(12) United States Patent
Ioannides et al.

(10) Patent No.: US 9,562,070 B2
(45) Date of Patent: *Feb. 7, 2017

(54) INDUCTION OF TUMOR IMMUNITY BY VARIANTS OF FOLATE BINDING PROTEIN

(71) Applicants: Board of Regents, The University of Texas System, Austin, TX (US); The Henry M. Jackson Foundation for the Advancement of Military Medicine, Inc., Bethesda, MD (US)

(72) Inventors: Constantin G. Ioannides, Houston, TX (US); George E. Peoples, Fulton, MD (US)

(73) Assignees: Board of Regents, The University of Texas System, Austin, TX (US); The Henry M. Jackson Foundation for the Advancement of Military Medicine, Inc., Bethesda, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/339,797

(22) Filed: Jul. 24, 2014

(65) Prior Publication Data
US 2015/0175658 A1 Jun. 25, 2015

Related U.S. Application Data

(60) Continuation of application No. 13/556,876, filed on Jul. 24, 2012, now Pat. No. 8,815,256, which is a continuation of application No. 12/422,600, filed on Apr. 13, 2009, now Pat. No. 8,258,261, which is a division of application No. 10/094,097, filed on Mar. 8, 2002, now Pat. No. 7,547,759.

(60) Provisional application No. 60/274,676, filed on Mar. 9, 2001.

(51) Int. Cl.
| | | |
|---|---|---|
| A61K 38/00 | (2006.01) | |
| C07K 7/06 | (2006.01) | |
| C07K 14/47 | (2006.01) | |
| A61K 39/17 | (2006.01) | |
| A61K 39/00 | (2006.01) | |

(52) U.S. Cl.
CPC ............ *C07K 7/06* (2013.01); *A61K 39/0011* (2013.01); *C07K 14/47* (2013.01); *A61K 38/00* (2013.01); *A61K 39/00* (2013.01); *A61K 39/17* (2013.01); *A61K 2039/54* (2013.01); *A61K 2039/545* (2013.01)

(58) Field of Classification Search
CPC .... A61K 39/0011; A61K 38/00; A61K 38/10; A61K 39/00; A61K 38/04; A61K 38/17
USPC ............................... 530/300, 328; 424/277.1
See application file for complete search history.

(56) References Cited

U.S. PATENT DOCUMENTS

| | | |
|---|---|---|
| 5,830,755 A | 11/1998 | Nishimura et al. |
| 5,846,538 A | 12/1998 | Cheever et al. |
| 6,153,430 A | 11/2000 | Pastan et al. |
| 6,514,942 B1 | 2/2003 | Ioannides et al. |
| 2003/0027766 A1 | 2/2003 | Ioannides et al. |
| 2003/0077248 A1 | 4/2003 | Moriarty et al. |

FOREIGN PATENT DOCUMENTS

WO 02/072766 A2 9/2002

OTHER PUBLICATIONS

National Center for Biotechnology Information GenBank Accession No. AAA37597, submitted Apr. 27, 2003; downloaded Sep. 7, 2004.
National Center for Biotechnology Information GenBank Accession No. AAA35824, submitted Apr. 27, 1993; downloaded Sep. 7, 2004.
National Center for Biotechnology Information GenBank Accession No. AAA37594, submitted Apr. 19, 1994; downloaded Sep. 7, 2004.
National Center for Biotechnology Information GenBank Accession No. AAA37596, submitted Apr. 27, 1993; downloaded Sep. 7, 2004.
National Center for Biotechnology Information GenBank Accession No. AAA37595, submitted Apr. 27, 1993; downloaded Sep. 7, 2004.
Pardoll, Drew M., "Therapeutic Vaccination for Cancer," Clinical Immunology, vol. 95(1):S44-S62 (2000).
Peoples, George E. et al., "Ovarian Cancer-associated Lymphocyte Recognition to Folate Binding Protein Peptides," Annals of Surgical Oncology, The Society of Surgical Oncology, Inc., Lippincott Williams & Wilkins, vol. 5(8):743-750 (1998).
Peoples, George E. et al., "Vaccine Implications of Folate Binding Protein, a Novel Cytotoxic T Lymphocyte-recognized Antigen System in Epithelial Cancers," Clin. Cancer Res., vol. 5(12):4214-4223 (1999).
Pietersz, G.A. et al., "Generation of Cellular Immune Responses to Antigenic Tumor Peptides," CMLS Cellular and Molecular Life Sciences, vol. 57:290-310 (2000).
Rosenberg, Steven A., "The Identification of Cancer Antigens: Impact on the Development of Cancer Vaccines," The Cancer Journal, vol. 6(Suppl. 2):S142-S149 (2000).
Ruppert, J. et al., "Prominent role of secondary anchor residues in peptide binding to HLA-A2.1 molecules," Cell, vol. 74(5):929-937 (1993).
Saijo, N., "What are the reasons for negative phase III trials of molecular-target-based drugs?" Cancer Science, vol. 95(10):772-776 (2004).
Schirle, Markus et al., "Combining computer algorithms with experimental approaches permits the rapid and accurate identification of T cell epitopes from defined antigens," Journal of Immunological Methods, vol. 257:1-16 (2001).
Skolnick, J. et al., "From genes to protein structure and function: novel applications of computational approaches in the genomic era," Trends in Biotechnology, vol. 18(1):34-39 (2000).

(Continued)

*Primary Examiner* — Stephen Rawlings
(74) *Attorney, Agent, or Firm* — Nelson Mullins Riley & Scarborough LLP; Jane E. Remillard, Esq.; Cynthia L. Kanik

(57) ABSTRACT

The present invention is directed to variants of antigens comprising folate binding protein epitopes as a composition associated with providing immunity against a tumor in an individual. The variant is effective in inducing cytotoxic T-lymphocytes but preferably not to the extent that they become sensitive to silencing by elimination, such as by apoptosis, or by anergy, as in unresponsiveness.

28 Claims, 6 Drawing Sheets

(56) References Cited

OTHER PUBLICATIONS

Spitler, L.E. et al., "Cancer vaccines: the interferon analogy," Cancer Biother., vol. 10(1):1-3 (1995).
Valmori, D. et al., "Diversity of the fine specificity displayed by HLA-A 0201-restricted CTL specific for the immunodominant Melan-A/MART-1 antigenic peptide," J. Immunol., vol. 161(12):6956-6962 (1998).
Valmori, Danila et al., "Enhanced Generation of Specific Tumor-Reactive CTL In Vitro by Selected Melan-A/MART-1 Immunodominant Peptide Analogues," The Journal of Immunology, vol. 160:1750-1758 (1998).
Van Der Burg, Sjoerd H. et al., "Immunogenicity of Peptide Bound to MHC Class I Molecules Depends on the MHC-Peptide Complex Stability," The Journal of Immunology, vol. 156:3308-3314 (1996).
Yamshchikov, G. et al., "Analysis of a natural immune response against tumor antigens in a melanoma survivor: lessons applicable to clinical trial evaluations," Clin. Cancer Res., vol. 7(3 Suppl.): 909s-916s (2001).
Yu, K. et al., "Methods for prediction of peptide binding to MHC molecules: a comparative study," Mol. Med., vol. 8 (3):137-148 (2002).
Zaks, T.Z. et al., "Immunization with a peptide epitope (p369-377) from HER-2/neu leads to peptide-specific cytotoxic T lymphocytes that fail to recognize HER-2/neu+ tumors," Cancer Res., vol. 58(21):4905-4908 (1998).
European Search Report for Application No. 11004714.9, 6 pages, dated Nov. 21, 2011.
Supplementary Partial European Search Report for Application No. 02750589.0, 5 pages, dated Jan. 29, 2008.
U.S. Appl. No. 10/094,097, filed Mar. 8, 2002, Constantin J. Ioannides.
U.S. Appl. No. 12/442,600, filed Apr. 13, 2009, Constantin J. Ioannides.
U.S. Appl. No. 13/556,876, filed Jul. 24, 2012, Constantin J. Ioannides.
U.S. Appl. No. 10/094,097, Jan. 5, 2009.
U.S. Appl. No. 10/094,097, Jun. 16, 2008.
U.S. Appl. No. 10/094,097, Oct. 18, 2007.
U.S. Appl. No. 10/094,097, Jun. 4, 2007.
U.S. Appl. No. 10/094,097, Nov. 7, 2006.
U.S. Appl. No. 10/094,097, May 12, 2006.
U.S. Appl. No. 10/094,097, Sep. 28, 2005.
U.S. Appl. No. 10/094,097, Apr. 1, 2004.
U.S. Appl. No. 12/442,600, Apr. 3, 2012.
U.S. Appl. No. 12/442,600, Nov. 8, 2011.
U.S. Appl. No. 12/442,600, Jun. 2, 2011.
U.S. Appl. No. 12/442,600, Feb. 4, 2011.
U.S. Appl. No. 13/556,876, May 16, 2014.
U.S. Appl. No. 13/556,876, Sep. 13, 2013.
U.S. Appl. No. 13/556,876, Apr. 24, 2013.
Abrams, Scott et al., "Rational Antigen Modification as a Strategy to Upregulate or Downregulate Antigen Recognition," Immunology, vol. 12:85-91 (2000).
Alexander, Richard B. et al., "Adoptively Transferred Tumor-Infiltrating Lymphocytes Can Cure Established Metastatic Tumor in Mice and Persist Long-Term In Vivo as Functional Memory T. Lymphocytes," Journal of Immunotherapy, vol. 10:389-397 (1991).
Andersen, M.H. et al., "Poor correspondence between predicted and experimental binding of peptides to class I MHC molecules," Tissue Antigens, vol. 55:519-531 (2000).
Bednarek, Maria A. et al., "Soluble HLA-A2.1 restricted peptides that are recognized by influenza virus specific cytotoxic T lymphocytes," Journal of Immunological Methods, vol. 139:41-47 (1991).
Bodey, B. et al., "Failure of cancer vaccines: the significant limitations of this approach to immunotherapy," Anticancer Res., vol. 20(4):2665-2676 (2000).
Boon, Thiery, "Toward a Genetic Analysis of Tumor Rejection Antigens," Advances in Cancer Research, vol. 58:177-210 (1992).

Bowie, James U. et al., "Deciphering the Message in Protein Sequences: Tolerance to Amino Acid Substitutions," Science, vol. 247:1306-1310 (1990).
Buelow, Roland et al., "Localization of the immunologic activity in the recognized by staphylococcal enterotoxin B using truncated recombinant fusion proteins," The Journal of Immunology, vol. 148(1):1-6 (1992).
Campbell, I.G. et al., "Folate-binding protein is a marker for ovarian cancer," Cancer Research, vol. 51 (19):5329-5338 (1991).
Castilleja, Agapito et al., "Induction of Tumor-Reactive CTL by C-Side Chain Variants of the CTL Epitope HER-2/neu Protooncogene (369-377) Selected by Molecular Modeling of the Peptide: HLA-A2 Complex," The Journal of Immunology, vol. 169(7):3545-3554 (2002).
Dalgleish, AG, "Cancer vaccines," British Journal of Cancer, vol. 82(10):1619-1624 (2000).
Deplaen, E. et al., "Structure, chromosomal localization, and expression of 12 genes of the MAGE family," Immunogenetics, vol. 40(5):360-369 (1994).
Ezzell, "Cancer 'Vaccines': An Idea Whose Time Has Come?" The Journal of NIH Research, vol. 7:46-49 (1995).
Falk, Kirsten et al., "Allele-specific motifs revealed by sequencing of self-peptides eluted from MHC molecules," Nature, vol. 351:290-296 (1991).
Feltkamp, Mariet C.W. et al., "Efficient MHC Class I-Peptide Binding is Required but Does Not Ensure MHC Class I-Restricted Immunogenicity," Molecular Immunology, vol. 31(18):1391-1401 (1994).
Fisk, B. et al., "Changes in an HER-2 peptide upregulating HLA-A2 expression affect both conformational epitopes and CTL recognition: implications for optimization of antigen presentation and tumor-specific CTL induction," J. Immunother. Emphasis Tumor Immunol., vol. 18(4):197-209 (1995).
Forni, G. et al., "Immunization in tumor prevention," Int. Immunopharmacol., vol. 3(8):1151-1158 (2003).
Gao, P. et al., "Tumor vaccination that enhances antitumor T-cell responses does not inhibit the growth of established tumors even in combination with interleukin-12 treatment: the importance of inducing intratumoral T-cell migration," J. Immunother., vol. 23(6):643-653 (2000).
Greenspan, N.S. et al., "Defining epitopes: It's not as easy as it seems," Nat. Biotechnol., vol. 17(10):936-937 (1999).
Guichard, Gilles et al., "Melanoma Peptide MART-1(27-35) Analogues with Enhanced Binding Capacity to the Human Class I Histocompatibility Molecule HLA-A2 by Introduction of a beta-Amino Acid Residue: Implications for Recognition by Tumor-Infiltrating Lymphocytes," J. Med. Chem., vol. 43:3803-3808 (2000).
Gura, T., "Systems for identifying new drugs are often faulty," Science, vol. 278(5340):1041-1042 (1997).
Holmes, E.H., "PSMA specific antibodies and their diagnostic and therapeutic use," Expert Opin. Investig. Drugs, vol. 10(3):511-519 (2001).
Huard, R. et al., "The critical role of a solvent-exposed residue of an MHC class I-restricted peptide in MHC-peptide binding," Int. Immunol., vol. 9(11):1701-1707 (1997).
Hudson, J. et al., "Growth and Antigen Recognition of Tumor-Infiltrating Lymphocytes from Human Breast Cancer," Journal of Interferon and Cytokine Research, vol. 18:529-536 (1998).
Ioannides, Constantin G., "Clarification of the Functional Significance of Human Folate-binding Protein-Peptide, 191-199, based on a Correct GenBank Sequence and on Other FBP (191-199) Sequences," Anticancer Res., vol. 27(4B):2251-2252 (2007).
Ioannides, Constantin G., "Cytotoxic T Cells from Ovarian Malignant Tumors Can Recognize Polymorphic Epithelial Mucin Core Peptides," The Journal of Immunology, vol. 151(7):3693-3703 (1993).
Ioannides, Constantin G. et al., "Cytotoxic T Cells Isolated from Ovarian Malignant Ascites Recognize a Peptide Derived from the HER-2/neu Proto-oncognee," Cellular Immunology, vol. 151:225-234 (1993).
Ioannides, Constantin G. et al., "Cytokine T Cell Clones Isolated From Ovarian Tumor-Infiltrating Lymphocytes Recognize Multiple

(56) References Cited

OTHER PUBLICATIONS

Antigenic Epitopes on Autologous Tumor Cells," The Journal of Immunology, vol. 146 (5):1700-1707 (1991).
Ioannides, Constantin G., "Induction of Interleukin-2 receptor by tumor necrosis factor a on cultured ovarian tumor-associated lymphocites," Cancer Immunol. Immunother, vol. 35:83-91 (1992).
Ioannides, Constantin G., "Lymphocites Infiltrating Ovarian Malignant Ascites: Modulation of IL-2-induced Proliferation by IL-4 and of Selective Increase in CD8+ T Cells by TNF-alpha," Lymphokine and Cytokine Research, vol. 10(4):307-315 (1991).
Ioannides, Constantin G. et al., "T-Cell Recognition on Oncogene Products: A New Strategy for Immunology," Molecular Carcinogenesis, vol. 6:77-82 (1992).
Kim, Dong-Kyu et al., "Folate Binding Protein Peptide 191-199 Presented on Dendritic Cells Can Stimulate CTL from Ovarian and Breast Cancer Patients," Anticancer Research, vol. 19:2907-2916 (1999).
Kim, Dong-Kyu et al., "The Comparison of Cytotoxic T-Lymphocyte Effects of Dendritic Cells Stimulated by the Folate Binding Protein Peptide Cultured with IL-15 and IL-2 in Solid Tumor," Yonsei Medical Journal, vol. 43(6):691-700 (2002).
Kos, Ferdynand J. et al., "Specific epitope-induced conversion of CD8+ memory cells into effector cytotoxic T lymphocytes in vitro: presentation of peptide antigen by CD8+ T cells," Eur. J. Immunol., vol. 22:1595-1601 (1992).
Lee, Tom V. et al., "Identification of Activated Tumor Antigen-Reactive CD8+ Cells in Healthy Individuals," Oncology Reports, vol. 7:455-466 (2000).
Lee, K.H. et al., "Increased vaccine-specific T cell frequency after peptide-based vaccination correlates with increased susceptibility to in vitro stimulation but does not lead to tumor regression," J. Immunol., vol. 163(11):6292-6300 (1999).
Li, Peng Young et al., "Local Concentration of Folate Binding Protein GP38 in Sections of Human Ovarian Carcinoma by In Vitro Quantitative Autoradiography," J. Nucl. Med., vol. 37:665-672 (1996).
Lollini, P.L. et al., "Cancer immunoprevention: tracking down persistent tumor antigens," Trends Immunol., vol. 24 (2):62-66 (2003).
Lu, Y. et al., "Immunotherapy of folate receptor-expressing tumors: review of recent advances and future prospects," J. Control Release, vol. 91(1-2):17-29 (2003).
Mantovani, L.T. et al., "Folate Binding Protein Distribution in Normal Tissues and Biological Fluids From Ovarian Carcinoma Patients as Detected by the Monoclonal Antibodies MOv18 and MOv19," European Journal of Cancer, vol. 30A(3):363-369 (1994).
Mazzoni, A. et al., "CD3-CD28 costimulation as a means to avoiding T cell preactivation in bispecific monoclonal antibody-based treatment of ovarian carcinoma," Cancer Res., vol. 56(23):5443-5449 (1996).
McCullough, K.C. et al., "Basic concepts of immune response and defense development," ILAR J., vol. 46(3):230-240 (2005).
National Center for Biotechnology Information GenBank Accession No. 1011184A, submitted Jun. 21, 1996; downloaded Sep. 7, 2004.
National Center for Biotechnology Information GenBank Accession No. 0908212A, submitted May 2, 1996; downloaded Sep. 7, 2004.
National Center for Biotechnology Information GenBank Accession No. CAA46610, submitted Feb. 19, 1992; downloaded Sep. 7, 2004.
National Center for Biotechnology Information GenBank Accession No. CAA83553, submitted Apr. 15, 1994; downloaded Sep. 7, 2004.
National Center for Biotechnology Information GenBank Accession No. AAA74896, submitted Aug. 25, 1995; downloaded Sep. 7, 2004.
National Center for Biotechnology Information GenBank Accession No. AAA49056, submitted Apr. 28, 1993; downloaded Sep. 7, 2004.
National Center for Biotechnology Information GenBank Accession No. AAA37599, submitted Apr. 27, 1993; downloaded Sep. 7, 2004.
National Center for Biotechnology Information GenBank Accession No. AAA37598, submitted Apr. 27, 1993; downloaded Sep. 7, 2004.

CTL Activity
E39 µg/mL
(% Specific Lysis)

|  | 0µg/mL | 5µg/mL | 25µg/mL |
|---|---|---|---|
| 1. J65x3, E39 | 0 | 24.5 | 17.4 |
| 2. J65x3, J77 | 0 | 4.2 | 8.2 |
| 3. J65x3, J65 | 0 | 20.9 | 23.2 |
| 4. E39x3, E39 | 0 | 11.1 | 14.6 |

Figure 2B

INDUCTION OF TUMOR IMMUNITY BY VARIANTS OF FOLATE BINDING PROTEIN

RELATED APPLICATIONS

This application is a continuation of U.S. application Ser. No. 13/556,876, which issued as U.S. Pat. No. 8,815,256, on Aug. 26, 2014, which is a continuation of U.S. application Ser. No. 12/422,600, which issued as U.S. Pat. No. 8,258,261, on Sep. 4, 2012, which is a divisional of U.S. application Ser. No. 10/094,097, which issued as U.S. Pat. No. 7,547,759, on Jun. 16, 2009, which claims priority to, and the benefit of, U.S. application Ser. No. 60/274,676, filed on Mar. 9, 2001. The contents of the aforementioned provisional application is hereby incorporated herein by reference.

The government owns rights in the present invention pursuant to United States Army grant number DAMD 17-94-J-4313.

FIELD OF THE INVENTION

The present invention is directed to the fields of cancer and immunology. Specifically, the present invention is directed to compositions and methods for tumor vaccines directed to tumor antigens and is directed to specific epitopes on these antigens that are recognized by cytotoxic T-lymphocytes (CTL). More specifically, the present invention regards compositions and methods for variants of folate binding protein (FBP).

BACKGROUND OF THE INVENTION

Tumor reactive T-cells have been reported to mediate therapeutic responses against human cancers (Rosenberg et al., 1988). In certain instances, in human immunotherapy trials with tumor infiltrating lymphocytes (TIL) or tumor vaccines, these responses correlated either with in vitro cytotoxicity levels against autologous tumors (Aebersold et al., 1991) or with expression of certain HLA-A,B,C gene products (Marincola et al., 1992). Recent studies (Ioannides et al., 1992) have proposed that in addition to virally encoded and mutated oncogenes, overexpressed self-proteins may elicit some degree of tumor-reactive cytotoxic T-lymphocytes (CTLs) in patients with various malignancies (Ioannides et al., 1992; Ioannides et al., 1993; Brichard et al., 1993; Jerome et al., 1991). Autologous tumor reactive CTLs can be generated from lymphocytes infiltrating ovarian malignant ascites (Ioannides et al., 1991), and overexpressed proteins, such as HER-2, may be targets for CTL recognition (Ioannides et al., 1992).

T-cells play an important role in tumor regression in most murine tumor models. Tumor infiltrating lymphocytes (TIL) that recognize unique cancer antigens can be isolated from many murine tumors. The adoptive transfer of these TIL in addition to interleukin-2 can mediate the regression of established lung and liver metastases (Rosenberg et al., 1986). In addition, the secretion of IFN-γ by injected TIL significantly correlates with in vivo regression of murine tumors suggesting activation of T-cells by the tumor antigens (Barth et al., 1991). The known ability of TIL to mediate the regression of metastatic cancer in 35 to 40% of melanoma patients when adoptively transferred into patients with metastatic melanoma attests to the clinical importance of the antigens recognized (Rosenberg et al., 1988; Rosenberg, 1992).

Strong evidence that an immune response to cancer exists in humans is provided by the existence of tumor reactive lymphocytes within melanoma deposits. These lymphocytes, when isolated, are capable of recognizing specific tumor antigens on autologous and allogeneic melanomas in an MHC restricted fashion. (Itoh et al., 1986; Muul et al., 1987; Topalian et al., 1989; Darrow et al., 1989; Horn et al., 1991; Kawakami et al., 1992; Horn et al., 1993; O'Neil et al., 1993). TIL from patients with metastatic melanoma recognize shared antigens including melanocyte-melanoma lineage specific tissue antigens in vitro (Kawakami et al., 1993; Anichini et al. 1993). Anti-melanoma T-cells appear to be enriched in TIL, probably as a consequence of clonal expansion and accumulation at the tumor site in vivo (Sensi et al., 1993). The transduction of T-cells with a variety of genes, such as cytokines, has been demonstrated. T-cells have been shown to express foreign gene products. (Blaese, 1993; Hwu et al., 1993; Culver et al., 1991) The fact that individuals mount cellular and humoral responses against tumor associated antigens suggests that identification and characterization of additional tumor antigens is important for immunotherapy of patients with cancer.

T-cell receptors on CD8$^+$ T-cells recognize a complex consisting of an antigenic peptide (9-10 amino acids for HLA-A2), β2 microglobulin and class I major histocompatibility complex (MHC) heavy chain (HLA-A, B, C, in humans). Peptides generated by digestion of endogenously synthesized proteins are transported into the endoplastic reticulum, bound to class I MHC heavy chain and β2 microglobulin, and finally expressed in the cell surface in the groove of the class I MHC molecule.

Information on epitopes of self-proteins recognized in the context of MHC Class I molecules remain limited, despite a few attempts to identify epitopes capable of in vitro priming and Ag-specific expansion of human CTLs. For example, peptide epitopes have been proposed which are likely candidates for binding on particular MHC Class I Ag (Falk et al., 1991), and some studies have attempted to define peptide epitopes which bind MHC Class I antigens.

Synthetic peptides have been shown to be a useful tool for T-cell epitope mapping. However in vivo and in vitro priming of specific CTLs has encountered difficulties (Alexander et al., 1991; Schild et al., 1991; Carbone et al., 1988). It is generally considered that in vitro CTL priming cannot necessarily be achieved with peptide alone, and in fact, a high antigen density is thought to be required for peptide priming (Alexander et al., 1991). Even in the limited instances when specific priming was achieved, APC or stimulators were also required at high densities (Alexander et al., 1991).

Short synthetic peptides have been used either as target antigens for epitope mapping or for induction of in vitro primary and secondary CTL responses to viral and parasitic Ags (Bednarek et al., 1991; Gammon et al., 1992; Schmidt et al., 1992; Kos and Müllbacher, 1992; Hill et al., 1992). Unfortunately, these studies failed to show the ability of proto-oncogene peptide analogs to stimulate in vitro human CTLs to lyse tumors endogenously expressing these antigens.

Identification of tumor antigens (Ag) and of specific epitopes on these Ag recognized by cytotoxic T-lymphocytes enables the development of tumor vaccines (for review of tumor antigens, see Rosenberg (2000), incorporated by reference herein). Tumor Ag are weak or partial agonists for activation of low-avidity (low-affinity) CTL. Attempts to activate CTL by increasing the affinity of peptide for MHC (by modifications in the anchor residues) has produced mixed successes even with powerful APC (dendritic cells, DC) and added B7 costimulation. Some of the resulting cross-reactive CTL recognized tumors with lower affinity than CTL induced by wild type Ag.

The limited ability of anchor-fixed immunogens to induce and expand high-affinity CTL raises the need for alternative approaches for CTL induction. One approach to this question is to design immunogens which activate "high-affinity" CTL from the existent pool of responders. In human tumor immunology, this approach has been successful in some instances. However, high-affinity CTL are expected to be more sensitive to silencing by elimination (e.g apoptosis) or by anergy (unresponsiveness or diminished reactivity to a specific antigen).

These processes occur as a consequence of recurrent stimulations with Ag (tumor Ag) and are amplified by a number of cytokines. The general mechanism of activation induced cell death (AICD) is that repeated stimulations with an Ag in the presence of cytokines such as IL-2 activates cell death pathways. This is because stimulation with Ag and IL-2 transduces a signal which is too strong to induce proliferation and instead leads to premature senescence. An alternative death pathway, passive cell death (PCD) occurs when cytokines involved in survival (IL-2, IL-4, IL-7, etc.) are withdrawn. Since tumor Ag are self-Ag, the corresponding responding cells should be even more sensitive to deletion than CTL responding to foreign Ag, because the body's defense mechanisms are programmed to avoid autoimmunity. There is little known as to how the survival of responders to tumor Ag can be induced, and how they can be protected from AICD or PCD.

Preclinical and clinical trials are underway for the utilization of tumor-specific peptide epitopes for melanoma (Rivoltini et al., 1999; Parkhurst et al., 1998; Kawakami et al., 1998; Lustgarten et al., 1997; Zeng et al., 1997; Reynolds et al., 1998; Nestle et al., 1998; Chakraborty et al., 1998; Rosenberg et al., 1998); breast cancer, such as with MUC1 (Gendler et al., 1998; Xing et al., 1989; Xing et al., 1990; Jerome et al., 1993; Apostolopoulos et al., 1994; Ding et al., 1993; Mang et al., 1996; Acres et al., 1993; Henderson et al., 1998; Henderson et al., 1996; Samuel et al., 1998; Gong et al., 1997; Apostolopoulos et al., 1995; Pietersz et al., 1998; Lofthouse et al., 1997; Rowse et al., 1998; Gong et al., 1998; Acres et al., 1999; Apostolopoulos et al., 1998; Lees et al., 1999; Xing et al., 1995; Goydos et al., 1996; Reddish et al., 1998; Karanikas et aL, 1997), p53 (DeLeo, 1998; McCarty et al., 1998; Hurpin et al., 1998; Gabrilovich et al., 1996), and Her-2/neu (Disis and Cheever, 1998; Ioannides et al., 1993; Fisk et al., 1995; Peoples et al., 1995; Kawashima et al., 1999; Disi et al., 1996); and colon cancer (Kantor et al., 1992; Kantor et al., 1992; Tsang et al., 1995; Hodge et al., 1997; Conry et al., 1998; Kass et al., 1999; Zaremba et al., 1997; Nukaya et al., 1999).

Recently, peptides of folate binding protein (FBP) were recognized by tumor-associated lymphocytes (Peoples et al., 1998; Peoples et al., 1999; Kim et al., 1999). FBP is a membrane-associated glycoprotein originally found as a mAb-defined Ag in placenta and trophoblastic cells but rarely in other normal tissues (Retrig et al., 1985; Elwood, 1989; Weitman et al., 1992; Garin-Chesa et al., 1993). Of interest, this protein has been found in greater than 90% of ovarian and endometrial carcinomas; in 20-50% of breast, colorectal, lung, and renal cell carcinomas; and in multiple other tumor types. When present in cancerous tissue, the level of expression is usually greater than 20-fold normal tissue expression and has been reported to be as high as 80-90-fold in ovarian carcinomas (Li et al., 1996).

U.S. Pat. No. 5,846,538 is directed to immune reactivity to peptides of HER-2/neu protein for treatment of malignancies.

Folate binding protein provides an ideal target for and satisfies a long-felt need in the art for compositions and methods of utilizing the compositions directed to tumor immunity.

SUMMARY OF THE INVENTION

It is an object of the present invention to provide as a composition of matter an antigen comprising a folate binding protein epitope of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

It is another object of the present invention to provide a composition comprising an antigen which includes a folate binding protein epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof in a pharmaceutically acceptable excipient.

It is another object of the present invention to provide a method for stimulating cytotoxic T-lymphocytes, comprising the step of contacting the cytotoxic T-lymphocytes with an amount of an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and a combination thereof, wherein the amount is effective to stimulate the cytotoxic T-lymphocytes. In a specific embodiment of the present invention, the cytotoxic T-lymphocytes are located within a human. In another specific embodiment, the method further comprises the step of administering to the human an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and a combination thereof. In another specific embodiment of the present invention, the epitope is formulated for administration parenterally, topically, or as an inhalant, aerosol or spray.

It is an additional object of the present invention to provide a method of generating an immune response, comprising the step of administering to a human a pharmaceutical composition comprising an immunologically effective amount of a composition comprising an antigen comprising a folate binding epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof.

It is another object of the present invention to provide a method of inducing immunity against a tumor in an individual, comprising the steps of administering to the individual an antigen comprising a folate binding protein epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof; and administering to the individual a cancer vaccine. In a specific embodiment of the present invention, the an antigen comprising a folate binding protein epitope is administered prior to the administration of the cancer vaccine. In a specific embodiment of the present invention, an antigen comprising a folate binding protein epitope is administered subsequent to the administration of the cancer vaccine. In another specific embodiment of the present invention, the antigen comprising a folate binding protein epitope is administered both prior to and subsequent to the administration of the cancer vaccine. In a further specific embodiment, the cancer vaccine comprises a polypeptide selected from the group consisting of SEQ ID NO:268 (E39) and SEQ ID NO:269 (E41).

It is another object of the present invention to provide a method of inducing memory cytotoxic T-lymphocytes in an individual comprising the step of administering an antigen comprising a folate binding epitope of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof. In a specific embodiment, the individual is substantially susceptible to recurrence of cancer.

It is another object of the present invention to provide a method of providing immunity against a tumor comprising the step of administering an antigen comprising a folate binding epitope vaccine of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof.

It is another object of the present invention to provide a method of treating an individual for cancer comprising the steps of administering to the individual a first cancer vaccine; and administering to the individual a second cancer vaccine comprising a peptide selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof. In a specific embodiment, the first cancer vaccine administration step precedes the second cancer vaccine administration step. In another specific embodiment, the first cancer vaccine administration step is subsequent to the second cancer vaccine administration step.

It is an additional object of the present invention to provide a pharmaceutical composition comprising an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof in a pharmaceutically acceptable excipient.

It is another object of the present invention to provide a method of treating a proliferative cell disorder in a human, comprising administering to the human a therapeutically effective amount of a pharmaceutical composition comprising an antigen comprising a folate binding protein epitope selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or a combination thereof in a pharmaceutically acceptable excipient. In a specific embodiment, the proliferative cell disorder is cancer. In an additional specific embodiment, the cancer is breast cancer, ovarian cancer, endometrial cancer, colorectal cancer, lung cancer, renal cancer, melanoma, kidney cancer, prostate cancer, brain cancer, sarcomas, or a combination thereof.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 2B illustrates CTL activity in PBMC with multiple stimulations with J65 or E39.

DETAILED DESCRIPTION OF THE INVENTION

I. Definitions

Figure 1:
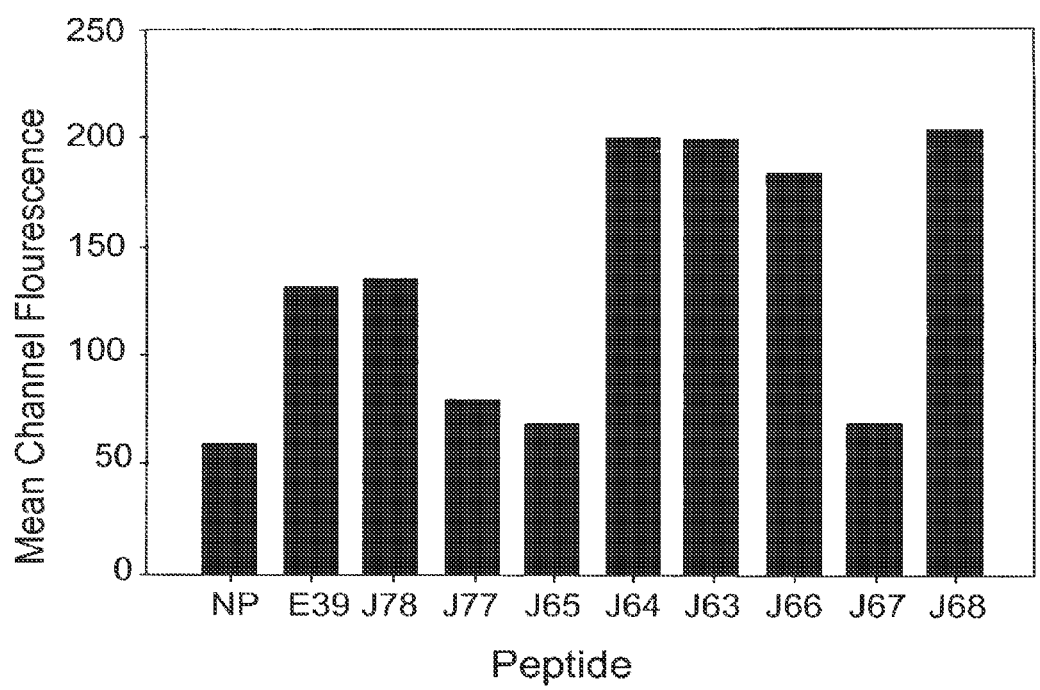
FIG. 1 demonstrates HLA-A2 stabilization by FBP epitope E39 variants.
Figure 2A:
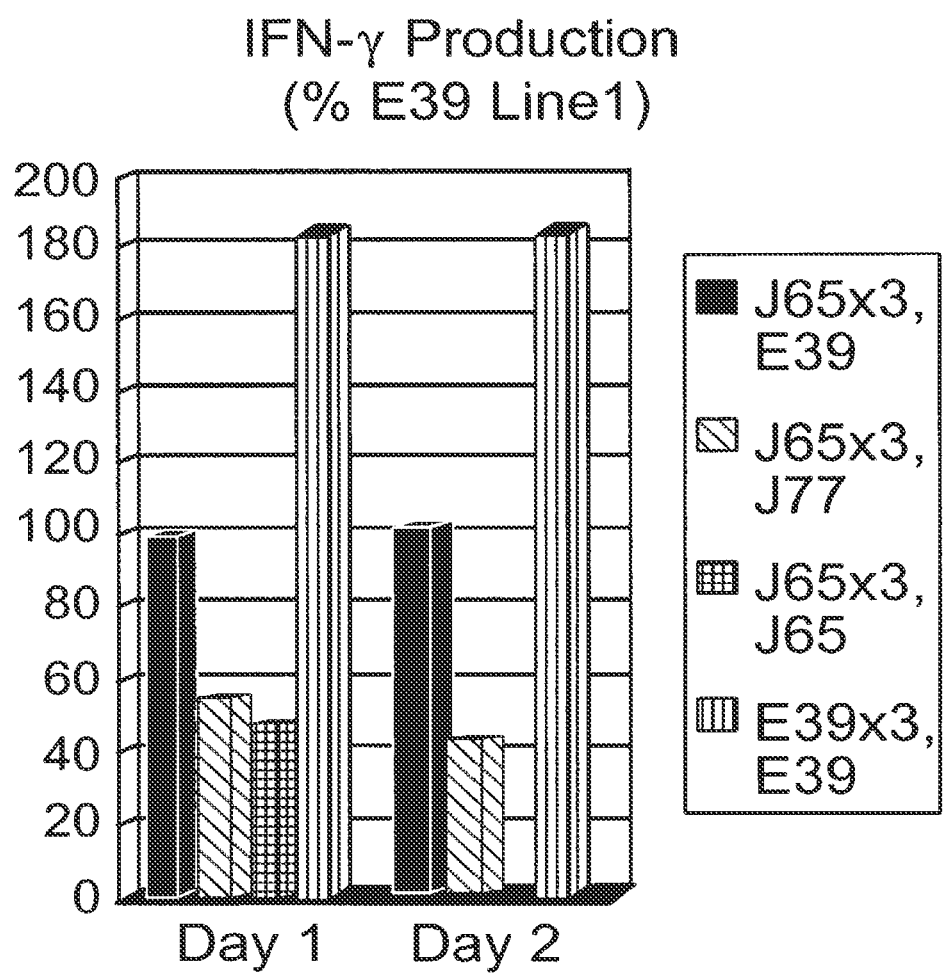
FIG. 2A illustrates IFN-γ induction in peripheral blood mononuclear cells (PBMC) with multiple stimulations with J65 or E39.
Figure 3:
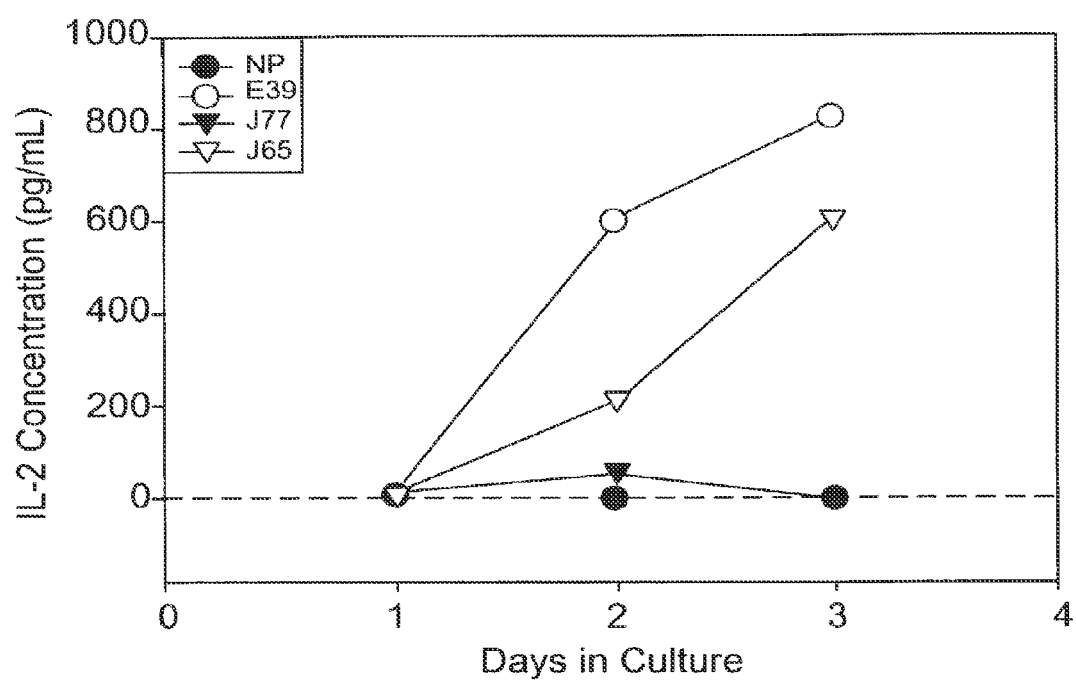
FIG. 3 illustrates specific interleukin 2 (IL-2) induction in PBMCs by priming with E39 variants.
Figure 4:
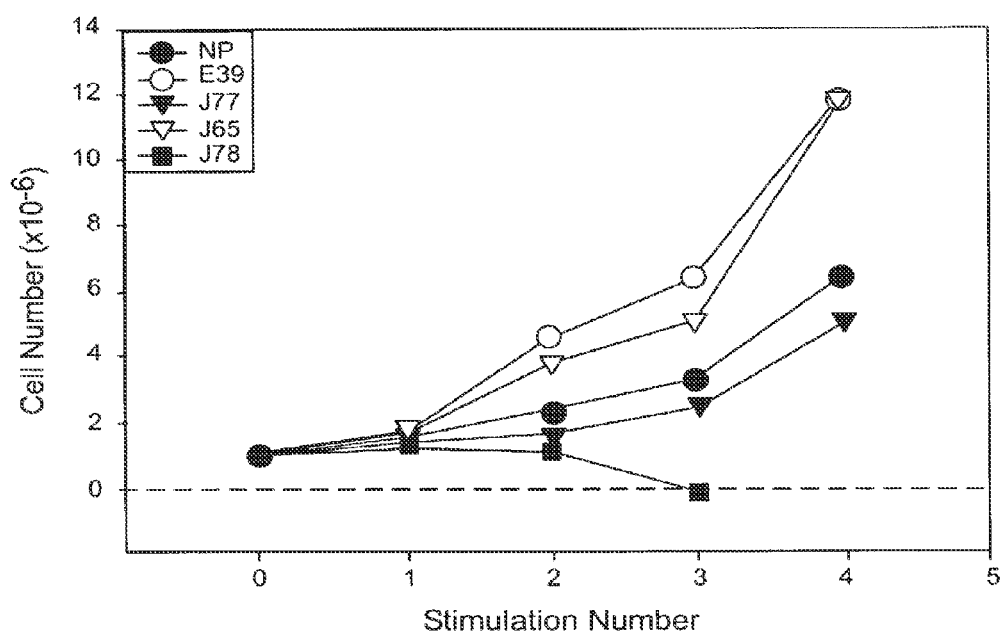
FIG. 4 illustrates expansion of PBMCs stimulated with FBP peptide E39 and its variants.
Figure 5:
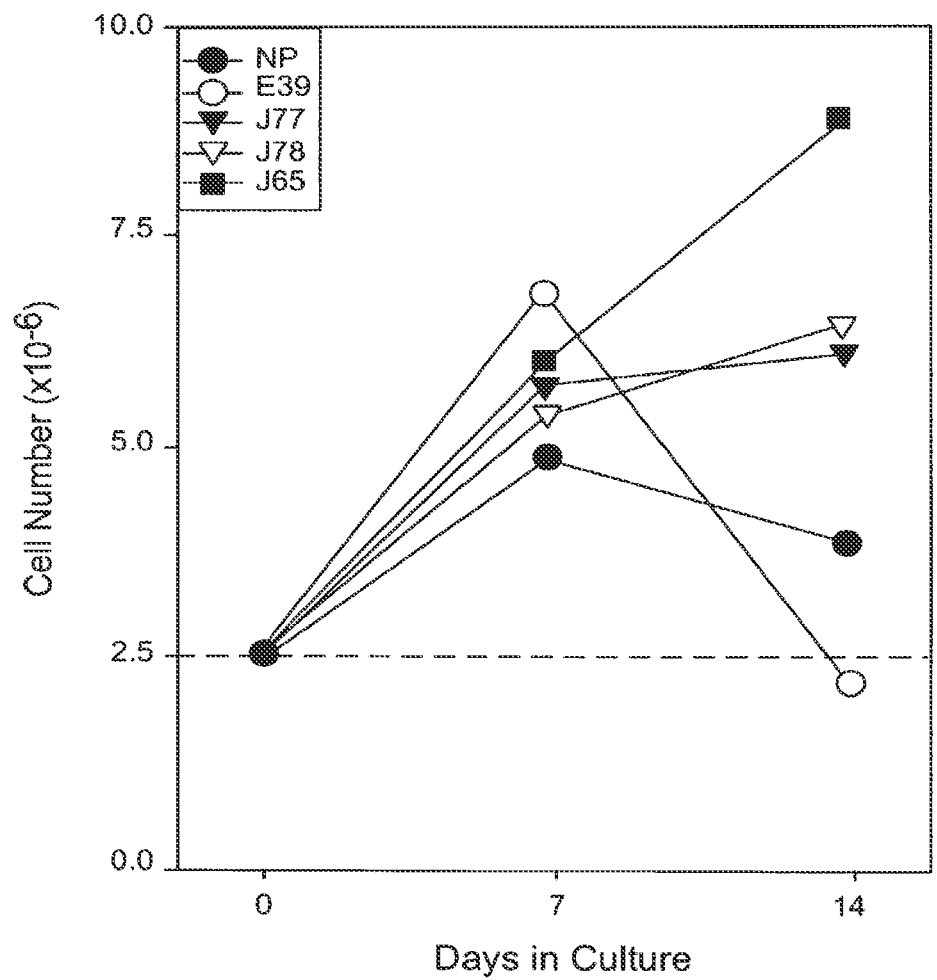
FIG. 5 demonstrates expansion of PBMC stimulated with variants of the FBP peptide E39.

As used herein the specification, "a" or "an" may mean one or more. As used herein in the claim(s), when used in conjunction with the word "comprising", the words "a" or "an" may mean one or more than one. As used herein "another" may mean at least a second or more.

The term "antigen" as used herein is defined as an entity which elicits an immune system response. The term herein may be abbreviated to "Ag."

The term "cancer" as used herein is defined as a tissue of uncontrolled growth or proliferation of cells, such as a tumor. In a specific embodiment, the cancer is an epithelial cancer. In specific embodiments, the cancer is breast cancer, ovarian cancer, endometrial cancer, colorectal cancer, lung cancer, renal cancer, melanoma, kidney cancer, prostate cancer, brain cancer, sarcomas, or a combination thereof. In specific embodiments, such cancers in mammals are caused by chromosomal abnormalities, degenerative growth and/or developmental disorders, mitogenic agents, ultraviolet radiation (uv), viral infections, inappropriate tissue expression of a gene, alterations in expression of a gene, carcinogenic agents, or a combination thereof. The term melanoma includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. The aforementioned cancers can be treated by methods described in the present application.

The term "epitope" as used herein is defined as a short peptide derived from a protein antigen which binds to an MHC molecule and is recognized by a particular T cell.

The term "folate binding protein variant" as used herein is defined as a folate binding protein and peptides thereof which are preferably recognized by helper T cells or cytotoxic T cells and may be naturally derived, synthetically produced, genetically engineered, or a functional equivalent thereof, e.g where one or more amino acids may be replaced by other amino acid(s) or non-amino acid(s) which do not substantially affect function. In specific embodiments, the peptides are epitopes which contain alterations, modifications, or changes in comparison to SEQ ID NO:268 (E39) or SEQ ID NO:269 (E41). In further specific embodiments, the variants are of SEQ ID NO:1 through SEQ ID NO:8.

The term "immune response" as used herein refers to a cellular immune response, including eliciting stimulation of T lymphocytes, macrophages, and/or natural killer cells.

The term "immunity" as used herein is defined as the ability to provide resistance to a tumor resulting from exposure to an antigen that is a folate binding protein epitope, such as the folate binding protein variants described herein.

The term "vaccine" as used herein is defined as a composition for generating immunity to a cancer. In specific embodiments, the cancer vaccine is a wild-type epitope of folate binding protein, such as E39 (FBP amino acid residues 191-199) (SEQ ID NO:268) or E41 (FBP amino acid residues 245-253) (SEQ ID NO:269). In other specific embodiments, the cancer vaccine comprises SEQ ID NO:1, SEQ ID NO:2, SEQ ID NO:3, SEQ ID NO:4, SEQ ID NO:5, SEQ ID NO:6, SEQ ID NO:7, or SEQ ID NO:8, or a combination thereof. In a preferred embodiment, administration of the vaccine alternates the signaling through the T cell receptor, thereby reducing the possibility of apoptosis.

The term "variant" as used herein is defined as a modified or altered form of a wildtype sequence, such as the folate binding protein E39 epitope (SEQ ID NO:268). The variant may contain replacement of at least one amino acid residue or may contain an altered side chain for at least one amino acid residue.

II. The Present Invention

A. Specific Embodiments

The present invention is directed to folate binding protein tumor Ag modified to attenuate the signaling through T cell receptors, compared with a wild-type folate binding protein tumor Ag, particularly for reducing the possibility of apoptosis that results following repeated exposure to strong antigens. Thus, variants of folate binding protein epitopes such as E39 (SEQ ID NO:268) and E41 (SEQ ID NO:269), which are "strong" antigens, are modified to act as a "weak" antigen. Thus, the present invention utilizes compositions and methods to attenuate signaling through the T cell receptors.

The invention works as (1) prestimulation prevaccine, to be administered before the tumor Ag; (2) as post vaccine to be given after the tumor Ag; and/or (3) in certain individuals will work as a priming vaccine. The situations (1) and (2) are more related to a protective role for SEQ ID NO:6 (J65) and its analogs for tumor reactive CTL. The situation (3) can be encountered in certain individuals where mutations in the histocompatibility Ag binding pocket may transform an attenuator into a strong immunogen.

The invention allows protection before and after vaccination of either precursors (stand-in) or activated effectors. In specific embodiments, administration of the variants of folate binding protein provide targeted induction of memory CTL.

The variants described herein, in a particular embodiment SEQ ID NO:6, are intended to attenuate the signaling at recurrent stimulation, thus inducing protection of CTL precursors as of activated T-cells from apoptosis, thereby enabling the immune response to expand, and, in preferred embodiments, have important implications in induction of memory CTL.

It is well known that the two major arms of the immune system are: (1) cell-mediated immunity with immune T cells; and (2) humoral immunity with antibodies. Further, the immune system normally functions to recognize and destroy any foreign or aberrant cells in the body. Since FBP is expressed by some normal cells, tolerance and/or anergy is expected.

Development of molecular therapies for cancer have historically focused on specific recognition of Ags by cellular immune effectors. The present invention discloses novel strategies aimed at identification of peptide targets for CTLs, and generation of T-cell immunity against specific epitopes (for a review of T-cell specific immunity, see, e.g, Ioannides et al., 1992; Houbiers et al., 1993).

To achieve this, the present invention provides novel naturally- and synthetically-derived peptides which bind human leucocyte antigen-(HLA) class I heavy chains. Appropriate criteria for epitope selection in vitro have been defined, and synthetic peptides based on immunogenic epitopes of FBP have also been produced.

Although the dominant anchors for peptide binding to HLA-A2 are Leu (P2) and Val (P9), a number of residues with similar charge and side chains, such as He and/or Met, were identified in CTL epitopes from viral proteins (Falk et al., 1991; Bednarek et al., 1991).

B. General Embodiments

1. CTL Epitopes

CTL epitopes reported to date are mainly derived from foreign (viral) proteins with little or no homology to self-proteins. With respect to CTL responses to self-proteins, it is expected that T-cells expressing TCR with high affinity for self-peptide-MHC class I complexes are eliminated in the thymus during development. Self-peptides eluted from HLA-A2.1 molecules of various cell lines show residues at P3-P5 and P7-P8 which are different from the sequences of viral epitopes recognized by human CTLs. Since these residues are likely to contact and interact with TCR, they may reflect peptides for which autologous T-cells are already tolerant/anergic.

For T-cell recognizing self-epitopes to be eliminated or anergized, a precondition exists that the peptide-MHC complex is stable enough to engage a sufficient number of TCRs, or at least more stable than other HLA-A2 peptide complexes, where one peptide can be easily displaced by other peptides. Consequently, this would suggest that for self-proteins with extension to FBP, the ones that can bind TCR with high affinity during development will be less likely to be recognized later when expressed on a tumor other target, than peptides that bind HLA-A2 with low affinity, which under appropriate conditions (e.g, high protein concentration) may occupy a higher number of HLA-A2 molecules. For low-affinity peptides, modification of the anchors resulting in stabilization of peptide—HLA-A2 interaction by replacing weak with dominant anchor residues (e.g, (P9) M⇒V should facilitate the reactivity of CTL with targets expressing such antigens, because TCR interacts mainly with the sequence P4-P8.

Tumor progression and metastasis are often associated with overexpression of specific cellular proteins. Epitopes of non-mutated overexpressed proteins can be targets of a specific cellular immune response against tumor mediated by T-cells. Moreover, when T-cell epitopes are present, distinction between tumor immunity/autoimmunity and unresponsiveness can be predicated on the protein concentration as a limiting factor of epitope supply.

2. Epitopic Core Sequences

The present invention is also directed to protein or peptide compositions, free from total cells and other peptides, which comprise a purified protein or peptide which incorporates an epitope that is immunologically recognized by a CTL.

As used herein, the term "incorporating an epitope(s) that is immunologically recognized by a CTL" is intended to refer to a peptide or protein antigen which includes a primary, secondary or tertiary structure similar to an epitope located within a FBP polypeptide. The level of similarity will generally be to such a degree that the same population of CTLs will also bind to, react with, or otherwise recognize, the cross-reactive peptide or protein antigen.

The identification of CTL-stimulating immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity.

The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of 8 to 20 amino acids in length, and more preferably about 8 to about 15 amino acids in length. It is proposed that shorter antigenic CTL-stimulating peptides will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to FBP sequences. These epitopic core sequences are identified herein in particular aspects as hydrophilic regions of the FBP polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, receptors on CTLs. It will be understood that in the context of the present disclosure, the term "complementary" refers to amino acids or peptides that exhibit an attractive force towards each other.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 9 or 10 being more preferred. Thus, this size will generally correspond to the smallest peptide antigens prepared in accordance with the invention. However, the size of the antigen may be larger where desired, so long as it contains a basic epitopic core sequence.

A skilled artisan recognizes that numerous computer programs are available for use in predicting antigenic portions of proteins (see e.g, Jameson & Wolf, 1988; Wolf et al., 1988). Computerized peptide sequence analysis programs (e.g, DNAStar Software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g, through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g, up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4°C, or more preferably, frozen. Of course, where the peptides are stored in a lyophilized or powdered state, they may be stored virtually indefinitely, e.g, in metered aliquots that may be rehydrated with a predetermined amount of water (preferably distilled) or buffer prior to use.

3. T Lymphocytes

T lymphocytes recognize antigen in the form of peptide fragments that are bound to class I and class II molecules of the major histocompatibility complex (MHC) locus. Major Histocompatibility Complex (MHC) is a generic designation meant to encompass the histocompatibility antigen systems described in different species including the human leucocyte antigens (HLA). The T-cell receptor for antigen (TCR) is a complex of at least 8 polypeptide chains. ("Basic and Clinical Immunology" (1994) Stites, Terr and Parslow (eds) Appleton and Lange, Nenmack Conn.) Two of these chains (the alpha and beta chains) form a disulfide-linked dimer that recognizes antigenic peptides bound to MHC molecules and therefore is the actual ligand-binding structure within the TCR. The TCR alpha and beta chains are similar in many respects to immunoglobulin proteins. The amino-terminal regions of the alpha and beta chains are highly polymorphic, so that within the entire T-cell population there are a large number of different TCR alpha/beta dimers, each capable of recognizing or binding a particular combination of antigenic peptide and MHC.

In general, $CD4^+$ T cell populations are considered to function as helpers/inducers through the release of lymphokines when stimulated by a specific antigen; however, a subset of $CD4^+$ cells can act as cytotoxic T lymphocytes (CTL). Similarly, $CD8^+$ T cells are considered to function by directly lysing antigenic targets; however, under a variety of circumstances they can secrete lymphokines to provide helper or DTH function. Despite the potential of overlapping function, the phenotypic CD4 and CD8 markers are linked to the recognition of peptides bound to class II or class I MHC antigens. The recognition of antigen in the context of class II or class I MHC mandates that $CD4^+$ and $CD8^+$ T cells respond to different antigens or the same antigen presented under different circumstances. The binding of immunogenic peptides to class II MHC antigens most commonly occurs for antigens ingested by antigen presenting cells. Therefore, $CD4^+$ T cells generally recognize antigens that have been external to the tumor cells. By contrast, under normal circumstances, binding of peptides to class I MHC occurs only for proteins present in the cytosol and synthesized by the target itself, proteins in the external environment are excluded. An exception to this is the binding of exogenous peptides with a precise class I binding motif which are present outside the cell in high concentration. Thus, $CD4^+$ and $CD8^+$ T cells have broadly different functions and tend to recognize different antigens as a reflection of where the antigens normally reside.

As disclosed within the present invention, the protein product expressed by FBP is recognized by T cells. Such a protein expression product "turns over" within cells, i.e., undergoes a cycle wherein a synthesized protein functions and then eventually is degraded and replaced by a newly synthesized molecule. During the protein life cycle, peptide fragments from the protein bind to major histocompatibility complex (MHC) antigens. By display of a peptide bound to MHC antigen on the cell surface and recognition by host T cells of the combination of peptide plus self MHC antigen, a malignant cell will be immunogenic to T cells. The exquisite specificity of the T cell receptor enables individual T cells to discriminate between protein fragments which differ by a single amino acid residue.

During the immune response to a peptide, T cells expressing a T cell receptor with high affinity binding of the peptide-MHC complex will bind to the peptide-MHC complex and thereby become activated and induced to proliferate. In the first encounter with a peptide, small numbers of immune T cells will secrete lymphokines, proliferate and differentiate into effector and memory T cells. Subsequent encounters with the same antigen by the memory T cell will lead to a faster and more intense immune response.

Intact folate binding protein or peptides thereof which are recognized by cytotoxic T cells may be used within the present invention. The peptides may be naturally derived or produced based upon an identified sequence. The peptides for CD8$^+$ T cell responses (elicited by peptides presented by folate binding protein class I MHC molecules) are generally about 8-10 amino acids in length. Peptides for CD8$^+$ T cell responses vary according to each individual's class I MHC molecules. Examples of peptides suitable within the present invention for CD8$^+$ T cell responses include peptides comprising or consisting of SEQ ID NO:1 through SEQ ID NO:8.

It will be evident to those of ordinary skill in the art that other peptides may be produced for use within the present invention, both for class I MHC molecules as well as for class II molecules. A variety of techniques are well known for isolating or constructing peptides. Suitable peptides are readily identified based upon the disclosure provided herein. Additional suitable peptides include those which are longer in length. Such peptides may be extended (e.g, by the addition of one or more amino acid residues and/or truncated (e.g, by the deletion of one or more amino acid residues from the carboxyl terminus). Alternatively, suitable peptides may be variations on other preferred peptides disclosed herein. Although this particular peptide variation may result in a peptide with the same number of total amino acids (such as nine), a peptide variation on a preferred peptide need not be identical in length. Variations in amino acid sequence that yield peptides having substantially the same desired biological activity are within the scope of the present invention.

Immunization of an individual with a FBP peptide (i.e., as a vaccine) can induce continued expansion in the number of T cells necessary for therapeutic attack against a tumor in which FBP is associated. Typically, about 0.01 µg/kg to about 100 mg/kg body weight will be administered by the intradermal, subcutaneous or intravenous route. A preferred dosage is about 1 µg/kg to about 1 mg/kg, with about 5 µg/kg to about 200 jag/kg particularly preferred. It will be evident to those skilled in the art that the number and frequency of administrations will be dependent upon the response of the patient. It may be desirable to administer the FBP peptide repetitively. It will be evident to those skilled in this art that more than one FBP peptide may be administered, either simultaneously or sequentially. For example, a combination of about 8-15 peptides may be used for immunization. Preferred peptides for immunization are those that include all or a portion of at least one FBP amino acid SEQ ID NO:1 through SEQ ID NO:68, or variants thereof. One or more peptides from other portions of the amino acid sequence shown in SEQ ID NO:1 through SEQ ID NO:68 may be added to one or more of the preferred peptides.

In addition to the FBP peptide (which functions as an antigen), it may be desirable to include other components in the vaccine, such as a vehicle for antigen delivery and immunostimulatory substances designed to enhance the protein's immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopolysaccharides (LPS), glucan, IL-12, GM-CSF, gamma interferon and IL-15. It will be evident to those skilled in this art that a FBP peptide may be prepared synthetically or that a portion of the protein (naturally-derived or synthetic) may be used. When a peptide is used without additional sequences, it may be desirable to couple the peptide hapten to a carrier substance, such as keyhole limpet hemocyanin.

The methods and compositions of the present invention are particularly well-suited for inducing an immune response in a patient who has developed resistance to conventional cancer treatments or who has a high probability of developing a recurrence following treatment. A skilled artisan recognizes that cancer cells are able to evade the immune system or evade an effective immune response because they look like self, they actively anergize the immune system to any antigens which may potentially differentiate between self and tumor, and they may create an immunosuppressive environment by secreting immunosuppressive factors and/or by expressing factors which can induce apoptosis of an offensive tumor antigen-specific killer cell.

A skilled artisan is aware of multiple reviews concerning cancer vaccines and the generation of cellular immune responses to antigenic tumor peptides (Pietersz et al., 2000; Pardoll, 2000; Rosenberg, 2000; Dalgleish, 2000, each of which are incorporated by reference herein).

A skilled artisan recognizes that the antigen can be produced in large amounts by recombinant technology, either as soluble molecules in eukaryotic systems or as fusion proteins in bacterial systems. In a specific embodiment, synthetic peptides are made from the tumor antigen. Furthermore, monoclonal antibodies to the tumor antigens are useful in their identification and purification.

In a peptide approach to tumor immunotherapy, peptides (such as about 8-9 mers) are presented by MHC class I molecules, leading to the generation of CD8$^+$-mediated cellular responses comprising CTLs and cytokine secretion, mostly in the form of IFN-γ and TNF-α.

A skilled artisan recognizes that the dendritic cell is important in generating CD8$^+$ CTLs following class I presentation. Esche et al. (1999) demonstrated techniques whereby dendritic cells are obtained from patients, isolated, expanded in vitro, exposed to the peptides and reintroduced into the patient. Others utilize similarly treated dendritic cells for generation of specifically activated T cells in vitro before transfer.

A crucial initial step in CD8$^+$ T cell generation is the uptake and presentation of peptides by MHC molecules by antigen-presenting cells. MHC class I proteins consist of three subunits, all of which are important for the formation of a stable complex. X-ray crystallography of MHC class I molecules has demonstrated that interaction of peptides with the MHC class I groove is determined by the peptide sequence, with discrete amino acids interacting with pockets in the MHC groove (which have a fixed spacing from each other) and also have specificity for anchoring amino acid side chains. Although there are exceptions, the amino and carboxy termini of the peptides are anchored at either end of the groove, often in positions 2 or 3, 5 or 7 (Apostolopoulos et al., 1997a; Apostolopoulos et al., 1997b). The peptides also interact with the T cell receptor, yet only a small amount of the peptide is exposed (Apostolopoulos et al., 1998).

Given that multiple peptide tumor antigens, such as folate binding protein, have been identified in addition to characterization of T cell epitopes, in a specific embodiment of the present invention peptide antigens are generated synthetically for immunization. The immunogenicity of small peptides can be improved upon by increasing the peptide size, by binding to carriers and also by using adjuvants to activate macrophages and other immune system factors. A skilled artisan is cognizant of recombinant cytokines being used to increase immunogenicity of a synthetic peptide (Tao and Levy, 1993) and furthermore that cytokines can also be directly fused to peptides (Nakao et al., 1994; Disis et al., 1996; Chen et al., 1994).

In specific embodiments of the present invention, mixtures of separate peptides are administered as a vaccine. Alternatively, multiple epitopes may be incorporated into the same molecule by recombinant technology well known in the art (Mateo et al., 1999; Astori and Krachenbuhl, 1996). In another embodiment, a combinatorial peptide library is used to increase binding peptides by utilizing different amino acids at least one anchor location.

In another embodiment of the present invention, natural amino acids of a peptide are replaced with unnatural D-amino acids; alternatively, the peptide residues are assembled in reverse order, which renders the peptides resistant to proteases (Briand et al., 1997; Herve et al., 1997; Bartnes et al., 1997; Guichard et al., 1996). In another embodiment, unnatural modified amino acids are incorporated into a peptide, such as α-aminoisobutyric acid or N-methylserine.

A skilled artisan recognizes that the binding strength of the 8- or 9-mer to the MHC complex and the subsequent recognition by the T cell receptor determines the immunogenicity of CTL peptides. Van Der Burg et al. (1993) determined that the longer the peptide remains bound to the MHC complex, the better the chance it will induce a T cell response. A skilled artisan also recognizes that there are methods for introducing extraneous peptides directly into the cytoplasm of a cell to allow generation of class I-restricted cellular immune responses. One example includes microbial toxins, which can carry peptides in their cytoplasm for delivery because they enter cells by receptor-mediated endocytosis and thereby deposit cellular toxins into the cytoplasm. Specific examples include shiga toxin (Lee et al., 1998), anthrax toxin (Goletz et al., 1997), diphtheria toxin (Stenmark et al., 1991), *Pseudomonas* exotoxin (Donnelly et al., 1993), and *Bordetella pertussis* toxin (Fayolle et al., 1996).

In alternative embodiments, peptides enter cells through membrane fusion and are beneficial for delivering tumor or other peptides into a cell cytoplasm, including *Antennapedia* (Derossi et al., 1994; Derossi et al., 1996; Schutze-Redelmeier et al., 1996), Tat protein (Kim et al., 1997), and Measles virus fusion peptide (Partidos et al., 1997).

In other embodiments, peptides are introduced into a cytoplasm through lipopeptides, which comprise both a lipid and a peptide, by direct insertion into the lipophilic cell membrane (BenMohamed et al., 1997; Obert et al., 1998; Deprez et al., 1996; Beekman et al., 1997). In alternative embodiments, the peptides are delivered in liposomes (for examples, see Nakanishi et al., 1997; Noguchi et al., 1991; Fukasawa et al., 1998; Guan et al., 1998), whereby the immunogenicity is dependent on the size, charge, lipid composition of the liposome itself, and whether or not the antigen is present on the surface of the liposome or within its interior.

A skilled artisan also recognizes that immune-stimulating complexes (ISCOMs), which comprise Quill A (a mixture of saponins), cholesterol, phospholipid, and proteins, are useful for delivering naturally hydrophobic antigens or antigens made hydrophobic by the addition of myristic or palmitic acid tails (for examples, see Hsu et al., 1996; Sjolander et al., 1997; Villacres-Eriksson, 1995; Tarpey et al., 1996; Rimmelzwaan et al., 1997). ISCOMs facilitate penetration into cells by fusion with their membranes, by endocytosis, or by phagocytosis.

Antigens may also be directed to particular subcellular compartments through incorporation of sorting signals to the antigen by recombinant technology, including Class II LAMP-I (Rowell et al., 1995; Wu et al., 1995), ER targeting peptide (Minev et al., 1994); CLIP (Malcherik et al., 1998), and heat shock proteins (Udono and Srivastava, 1993; Heike et al., 1996; Zhu et al., 1996; Suzue et al., 1997; Ciuputu et al., 1998).

A skilled artisan recognizes that the present invention provides anti-cancer therapeutic compositions comprising a variety of peptides designated for CD8$^+$ T cell responses comprising SEQ ID NO:1 through SEQ ID NO:8, or a combination thereof. A skilled artisan also recognizes that the present invention provides anti-cancer therapeutic compositions comprising a variety of peptides designated for CD8$^+$ T cell responses consisting essentially of SEQ ID NO:1 through SEQ ID NO:8, or a combination thereof.

A skilled artisan recognizes that references such as Abrams and Schlom (2000) summarize the current views on rational Ag modification. Two types of peptides are described: (1) agonistic peptides which upregulate Ag-specific responses; (2) antagonistic/partial agonistic peptides which downregulate the same responses. However, it is an object of the present invention to provide therapy which stimulate Ag-specific immune responses while at the same time does not elicit activation induced-cell death or death by neglect.

A skilled artisan recognizes that sequences that encode folate binding protein epitopes for induction of tumor immunity can be obtained from databases such as the National Center for Biotechnology Informations's GenBank® database or commercially available databases, such as that of Celera Genomics, Inc. (Rockville, Md.). Examples of folate binding protein sequences which may comprise an epitope or which can be altered to comprise an epitope include the following, denoted by GenBank® Accession numbers: P14207 (SEQ ID NO:9); P15328 (SEQ ID NO:10); P13255 (SEQ ID NO:11); NP—000793 (SEQ ID NO:12); AAB05827 (SEQ ID NO:13); AAG36877 (SEQ ID NO:14); 542627 (SEQ ID NO:15); S00112 (SEQ ID NO:16); BFBO (SEQ ID NO:17); S62670 (SEQ ID NO:18); S62669 (SEQ ID NO:19); A55968 (SEQ ID NO:20); A45753 (SEQ ID NO:21); A33417 (SEQ ID NO:22); B40969 (SEQ ID NO:23); A40969 (SEQ ID NO:24); NP_057943 (SEQ ID NO:25); NP_057942 (SEQ ID NO:26); NP_057941 (SEQ ID NO:27); NP_057937 (SEQ ID NO:28); NP_057936 (SEQ ID NO:29); NP_037439 (SEQ ID NO:30); NP_032061 (SEQ ID NO:31); NP_032060 (SEQ ID NO:32); NP_000795 (SEQ ID NO:33); NP_000794 (SEQ ID NO:34); AAF66225 (SEQ ID NO:35); BAA37125 (SEQ ID NO:36); P02752 (SEQ ID NO:37); Q05685 (SEQ ID NO:38); P35846 (SEQ ID NO:39); P02702 (SEQ ID NO:40); AAD53001 (SEQ ID NO:41); AAD33741 (SEQ ID NO:42); AAD33740 (SEQ ID NO:43); AAD19354 (SEQ ID NO:44); AAD19353 (SEQ ID NO:45); AAC98303 (SEQ ID NO:46); AAB81938 (SEQ ID NO:47); AAB81937 (SEQ ID NO:48); AAB49703 (SEQ ID NO:49); AAB35932 (SEQ ID NO:50); 1011184A (SEQ ID NO:51); 0908212A (SEQ ID NO:52); CAA44610 (SEQ ID NO:53); CAA83553 (SEQ ID NO:54); AAA74896 (SEQ ID NO:55); AAA49056 (SEQ ID NO:56); AAA37599 (SEQ ID NO:57); AAA37598 (SEQ ID NO:58); AAA37597 (SEQ ID NO:59); AAA37594 (SEQ ID NO:60); AAA37596 (SEQ ID NO:61); AAA37595 (SEQ ID NO:62); AAA35824 (SEQ ID NO:63); AAA35823 (SEQ ID NO:64); AAA35822 (SEQ ID NO:65); AAA35821 (SEQ ID NO:66); AAA18382 (SEQ ID NO:67); and AAA17370 (SEQ ID NO:68).

A skilled artisan also recognizes that epitopes of folate binding protein, nucleic acid sequences are encoded by, or altered to encode a variant of, for example, one of the following: U02715 (SEQ ID NO:69); BE518506 (SEQ ID NO:70); BG058247 (SEQ ID NO:71); BG017460 (SEQ ID NO:72); NM_000802 (SEQ ID NO:73); U20391 (SEQ ID NO:74); NM_016731 (SEQ ID NO:75); NM_016730 (SEQ ID NO:76); NM_016729 (SEQ ID NO:77); NM_016725 (SEQ ID NO:78); NM_016724 (SEQ ID NO:79); NM_013307 (SEQ ID NO:80); NM_008035 (SEQ ID NO:81); NM_008034 (SEQ ID NO:82); BF153292 (SEQ ID NO:83); BF114518 (SEQ ID NO:84); BE940806 (SEQ ID NO:85); BE858996 (SEQ ID NO:86); AF219906 (SEQ ID NO:87); AF219905 (SEQ ID NO:88); AF219904 (SEQ ID NO:89); BE687177 (SEQ ID NO:90); BE636622 (SEQ ID NO:91); BE627230 (SEQ ID NO:92); BE506561 (SEQ ID NO:93); BE505048 (SEQ ID NO:94); BE496754 (SEQ ID NO:95); BB114010 (SEQ ID NO:96); BB109527 (SEQ ID NO:97); BB107219 (SEQ ID NO:98); BE206324 (SEQ ID NO:99); BE448392 (SEQ ID NO:100); BE207596 (SEQ ID NO:101); BE206635 (SEQ ID NO:102); BE240998 (SEQ ID NO:103); BE228221 (SEQ ID NO:104); BE225416 (SEQ ID NO:105); BE225404 (SEQ ID NO:106); BB214040 (SEQ ID NO:107); BE199619 (SEQ ID NO:108); BE199597 (SEQ ID NO:109); BE198610 (SEQ ID NO:110); BE198571 (SEQ ID NO:111); BE188055 (SEQ ID NO:112); BE187804 (SEQ ID NO:113); BB032646 (SEQ ID NO:114); BE037278 (SEQ ID NO:115); BE037125 (SEQ ID NO:116); BE037110 (SEQ ID NO:117); BE037009 (SEQ ID NO:118); BE036024 (SEQ ID NO:119); BE035828 (SEQ ID NO:120); BE035751 (SEQ ID NO:121); BE019724 (SEQ ID NO:122); AW913291 (SEQ ID NO:123); AW912445 (SEQ ID NO:124); AW823912 (SEQ ID NO:125); AW823418 (SEQ ID NO:126); AB023803 (SEQ ID NO:127); AB022344 (SEQ ID NO:128); AW475385 (SEQ ID NO:129); AW323586 (SEQ ID NO:130); AW319308 (SEQ ID NO:131); AW239668 (SEQ ID NO:132); AV253136 (SEQ ID NO:133); AW013716 (SEQ ID NO:134); AW013704 (SEQ ID NO:135); AW013702 (SEQ ID NO:136); AW013696 (SEQ ID NO:137); AW013669 (SEQ ID NO:138); AW013647 (SEQ ID NO:139); AW013501 (SEQ ID NO:140); AW013484 (SEQ ID NO:141); AW013428 (SEQ ID NO:142); AW013404 (SEQ ID NO:143); AW013386 (SEQ ID NO:144); AW013284 (SEQ ID NO:145); AW013183 (SEQ ID NO:146); AF061256 (SEQ ID NO:147); AI956572 (SEQ ID NO:148); AI882550 (SEQ ID NO:149); AI822932 (SEQ ID NO:150); AI785988 (SEQ ID NO:151); AI744273 (SEQ ID NO:152); AI727302 (SEQ ID NO:153); AI725714 (SEQ ID NO:154); AF137375 (SEQ ID NO:155); AF137374 (SEQ ID NO:156); AF137373 (SEQ ID NO:157); AF096320 (SEQ ID NO:158); AF096319 (SEQ ID NO:159); AI663857 (SEQ ID NO:160); AI647841 (SEQ ID NO:161); A1646950 (SEQ ID NO:162); AI607910 (SEQ ID NO:163); AI529173 (SEQ ID NO:164); AI509734 (SEQ ID NO:165); AI506267 (SEQ ID NO:166); AI498269 (SEQ ID NO:167); AI000444 (SEQ ID NO:168); AA956337 (SEQ ID NO:169); AA955042 (SEQ ID NO:170); AA899838 (SEQ ID NO:171); AA899718 (SEQ ID NO:172); AA858756 (SEQ ID NO:173); AI311561 (SEQ ID NO:174); AI385951 (SEQ ID NO:175); AI352406 (SEQ ID NO:176); AF100161 (SEQ ID NO:177); AI326503 (SEQ ID NO:178); AI325517 (SEQ ID NO:179); AI325453 (SEQ ID NO:180); AI325382 (SEQ ID NO:181); AI323700 (SEQ ID NO:182); AI323374 (SEQ ID NO:183); AI313973 (SEQ ID NO:184); AI196928 (SEQ ID NO:185); AF091041 (SEQ ID NO:186); AI156212 (SEQ ID NO:187); AI120374 (SEQ ID NO:188); AI119000 (SEQ ID NO:189); AA408670 (SEQ ID NO:190); AA408072 (SEQ ID NO:191); AA407615 (SEQ ID NO:192); AA995272 (SEQ ID NO:193); C78593 (SEQ ID NO:194); AA999910 (SEQ ID NO:195); AA991491 (SEQ ID NO:196); X99994 (SEQ ID NO:197); X99993 (SEQ ID NO:198); X99992 (SEQ ID NO:199); X99991 (SEQ ID NO:200); X99990 (SEQ ID NO:201); AA958985 (SEQ ID NO:202); AA873222 (SEQ ID NO:203); AA930051 (SEQ ID NO:204); AA895334 (SEQ ID NO:205); AA796142 (SEQ ID NO:206); AA798223 (SEQ ID NO:207); AA734325 (SEQ ID NO:208); AA690871 (SEQ ID NO:209); AA674988 (SEQ ID NO:210); AA674863 (SEQ ID NO:211); AA674821 (SEQ ID NO:212); AA674744 (SEQ ID NO:213); AA671558 (SEQ ID NO:214); AF000381 (SEQ ID NO:215); AF000380 (SEQ ID NO:216); AA637071 (SEQ ID NO:217); AA616314 (SEQ ID NO:218); AA109687 (SEQ ID NO:219); AA608235 (SEQ ID NO:220); AA589050 (SEQ ID NO:221); AA544782 (SEQ ID NO:222); AA522095 (SEQ ID NO:223); AA386821 (SEQ ID NO:224); AA386818 (SEQ ID NO:225); AA386495 (SEQ ID NO:226); AA289278 (SEQ ID NO:227); AA286342 (SEQ ID NO:228); AA276302 (SEQ ID NO:229); AA276123 (SEQ ID NO:230); AA277280 (SEQ ID NO:231); AA273543 (SEQ ID NO:232); U89949 (SEQ ID NO:233); AA208306 (SEQ ID NO:234); AA208089 (SEQ ID NO:235); AA242285 (SEQ ID NO:236); AA139715 (SEQ ID NO:237); AA139709 (SEQ ID NO:238); AA139675 (SEQ ID NO:239); AA139593 (SEQ ID NO:240); AA124010 (SEQ ID NO:241); AA108790 (SEQ ID NO:242); AA108350 (SEQ ID NO:243); AA028831 (SEQ ID NO:244); AA061275 (SEQ ID NO:245); W82933 (SEQ ID NO: 246); AA015571 (SEQ ID NO:247); W71715 (SEQ ID NO:248); W59165 (SEQ ID NO:249); X62753 (SEQ ID NO:250); Z32564 (SEQ ID NO:251); T29279 (SEQ ID NO:252); M25317 (SEQ ID NO:253); M86438 (SEQ ID NO:254); J03922 (SEQ ID NO:255); M64817 (SEQ ID NO:256); L25338 (SEQ ID NO:257); M97701 (SEQ ID NO:258); M97700 (SEQ ID NO:259); M64782 (SEQ ID NO:260); M35069 (SEQ ID NO:261); J05013 (SEQ ID NO:262); M28099 (SEQ ID NO:263); J02876 (SEQ ID NO:264); U08471 (SEQ ID NO:265); UO2714 (SEQ ID NO:266); and UO2716 (SEQ ID NO:267).

A skilled artisan also recognizes that the scope of the invention is not limited to the specific nonapeptides described in SEQ ID NO:1 through SEQ ID NO:8. The antigens comprising a FBP epitope may be at least about 7, 8, 9, 10, 11, 12, 13, 14, 15, 16, 17, 18, 19, 20, 25, or up to about 30. It is contemplated that any amino acid may be used for additions or filling in for the remainder of sequences in addition to the specific variant sequence provided herein.

However, it is preferred that they will be those that will maintain the underlying sequence of FBP.

III. Rational Vaccine Design

The goal of rational vaccine design is to produce structural analogs of biologically active compounds. By creating such analogs, it is possible to fashion vaccines which are more active or stable than the natural molecules, which have different susceptibility to alteration or which may affect the function of various other molecules. In one approach, a skilled artisan generates a three-dimensional structure for the folate binding protein variant of the invention or a fragment thereof. This could be accomplished by X-ray crystallography, computer modeling, or by a combination of both approaches. An alternative approach involves the random replacement of functional groups throughout the folate binding protein variant, and the resulting affect on function is determined.

It also is possible to isolate a folate binding protein variant specific antibody, selected by a functional assay, and then solve its crystal structure. In principle, this approach yields a pharmacore upon which subsequent vaccine design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the vaccine.

Thus, one may design vaccines which have enhanced and improved biological activity, for example, anti-tumor activity, relative to a starting folate binding protein variant of the invention. By virtue of standard chemical isolation procedures and other descriptions herein, sufficient amounts of the folate binding protein variants of the invention can be produced to perform crystallographic studies. In addition, knowledge of the chemical characteristics of these compounds permits computer-employed predictions of structure-function relationships.

IV. Immunological Reagents

It is well known in the art that the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as g-interferon, IL-2, or IL-12 or genes encoding proteins involved in immune helper functions, such as B-7.

A variety of routes can be used to administer the vaccines including but not limited to subcutaneous, intramuscular, intradermal, intraepidermal, intravenous and intraperitoneal.

An individual, such as a patient, is injected with vaccine generally as described above. The antigen may be mixed with adjuvant, such as Freund's complete or incomplete adjuvant. Booster administrations with the same vaccine or DNA encoding the same may occur at approximately two-week intervals.

V. Immunotherapeutic Agents

An immunotherapeutic agent generally relies on the use of immune effector cells and molecules to target and destroy cancer cells. The immune effector may be, for example, a folate binding protein variant which is or is similar to a tumor cell antigen. The variant alone may serve as an effector of therapy or it may recruit other cells to actually effect cell killing. The variant also may be conjugated to a drug or toxin (e.g, a chemotherapeutic, a radionuclide, a ricin A chain, a cholera toxin, a pertussis toxin, etc.) and serve merely as a targeting agent. Such antibody conjugates are called immunotoxins, and are well known in the art (see U.S. Pat. Nos. 5,686,072, 5,578,706, 4,792,447, 5,045,451, 4,664,911, and 5,767,072, each incorporated herein by reference). Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist in addition to folate binding protein described herein, and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

The disclosures presented herein have significant relevance to immunotherapy of human diseases and disorders, including cancer. In using the immunotherapeutic compositions derived from the antigen of the present invention in treatment methods, other standard treatments also may be employed, such as radiotherapy or chemotherapy. However, it is preferred that the immunotherapy be used alone initially as its effectiveness can be readily assessed. Immunotherapies of cancer can broadly be classified as adoptive, passive and active, as described in the following sections, and may be used or produced with the folate binding protein variant antigen of the present invention.

A. Immune Stimulators

A specific aspect of immunotherapy is to use an immune stimulating molecule as an agent, or more preferably in conjunction with another agent, such as, for example, a cytokine such as IL-2, IL-4, IL-12, GM-CSF, tumor necrosis factor; interferons alpha, beta, and gamma; F42K and other cytokine analogs; a chemokine such as, for example, MIP-1, MIP-1beta, MCP-1, RANTES, IL-8; or a growth factor such as, for example, FLT3 ligand.

One particular cytokine contemplated for use in the present invention is tumor necrosis factor. Tumor necrosis factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-a also has been found to possess anticancer activity.

Another cytokine specifically contemplate is interferon alpha. Interferon alpha has been used in treatment of hairy cell leukemia, Kaposi's sarcoma, melanoma, carcinoid, renal cell cancer, ovary cancer, bladder cancer, non-Hodgkin's lymphomas, mycosis fungoides, multiple myeloma, and chronic granulocytic leukemia.

B. Passive Immunotherapy

A number of different approaches for passive immunotherapy of cancer exist. They may be broadly categorized into the following: injection of vaccine alone; injection of vaccine coupled to toxins or chemotherapeutic agents; injection of vaccine coupled to radioactive isotopes; injection of anti-idiotype vaccine; and finally, purging of tumor cells in bone marrow.

It may be favorable to administer more than one vaccine associated with two different antigens or even vaccine with multiple antigen specificity. Treatment protocols also may include administration of lymphokines or other immune enhancers (Bajorin et al. 1988).

C. Active Immunotherapy

In some embodiments of the invention, active immunotherapy may be employed. In active immunotherapy, a folate binding protein variant (e.g., a peptide or polypeptide), a nucleic acid encoding a folate binding protein variant, and/or additional vaccine components, such as for example, a cell expressing the folate binding protein variant (e.g a dendritic cell fused with a tumor cell, or an autologous or allogeneic tumor cell composition expressing the antigen), an adjuvant, a recombinant protein, an immunomodulator, and the like is administered (Ravindranath and Morton, 1991; Morton and Ravindranath, 1996; Morton et al., 1992; Okamoto et al., 1997; Kugler et al., 2000; Trefzer et al., 2000; Mitchell et al., 1990; Mitchell et al., 1993).

An antigenic peptide, polypeptide or protein, or an autologous or allogenic tumor cell composition or "vaccine" is administered generally with a distinct bacterial adjuvant (Ravindranath and Morton, 1991; Morton and Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anti-carbohydrate antibodies.

D. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. In certain embodiments, the patient's lymphocytes are cultured or expanded in number or selected for activity, such as immunoreactivity to the antigen. This form of immunotherapy has produced several cases of regression of melanoma and renal carcinoma.

VI. Vaccines

The present invention contemplates vaccines for use in both active and passive immunization embodiments. Immunogenic compositions, proposed to be suitable for use as a vaccine, may be prepared most readily directly from immunogenic CTL-stimulating peptides prepared in a manner disclosed herein. Preferably the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4.578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g, the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel A) or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

For an antigenic composition to be useful as a vaccine, an antigenic composition must induce an immune response to the antigen in a cell, tissue or animal (e.g, a human). As used herein, an "antigenic composition" may comprise an antigen (e.g, a peptide or polypeptide), a nucleic acid encoding an antigen (e.g, an antigen expression vector), or a cell expressing or presenting an antigen. In particular embodiments, the antigenic composition comprises or encodes a folate binding protein variant, or an immunologically functional equivalent thereof. In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent, may be used as an effective vaccine in inducing an anti-folate binding protein variant humoral and/or cell-mediated immune response in an animal. The present invention contemplates one or more antigenic compositions or vaccines for use in both active and passive immunization embodiments.

A vaccine of the present invention may vary in its composition of proteinaceous, nucleic acid and/or cellular components. In a non-limiting example, a nucleic acid encoding an antigen might also be formulated with a proteinaceous adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

A. Proteinaceous Antigens

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g, a DNA sequence) encoding a peptide or polypeptide comprising an antigen of the present invention in an in vitro translation system or in a living cell. Preferably the antigenic composition is isolated and extensively dialyzed to remove one or more undesired small molecular weight molecules and/or lyophilized for more ready formulation into a desired vehicle. It is further understood that additional amino acids, mutations, chemical modification and the like, if any, that are made in a vaccine component will preferably not substantially interfere with the antibody recognition of the epitopic sequence.

A peptide or polypeptide corresponding to one or more antigenic determinants of the folate binding protein variant of the present invention should generally be at least five or six amino acid residues in length, and may contain up to about 10, about 15, about 20, or more. A peptide sequence may be synthesized by methods known to those of ordinary skill in the art, for example, peptide synthesis using automated peptide synthesis machines, such as those available from Applied Biosystems (Foster City, Calif.).

Longer peptides or polypeptides also may be prepared, e.g, by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

B. Genetic Vaccine Antigens

In certain embodiments, an immune response may be promoted by transfecting or inoculating an animal with a nucleic acid encoding an antigen. One or more cells comprised within a target animal then expresses the sequences encoded by the nucleic acid after administration of the nucleic acid to the animal. Thus, the vaccine may comprise "genetic vaccine" useful for immunization protocols. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In preferred aspects, the nucleic acid comprises a coding region that encodes all or part of the sequences disclosed as SEQ ID NO:1 through SEQ ID NO:9, or an immunologically functional equivalent thereof. Of course, the nucleic acid may comprise and/or encode additional sequences, including but not limited to those comprising one or more immunomodulators or adjuvants. The nucleotide and protein, polypeptide and peptide encoding sequences for various genes have been previously disclosed, and may be found at computerized databases known to those of ordinary skill in the art. One such database is the National Center for Biotechnology Information's Genbank® and GenPept databases. The coding regions for these known genes may be amplified, combined with the nucleic acid sequences encoding the folate binding protein variant disclosed herein (e.g., ligated) and/or expressed using the techniques disclosed herein or by any technique that would be know to those of ordinary skill in the art (e.g, Sambrook et al., 1987). Though a nucleic acid may be expressed in an in vitro expression system, in preferred embodiments the nucleic acid comprises a vector for in vivo replication and/or expression.

C. Cellular Vaccine Antigens

In another embodiment, a cell expressing the antigen may comprise the vaccine. The cell may be isolated from a culture, tissue, organ or organism and administered to an animal as a cellular vaccine. Thus, the present invention contemplates a "cellular vaccine." The cell may be transfected with a nucleic acid encoding an antigen to enhance its expression of the antigen. Of course, the cell may also express one or more additional vaccine components, such as immunomodulators or adjuvants. A vaccine may comprise all or part of the cell.

D. Immunologically Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | Codons |
|---|---|
| Alanine | Ala A GCA GCC GCG GCU |
| Cysteine | Cys C UGC UGU |
| Aspartic acid | Asp D GAC GAU |
| Glutamic acid | Glu E GAA GAG |
| Phenylalanine | Phe F UUC UUU |
| Glycine | Gly G GGA GGC GGG GGU |
| Histidine | His H CAC CAU |
| Isoleucine | Ile I AUA AUC AUU |
| Lysine | Lys K AAA AAG |

TABLE 1-continued

| Amino Acids | Codons |
|---|---|
| Leucine | Leu L UUA UUG CUA CUC CUG CUU |
| Methionine | Met M AUG |
| Asparagine | Asn N AAC AAU |
| Proline | Pro P CCA CCC CCG CCU |
| Glutamine | Gln Q CAA CAG |
| Arginine | Arg R AGA AGG CGA CGC CGG CGU |
| Serine | Ser S AGC AGU UCA UCC UCG UCU |
| Threonine | Thr T ACA ACC ACG ACU |
| Valine | Val V GUA GUC GUG GUU |
| Tryptophan | Trp W UGG |
| Tyrosine | Tyr Y UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode the peptides without appreciable loss of their biological utility or activity. Amino acid substitutions may be based on the relative similarity of the amino acid side-chain substituents, for example, their hydrophobicity, hydrophilicity, charge, size, and the like. Exemplary substitutions which take various of the foregoing characteristics into consideration are well known to those of skill in the art.

Numerous scientific publications have also been devoted to the prediction of secondary structure, and to the identification of an epitope, from analyses of an amino acid sequence (Chou and Fasman, 1974a,b; 1978a,b, 1979). Any of these may be used, if desired, to supplement the teachings of U.S. Pat. No. 4,554,101.

Moreover, computer programs are currently available to assist with predicting an antigenic portion and an epitopic core region of one or more proteins, polypeptides or peptides. Examples include those programs based upon the Jameson-Wolf analysis (Jameson & Wolf, 1988; Wolf et al., 1988), the program PepPlot.RTM. (Brutlag et al., 1990; Weinberger et al., 1985), and other new programs for protein tertiary structure prediction (Fetrow & Bryant, 1993). Another commercially available software program capable of carrying out such analyses is MacVector® (IBI, New Haven, Conn.).

As modifications and changes may be made in the structure of an antigenic composition (e.g., a folate binding protein variant) of the present invention, and still obtain molecules having like or otherwise desirable characteristics, such immunologically functional equivalents are also encompassed within the present invention.

For example, certain amino acids may be substituted for other amino acids in a peptide, polypeptide or protein structure without appreciable loss of interactive binding capacity with structures such as, for example, antigen-binding regions of antibodies, binding sites on substrate molecules or receptors, DNA binding sites, or such like. Since it is the interactive capacity and nature of a peptide, polypeptide or protein that defines its biological (e.g., immunological) functional activity, certain amino acid sequence substitutions can be made in a amino acid sequence (or, of course, its underlying DNA coding sequence) and nevertheless obtain a peptide or polypeptide with like (agonistic) properties. It is thus contemplated by the inventors that various changes may be made in the sequence of an antigenic composition such as, for example a folate binding protein variant peptide or polypeptide, or underlying DNA, without appreciable loss of biological utility or activity.

Accordingly, antigenic composition, particularly an immunologically functional equivalent of the sequences disclosed herein, may encompass an amino molecule sequence comprising at least one of the 20 common amino acids in naturally synthesized proteins, or at least one modified or unnatural amino acid, including but not limited to those shown on Table 2 below.

TABLE 2

Modified, Unnatural or Rare Amino Acids

| Abbr. | Amino Acid |
|---|---|
| Aad | 2-Aminoadipic acid |
| Baad | 3-Aminoadipic acid |
| Bala | β-alanine, b-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| Ahyl | Allo-Hydroxylysine |
| 3Hyp | 3-Hydroxyproline |
| 4Hyp | 4-Hydroxyproline |
| Ide | Isodesmosine |
| Aile | Allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In terms of immunologically functional equivalent, it is well understood by the skilled artisan that, inherent in the definition is the concept that there is a limit to the number of changes that may be made within a defined portion of the molecule and still result in a molecule with an acceptable level of equivalent immunological activity. An immunologically functional equivalent peptide or polypeptide are thus defined herein as those peptide(s) or polypeptide(s) in which certain, not most or all, of the amino acid(s) may be substituted.

In particular, where a shorter length peptide is concerned, it is contemplated that fewer amino acid substitutions should be made within the given peptide. A longer polypeptide may have an intermediate number of changes. The full-length protein will have the most tolerance for a larger number of changes. Of course, a plurality of distinct polypeptides/peptides with different substitutions may easily be made and used in accordance with the invention.

It also is well understood that where certain residues are shown to be particularly important to the immunological or structural properties of a protein or peptide, e.g., residues in binding regions or active sites, such residues may not generally be exchanged. This is an important consideration in the present invention, where changes in the folate binding protein variant antigenic site should be carefully considered and subsequently tested to ensure maintenance of immunological function (e.g., antigenicity), where maintenance of immunological function is desired. In this manner, functional equivalents are defined herein as those peptides or polypeptides which maintain a substantial amount of their native immunological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Careful selection of a particular amino acid substitution for a peptide, as opposed to a protein, must be considered given the differences in size between peptides and proteins.

In further embodiments, major antigenic determinants of a peptide or polypeptide may be identified by an empirical approach in which portions of a nucleic acid encoding a peptide or polypeptide are expressed in a recombinant host, and the resulting peptide(s) or polypeptide(s) tested for their ability to elicit an immune response. For example, PCR™ can be used to prepare a range of peptides or polypeptides lacking successively longer fragments of the C-terminus of the amino acid sequence. The immunoactivity of each of these peptides or polypeptides is determined to identify those fragments or domains that are immunodominant. Further studies in which only a small number of amino acids are removed at each iteration then allows the location of the antigenic determinant(s) of the peptide or polypeptide to be more precisely determined.

Another method for determining a major antigenic determinant of a peptide or polypeptide is the SPOTs™ system (Genosys Biotechnologies, Inc., The Woodlands, Tex.). In this method, overlapping peptides are synthesized on a cellulose membrane, which following synthesis and deprotection, is screened using a polyclonal or monoclonal antibody. An antigenic determinant of the peptides or polypeptides which are initially identified can be further localized by performing subsequent syntheses of smaller peptides with larger overlaps, and by eventually replacing individual amino acids at each position along the immunoreactive sequence.

Once one or more such analyses are completed, an antigenic composition, such as for example a peptide or a polypeptide is prepared that contain at least the essential features of one or more antigenic determinants. An antigenic composition is then employed in the generation of antisera against the composition, and preferably the antigenic determinant(s).

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. Nucleic acids encoding these antigenic compositions also can be constructed and inserted into one or more expression vectors by standard methods (Sambrook et al., 1987), for example, using PCR™ cloning methodology.

In addition to the peptidyl compounds described herein, the inventors also contemplate that other sterically similar compounds may be formulated to mimic the key portions of the peptide or polypeptide structure or to interact specifically with, for example, an antibody. Such compounds, which may be termed peptidomimetics, may be used in the same manner as a peptide or polypeptide of the invention and hence are also immunologically functional equivalents.

Certain mimetics that mimic elements of protein secondary structure are described in Johnson et al. (1993). The underlying rationale behind the use of peptide mimetics is that the peptide backbone of proteins exists chiefly to orientate amino acid side chains in such a way as to facilitate molecular interactions, such as those of antibody and antigen. A peptide mimetic is thus designed to permit molecular interactions similar to the natural molecule.

E. Antigen Mutagenesis

In particular embodiments, an antigenic composition is mutated for purposes such as, for example, enhancing its immunogenicity or producing or identifying an immunologically functional equivalent sequence. Methods of mutagenesis are well known to those of skill in the art (Sambrook et al., 1987).

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In a preferred embodiment, site directed mutagenesis is used. Site-specific mutagenesis is a technique useful in the preparation of an antigenic composition (e.g, a folate binding protein variant-comprising peptide or polypeptide, or immunologically functional equivalent protein, polypeptide or peptide), through specific mutagenesis of the underlying DNA. In general, the technique of site-specific mutagenesis is well known in the art. The technique further provides a ready ability to prepare and test sequence variants, incorporating one or more of the foregoing considerations, by introducing one or more nucleotide sequence changes into the DNA. Site-specific mutagenesis allows the production of a mutant through the use of specific oligonucleotide sequence(s) which encode the DNA sequence of the desired mutation, as well as a sufficient number of adjacent nucleotides, to provide a primer sequence of sufficient size and sequence complexity to form a stable duplex on both sides of the position being mutated. Typically, a primer of about 17 to about 75 nucleotides in length is preferred, with about 10 to about 25 or more residues on both sides of the position being altered, while primers of about 17 to about 25 nucleotides in length being more preferred, with about 5 to 10 residues on both sides of the position being altered.

In general, site-directed mutagenesis is performed by first obtaining a single-stranded vector, or melting of two strands of a double stranded vector which includes within its sequence a DNA sequence encoding the desired protein. As will be appreciated by one of ordinary skill in the art, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

This mutagenic primer is then annealed with the single-stranded DNA preparation, and subjected to DNA polymerizing enzymes such as, for example, E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

Alternatively, a pair of primers may be annealed to two separate strands of a double stranded vector to simultaneously synthesize both corresponding complementary strands with the desired mutation(s) in a PCR™ reaction. A genetic selection scheme to enrich for clones incorporating the mutagenic oligonucleotide has been devised (Kunkel et al., 1987). Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector (Tomic et al., 1990; Upender et al., 1995). A PCR™ employing a thermostable ligase in addition to a thermostable polymerase also may be used to incorporate a phosphorylated mutagenic oligonucleotide into an amplified DNA fragment that may then be cloned into an appropriate cloning or expression vector (Michael 1994).

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

Additionally, one particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

F. Vectors

In order to effect replication, expression or mutagenesis of a nucleic acid, the nucleic acid may be delivered ("transfected") into a cell. The transfection of cells may be used, in certain embodiments, to recombinately produce one or more vaccine components for subsequent purification and preparation into a pharmaceutical vaccine. In other embodiments, the nucleic acid may be comprised as a genetic vaccine that is administered to an animal. In other embodiments, the nucleic acid is transfected into a cell and the cell administered to an animal as a cellular vaccine component. The nucleic acid may consist only of naked recombinant DNA, or may comprise, for example, additional materials to protect the nucleic acid and/or aid its targeting to specific cell types.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g, YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell.

The nucleic acid encoding the antigenic composition or other vaccine component may be stably integrated into the genome of the cell, or may be stably maintained in the cell as a separate, episomal segment of DNA. Such nucleic acid segments or "episomes" encode sequences sufficient to permit maintenance and replication independent of or in synchronization with the host cell cycle. Vectors and expression vectors may contain nucleic acid sequences that serve other functions as well and are described infra. How the expression construct is delivered to a cell and where in the cell the nucleic acid remains is dependent on the type of expression construct employed.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 by upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 by apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 3 lists non-limiting examples of elements/promoters that may be employed, in the context of the present invention, to regulate the expression of a RNA. Table 4 provides non-limiting examples of inducible elements, which are regions of a nucleic acid sequence that can be activated in response to a specific stimulus.

TABLE 3

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |

TABLE 3-continued

Promoter and/or Enhancer

| Promoter/Enhancer | References |
|---|---|
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 4

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al, 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et at, 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEMTMλ11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g, by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Vaccine components of the present invention may be a viral vector that encode one or more folate binding protein variant antigenic compositions or other components such as, for example, a folate binding protein variant immunomodulator or adjuvant. Non-limiting examples of virus vectors that may be used to deliver a nucleic acid of the present invention are described below.

a. Adenoviral Vectors

A particular method for delivery of the nucleic acid involves the use of an adenovirus expression vector, Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

b. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in the folate binding protein variant vaccines of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

c. Retroviral Vectors

Retroviruses have promise as folate binding protein variant antigen delivery vectors in vaccines due to their ability to integrate their genes into the host genome, transferring a large amount of foreign genetic material, infecting a broad spectrum of species and cell types and of being packaged in special cell lines (Miller, 1992).

In order to construct a folate binding protein variant vaccine retroviral vector, a nucleic acid (e.g, one encoding an folate binding protein variant antigen of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g, by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

d. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

e. Vaccine Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989). Thus, it is contemplated that antibodies, specific binding ligands and/or other targeting moieties may be used to specifically transfect APC types.

11. Vector Delivery and Cell Transformation

Suitable methods for nucleic acid delivery for transformation of an organelle, a cell, a tissue or an organism for use with the current invention are believed to include virtually any method by which a nucleic acid (e.g, DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Injection

In certain embodiments, a nucleic acid may be delivered to an organelle, a cell, a tissue or an organism via one or more injections (i.e., a needle injection). Methods of injection of nucleic acids are described herein, and are well known to those of ordinary skill in the art. Further embodiments of the present invention include the introduction of a nucleic acid by direct microinjection to a cell. Direct microinjection has been used to introduce nucleic acid constructs into *Xenopus* oocytes (Harland and Weintraub, 1985). The amount of folate binding protein variant used may vary upon the nature of the antigen as well as the organelle, cell, tissue or organism used b. Electroporation In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

c. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Liposome-Mediated Transfection

In a further embodiment of the invention, one or more vaccine components or nucleic acids may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

f. Receptor Mediated Transfection

One or more vaccine components or nucleic acids, may be employed to delivered using a receptor-mediated delivery vehicle. These take advantage of the selective uptake of macromolecules by receptor-mediated endocytosis that will be occurring in the target cells. In view of the cell type-specific distribution of various receptors, this delivery method adds another degree of specificity to the present invention. Specific delivery in the context of another mammalian cell type has been described (Wu and Wu, 1993, incorporated herein by reference).

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

g. Microprojectile Bombardment

Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et at, 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

12. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a folate binding protein variant. The tissue may be part or separated from an organism. In certain embodiments, a tissue may comprise, but is not limited to, adipocytes, alveolar, ameloblasts, axon, basal cells, blood (e.g, lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g, a eubacteria, an archaea) or an eukaryote, as would be understood by one of ordinary skill in the art.

Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g, *E. coli* strain RR1, *E. coli* LE392, *E. coli* B, *E. coli* X 1776 (ATCC No. 31537) as well as *E. coli* W3110 (F', lambda, prototrophic, ATCC No. 273325), bacilli such as *Bacillus subtilis*; and other enterobacteriaceae such as *Salmonella typhimurium, Serratia marcescens*, various *Pseudomonas specie*, DH5a, JM109, and KCB, as well as a number of commercially available bacterial hosts such as SURE.RTM. Competent Cells and SOLOPACKa Gold Cells (STRATA-GENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

13. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROLä Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radiolabeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g, visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

G. Vaccine Component Purification

In any case, a vaccine component (e.g, an antigenic peptide or polypeptide or nucleic acid encoding a proteinaceous composition) may be isolated and/or purified from the chemical synthesis reagents, cell or cellular components. In a method of producing the vaccine component, purification is accomplished by any appropriate technique that is described herein or well known to those of skill in the art (e.g, Sambrook et al., 1987). Although preferred for use in certain embodiments, there is no general requirement that an antigenic composition of the present invention or other vaccine component always be provided in their most purified state. Indeed, it is contemplated that a less substantially purified vaccine component, which is nonetheless enriched in the desired compound, relative to the natural state, will have utility in certain embodiments, such as, for example, total recovery of protein product, or in maintaining the activity of an expressed protein. However, it is contemplate that inactive products also have utility in certain embodiments, such as, e.g, in determining antigenicity via antibody generation.

The present invention also provides purified, and in preferred embodiments, substantially purified vaccines or vaccine components. The term "purified vaccine component" as used herein, is intended to refer to at least one vaccine component (e.g, a proteinaceous composition, isolatable from cells), wherein the component is purified to any degree relative to its naturally-obtainable state, e.g, relative to its purity within a cellular extract or reagents of chemical synthesis. In certain aspects wherein the vaccine component is a proteinaceous composition, a purified vaccine component also refers to a wild-type or mutant protein, polypeptide, or peptide free from the environment in which it naturally Occurs.

Where the term "substantially purified" is used, this will refer to a composition in which the specific compound (e.g, a protein, polypeptide, or peptide) forms the major component of the composition, such as constituting about 50% of the compounds in the composition or more. In preferred embodiments, a substantially purified vaccine component will constitute more than about 60%, about 70%, about 80%, about 90%, about 95%, about 99% or even more of the compounds in the composition.

In certain embodiments, a vaccine component may be purified to homogeneity. As applied to the present invention, "purified to homogeneity," means that the vaccine component has a level of purity where the compound is substantially free from other chemicals, biomolecules or cells. For example, a purified peptide, polypeptide or protein will often be sufficiently free of other protein components so that degradative sequencing may be performed successfully. Various methods for quantifying the degree of purification of a vaccine component will be known to those of skill in the art in light of the present disclosure. These include, for example, determining the specific protein activity of a fraction (e.g, antigenicity), or assessing the number of polypeptides within a fraction by gel electrophoresis.

Various techniques suitable for use in chemical, biomolecule or biological purification, well known to those of skill in the art, may be applicable to preparation of a vaccine component of the present invention. These include, for example, precipitation with ammonium sulfate, PEG, antibodies and the like or by heat denaturation, followed by centrifugation; fractionation, chromatographic procedures, including but not limited to, partition chromatograph (e.g, paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 1989; and Freifelder, Physical Biochemistry, Second Edition, pages 238-246, incorporated herein by reference).

Given many DNA and proteins are known (see for example, the National Center for Biotechnology Information's Genbank® and GenPept databases), or may be identified and amplified using the methods described herein, any purification method for recombinately expressed nucleic acid or proteinaceous sequences known to those of skill in the art can now be employed. In certain aspects, a nucleic acid may be purified on polyacrylamide gels, and/or cesium chloride centrifugation gradients, or by any other means known to one of ordinary skill in the art (see for example, Sambrook et al. 1989, incorporated herein by reference). In further aspects, a purification of a proteinaceous sequence may be conducted by recombinately expressing the sequence as a fusion protein. Such purification methods are routine in the art. This is exemplified by the generation of an specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. In particular aspects, cells or other components of the vaccine may be purified by flow cytometry. Flow cytometry involves the separation of cells or other particles in a liquid sample, and is well known in the art (see, for example, U.S. Pat. Nos. 3,826,364, 4,284,412, 4,989,977, 4,498,766, 5,478,722, 4,857,451, 4,774,189, 4,767,206, 4,714,682, 5,160,974 and 4,661,913). Any of these techniques described herein, and combinations of these and any other techniques known to skilled artisans, may be used to purify and/or assay the purity of the various chemicals, proteinaceous compounds, nucleic acids, cellular materials and/or cells that may comprise a vaccine of the present invention. As is generally known in the art, it is believed that the order of conducting the various purification steps may be changed, or that certain steps may be omitted, and still result in a suitable method for the preparation of a substantially purified antigen or other vaccine component.

H. Additional Vaccine Components

It is contemplated that an antigenic composition of the invention may be combined with one or more additional components to form a more effective vaccine. Non-limiting examples of additional components include, for example, one or more additional antigens, immunomodulators or adjuvants to stimulate an immune response to an antigenic composition of the present invention and/or the additional component(s).

1. Immunomodulators

For example, it is contemplated that immunomodulators can be included in the vaccine to augment a cell's or a patient's (e.g, an animal's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g, a cytokine and a chemokine).

In another aspects of the invention, it is contemplated that the folate binding protein variant composition may further comprise a therapeutically effective composition of an immunomodulator. It is envisioned that an immunomodulator would constitute a cytokine, hematapoietin, colony stimulating factor, interleukin, interferon, growth factor or combination thereof. As used herein certain embodiments, the terms "cytokine" are the same as described in U.S. Pat. No. 5,851,984, incorporated herein by reference in its entirety, which reads in relevant part:

"The term 'cytokine' is a generic term for proteins released by one cell population which act on another cell as intercellular mediators. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-.alpha. and -.beta.; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-a, -.b, and -g; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-11, IL-12; IL-13, IL-14, IL-15, IL-16, IL-17, IL-18, LIF, G-CSF, GM-CSF, M-CSF, EPO, kit-ligand or FLT-3. As used herein, the term cytokine includes proteins from natural sources or from recombinant cell culture and biologically active equivalents of the native sequence cytokines.

a. β-Interferon

β-interferon (IFN-b) is low molecular weight protein that is produced by many cell types, including epithelial cells, fibroblasts and macrophages. Cells that express endogenous IFN-b are resistant to viral infection and replication. The b-interferon genes from mouse (GenBank® accession numbers X14455, X14029) and human (GenBank® accession numbers J00218, K00616 and M11029) have been isolated and sequenced. IFN-b is a multifunctional glycoprotein that can inhibit tumor growth both directly, by suppressing cell replication and inducing differentiation or apoptosis and indirectly by activating tumoricidal properties of macrophages and NK cells, by suppressing tumor angiogenesis and by stimulating specific immune response.

b. Interleukin-2

Interleukin-2 (IL-2), originally designated T-cell growth factor I, is a highly proficient inducer of T-cell proliferation and is a growth factor for all subpopulations of T-lymphocytes. IL-2 is an antigen independent proliferation factor that induces cell cycle progression in resting cells and thus allows clonal expansion of activated T-lymphocytes. Since freshly isolated leukemic cells also secrete IL2 and respond to it IL2 may function as an autocrine growth modulator for these cells capable of worsening ATL. IL2 also promotes the proliferation of activated B-cells although this requires the presence of additional factors, for example, IL4. In vitro IL2 also stimulates the growth of oligodendroglial cells. Due to its effects on T-cells and B-cells IL2 is a central regulator of immune responses. It also plays a role in anti-inflammatory reactions, in hematopoiesis and in tumor surveillance. IL-2 stimulates the synthesis of IFN-g in peripheral leukocytes and also induces the secretion of IL-1, TNF-α and TNF-b. The induction of the secretion of tumoricidal cytokines, apart from the activity in the expansion of LAK cells, (lymphokine-activated killer cells) are probably the main factors responsible for the antitumor activity of IL2.

c. GM-CSF

GM-CSF stimulates the proliferation and differentiation of neutrophilic, eosinophilic, and monocytic lineages. It also functionally activates the corresponding mature forms, enhancing, for example, to the expression of certain cell surface adhesion proteins (CD-11A, CD-11C). The overexpression of these proteins could be one explanation for the observed local accumulation of granulocytes at sites of inflammation. In addition, GM-CSF also enhances expression of receptors for fMLP (Formyl-Met-Leu-Phe) which is a stimulator of neutrophil activity.

d. Cytokines

Interleukins, cytokines, nucleic acids encoding interleukins or cytokines, and/or cells expressing such compounds are contemplated as possible vaccine components. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH-1, METH-2, tumor necrosis factor, TGFb, LT and combinations thereof.

e. Chemokines

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines.

f. Immunogenic Carrier Proteins

In certain embodiments, an antigenic composition's may be chemically coupled to a carrier or recombinantly expressed with a immunogenic carrier peptide or polypeptide (e.g, a antigen-carrier fusion peptide or polypeptide) to enhance an immune reaction. Exemplary and preferred immunogenic carrier amino acid sequences include hepatitis B surface antigen, keyhole limpet hemocyanin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine.

g. Biological Response Modifiers

It may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m2) (Johnson/Mead, NJ), or a gene encoding a protein involved in one or more immune helper functions, such as B-7.

2. Adjuvants

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent such as alum used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cell(s) such as *C. parvum* or an endotoxin or a lipopolysaccharide components of Gram-negative bacteria, emulsion in physiologically acceptable oil vehicles such as mannide mono-oleate (Aracel A) or emulsion with a 20% solution of a perfluorocarbon (Fluosol-DA®) used as a block substitute also may be employed.

Some adjuvants, for example, are certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g, U.S. Pat. No. 4,877,611). This has been attempted particularly in the treatment of cancer. For many cancers, there is compelling evidence that the immune system participates in host defense against the tumor cells, but only a fraction of the likely total number of tumor-specific antigens are believed to have been identified to date. However, using the present invention, the inclusion of a suitable adjuvant into the membrane of an irradiated tumor cell will likely increase the anti-tumor response irrespective of the molecular identification of the prominent antigens. This is a particularly important and time-saving feature of the invention.

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed.

Various polysaccharide adjuvants may also be used. For example, the use of various pneumococcal polysaccharide adjuvants on the antibody responses of mice has been described (Yin et al., 1989). The doses that produce optimal responses, or that otherwise do not produce suppression, should be employed as indicated (Yin et al., 1989). Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is described for use in artificial liposomes formed from phosphatidyl choline and phosphatidyl glycerol. It is the to be effective in activating human monocytes and destroying tumor cells, but is non-toxic in generally high doses. The compounds of U.S. Pat. No. 4,950,645 and PCT Patent Application WO 91/16347, are contemplated for use with cellular carriers and other embodiments of the present invention.

Another adjuvant contemplated for use in the present invention is BCG. BCG (*bacillus* Calmette-Guerin, an attenuated strain of *Mycobacterium*) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

BCG is an important clinical tool because of its immunostimulatory properties. BCG acts to stimulate the reticuloendothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG (Jacobs et al., 1987; Snapper et al., 1988; Husson et al., 1990; Martin et al., 1990).

Live BCG is an effective and safe vaccine used worldwide to prevent tuberculosis. BCG and other mycobacteria are highly effective adjuvants, and the immune response to mycobacteria has been studied extensively. With nearly 2 billion immunizations, BCG has a long record of safe use in man (Luelmo, 1982; Lotte et al., 1984). It is one of the few vaccines that can be given at birth, it engenders long-lived immune responses with only a single dose, and there is a worldwide distribution network with experience in BCG vaccination. An exemplary BCG vaccine is sold as TICE™ BCG (Organon Inc., West Orange, N.J.).

In a typical practice of the present invention, cells of *Mycobacterium bovis*-BCG are grown and harvested by methods known in the art. For example, they may be grown as a surface pellicle on a Sauton medium or in a fermentation vessel containing the dispersed culture in a Dubos medium (Dubos et al., 1947; Rosenthal, 1937). All the cultures are harvested after 14 days incubation at about 37° C. Cells grown as a pellicle are harvested by using a platinum loop whereas those from the fermenter are harvested by centrifugation or tangential-flow filtration. The harvested cells are resuspended in an aqueous sterile buffer medium. A typical suspension contains from about $2 \times 10^{10}$ cells/ml to about $2 \times 10^{12}$ cells/ml. To this bacterial suspension, a sterile solution containing a selected enzyme which will degrade the BCG cell covering material is added. The resultant suspension is agitated such as by stirring to ensure maximal dispersal of the BCG organisms. Thereafter, a more concentrated cell suspension is prepared and the enzyme in the concentrate removed, typically by washing with an aqueous buffer, employing known techniques such as tangential-flow filtration. The enzyme-free cells are adjusted to an optimal immunological concentration with a cryoprotectant solution, after which they are filled into vials, ampoules, etc., and lyophilized, yielding BCG vaccine, which upon reconstitution with water is ready for immunization.

Amphipathic and surface active agents, e.g, saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention.

One group of adjuvants preferred for use in the invention are the detoxified endotoxins, such as the refined detoxified endotoxin of U.S. Pat. No. 4,866,034. These refined detoxified endotoxins are effective in producing adjuvant responses in mammals. Of course, the detoxified endotoxins may be combined with other adjuvants to prepare multi-adjuvant-incorporated cells. For example, combination of detoxified endotoxins with trehalose dimycolate is particularly contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436, 728 and 4,505,900. Combinations of just CWS and trehalose dimycolate, without detoxified endotoxins, is also envisioned to be useful, as described in U.S. Pat. No. 4,520,019.

In other embodiments, the present invention contemplates that a variety of adjuvants may be employed in the membranes of cells, resulting in an improved immunogenic composition. The only requirement is, generally, that the adjuvant be capable of incorporation into, physical association with, or conjugation to, the cell membrane of the cell in question. Those of skill in the art will know the different kinds of adjuvants that can be conjugated to cellular vaccines in accordance with this invention and these include alkyl lysophosphilipids (ALP); BCG; and biotin (including biotinylated derivatives) among others. Certain adjuvants particularly contemplated for use are the teichoic acids from Gram positive cells. These include the lipoteichoic acids (LTA), ribitol teichoic acids (RTA) and glycerol teichoic acid (GTA). Active forms of their synthetic counterparts may also be employed in connection with the invention (Takada et al., 1995a).

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g, as may occur using non-irradiated tumor cells, is irrelevant in such circumstances.

One group of adjuvants preferred for use in some embodiments of the present invention are those that can be encoded by a nucleic acid (e.g, DNA or RNA). It is contemplated that such adjuvants may be encoded in a nucleic acid (e.g, an expression vector) encoding the antigen, or in a separate vector or other construct. These nucleic acids encoding the adjuvants can be delivered directly, such as for example with lipids or liposomes.

3. Excipients, Salts and Auxiliary Substances

An antigenic composition of the present invention may be mixed with one or more additional components (e.g., excipients, salts, etc.) which are pharmaceutically acceptable and compatible with at least one active ingredient (e.g, antigen). Suitable excipients are, for example, water, saline, dextrose, glycerol, ethanol and combinations thereof.

An antigenic composition of the present invention may be formulated into the vaccine as a neutral or salt form. A pharmaceutically-acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2-ethylamino ethanol, histidine, procaine, and combinations thereof.

In addition, if desired, an antigenic composition may comprise minor amounts of one or more auxiliary substances such as for example wetting or emulsifying agents, pH buffering agents, etc. which enhance the effectiveness of the antigenic composition or vaccine.

I. Vaccine Preparations

Once produced, synthesized and/or purified, an antigen or other vaccine component may be prepared as a vaccine for administration to a patient. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine comprising an antigenic composition comprising folate binding protein epitopes and/or variants as active ingredient(s), in light of the present disclosure. In preferred embodiments, the compositions of the present invention are prepared to be pharmacologically acceptable vaccines.

Pharmaceutical vaccine compositions of the present invention comprise an effective amount of one or more folate binding protein epitopes and/or variants or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one folate binding protein epitope or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g, human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g, antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The folate binding protein variant may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g, methylparabens, propylparabens), chlorobutanol, phenol, sorbic acid, thimerosal or combinations thereof.

The folate binding protein variant may be formulated into a composition in a free base, neutral or salt form. Pharmaceutically acceptable salts, include the acid addition salts, e.g, those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g, glycerol, propylene glycol, liquid polyethylene glycol, etc.), lipids (e.g, triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the folate binding protein variant is prepared for administration by such routes as oral ingestion. In these embodiments, the solid composition may comprise, for example, solutions, suspensions, emulsions, tablets, pills, capsules (e.g, hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

J. Vaccine Administration

The manner of administration of a vaccine may be varied widely. Any of the conventional methods for administration of a vaccine are applicable. For example, a vaccine may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in cremes, in lipid compositions (e.g, liposomes), or by other method or any combination of the forgoing as would be known to one of ordinary skill in the art (see, for example, Remington's Pharmaceutical Sciences, 18th Ed. Mack Printing Company, 1990, incorporated herein by reference).

A vaccination schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g, the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g, inoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the folate binding protein variant can be performed, following immunization.

K. Enhancement of an Immune Response

The present invention includes a method of enhancing the immune response in a subject comprising the steps of contacting one or more lymphocytes with a folate binding protein variant antigenic composition, wherein the antigen comprises as part of its sequence a sequence in accordance with SEQ ID NO:1 through SEQ ID NO:8, or a immunologically functional equivalent thereof. In certain embodiments the one or more lymphocytes is comprised in an animal, such as a human. In other embodiments, the lymphocyte(s) may be isolated from an animal or from a tissue (e.g, blood) of the animal. In certain preferred embodiments, the lymphocyte(s) are peripheral blood lymphocyte(s). In certain embodiments, the one or more lymphocytes comprise a T-lymphocyte or a B-lymphocyte. In a particularly preferred facet, the T-lymphocyte is a cytotoxic T-lymphocyte.

The enhanced immune response may be an active or a passive immune response. Alternatively, the response may be part of an adoptive immunotherapy approach in which lymphocyte(s) are obtained with from an animal (e.g, a patient), then pulsed with composition comprising an antigenic composition. In a preferred embodiment, the lymphocyte(s) may be administered to the same or different animal (e.g, same or different donors).

1. Cytotoxic T Lymphocytes

In certain embodiments, T-lymphocytes are specifically activated by contact with an antigenic composition of the present invention. In certain embodiments, T-lymphocytes are activated by contact with an antigen presenting cell that is or has been in contact with an antigenic composition of the invention.

T cells express a unique antigen binding receptor on their membrane (T-cell receptor), which can only recognize antigen in association with major histocompatibility complex (MHC) molecules on the surface of other cells. There are several populations of T cells, such as T helper cells and T cytotoxic cells. T helper cells and T cytotoxic cells are primarily distinguished by their display of the membrane bound glycoproteins CD4 and CD8, respectively. T helper cells secret various lymphokines, that are crucial for the activation of B cells, T cytotoxic cells, macrophages and other cells of the immune system. In contrast, a T cytotoxic cell that recognizes an antigen-MHC complex proliferates and differentiates into an effector cell called a cytotoxic T lymphocyte (CTL). CTLs eliminate cells of the body displaying antigen by producing substances that result in cell lysis.

CTL activity can be assessed by methods described herein or as would be known to one of skill in the art. For example, CTLs may be assessed in freshly isolated peripheral blood mononuclear cells (PBMC), in a phytohaemaglutinin-stimulated IL-2 expanded cell line established from PBMC (Bernard et al., 1998) or by T cells isolated from a previously immunized subject and restimulated for 6 days with DC infected with an adenovirus vector containing antigen using standard 4 h $51^{Cr}$ release microtoxicity assays. In another fluorometric assay developed for detecting cell-mediated cytotoxicity, the fluorophore used is the non-toxic molecule ALAMARBLUE (dye) (Nociari et al., 1998). The ALAMARBLUE (dye) is fluorescently quenched (i.e., low quantum yield) until mitochondrial reduction occurs, which then results in a dramatic increase in the alamarBlue fluorescence intensity (i.e., increase in the quantum yield). This assay is reported to be extremely sensitive, specific and requires a significantly lower number of effector cells than the standard $51^{Cr}$ release assay.

In certain aspects, T helper cell responses can be measured by in vitro or in vivo assay with peptides, polypeptides or proteins. In vitro assays include measurement of a specific cytokine release by enzyme, radioisotope, chromaphore or fluorescent assays. In vivo assays include delayed type hypersensitivity responses called skin tests, as would be known to one of ordinary skill in the art.

2. Antigen Presenting Cells

In general, the term "antigen presenting cell" can be any cell that accomplishes the goal of the invention by aiding the enhancement of an immune response (i.e., from the T-cell or -B-cell arms of the immune system) against an antigen (e.g, a folate binding protein variant or a immunologically functional equivalent) or antigenic composition of the present invention. Such cells can be defined by those of skill in the art, using methods disclosed herein and in the art. As is understood by one of ordinary skill in the art (see for example Kuby, 1993, incorporated herein by reference), and used herein certain embodiments, a cell that displays or presents an antigen normally or preferentially with a class II major histocompatability molecule or complex to an immune cell is an "antigen presenting cell." In certain aspects, a cell (e.g, an APC cell) may be fused with another cell, such as a recombinant cell or a tumor cell that expresses the desired antigen. Methods for preparing a fusion of two or more cells is well known in the art, such as for example, the methods disclosed in Goding, pp. 65-66, 71-74 1986; Campbell, pp. 75-83, 1984; Kohler and Milstein, 1975; Kohler and Milstein, 1976, Gefter et al., 1977, each incorporated herein by reference. In some cases, the immune cell to which an antigen presenting cell displays or presents an antigen to is a CD4$^+$ TH cell. Additional molecules expressed on the APC or other immune cells may aid or improve the enhancement of an immune response. Secreted or soluble molecules, such as for example, immunomodulators and adjuvants, may also aid or enhance the immune response against an antigen. Such molecules are well known to one of skill in the art, and various examples are described herein.

VII. Peptide Formulations

Peptides containing the epitope motifs described herein are contemplated for use in therapeutics to provide universal FBP targets and antigens for CTLs in the HLA-A2 system. The development of therapeutics based on these novel sequences provides induction of tumor reactive immune cells in vivo through the formulation of synthetic cancer vaccines, as well as induction of tumor-reactive T-cells in vitro through either peptide-mediated (e.g, lipopeptide) or cell-mediated (e.g, EBV-B lines using either autologous or HLA-A2 transfectants where the gene for the peptide of interest is introduced, and the peptide is expressed associated with HLA-A2 on the surface). The use of these novel peptides as components of vaccines to prevent, or lessen the chance of cancer progression is also contemplated.

The peptides contemplated for use, being smaller than other compositions, such as envelope proteins, will have improved bioavailability and half lives. If desired, stability examinations may be performed on the peptides, including, e.g, pre-incubation in human serum and plasma; treatment with various proteases; and also temperature- and pH-stability analyses. If found to be necessary, the stability of the synthetic peptides may be enhanced by any one of a variety of methods such as, for example, employing D-amino acids in place of L-amino acids for peptide synthesis; using blocking groups like t-boc and the like; or encapsulating the peptides within liposomes. The bio-availability of select mixtures of peptides may also be determined by injecting radio-labeled peptides into experimental animals, such as mice and/or Rhesus monkeys, and subsequently analyzing their tissue distribution.

If stability enhancement was desired, it is contemplated that the use of dextrorotary amino acids (D-amino acids) would be advantageous as this would result in even longer bioavailability due to the inability of proteases to attack these types of structures. The peptides of the present invention may also be further stabilized, for example, by the addition of groups to the N- or C-termini, such as by acylation or amination. If desired, the peptides could even be in the form of lipid-tailed peptides, formulated into surfactant-like micelles, or other peptide multimers. The preparation of peptide multimers and surfactant-like micelles is described in detail in U.S. Ser. No. 07/945,865, incorporated herein by reference. The compositions of the present invention are contemplated to be particularly advantageous for use in economical and safe anti-tumor/anti-cancer therapeutics, and specific therapeutic formulations may be tested in experimental animal models, such as mice, rats, rabbits, guinea pigs, cats, goats, Rhesus monkeys, chimpanzees, and the like, in order to determine more precisely the dosage forms required.

In addition to the peptidyl compounds described herein, the inventors also contemplate that other sterically similar compounds may be formulated to mimic the key portions of the peptide structure and that such compounds may also be used in the same manner as the peptides of the invention. This may be achieved by the techniques of modelling and chemical design known to those of skill in the art. For example, esterification and other alkylations may be employed to modify the terminus of a peptide to mimic a particular terminal motif structure. It will be understood that all such sterically similar constructs fall within the scope of the present invention.

Therapeutic or pharmacological compositions of the present invention will generally comprise an effective amount of a CTL-stimulating peptide or peptides, dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

Supplementary active ingredients can also be incorporated into the therapeutic compositions of the present invention. For example, the stimulatory peptides may also be combined with peptides including cytotoxic T-cell- or T-helper-cell-inducing epitopes (as disclosed in U.S. Ser. No. 07/945,865; incorporated herein by reference) to create peptide cocktails for immunization and treatment.

The preparation of pharmaceutical or pharmacological compositions containing a CTL-stimulating peptide or peptides, including dextrorotatory peptides, as active ingredients will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalents and the like.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile solutions suitable for intravenous administration are preferred in certain embodiments and are contemplated to be particularly effective in stimulating CTLs and/or producing an immune response in an animal. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A peptide or peptides can be formulated into a composition in a neutral or salt form. Pharmaceutically acceptable salts, include the acid addition salts (formed with the free amino groups of the peptide) and which are formed with inorganic acids such as, e.g, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

The carrier can also be a solvent or dispersion medium containing, e.g., water, ethanol, polyol (for example, glycerol, propylene glycol, and liquid polyethylene glycol, and the like), suitable mixtures thereof, and vegetable oils. The proper fluidity can be maintained by inter alia the use of a coating, such as lecithin, by the maintenance of the required particle size in the case of dispersion and by the use of surfactants. The prevention of the action of microorganisms can be brought inter alia by various antibacterial ad antifungal agents, for example, parabens, chlorobutanol, phenol, sorbic acid, thimerosal, and the like. In many cases, it will be preferable to include isotonic agents, e.g, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more- or highly-concentrated solutions for intramuscular injection is also contemplated. This is envisioned to have particular utility in facilitating the treatment of needle stick injuries to animals or even humans. In this regard, the use of DMSO as solvent is preferred as this will result in extremely rapid penetration, delivering high concentrations of the active peptide, peptides or agents to a small area.

The use of sterile formulations, such as saline-based washes, by veterinarians, technicians, surgeons, physicians or health care workers to cleanse a particular area in the operating field may also be particularly useful. Therapeutic formulations in accordance with the present invention may also be reconstituted in the form of mouthwashes, including the peptides alone, or in conjunction with antifungal reagents. Inhalant forms are also envisioned, which again, may contain active peptides or agents alone, or in conjunction with other agents, such as, e.g, pentamidine. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9±0.2%. Suitable antioxidants and stabilizers include sodium bisulfite, sodium metabisulfite, sodium thiosulfate, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethyl-propylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed. As used herein, "pharmacologically effective amount" means an amount of composition is used that contains an amount of a peptide or peptides sufficient to significantly stimulate a CTL or generate an immune response in an animal.

In this context, the quantity of peptide(s) and volume of composition to be administered depends on the host animal to be treated, such as, the capacity of the host animal's immune system to produce an immune response. Precise amounts of active peptide required to be administered depend on the judgment of the practitioner and are peculiar to each individual.

A minimal volume of a composition required to disperse the peptide is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

In certain embodiments, active compounds may be administered orally. This is contemplated for agents that are generally resistant, or have been rendered resistant, to proteolysis by digestive enzymes. Such compounds are contemplated to include chemically designed or modified agents; dextrorotatory peptides; and peptide and liposomal formulations in timed-release capsules to avoid peptidase, protease and/or lipase degradation.

Oral formulations may include compounds in combination with an inert diluent or an edible carrier which may be assimilated; those enclosed in hard- or soft-shell gelatin capsules; those compressed into tablets; or those incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should generally contain at least 0.1% of active compound.

The percentage of the compositions and preparations may, of course, be varied and may conveniently be between about 2 to about 60% of the weight of the unit. The amount of active compounds in such therapeutically useful compositions is such that a suitable dosage will be obtained.

Tablets, troches, pills, capsules and the like may also contain the following: a binder, as gum tragacanth, acacia, corn starch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparaben as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The peptides may be used in their immunizing capacity by administering an amount effective to generate an immune response in an animal. In this sense, such an "amount effective to generate an immune response" means an amount of composition that contains a peptide or peptide mixture sufficient to significantly produce an antigenic response in the animal.

VIII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Rationale for Variant Design

Studies in experimental models regarding lymphocyte development in the thymus show that interaction of thymocytes with weak or null (no apparent effect) agonists lead to positive selection (i.e. survival) of responders for a specific Ag, while stimulation with strong agonists leads to negative selection (deletion of reactive CTL). Similarly, recent studies on CD8+ cell responses from peripheral blood show that Ag variants with null or weak agonistic activity induced expansion of precursors of CTL responding to a model Ag, but not effector function. These results were obtained with transgenic animals, and the recipients for the CTL were heavily irradiated. There is little information concerning how the responders to tumor, and/or their precursors, can be maintained and avoid elimination in healthy individuals, or patients without evidence of disease. However, the presence of such precursors, or of activated CTL recognizing tumor Ag, (Peoples et al., 1998; Hudson et al., 1998; Peoples et al, 1998; Kim et al., 1999; Lee et al., 2000) is proof that such responders exist in the peripheral blood. Approaches to promote their survival, expansion and induction of lytic formation is beneficial for the patients. If the responders targeted for survival are low-affinity CTL, the weak affinity is expected to be compensated by a significant increase in effector numbers. If the responders are of high affinity, protection from AICD will also allow their expansion.

To design "survival inducing" Ag, the present invention focuses on the FBP epitope E39: EIWTHSYKV (SEQ ID NO: 268). This epitope is recognized, although with low affinity, by ovarian and breast tumor reactive CTL. It was predicted that improved immunogenicity in terms of net gain in cell numbers reacting with the wild-type Ag is achieved by reducing the positive charge at the amino acid in position 5 (histidine) and replacement of histidine with phenylalanine (Phe). Phe is not charged, but its benzene aromatic ring is a close substitution for the imidazole ring of histidine. To ensure a better flexibility of the residues in the peptide, the phenolic structure of tyrosine was replaced with the aliphatic core chain of Threonine (Thr). Both Tyr and Thr contain an OH (hydroxyl) side chain group. Thus, the positive charge in position 5 and the rigid structure of Tyr were eliminated. In a specific embodiment, this increases the flexibility of the residues 5-9 (SYKV) (SEQ ID NO: 270) in the peptide and allows for a better fitting of the TCR with the peptide MHC complex. The variant: E I W T F S T K V (SEQ ID NO: 5) was designated J65. Additional variants of J65 were created with changes in position 7 (Tyr)→Thr only=designated J77, in position 5 only Phe→His=designated J78, and in positions 1 and 6. These analogs/variants are listed in Table 5.

TABLE 5

Variants of Folate Binding Protein

| VARIANT | SEQUENCE | CHANGE |
|---|---|---|
| E39 | EIWTHSYKV (SEQ ID NO: 268) | wild type |
| J77 | EIWTHSTKV (SEQ ID NO: 1) | Y7 → T |
| J78 | EIWTFSYKV (SEQ ID NO: 2) | H5 → F |
| J68 | FIWTFATKV (SEQ ID NO: 3) | E1 → F, H5 → F, S6 → A; Y7 → T |
| J67 | EIWTHATKV (SEQ ID NO: 4) | S6 → A, Y7 → T |
| J66 | FIWTFSTKV (SEQ ID NO: 271) | E1 → F, H5 → F, Y7 → T |
| J65 | EIWTFSTKV (SEQ ID NO: 5) | H5 → F, Y7 → T |
| J64 | GIWTHSTKV (SEQ ID NO: 7) | E1 → G, Y7 → T |
| J63 | FIWTHSTKV (SEQ ID NO: 8) | E1 → F, Y7 → T |

Selection of these Ag variants was made on the principle of Ag alteration aiming to alternate signaling. In addition to substitutions H→F (Pos. 5) and Y→T (pos. 7), substitutions were introduced in the other positions: S→A (Pos. 6 and Glu (B)→F and E→Gly (G) (in Pos. 1). The purpose of these substitutions was to remove potential reacting groups with the TCR. In the substitution S→A (Pos. A), this change removes a side chain OH group. In position 1, the substitution E (glutamic acid)→glycine, removes the entire aliphatic side chain plus the charged COO group. Also in position 1, the substitution E→F (removes the charged group COO, but introduces an aromatic ring). These substitutions aim to diminish the reactivity of the peptide with the TCR.

Example 2

IFN-γ Induction and CRL Activity

The HLA-A2 stabilizing ability of the variant peptides has also been determined (FIG. 1). The results show that the stabilizing ability of J65 is almost half of the stabilizing ability of E39. In contrast, substitutions at position 1 increase the binding affinity of the peptide. The results in FIG. 2 show the cytolytic activity of J65-induced CTL compared with E39-induced CTL. The results indicate that J65 was a weaker inducer of IFN-y from 3×J65 stimulated cultures than J77 and E39, suggesting that the changes in the sequence had cumulative effects in decreasing IFN-y induction.

To address the effects of FBP variants on induction of CTL activity, PBMC cultures from the healthy donor stimulated three times with J65 were split in three and restimulated with either E39 or J65 or J77. A control culture was made of the same PBMC stimulated three times with E39 and restimulated with E39 for the fourth time. PBMC stimulated three times with E39 (3×E39) followed by E39 showed moderate weak recognition of E39. In contrast, 3×J65 stimulated CTL showed significantly higher recognition of E39 after stimulation with E39. A similar picture was observed with 3×J65 cells restimulated with J65, while 3×J65 restimulated with J77 showed significantly lower CTL activity than 3×J65 stimulated with the other peptides. It was recently reported that memory CTL reacting with the tumor Ag such as FBP are present in the blood of healthy individuals (Lee et al., 2000). These cells can be easily activated by stimulation with the corresponding peptide presented on dendritic cells (Kim et al., 1999). To evaluate the stimulating ability of the analogs J65 and J77, PBMC from a responding donor were stimulated with E39, J65 and J77. These results show that the potentiating role of J65 in responder proliferation and cytotoxicity does not reflect enhanced IL-2 and/or IFN-γ secretion compared with the wild-type Ag, but its weaker cytokine-inducing activity appears to protect CTL of higher affinity from apoptosis by avoiding overstimulation.

Example 3

Specific IL-2 Induction by Priming with FBP Variants

In J65-primed CTL, higher CTL activity and IFN-γ secretion can be elicited by the wild-type epitope E39, suggesting a protective effect of the previous stimulations. The results in FIG. 3 show that J65 and J77 induced lower levels of IL-2 in the PBMC of this donor compared with the wild-type peptide E39. To identify which of E39 variants induced higher cell expansion, PBMC from the same donor were stimulated three times with the corresponding peptide, and the resulting live cells were counted a week after each stimulation. The results in FIG. 4 show that cultures stimulated with E39 initially expanded faster than other cultures; however, after the third stimulation, cultures stimulated with J65 increased faster in numbers. In contrast, cultures stimulated with J78 (H→F) and J77 (Y→T) proliferated slower than control cultures which were not stimulated with peptide. Similar results were obtained with J65 in another donor (FIG. 5). In this donor, cells stimulated with E39 died after the third stimulation while cells stimulated by J65 expanded faster. Cells stimulated with J77 and J78 also expanded, but at a slower rate.

* * *

REFERENCES

The following references, to the extent that they provide exemplary procedural or other details supplementary to those set forth herein, are specifically incorporated herein by reference.

Patents

U.S. Pat. No. 3,826,364; issued Jul. 30, 1974.
U.S. Pat. No. 4,284,412; issued Aug. 18, 1981.
U.S. Pat. No. 4,498,766; issued Feb. 12, 1985.
U.S. Pat. No. 4,578,770; issued Mar. 25, 1986.
U.S. Pat. No. 4,596,792; issued Jun. 24, 1986.
U.S. Pat. No. 4,599,230; issued Jul. 8, 1986.
U.S. Pat. No. 4,599,231; issued Jul. 8, 1986.
U.S. Pat. No. 4,601,903; issued Jul. 22, 1986.
U.S. Pat. No. 4,608,251; issued Aug. 26, 1986.
U.S. Pat. No. 4,661,913; issued Apr. 28, 1987.
U.S. Pat. No. 4,714,682; issued Dec. 22, 1987.
U.S. Pat. No. 4,767,206; issued Aug. 30, 1988.
U.S. Pat. No. 4,774,189; issued Sep. 27, 1988.
U.S. Pat. No. 4,857,451; issued Aug. 15, 1989.
U.S. Pat. No. 4,989,977; issued Feb. 5, 1991.
U.S. Pat. No. 5,160,974; issued Nov. 3, 1992.
U.S. Pat. No. 5,478,722; issued Dec. 26, 1995.

Publications

Acres B., Hareuveni M., Balloul J. M. and Kieny M. P. (1993) VV-MUC1 immunisation of mice-immune response and protection against the growth of murine tumours bearing the MUC1 antigen J. Immunother. 14:136-143.

Acres B., Apostolopoulos V., Balloul J. M., Wreschner D, Xing P. X., Hadi D. A. et al. (1999) MUC1 specific cytotoxic T cell precursor analysis in human MUC1 transgenic mice immunised with human MUC1 vaccines. Cancer Immunol. Immunother. 2000 January; 48(10):588-94.

Almendro et al., "Cloning of the human platelet endothelial cell adhesion molecule-1 promoter and its tissue-specific expression. Structural and functional characterization," J Immunol. 157(12):5411-5421, 1996.

Anichini, A. et al., (1993) et al., J. Exp. Med. 177:989-998.

Apostolopoulos V., Haurum J. S. and McKenzie I. F. C. (1997) MUCI peptide epitopes associated with 5 different H2 class I molecules. Eur. J. Immunol. 27:2579-2587.

Apostolopoulos V., Karanikas V., Haurum J. and McKenzie I. F. C. (1997) Induction of HLA-A2 restricted cytotoxic T lymphocytes to the MUCI human breast cancer antigen J. Immunol. 159:56211-5218.

Apostolopoulos V., Chelvanayagam G., Xing P.-X and McKenzie I. F. C. (1998) Anti-MUCI antibodies react directly with MUC1 peptides presented by class I and HLA molecules J. Immunol. 161:767-775.

Apostolopoulus V. Xing P.-X. and McKenzie I. F. C. (1994) Murine immuno response to cells transfected with human MUC1: Immunisation with cellular and synthetic antigens. Cancer Res. 54: 5186-5193.

Apostolopoulos V., Pietersz G. A., Loveland B. E., Sandrin M. S. and McKenzie I. F. C. (1995) Oxidative/reductive conjugation of mannan to antigen selects for T1 or T2 immune responses. Proc. Natl. Acad. Sci. USA 92: 10128-10132.

Apostolopoulos V., Popovski V. and McKenzie I. F. C. (1998) Cyclophosphamide enhances the CTL precursor frequency in mice immunized with MUC1-mannan fusion protein (M-FP). J. Immunother. 21:109-113.

Astori M. and Krachenbuhl J. P. (1996) Recombinant fusion peptices containing single or multiple repeats of a ubiquitous T-helper epitope are highly immunogenic. Mol. Immunol. 33: 1017-1024.

Barth, R. J., et al., (1991) J. Exp. Med. 173:647-658.

Bartnes K., Hannestad K., Guichard G. and Briand J. P. (1997) A retro-inverso analog mimics the cognate peptide epitope of a CD4+ T cell clone. Eur. J. Immunol. 27:1387-1391.

Beekman N. J., Schaaper W. M., Tesser G. I., Dalsgaard K., Kamstrup S., Langeveld J. P. et al. (1997) Synthetic peptide vaccines: palmitoylation of peptide antigens by a thioester bond increases immunogenicity. J. Pept. Res. 50: 357-364.

BenMohamed L., Gras-Masse H., Tarter A., Daubersies P., Bahimi K., Bossus M. et al. (1997) Lipopeptide immunization without adjuvant induces potent and long-lasting B. T. helper, and cytotoxic T lymphocyte responses against a malaria liver stage antigen in mice and chimpanzees. Eur. J. Immunol. 27: 1242-1253.

Blaese, R. M., Pediatr. Res., 33 (1 Suppl):S49-S53 (1993).

Briand J. P., Benkirane N., Guichard G., Newman J. F. E., Van Regenmortel M. H., Brown F. et al. (1997) A retro-inverso peptide corresponding to the GH loop of foot-and-mouth disease virus elicits high levels of long-lasting protective neutralizing antibodies. Proc. Natl. Acad. Sci. USA 94: 12545-12550.

Chakraborty N. G., Sporn J. R., Tortora A. F., Kurtzman S. H., Yamase H., Ergin M. T. et al. (1998) Immunization with a tumor-cell-lysate-loaded autologous-antigen-presenting-cell-based vaccine in melanoma. Cancer Immunol. Immunother, 47: 58-64.

Chen T. T., Tao M. H. and Levy R. (1994) Idiotype-cytokine fusion proteins as cancer vaccines. Relative efficacy of IL-2, IL-4 and granulocyte-macrophage colony-stimulating factor. J. Immunol. 153:4775-4787.

Ciupitu A. M. Petersson M., O'Donnell C. L., Williams K., Jindal S., Kiessling R. et al. (1998) Immunization with a lymphocytic choriomeningitis virus peptide mixed with heat shock protein 70 results in protective antiviral immunity and specific cytotoxic T lymphocytes. J. Exp. Med. 187:685-691.

Creswell P. (1994) Assembly, transport and function of MHC class I molecules. Ann. Rev. Immunol. 12:259-293.

Culver, L., et al. Proc. Natl. Acad. Sci. USA, 88:3155-3159 (1991).

Dalgleish, A. G. Cancer vaccines. Br. J. Cancer 82(10): 1619-1624.

Darrow, T. L., et al., (1989) J. Immunol. 142:3329-3335.

DeLeo A. B. (1998) p53-based immunotherapy of cancer. Crit. Rev. Immunol. 18: 29-35.

Deprez B., Sauzet J. P., Boutillon C., Martinon F., Tartar A., Sergheraert C. et al. (1996) Comparative efficiency of simple lipopeptide constructs for in vivo induction of virus-specific CTL. Vaccine 14: 375-382.

Derossi D., Joliot G., Chassaing G. and Prochiantz A. (1994) The third helix of the *Antennapedia* homeodomain translocates through biological membranes. J. Biol. Chem. 269: 10444-10450.

Derossi D., Calvet S., Trembleau A., Brunissen A., Chassaing G. and Prochiantz A. (1996) Cell internalization of the helix of the *Antennapedia* homeodomain is receptor-independent. J. Biol. Chem. 271: 18188-18193.

Ding L., Lalani E. N. and Reddish M. (1993) Immunogenicity of synthetic peptides related to the core peptide sequence encoded by the human MUC1 gene: effect of immunisation on the growth of murine mammary adenocarcinoma cells transfected with the human MUC1 gene. Cancer Immunol. Immunother. 36:9-17.

Disis M. L., Bernhard H., Shiota F. M., Hand S. L., Gralow J. R., Huseby E. S. et al. (1996) Granulocyte macrophage colony-stimulating factor: an effective adjuvant for protein and peptide-based vaccines Blood 88:-202-210

Donnelly J. J., Ulmer J. B., Hawe L. A., Friedman A., Shi X. P., Leander K. R. et al. (1993) Targeted delivery of peptide epitopes to class I major histocompatibility molecules by a modified *Pseudomonas* exotoxin. Proc. Natl. Acad. Sci. USA 90: 3530-3534.

Elwood, P. C. Molecular cloning and characterization of the human folate binding protein cDNA from placenta and malignant tissue culture (KB) cells. J. Biol. Chem. 264: 14893-14901, 1989.

Fayolle C., Sebo P., Ladant D., Ullmann A. and Leclerc C. (1996) In vivo induction of CTL responses by recombinant adenylate cyclase of *Bordetella pertussis* carrying viral CD8+ T cell epitopes. J. Immunol. 156:4697-4706.

Fukasawa M., Shimizu Y., Shikata K., Nakata M., Sakakibara R., Yamamoto N. et al. (1998) Liposome oligomannase-coated with neoglycolipid, a new candidate for a safe adjuvant for induction of CD8+ cytotoxic T lymphocytes. FEBS Lett. 441: 353-356.

Garin-Chesa, P., Campbell, I. Suigo, P. E., Lewis, J. L., Old, L. J., and Rettig, W. J. Trophoblast and ovarian cancer antigen LK26. Sensitivity and specificity in immunopathology and molecular identification as a folate binding protein. Am. J. Pathol., 142: 557-567, 1993.

Gendler S. J., Papadimitriou J. T., Duhig T., Rothbard J. and Burchell J. (1998) A highly immunogenic region of human polymorphic epithelial mucin expressed by carcinomas is made up of tandem repeats, J. Biol. Chem. 263:12820-12823.

Goletz T. J., Klimpel K. R., Arora N., Leppla S. H., Keith J. M. and Berzofsky J. A. (1997) Targeting HIV proteins to the major histocompatibility complex class I processing pathway with a novel gp120-antrax toxin fusion protein, Proc. Natl. Acad. Sci. USA 94: 12059-12064.

Gong J., Chen D., Kashiwaba M. and Kufe D. (1997) Induction of antitumour activity by immunization with fusions of dendritic and carcinoma cells. Nature Med. 3: 558-561.

Gong J., Chen D., Kashiwaba M., Li Y., Chen L., Takeuchi H. et al. (1998) Reversal of tolerance to human MUC1 antigen in MUC1 transgenic mice immunized with fusions of dendritic and carcinoma cells. Proc. Natl. Acad. Sci. USA 95: 6279-6283.

Goydos J. S., Elder E., Whiteside T. L., Finn 0. J. and Lotze M. T. (1996) A phase I trial of a synthetic mucin peptide vaccine. Induction of specific immune reactivity in patients with adenocarcinoma. J. Surg. Res. 63: 298-304.

Gras-Masse H., Boutillon C., Diesis E., Deprez B. and Tartar A. (1997) Confronting the degeneracy of convergent combinatorial immunogens or 'mixotopes', with the specificity of recognition of the target sequences. Vaccine 15:1568-1578.

Guan H. H., Budzynski W., Koganty R. R., Kantz M. J., Reddish M. A., Rogers J. A. et al (1998) Liposomal formulations of synthetic MUC1 peptides: effects of encapsulation versus surface display of peptides on immune responses. Bioconjug. Chem. 9:451-458.

Guichard G., Connan F., Graff R., Ostankovitch M., Muller S., Guillet J. G. et al. (1996) A partially modified retro-inverso pseudopeptide as a non-natural ligand for the human class I histocompatibility molecule HLA-A2. J. Med. Chem. 39: 2030-3039.

Hurpin C, Rotarioa C, Bisceglia H, Chevalier M, Tartaglia J, Erdile L. The mode of presentation and route of administration are critical for the induction of immune responses to p53 and antitumor immunity. Vaccine. 1998 January-February; 16(2-3):208-15.

Heeg K., Kuon W. and Wagner H. (1991) Vaccination of class I major histocompatibility complex (MHC)-restricted murine CD8+ cytotoxic T lymphocytes towards soluble antigens: immunostimulating-ovalbumin complexes enter the class I MHC-restricted antigen pathway and allow sensitization against the immunodominant peptide. Eur. J. Immunol. 21: 1523-1527.

Heike M., Noll B. and Meyer zum Buschenfelde K. H. (1996) Heat shock protein-peptide completes for use in vaccines. J. Leukoc. Biol. 60: 153-158.

Henderson R. A., Konitsky W. M., Barratt-Boyes S. M., Soares M., Robbins P. D. and Finn O. J. (1998) Retroviral expression of MUC-1 human tumor antigen with intact repeat structure and capacity to elicit immunity in vivo. J. Immunother. 21:247-256.

Henderson R. A., Nimgaonkar M. T., Watkins S. C., Robbins P. D., Ball E. D. and Finn O. J. (1996) Human dendritic cells genetically engineered to express high levels of the human epithelial tumor antigen mucin (MUC-1). Cancer Res. 56:3763-3770.

Herve M., Maillere B., Mourier G., Texier C., Leroy S. and Menez A. (1997) On the immunogenic properties of retro-inverso peptides. Total retro-inversion of T-cell epitopes causes a loss of binding to MHC II molecules. Mol. Immunol. 34:157-163.

Hom, S. S., et al., (1991) J. Immunother. 10:153-164.

Hom, S. S., et al., (1993) J. Immunother. 13:18-30.

Hsu S. C., Schadeck E. B., Delmas A., Shaw M. and Stewart M. W., (1996) Linkage of a fusion peptide to a CTL epitope from the nucleoprotein of measles virus enables incorporation into ISCOMs and induction of CTL responses following intranasal immunization. Vaccine 14: 1159-1166.

Hwu, P., et al. J. Immunol, 150:4104-415 (1993).

Itoh, K. et al. (1986), Cancer Res. 46:3011-3017.

Jerome K. R., Domenech N. and Finn 0. J. (1993) Rumor-specific CTL clones from patients with breast and pancreatic adenocarcinoma recognize EBV-immortalized B cells transfected with polymorphic epithelial mucin cDNA. J. Immunol. 151: 1654-1662.

Karanikas V., Hwang L., Pearson J., Ong C. S., Apostolopoulos V., Vaughan H. et al. (1997) Antibody and T cell responses of patients with adenocarcinoma immunized with mannan-MUC1 fusion protein. J. Clinical Invest. 100: 2783-2792.

Kawakami, Y., et al., (1992) J. Immunol. 148:638-643.

Kawakami, Y., et al., (1993) J. Immunother. 14:88-93.

Kawakami Y., Robbins P. F., Wanx X., Tupesis J. P., Parkhurst M. R., Kang X. et al. (1998) Identification of New melanoma epitopes on melanosomal proteins recognized by tumor infiltrating T lymphocytes restricted by HLA-A1, -A2, and -A3 alleles J. Immunology 161:6985-6992.

Kim, D., Lee, T. V., Castilleja, A., Anderson, B. W., Papier, G. E. Kudella, A. P., Murray, J. L., Sittisomwong, T., Wharton, J. T., Kim, J. Ioannides, C. G. Folate binding protein peptide 191-199 presented on dendritic cells can simulate CTL from ovarian and breast cancer patients. *Anticancer Res.*, 18:2907-2916, 1999.

Kim D. T., Mitchell D. J., Brockstedt D. G., Fong L., Nolan G. P., Fathman C. G. et al. (1997) Introduction of soluble proteins into the MHC class I pathway by conjugation to an HIV tat peptide. J. Immunol: 159: 1666-1668.

Kraus et al., "Alternative promoter usage and tissue specific expression of the mouse somatostatin receptor 2 gene," FEBS Lett., 428(3):165-170, 1998.

Lareyre et al., "A 5-kilobase pair promoter fragment of the murine epididymal retinoic acid-binding protein gene drives the tissue-specific, cell-specific, and androgen-regulated expression of a foreign gene in the epididymis of transgenic mice," J Biol Chem., 274(12): 8282-8290,1999.

Lee et al., "Activation of beta3-adrenoceptors by exogenous dopamine to lower glucose uptake into rat adipocytes," J Auton Nery Syst. 74(2-3):86-90, 1997.

Lee, T. V., Anderson, B. W., Peoples, G. E., Castilleja, A., Murray, J. L., Gershenson, D. M., and Ioannides, C. G. Identification of activated tumor-Ag-rective CD8+ cells in healthy individuals, *Oncology Reports*, 7:455-466, 2000.

Lee R. S., Tartour E., van der Bruggen P., Vantomme V., Joyeaux I., Goud B. et al., (1998) Major histocompatibility complex class I presentation of exogenous soluble tumour antigen fused to the B-fragment of Shiga toxin. Eur. J. Immunol. 28:2726-2737.

Lees C. J. Apostolopoulos V., Acres B. A., Ong C.-S., and T2 cytokines on the cytotoxic T cell response to mannan-MUC1. Cancer Immuno. Immother. 2000 February; 48(11):644-52.

Li, P. Y., Del Vecchio, S., Fonti, R., Carrieto, M. V., Potena, M. I., Botti, G., Miotti, S., Lastoria, S., Menard, S., Colnaghi, M. I. and Salvatore, M. Local characterization of folate binding protein GP38 in sections of human ovarian carcinoma by in vitro quantitative autoradiography. J. Nucl. Med. 37:665-672, 1996.

Lofthouse S. A., Apostolopoulos V., Piertersz G. A. and McKenzie I. F. C. (1997) Induction of T1 (CTL) and/or T2 (antibody) response to a mucin 1 tumor antigen, Vaccine 25: 1586-1593.

Lustgarten J., Theobald M., Labadic C., LaFacc D., Peterson P., Disis M. L. et al. (1997) Identification of Her-2/NeuCTL epitopes using double transgenic mice expressing HLA-A2.1 and human CD*. Hum. Immunol. 52: 109-118.

Malcherek G., Wirblich C., Willcox N., Rammensee H. G., Trowsdale J. and Melms A. (1998) MHC class II-associated invariant chain peptice replacement by T cell epitopes: engineered invariant chain as a vehicle for directed and enhanced MHC class II antigen processing and presentation. Eur. J. Immunol. 28:1524-1533.

Matco, L., Gardner J., Chen Q., Schmidt C., Down M., Elliott S. L. et al. (1999) An HLA-A2 polyepitope vaccine for melanoma immunotherapy. J. Immunol. 163:4058-4063.

McCarty T. M., Liu X., Sun J. Y., Peralta E. A., Diamond D. J. and Ellenhom J. D. (1998) Targeting p53 for adoptive T-cell immunotherapy. Cancer Res. 58: 2601-2605.

Minev B. R., McFarland B. J., Spiess P. J., Rosenberg S. A. and Restifo N. P. (1994) Insertion signal sequence fused to minimal peptides elicits specific CD8+ T-cell responses and prolongs survival of thymoma-bearing mice. Cancer Res. 54:4155-4161.

Muul, L. M., et al. (1987), J. Immunol. 138:989-995.

Nakanishi T., Kunisawa J., Hayashi A., Tsutsumi Y., Kubo K., Nakagawa S. et al. (1997) Positively charged liposome functions as an efficient immunoadjuvant in inducing immune responses to soluble proteins. Biochem. Biophys. Res. Commun. 240:793-797.

Nakao M., Hazama M., Mayumi-Aono A., Hinuma S. and Fujisawa Y. (1994) Immunotherapy of acute and recurrent herpes simplex virus type 2 infection with an adjuvant-free form of recombinant glycoprotein D-interleukin-2 fusion protein. J. Infect Dis. 169:787-791.

Nestle F. O., Alijagic S., Gilliet M., Sun V., Grabbe S., Dumer R. et. al, (1998) Vaccination of melanoma patients with peptide- or tumor lysate-pursued dendritic cells, Nature Med. 4:328-332.

Noguchi Y., Noguchi T., Sata T., Yokoo Y., Itoh S., Yoshida M. et al. (1991) Printing for in vitro and in vivo anti-human T lymphotropic virus type 1 cellular immunity by virus-related protein reconstituted into liposome. J. Immunol. 146: 3599-3603.

Nomoto et al., "Cloning and characterization of the alternative promoter regions of the human LIMK2 gene responsible for alternative transcripts with tissue-specific expression," Gene, 236(2):259-271, 1999.

Obert M., Plkeuger H., Hanagarth II. G., Schulte-Monting J., Wiesmuller K. H., Braun D. G., et al. (1998) Protection of mice against SV40 tumors by Pam3Cys, MTP-PE and Pam3Cys conjugated with the SV40 T antigen-derived peptide K(698)-T(708). Vaccine 16: 161-169.

O'Neil, B. H., et al., (1993) J. Immunol. 151:1410-1418.

Pardoll, D. M. (2000) Clin. Immunol. 95 (1): S44-S62.

Parkhurst M. R., Fitzgerald E. B., Southwood S., Sette A., Rosenberg S. A. and Kawakami Y. (1998) Identification of a shared HLA-A*020-restricted T-cell epitope from the melanoma antigen tyrosinase related protein 2 (TRP2). Cancer Res. 58:4895-4901.

Partidos C. D., Vohra P. and Stewart M. W. (1996) Priming of measles virus-specific CTL responses after immunization with a CTL epitope linked to a fusogenic peptide. Virology 215: 107-110.

Peoples, G. E., Anderson, B. W., Fisk, B., Kudelka, A. P., Wharton, J. T., and Ioannides, C. G. Ovarian cancer-associated lymphocytes recognize folate binding protein (FBP) peptides. Ann. Surg Oncol., 5(8):743-750, 1998.

Peoples, G. E., Anderson, B. W., Murray, J. L., Kudelka, A. P., Eberlein, T. J., Wharton, J. T., and Ioannides, C. G. Vaccine implications of folate binding protein in epithelial cancers. Clin. Cancer Res., 5:4214-4223, 1999.

Pietersz, G. A. et al. (2000) Generation of cellular immune responses to antigenic tumor peptides. Cell. Mol. Life Sci. 57:290-310.

Pietersz G. A., Wenjun L., Popovski V., Caruana J. A. Apostolopoulos V. and McKenzie I. F. C. (1998) Parameters in using mannan-fusion protein (M-FP) to induce cellular immunity. Cancer Immunol. Immunother. 45: 321-326.

Rammensee H. G. (1995) Chemistry of peptides associated with MHC class I and class I molecules. Curr. Opin. Immunol. 7:85-96.

Rammensee H. G., Friede T. and Stevanovic S. (1995) MHC ligands and peptide motiffs: first listing. Immunogenetics 41:178-228.

Reddish M., MacLean G. D., Koganty R. R., Kan-Mitchell J., Jones V., Mitchell M. S. et al. (1998) Anti-MUC1 class I restricted CTLs in metastatic breast cancer patients immunized with a synthetic MUC1 peptide. Int. J. Cancer 76: 817-823.

Remington's Pharmaceutical Sciences, 18th Ed. Mack Printing Company, 1990.

Retrig, W. J., Cordon-Cardo, C., Koulos, J. P., Lewis, J. L., Oertgen, H. F., and Old, L. J. Cell surface antigens of human trophoblast and choriocarcinoma defined by monoclonal antibodies. Int. J. Cancer 35: 469-475, 1985.

Reynolds S. R., Celis E., Sette A., Gratz R., Shapiro R. L., Johnston D. et al, (1998) HLA-independent heterogeneity of CDS+ T cell responses to MAGE-3, Melan-A/MART-1, gp 100, tyronsinase, MCIR and TRP-2 in vaccine-treated melanoma patients, J. Immunol. 161: 6970-6976.

Rimmelzwaan G. F., Baars M., van Beek R., van Amerongen G., Lovgren-Bengtsson K., Claas E. C. et al. (1997) Induction of protective immunity against influenza virus in a macaque model: comparison of conventional and iscom vaccines. J. Gen. Virol. 78:757-765.

Rivoltini L., Squarcina P., Loftus D. J., Castelli C., Tarsini P., Mazzocchi A. et al. (1999) A superagonist variant of peptide—MART1/Melan A27-35 elicits anti-melanoma CD8+ T cells with enhanced functional characteristics: implication for more effective immunotherapy. Cancer Res. 59:301-306.

Rosenberg, S. A., et al., (1986) Science 3233:1318-1321.

Rosenberg, S. A., et al., (1988) N Engl J Med 319:1676-1680.

Rosenberg S. A. (1992) J. Clin. Oncol. 10:180-199.

Rosenberg, S. A. (2000) Cancer J. 6, Supp. 2: S142-S149.

Rosenberg S. A., Yang J. C., Schwartzentruber D. J., Hwu P., Marincola F. M., Topalian S. L. et al. (1998) Immunologic and therapeutic evaluation of a synthetic peptide vaccine for the treatment of patients with metastatic melanoma, Nature Med. 4: 321-327.

Rowell J. F., Ruff A. L., Guarnieri G. G., Stavely-O'Carroll K., Lin X., Tang J. et al. (1995) Lysosome-associated membrane protein-1-mediated targeting of the HIV-1 envelope protein to an endosomal/lysosomal compartment enhances its presentation to MHC class II-restricted T cells. J. Immunol. 155: 1818-1828.

Rowse G. J., Tempero R. M., VanLith M. L., Hillingsworth M. A. and Gendler S. J. (1998) Tolerance and immunity to MUC1 in a human MUC1 transgenic murine model. Cancer Res. 58: 315-321.

Samuel J., Budynski W. A., Reddish M. A., Ding L., Zimmermann G. I., Krantz M. I. et al. (1998) Immunogenicity and antitumour activity of a liposomal MUC1 peptide-based vaccine. Int. J. Cancer 75: 295-302.

Schutze-Redelmeier M. P., Gournier H., Garcia-Pons F., Moussa M., Joliot A. H., Volovitch M. et al. (1996) Introduction of exogenous antigens into the MHC class I processing and presentation pathway by *Drosophila antennapedia* homeodomain primes cytotoxic T. cells in vivo. J. Immunol. 157:650-655.

Sensi, M., et al., (1993) J. Exp. Med. 178:1231-1246.

Sjolander A., van't Land B. and Lovgren Bengtsson K., (1997) Iscoms containing purified Quillaja saponins upregulate both Th1-like and Th2-like immune responses. Cell Immunol. 10:69-76.

Speir J. A., Abdel-Motal U. M., Jondal M. and Wilson I. A. (1999) Crystal structure of an MHC class I presented glycopeptide that generates carbohydrates-specific CTL. Immunity 10:51-61.

Stenmark H., Moskaug J. 0., Madshus I. H., Sandvig K. and Olsnes S. (1991) Peptices fused on the amino-terminal end of diphtheria toxin are translocated to the cytosol. J. Cell Biol. 113: 1025-1032.

Suzue K., Thou X., Eisen H. N. and Young R. A. (1997) Heat shock fusion proteins as vehicles for antigen delivery into the major histocompatibility complex class I presentation pathway. Proc. Nal. Acad. Sci. USA 94: 13146-13151.

Tao M. H. and Levy R. (1993) Idiotype/granulocyte-macrophage colony-stimulating factor fusion protein as a vaccine: for B-cell lymphoma. Nature 362:755-758.

Tarpey I., Stacey S. N., McIndoe A. and Davies D. H. (1996) Priming in vivo and quantification in vitro of class I MHC-restricted cytotoxic T cells to human papilloma virus type 11 early proteins (E6 and E7) using immunostimulating complexes (ISCOMs). Vaccine 14: 230-236.

Theobald M., Biggs J., Dittmer D., Levine A. J. and Sherman L. A. (1995) Targeting p53 as a general tumor antigen. Proc. Natl. Acad. Sci. USA 92: 11993-11997.

Topalian, S. L., et al., (1989) J. Immunol. 142:3714-3725.

Tsumaki et al., "Modular arrangement of cartilage- and neural tissue-specific cis-elements in the mouse alpha2 (XI) collagen promoter," J Biol Chem. 273(36):22861-22864, 1998.

Udono H. and Srivastava P. K. (1993) Heat shock protein 70 associated peptides elicit specific cancer immunity. J. Exp. Med. 178: 1391-1396.

Van Der Burg S. H., Vissern M. J., Brandt R. M., Kast W. M. and Melief C. J. (1996) Immunogenicity of peptices bound to MHC class I molecules depends on the MHC peptide complex stability. J. Immunol. 156:3308-3314.

Villacres-Eriksson M. (1995) Antigen presentation by naïve macrophages, dendritic cells and B cells primed T lymphocytes and their cytokine production following exposure to immunostimulating complexes. Clin. Exp. Immunol. 102:46-52.

Vogel F. R. and Powell M. F. (1995) A compendium of vaccine adjuvants and excipients. In: Vaccine Deign: The Subunit and Adjuvant Approach. Pharmaceutical Biotechnology, vol. 6, pp. 141-228, Powell M. F. and Newman M. J. (eds), Plenum Press, New York.

Weitman, S. D., Lark, R. H., Coney, L. R., Fort, D. W., Frasca, V., Zurawski, V. R., and Kamen, B. A. Distribution of the folate receptor GP38 in normal and malignant cell lines and tissues. Cancer Res. 52: 3396-3401, 1992.

Wu et al., "Promoter-dependent tissue-specific expressive nature of imprinting gene, insulin-like growth factor II, in human tissues," Biochem Biophys Res Commun. 233(1):221-226, 1997.

Wu T. C., Guarnieri F. G., Staveley-O'Carroll K. F., Viscidi R. P., Levitsky H. I., Hedrick I., et al. (1995) Engineering an intracellular pathway for major histocompatibility complex class II presentation of antigens. Proc. Natl. Acad. Sci. USA 92:11671-11675.

Xing P.-X., Tjandra J. J., Stacker S. A., T. J. G., Thompson C. H., McLaughlin P. J. et al, (1989) Monoclonal antibodies reactive with mucin expressed in breast cancer. Immunol. Cell. Biol. 67: 183-195.

Xing P.-X., Apostolopoulos V., Michaels M., Prenzoska J., Bishop J. and McKenzie I. F. C. (1995) Phase I study of synthetic MUC1 peptides in cancer. Int:J. OncoL 6:1283-1289.

Xing P.-X, Reynolds K., Tjandra J. J., Tang X. L. and McKenzie I. F. C. (1990) Synthetic peptides reactive with anti-human milk fat globule membrane monoclonal antibodies. Cancer Res. 50:89-96.

Zeng Z. H., Castano A. R., Segelke B. W., Stura E. A. Peterson P. A. and Wilson I. A. (1997) Crystal structure of mouse CD1: an MHC-like fold with a large hydrophobic binding groove. Science 277: 339-345.

Zhang S., Graeber L. A., Helling F., Ragupathi G., Adluri S., Lloyd K. O. et al. (1996) Augmenting the immunogenicity of synthetic MUC1 peptide vaccines in mice. Cancer Res. 56: 3315-3319.

Zhao-Emonet et al., "The equine herpes virus 4 thymidine kinase is a better suicide gene than the human herpes virus 1 thymidine kinase," Gene Ther. 6(9):1638-1642, 1999.

Zhu X., Zhao X., Burkholder W. F., Gragemv A., Ogata C. M., Gottesman M. E. et al. (1996) Structural analysis of substrate binding by the molecular chaperone DnaK. Science 272: 1606-1614.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as described herein.

The invention claimed is:

1. A method of inducing immunity against a cancer expressing folate binding protein (SEQ ID NO:10) in an individual, the method comprising administering to the individual an effective amount a first vaccine composition comprising a peptide consisting of the amino acid sequence EIWTFSTKV (SEQ ID NO: 5).

2. The method of claim 1, further comprising administering a second vaccine composition comprising a peptide consisting of the amino acid sequence EIWTHSYKV (SEQ ID NO: 268).

3. The method of claim 2, wherein the first vaccine composition is administered prior to the administration of the second composition.

4. The method of claim 2, wherein the second vaccine composition is administered prior to the administration of the first composition.

5. The method of claim 1, wherein the first vaccine composition further comprises an adjuvant.

6. The method of claim 2, wherein the second vaccine composition further comprises an adjuvant.

7. The method of claim 1, wherein the first vaccine composition is formulated for intradermal, subcutaneous or intravenous administration.

8. The method of claim 2, wherein the second vaccine composition is formulated for intradermal, subcutaneous or intravenous administration.

9. The method of claim 1, further comprising multiple administrations of the first peptide vaccine at two to twelve week intervals.

10. The method of claim 2, further comprising multiple administration of the second peptide vaccine at two to twelve week intervals.

11. The method of claim 1, further comprising administering a booster composition comprising a peptide consisting of amino acid sequence EIWTFSTKV (SEQ ID NO: 5).

12. The method of claim 1, further comprising administering a booster composition comprising a peptide consisting of amino acid sequence EIWTHSYKV (SEQ ID NO: 268).

13. The method of claim 2, further comprising administering a booster composition comprising a peptide consisting of amino acid sequence EIWTFSTKV (SEQ ID NO: 5).

14. The method of claim 2, further comprising administering a booster composition comprising a peptide consisting of amino acid sequence EIWTHSYKV (SEQ ID NO: 268).

15. The method of claim 1, wherein the cancer is breast cancer, ovarian cancer, endometrial cancer, colorectal cancer, lung cancer, renal cancer, melanoma, kidney cancer, prostate cancer, brain cancer, sarcomas, or a combination thereof.

16. The method of claim 2, wherein the cancer is breast cancer, ovarian cancer, endometrial cancer, colorectal cancer, lung cancer, renal cancer, melanoma, kidney cancer, prostate cancer, brain cancer, sarcomas, or a combination thereof.

17. A method of inducing immunity against a cancer expressing folate binding protein (SEQ ID NO:10) in an individual, the method comprising administering to the individual an effective amount a first vaccine composition comprising a peptide consisting of the amino acid sequence EIWTFSTKV (SEQ ID NO: 5), and subsequently administering an effective amount of a second vaccine composition comprising a peptide consisting of the amino acid sequence EIWTHSYKV (SEQ ID NO: 268).

18. The method of claim 17, wherein the first vaccine composition and the second vaccine composition further comprise an adjuvant.

19. The method of claim 17, wherein the first vaccine composition and the second vaccine composition are formulated for intradermal, subcutaneous or intravenous administration.

20. The method of claim 17, further comprising administering a booster composition comprising a peptide consisting of amino acid sequence EIWTFSTKV (SEQ ID NO: 5).

21. The method of claim 17, further comprising administering a booster composition comprising a peptide consisting of amino acid sequence EIWTHSYKV (SEQ ID NO: 268).

22. The method of claim 17, wherein the cancer is breast cancer, ovarian cancer, endometrial cancer, colorectal cancer, lung cancer, renal cancer, melanoma, kidney cancer, prostate cancer, brain cancer, sarcomas, or a combination thereof.

23. A method of inducing immunity against a cancer expressing folate binding protein (SEQ ID NO:10) in an individual, the method comprising administering to the individual an effective amount a first vaccine composition comprising a peptide consisting of the amino acid sequence EIWTHSYKV (SEQ ID NO: 268), and subsequently administering an effective amount of a second vaccine composition comprising a peptide consisting of the amino acid sequence EIWTFSTKV (SEQ ID NO: 5).

24. The method of claim 23, wherein the first vaccine composition and the second vaccine composition further comprise an adjuvant.

25. The method of claim 23, wherein the first vaccine composition and the second vaccine composition are formulated for intradermal, subcutaneous or intravenous administration.

26. The method of claim 23, further comprising administering a booster composition comprising a peptide consisting of amino acid sequence EIWTFSTKV (SEQ ID NO: 5).

27. The method of claim 23, further comprising administering a booster composition comprising a peptide consisting of amino acid sequence EIWTHSYKV (SEQ ID NO: 268).

28. The method of claim 23, wherein the cancer is breast cancer, ovarian cancer, endometrial cancer, colorectal cancer, lung cancer, renal cancer, melanoma, kidney cancer, prostate cancer, brain cancer, sarcomas, or a combination thereof.

* * * * *

SEQUENCE LISTING

<160> NUMBER OF SEQ ID NOS: 271

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Glu Ile Trp Thr His Ser Thr Lys Val
 1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Glu Ile Trp Thr Phe Ser Tyr Lys Val
 1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Phe Ile Trp Thr Phe Ala Thr Lys Val
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Glu Ile Trp Thr His Ala Thr Lys Val
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Glu Ile Trp Thr Phe Ser Thr Lys Val
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 6

Glu Ile Trp Thr Phe Ser Tyr Lys Val
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Gly Ile Trp Thr His Ser Thr Lys Val
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Phe Ile Trp Thr His Ser Thr Lys Val
 1               5

<210> SEQ ID NO 9
<211> LENGTH: 255
<212> TYPE: PRT
<213> ORGANISM: Homo sapiens

<400> SEQUENCE: 9

Met Val Trp Lys Trp Met Pro Leu Leu Leu Leu Val Cys Val Ala
 1               5                  10                  15

Thr Met Cys Ser Ala Gln Asp Arg Thr Asp Leu Leu Asn Val Cys Met
                 20                  25                  30

Asp Ala Lys His His Lys Thr Lys Pro Gly Pro Glu Asp Lys Leu His
             35                  40                  45

Asp Gln Cys Ser Pro Trp Lys Lys Asn Ala Cys Cys Thr Ala Ser Thr
         50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

```
Val Ser Asn Tyr Ser Arg Gly Ser Gly Arg Cys Ile Gln Met Trp Phe
            195                 200                 205

Asp Ser Ala Gln Gly Asn Pro Asn Glu Glu Val Ala Arg Phe Tyr Ala
        210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
            245                 250                 255

<210> SEQ ID NO 10
<211> LENGTH: 257
<212> TYPE: PRT
<213> ORGANISM: Homo sapiens

<400> SEQUENCE: 10

Met Ala Gln Arg Met Thr Thr Gln Leu Leu Leu Leu Val Trp Val
  1               5                  10                  15

Ala Val Val Gly Glu Ala Gln Thr Arg Ile Ala Trp Ala Arg Thr Glu
             20                  25                  30

Leu Leu Asn Val Cys Met Asn Ala Lys His His Lys Glu Lys Pro Gly
         35                  40                  45

Pro Glu Asp Lys Leu His Glu Gln Cys Arg Pro Trp Arg Lys Asn Ala
     50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
             85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
            165                 170                 175

Pro Phe His Phe Tyr Phe Pro Thr Pro Thr Val Leu Cys Asn Glu Ile
        180                 185                 190

Trp Thr His Ser Tyr Lys Val Ser Asn Tyr Ser Arg Gly Ser Gly Arg
    195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
            245                 250                 255

Ser

<210> SEQ ID NO 11
<211> LENGTH: 293
<212> TYPE: PRT
<213> ORGANISM: RAT

<400> SEQUENCE: 11

Met Val Asp Ser Val Tyr Arg Thr Arg Ser Leu Gly Val Ala Ala Glu
```

```
            1               5                  10                 15
          Gly Ile Pro Asp Gln Tyr Ala Asp Gly Glu Ala Ala Arg Val Trp Gln
                        20                 25                 30

Leu Tyr Ile Gly Asp Thr Arg Ser Arg Thr Ala Glu Tyr Lys Ala Trp
                        35                 40                 45

Leu Leu Gly Leu Leu Arg Gln His Gly Cys His Arg Val Leu Asp Val
                        50                 55                 60

Ala Cys Gly Thr Gly Val Asp Ser Ile Met Leu Val Glu Gly Phe
          65                 70                 75                 80

Ser Val Thr Ser Val Asp Ala Ser Asp Lys Met Leu Lys Tyr Ala Leu
                        85                 90                 95

Lys Glu Arg Trp Asn Arg Arg Lys Glu Pro Ala Phe Asp Lys Trp Val
                        100                105                110

Ile Glu Glu Ala Asn Trp Leu Thr Leu Asp Lys Asp Val Pro Ala Gly
                        115                120                125

Asp Gly Phe Asp Ala Val Ile Cys Leu Gly Asn Ser Phe Ala His Leu
                        130                135                140

Pro Asp Ser Lys Gly Asp Gln Ser Glu His Arg Leu Ala Leu Lys Asn
          145                150                155                160

Ile Ala Ser Met Val Arg Pro Gly Gly Leu Leu Val Ile Asp His Arg
                        165                170                175

Asn Tyr Asp Tyr Ile Leu Ser Thr Gly Cys Ala Pro Gly Lys Asn
                        180                185                190

Ile Tyr Tyr Lys Ser Asp Leu Thr Lys Asp Ile Thr Thr Ser Val Leu
                        195                200                205

Thr Val Asn Asn Lys Ala His Met Val Thr Leu Asp Tyr Thr Val Gln
          210                215                220

Val Pro Gly Ala Gly Arg Asp Gly Ala Pro Gly Phe Ser Lys Phe Arg
          225                230                235                240

Leu Ser Tyr Tyr Pro His Cys Leu Ala Ser Phe Thr Glu Leu Val Gln
                        245                250                255

Glu Ala Phe Gly Gly Arg Cys Gln His Ser Val Leu Gly Asp Phe Lys
                        260                265                270

Pro Tyr Arg Pro Gly Gln Ala Tyr Val Pro Cys Tyr Phe Ile His Val
                        275                280                285

Leu Lys Lys Thr Gly
                        290

<210> SEQ ID NO 12
<211> LENGTH: 257
<212> TYPE: PRT
<213> ORGANISM: Homo sapiens

<400> SEQUENCE: 12

Met Ala Gln Arg Met Thr Thr Gln Leu Leu Leu Leu Leu Val Trp Val
          1               5                  10                 15

Ala Val Val Gly Glu Ala Gln Thr Arg Ile Ala Trp Ala Arg Thr Glu
                        20                 25                 30

Leu Leu Asn Val Cys Met Asn Ala Lys His His Lys Glu Lys Pro Gly
                        35                 40                 45

Pro Glu Asp Lys Leu His Glu Gln Cys Arg Pro Trp Arg Lys Asn Ala
                        50                 55                 60

Cys Cys Ser Thr Asn Thr Ser Gln Glu Ala His Lys Asp Val Ser Tyr
          65                 70                 75                 80
```

```
Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 13
<211> LENGTH: 257
<212> TYPE: PRT
<213> ORGANISM: Homo sapiens

<400> SEQUENCE: 13

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190
```

```
Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                    245                 250                 255

Ser

<210> SEQ ID NO 14
<211> LENGTH: 244
<212> TYPE: PRT
<213> ORGANISM: Mus musculus

<400> SEQUENCE: 14

Met Ala Gln Trp Trp Gln Ile Leu Leu Gly Leu Trp Ala Val Leu Pro
1               5                   10                  15

Thr Leu Ala Gly Asp Lys Leu Leu Ser Val Cys Met Asn Ser Lys Arg
                20                  25                  30

His Lys Gln Glu Pro Gly Pro Glu Asp Glu Leu Tyr Gln Glu Cys Arg
            35                  40                  45

Pro Trp Glu Asp Asn Ala Cys Cys Thr Arg Ser Thr Ser Trp Glu Ala
    50                  55                  60

His Leu Glu Glu Pro Leu Leu Phe Asn Phe Ser Met Met His Cys Gly
65                  70                  75                  80

Leu Leu Thr Pro Ala Cys Arg Lys His Phe Ile Gln Ala Ile Cys Phe
                85                  90                  95

His Glu Cys Ser Pro Asn Leu Gly Pro Trp Ile Gln Pro Val Val Pro
            100                 105                 110

Asn Gly Gln Glu Glu Gln Arg Val Trp Gly Val Pro Leu Cys Gln Glu
    115                 120                 125

Asp Cys Glu Asp Trp Trp Arg Ala Cys His Ser Ser Leu Thr Cys Lys
130                 135                 140

Ser Asn Trp Leu His Gly Trp Asp Trp Ser Glu Lys Lys His Cys
145                 150                 155                 160

Pro Ala His Glu Pro Cys Leu Pro Phe Ser Tyr His Phe Pro Thr Pro
                165                 170                 175

Asp Asp Leu Cys Glu Lys Ile Trp Asn Asn Thr Phe Lys Ala Ser Pro
            180                 185                 190

Glu Arg Arg Asn Ser Gly Arg Cys Leu Gln Lys Trp Phe Glu Pro Thr
    195                 200                 205

Leu Ser Asn Pro Asn Val Glu Val Ala Leu His Phe Ala Gly Ser Ala
210                 215                 220

Leu Ala Pro Gln Leu Ser Tyr Thr Leu Pro Ala Phe Ser Leu Cys Leu
225                 230                 235                 240

Leu Phe His Pro

<210> SEQ ID NO 15
<211> LENGTH: 295
<212> TYPE: PRT
<213> ORGANISM: Homo sapiens

<400> SEQUENCE: 15

Met Val Asp Ser Val Tyr Arg Thr Arg Ser Leu Gly Val Ala Ala Glu
1               5                   10                  15
```

```
Gly Leu Pro Asp Gln Tyr Ala Glu Gly Glu Ala Ala Arg Val Trp Gln
             20                  25                  30

Leu Tyr Ile Gly Asp Thr Arg Ser Arg Thr Ala Glu Tyr Lys Ala Trp
         35                  40                  45

Leu Leu Gly Leu Leu Arg Gln His Gly Cys Gln Arg Val Leu Asp Val
 50                  55                  60

Ala Cys Gly Thr Gly Val Asp Ser Ile Met Leu Val Glu Gly Phe
 65                  70                  75                  80

Ser Val Thr Ser Val Asp Ala Ser Asp Lys Met Leu Lys Tyr Ala Leu
                 85                  90                  95

Lys Glu Arg Trp Asn Arg Arg His Glu Pro Ala Phe Asp Lys Trp Val
             100                 105                 110

Ile Glu Glu Ala Asn Trp Met Thr Leu Asp Lys Asp Val Pro Gln Ser
         115                 120                 125

Ala Glu Gly Gly Phe Asp Ala Val Ile Cys Leu Gly Asn Ser Phe Ala
 130                 135                 140

His Leu Pro Asp Cys Lys Gly Asp Gln Ser Glu His Arg Leu Ala Leu
145                 150                 155                 160

Lys Asn Ile Ala Ser Met Val Arg Ala Gly Gly Leu Leu Val Ile Asp
                165                 170                 175

His Arg Asn Tyr Asp His Ile Leu Ser Thr Gly Cys Ala Pro Pro Gly
             180                 185                 190

Lys Asn Ile Tyr Tyr Lys Ser Asp Leu Thr Lys Asp Val Thr Thr Ser
         195                 200                 205

Val Leu Ile Val Asn Asn Lys Ala His Met Val Thr Leu Asp Tyr Thr
 210                 215                 220

Val Gln Val Pro Gly Ala Gly Gln Asp Gly Ser Pro Gly Leu Ser Lys
225                 230                 235                 240

Phe Arg Leu Ser Tyr Tyr Pro His Cys Leu Ala Ser Phe Thr Glu Leu
                245                 250                 255

Leu Gln Ala Ala Phe Gly Gly Lys Cys Gln His Ser Val Leu Gly Asp
             260                 265                 270

Phe Lys Pro Tyr Lys Pro Gly Gln Thr Tyr Ile Pro Cys Tyr Phe Ile
         275                 280                 285

His Val Leu Lys Arg Thr Asp
 290                 295

<210> SEQ ID NO 16
<211> LENGTH: 293
<212> TYPE: PRT
<213> ORGANISM: RAT

<400> SEQUENCE: 16

Met Val Asp Ser Val Tyr Arg Thr Arg Ser Leu Gly Val Ala Ala Glu
 1               5                  10                  15

Gly Ile Pro Asp Gln Tyr Ala Asp Gly Glu Ala Ala Arg Val Trp Gln
             20                  25                  30

Leu Tyr Ile Gly Asp Thr Arg Ser Arg Thr Ala Glu Tyr Lys Ala Trp
         35                  40                  45

Leu Leu Gly Leu Leu Arg Gln His Gly Cys His Arg Val Leu Asp Val
 50                  55                  60

Ala Cys Gly Thr Gly Val Asp Ser Ile Met Leu Val Glu Glu Gly Phe
 65                  70                  75                  80

Ser Val Thr Ser Val Asp Ala Ser Asp Lys Met Leu Lys Tyr Ala Leu
```

```
                85                  90                  95
Lys Glu Arg Trp Asn Arg Arg Lys Glu Pro Ala Phe Asp Lys Trp Val
            100                 105                 110

Ile Glu Glu Ala Asn Trp Leu Thr Leu Asp Lys Asp Val Pro Ala Gly
            115                 120                 125

Asp Gly Phe Asp Ala Val Ile Cys Leu Gly Asn Ser Phe Ala His Leu
        130                 135                 140

Pro Asp Ser Lys Gly Asp Gln Ser Glu His Arg Leu Ala Leu Lys Asn
145                 150                 155                 160

Ile Ala Ser Met Val Arg Pro Gly Gly Leu Leu Val Ile Asp His Arg
                165                 170                 175

Asn Tyr Asp Tyr Ile Leu Ser Thr Gly Cys Ala Pro Pro Gly Lys Asn
            180                 185                 190

Ile Tyr Tyr Lys Ser Asp Leu Thr Lys Asp Ile Thr Thr Ser Val Leu
        195                 200                 205

Thr Val Asn Asn Lys Ala His Met Val Thr Leu Asp Tyr Thr Val Gln
    210                 215                 220

Val Pro Gly Ala Gly Arg Asp Gly Ala Pro Gly Phe Ser Lys Phe Arg
225                 230                 235                 240

Leu Ser Tyr Tyr Pro His Cys Leu Ala Ser Phe Thr Glu Leu Val Gln
                245                 250                 255

Glu Ala Phe Gly Gly Arg Cys Gln His Ser Val Leu Gly Asp Phe Lys
            260                 265                 270

Pro Tyr Arg Pro Gly Gln Ala Tyr Val Pro Cys Tyr Phe Ile His Val
        275                 280                 285

Leu Lys Lys Thr Gly
        290

<210> SEQ ID NO 17
<211> LENGTH: 222
<212> TYPE: PRT
<213> ORGANISM: bovidae
<220> FEATURE:
<221> NAME/KEY: MOD_RES
<222> LOCATION: (55)
<223> OTHER INFORMATION: Xaa = anything

<400> SEQUENCE: 17

Ala Gln Ala Pro Arg Thr Pro Arg Ala Arg Thr Asp Leu Leu Asn Val
1               5                   10                  15

Cys Met Asp Ala Lys His His Lys Ala Glu Pro Gly Pro Glu Asp Ser
            20                  25                  30

Leu His Glu Gln Cys Ser Pro Trp Arg Lys Asn Ala Cys Cys Ser Val
        35                  40                  45

Asn Thr Ser Ile Glu Ala Xaa Lys Asp Ile Ser Tyr Leu Tyr Arg Phe
    50                  55                  60

Asn Trp Asp His Cys Gly Lys Met Glu Pro Ala Cys Lys Arg His Phe
65                  70                  75                  80

Ile Gln Asp Thr Cys Leu Tyr Glu Cys Ser Pro Asn Leu Gly Pro Trp
                85                  90                  95

Ile Arg Glu Val Asn Gln Arg Trp Arg Lys Glu Arg Val Leu Gly Val
            100                 105                 110

Pro Leu Cys Lys Glu Asp Cys Gln Ser Trp Trp Glu Asp Cys Arg Thr
        115                 120                 125

Ser Tyr Thr Cys Lys Ser Asn Trp His Lys Gly Trp Asn Trp Thr Ser
    130                 135                 140
```

-continued

Gly Tyr Asn Gln Cys Pro Val Lys Ala Ala His Cys Arg Phe Asp Phe
145                 150                 155                 160

Tyr Phe Pro Thr Pro Ala Ala Leu Cys Asn Glu Ile Trp Ser His Ser
                165                 170                 175

Tyr Lys Val Ser Asn Tyr Ser Arg Gly Ser Gly Arg Cys Ile Gln Met
            180                 185                 190

Trp Phe Asp Pro Phe Gln Gly Asn Pro Asn Glu Glu Val Ala Arg Phe
        195                 200                 205

Tyr Ala Glu Asn Pro Thr Ser Gly Ser Thr Pro Gln Gly Ile
    210                 215                 220

<210> SEQ ID NO 18
<211> LENGTH: 22
<212> TYPE: PRT
<213> ORGANISM: RAT

<400> SEQUENCE: 18

Gln Ala Thr Arg Ala Arg Thr Glu Leu Leu Asn Val Phe Ala Asp Ala
1               5                   10                  15

Lys Arg Glu Lys Pro Lys
            20

<210> SEQ ID NO 19
<211> LENGTH: 22
<212> TYPE: PRT
<213> ORGANISM: RAT

<400> SEQUENCE: 19

Gln Ala Thr Arg Ala Glu Thr Glu Asn Leu Asn Val Asp Met Asp Ala
1               5                   10                  15

Lys His His Lys Glu Lys
            20

<210> SEQ ID NO 20
<211> LENGTH: 589
<212> TYPE: PRT
<213> ORGANISM: Homo sapiens

<400> SEQUENCE: 20

Met Val Pro Ser Ser Pro Ala Val Glu Lys Gln Val Pro Val Glu Pro
1               5                   10                  15

Gly Pro Asp Pro Glu Leu Arg Ser Trp Arg His Leu Val Cys Tyr Leu
                20                  25                  30

Cys Phe Tyr Gly Phe Met Ala Gln Ile Arg Pro Gly Glu Ser Phe Ile
            35                  40                  45

Thr Pro Tyr Leu Leu Gly Pro Asp Lys Asn Phe Thr Arg Glu Gln Val
        50                  55                  60

Thr Asn Glu Ile Thr Pro Val Leu Ser Tyr Ser Tyr Leu Ala Val Leu
65                  70                  75                  80

Val Pro Val Phe Leu Leu Thr Asp Tyr Leu Arg Tyr Thr Pro Val Leu
                85                  90                  95

Leu Leu Gln Gly Leu Ser Phe Val Ser Val Trp Leu Leu Leu Leu Leu
            100                 105                 110

Gly His Ser Val Ala His Met Gln Leu Met Glu Leu Phe Tyr Ser Val
        115                 120                 125

Thr Met Ala Ala Arg Ile Ala Tyr Ser Ser Tyr Ile Phe Ser Leu Val
    130                 135                 140

```
Arg Pro Ala Arg Tyr Gln Arg Val Ala Gly Tyr Ser Arg Ala Ala Val
145                 150                 155                 160

Leu Leu Gly Val Phe Thr Ser Ser Val Leu Gly Gln Leu Leu Val Thr
            165                 170                 175

Val Gly Arg Val Ser Phe Ser Thr Leu Asn Tyr Ile Ser Leu Ala Phe
            180                 185                 190

Leu Thr Phe Ser Val Val Leu Ala Leu Phe Leu Lys Arg Pro Lys Arg
        195                 200                 205

Ser Leu Phe Phe Asn Arg Asp Asp Arg Gly Arg Cys Glu Thr Ser Ala
        210                 215                 220

Ser Glu Leu Glu Arg Met Asn Pro Gly Pro Gly Lys Leu Gly His
225                 230                 235                 240

Ala Leu Arg Val Ala Cys Gly Asp Ser Val Leu Ala Arg Met Leu Arg
            245                 250                 255

Glu Leu Gly Asp Ser Leu Arg Arg Pro Gln Leu Arg Leu Trp Ser Leu
            260                 265                 270

Trp Trp Val Phe Asn Ser Ala Gly Tyr Tyr Leu Val Val Tyr Tyr Val
        275                 280                 285

His Ile Leu Trp Asn Glu Val Asp Pro Thr Thr Asn Ser Ala Arg Val
    290                 295                 300

Tyr Asn Gly Ala Ala Asp Ala Ala Ser Thr Leu Leu Gly Ala Ile Thr
305                 310                 315                 320

Ser Phe Ala Ala Gly Phe Val Lys Ile Arg Trp Ala Arg Trp Ser Lys
                325                 330                 335

Leu Leu Ile Ala Gly Val Thr Thr Gln Ala Gly Leu Val Phe Leu
        340                 345                 350

Leu Ala His Thr Arg His Pro Ser Ser Ile Trp Leu Cys Tyr Ala Ala
            355                 360                 365

Phe Val Leu Phe Arg Gly Ser Tyr Gln Phe Leu Val Pro Ile Ala Thr
        370                 375                 380

Phe Gln Ile Ala Ser Ser Leu Ser Lys Glu Leu Cys Ala Leu Val Phe
385                 390                 395                 400

Gly Val Asn Thr Phe Phe Ala Thr Ile Val Lys Thr Ile Ile Thr Phe
            405                 410                 415

Ile Val Ser Asp Val Arg Gly Leu Gly Leu Pro Val Arg Lys Pro Val
            420                 425                 430

Ile Leu Arg Val Leu Pro Asp Pro Val His His Leu Leu Gly Gly
        435                 440                 445

His Ala Gly Trp Pro Ala Ala Leu Pro Ala Gly Pro Pro Ala Ala
450                 455                 460

Ala Pro Gly Pro Gly Pro Glu Glu Cys Arg Gly Gly Glu Gly Ser Thr
465                 470                 475                 480

Gly Thr Glu Arg Ala Gly Gln Gly Pro Arg Arg Leu Gln Pro Ala Gln
            485                 490                 495

Ser Pro Pro Leu Ser Pro Glu Asp Ser Leu Gly Ala Val Gly Pro Ala
        500                 505                 510

Ser Leu Glu Gln Arg Gln Ser Asp Pro Tyr Leu Ala Gln Ala Pro Ala
        515                 520                 525

Pro Gln Ala Ala Glu Phe Leu Ser Pro Val Thr Thr Pro Ser Pro Cys
        530                 535                 540

Thr Leu Ser Ser Ala Gln Ala Ser Gly Pro Glu Ala Ala Asp Glu Thr
545                 550                 555                 560

Cys Pro Gln Leu Ala Val His Pro Pro Gly Val Ser Lys Leu Gly Leu
```

-continued

```
                       565                 570                 575

Gln Cys Leu Pro Ser Asp Gly Val Gln Asn Val Asn Gln
            580                 585

<210> SEQ ID NO 21
<211> LENGTH: 257
<212> TYPE: PRT
<213> ORGANISM: Homo sapiens

<400> SEQUENCE: 21

Met Ala Gln Arg Met Thr Thr Gln Leu Leu Leu Leu Val Trp Val
 1               5                  10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 22
<211> LENGTH: 255
<212> TYPE: PRT
<213> ORGANISM: Homo sapiens

<400> SEQUENCE: 22

Met Val Trp Lys Trp Met Pro Leu Leu Leu Leu Leu Val Cys Val Ala
 1               5                  10                  15

Thr Met Cys Ser Ala Gln Asp Arg Thr Asp Leu Leu Asn Val Cys Met
                20                  25                  30

Asp Ala Lys His His Lys Thr Lys Pro Gly Pro Glu Asp Lys Leu His
            35                  40                  45
```

```
Asp Gln Cys Ser Pro Trp Lys Lys Asn Ala Cys Cys Thr Ala Ser Thr
            50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
            115                 120                 125

Cys Lys Glu Asp Cys Gln Arg Trp Trp Glu Asp Cys His Thr Ser His
        130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
        210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 23
<211> LENGTH: 251
<212> TYPE: PRT
<213> ORGANISM: Mus musculus

<400> SEQUENCE: 23

Met Ala Trp Lys Gln Thr Pro Leu Leu Leu Leu Val Tyr Met Val Thr
 1               5                  10                  15

Thr Gly Ser Gly Arg Asp Arg Thr Asp Leu Leu Asn Val Cys Met Asp
                 20                  25                  30

Ala Lys His His Lys Thr Lys Pro Gly Pro Glu Asp Lys Leu His Asp
             35                  40                  45

Gln Cys Ser Pro Trp Lys Lys Asn Ala Cys Cys Ser Val Asn Thr Ser
        50                  55                  60

Gln Glu Leu His Lys Ala Asp Ser Arg Leu Tyr Phe Asn Trp Asp His
 65                  70                  75                  80

Cys Gly Lys Met Glu Pro Ala Cys Lys Ser His Phe Ile Gln Asp Ser
                 85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
            115                 120                 125

Glu Asp Cys His Gln Trp Trp Glu Ala Cys Arg Thr Ser Phe Thr Cys
        130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
```

```
                    165                 170                 175

Pro Ala Ser Leu Cys Glu Gly Leu Trp Ser His Ser Tyr Lys Val Ser
                180                 185                 190

Asn Tyr Ser Arg Gly Ser Gly Arg Cys Ile Gln Met Trp Phe Asp Ser
            195                 200                 205

Thr Gln Gly Asn Pro Asn Glu Asp Val Val Lys Phe Tyr Ala Ser Phe
        210                 215                 220

Met Thr Ser Gly Thr Val Pro His Ala Ala Val Leu Leu Val Pro Ser
225                 230                 235                 240

Leu Ala Pro Val Leu Ser Leu Trp Leu Pro Gly
                245                 250

<210> SEQ ID NO 24
<211> LENGTH: 255
<212> TYPE: PRT
<213> ORGANISM: Mus musculus

<400> SEQUENCE: 24

Met Ala His Leu Met Thr Val Gln Leu Leu Leu Val Met Trp Met
  1               5                  10                  15

Ala Glu Cys Ala Gln Ser Arg Ala Thr Arg Ala Arg Thr Glu Leu Leu
                 20                  25                  30

Asn Val Cys Met Asp Ala Lys His His Lys Glu Lys Pro Gly Pro Glu
             35                  40                  45

Asp Asn Leu His Asp Gln Cys Ser Pro Trp Lys Thr Asn Ser Cys Cys
         50                  55                  60

Ser Thr Asn Thr Ser Gln Glu Ala His Lys Asp Ile Ser Tyr Leu Tyr
 65                  70                  75                  80

Arg Phe Asn Trp Asn His Cys Gly Thr Met Thr Ser Glu Cys Lys Arg
                 85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Gln Gln Trp Trp Glu Asp Cys
    130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                245                 250                 255

<210> SEQ ID NO 25
<211> LENGTH: 257
<212> TYPE: PRT
<213> ORGANISM: Homo sapiens
```

```
<400> SEQUENCE: 25

Met Ala Gln Arg Met Thr Thr Gln Leu Leu Leu Leu Val Trp Val
  1               5                  10                  15

Ala Val Val Gly Glu Ala Gln Thr Arg Ile Ala Trp Ala Arg Thr Glu
             20                  25                  30

Leu Leu Asn Val Cys Met Asn Ala Lys His His Lys Glu Lys Pro Gly
             35                  40                  45

Pro Glu Asp Lys Leu His Glu Gln Cys Arg Pro Trp Arg Lys Asn Ala
 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
                180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 26
<211> LENGTH: 257
<212> TYPE: PRT
<213> ORGANISM: Homo sapiens

<400> SEQUENCE: 26

Met Ala Gln Arg Met Thr Thr Gln Leu Leu Leu Leu Val Trp Val
  1               5                  10                  15

Ala Val Val Gly Glu Ala Gln Thr Arg Ile Ala Trp Ala Arg Thr Glu
             20                  25                  30

Leu Leu Asn Val Cys Met Asn Ala Lys His His Lys Glu Lys Pro Gly
             35                  40                  45

Pro Glu Asp Lys Leu His Glu Gln Cys Arg Pro Trp Arg Lys Asn Ala
 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
```

```
            100                 105                 110
Leu Gly Pro Trp Ile Gln Gln Val Asp Gln Ser Trp Arg Lys Glu Arg
            115                 120                 125
Val Leu Asn Val Pro Leu Cys Lys Glu Asp Cys Glu Gln Trp Trp Glu
        130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Ala Val Gly Ala Ala Cys Gln
                165                 170                 175
Pro Phe His Phe Tyr Phe Pro Thr Pro Thr Val Leu Cys Asn Glu Ile
            180                 185                 190
Trp Thr His Ser Tyr Lys Val Ser Asn Tyr Ser Arg Gly Ser Gly Arg
            195                 200                 205
Cys Ile Gln Met Trp Phe Asp Pro Ala Gln Gly Asn Pro Asn Glu Glu
        210                 215                 220
Val Ala Arg Phe Tyr Ala Ala Ala Met Ser Gly Ala Gly Pro Trp Ala
225                 230                 235                 240
Ala Trp Pro Phe Leu Leu Ser Leu Ala Leu Met Leu Leu Trp Leu Leu
                245                 250                 255
Ser

<210> SEQ ID NO 27
<211> LENGTH: 257
<212> TYPE: PRT
<213> ORGANISM: Homo sapiens

<400> SEQUENCE: 27

Met Ala Gln Arg Met Thr Thr Gln Leu Leu Leu Leu Val Trp Val
1               5                   10                  15
Ala Val Val Gly Glu Ala Gln Thr Arg Ile Ala Trp Ala Arg Thr Glu
                20                  25                  30
Leu Leu Asn Val Cys Met Asn Ala Lys His His Lys Glu Lys Pro Gly
            35                  40                  45
Pro Glu Asp Lys Leu His Glu Gln Cys Arg Pro Trp Arg Lys Asn Ala
        50                  55                  60
Cys Cys Ser Thr Asn Thr Ser Gln Glu Ala His Lys Asp Val Ser Tyr
65                  70                  75                  80
Leu Tyr Arg Phe Asn Trp Asn His Cys Gly Glu Met Ala Pro Ala Cys
                85                  90                  95
Lys Arg His Phe Ile Gln Asp Thr Cys Leu Tyr Glu Cys Ser Pro Asn
            100                 105                 110
Leu Gly Pro Trp Ile Gln Gln Val Asp Gln Ser Trp Arg Lys Glu Arg
            115                 120                 125
Val Leu Asn Val Pro Leu Cys Lys Glu Asp Cys Glu Gln Trp Trp Glu
        130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Ala Val Gly Ala Ala Cys Gln
                165                 170                 175
Pro Phe His Phe Tyr Phe Pro Thr Pro Thr Val Leu Cys Asn Glu Ile
            180                 185                 190
Trp Thr His Ser Tyr Lys Val Ser Asn Tyr Ser Arg Gly Ser Gly Arg
            195                 200                 205
Cys Ile Gln Met Trp Phe Asp Pro Ala Gln Gly Asn Pro Asn Glu Glu
```

```
            210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                    245                 250                 255

Ser

<210> SEQ ID NO 28
<211> LENGTH: 257
<212> TYPE: PRT
<213> ORGANISM: Homo sapiens

<400> SEQUENCE: 28

Met Ala Gln Arg Met Thr Thr Gln Leu Leu Leu Leu Val Trp Val
 1               5                  10                  15

Ala Val Val Gly Glu Ala Gln Thr Arg Ile Ala Trp Ala Arg Thr Glu
                    20                  25                  30

Leu Leu Asn Val Cys Met Asn Ala Lys His His Lys Glu Lys Pro Gly
                35                  40                  45

Pro Glu Asp Lys Leu His Glu Gln Cys Arg Pro Trp Arg Lys Asn Ala
         50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                    85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
                180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                    245                 250                 255

Ser

<210> SEQ ID NO 29
<211> LENGTH: 257
<212> TYPE: PRT
<213> ORGANISM: Homo sapiens

<400> SEQUENCE: 29

Met Ala Gln Arg Met Thr Thr Gln Leu Leu Leu Leu Leu Val Trp Val
 1               5                  10                  15
```

```
Ala Val Val Gly Glu Ala Gln Thr Arg Ile Ala Trp Ala Arg Thr Glu
             20                  25                  30

Leu Leu Asn Val Cys Met Asn Ala Lys His His Lys Glu Lys Pro Gly
         35                  40                  45

Pro Glu Asp Lys Leu His Glu Gln Cys Arg Pro Trp Arg Lys Asn Ala
     50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                 85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 30
<211> LENGTH: 254
<212> TYPE: PRT
<213> ORGANISM: Homo sapiens

<400> SEQUENCE: 30

Met Ala Ser Val Pro Lys Thr Asn Lys Ile Glu Pro Arg Ser Tyr Ser
  1               5                  10                  15

Ile Ile Pro Ser Cys Ser Ile Arg Arg Leu Gly Pro Ala Leu Asn Thr
             20                  25                  30

Pro Ile Phe Gln Ser Lys Arg Asn Gly Pro Arg Gly His Ser Ala Tyr
         35                  40                  45

Ser Ile Glu Gly Arg Gln Arg Gln Gly Ala Gly Arg Ala Val Val Pro
     50                  55                  60

Arg Ala Asp Arg Pro Pro Ala Pro Lys Ile Gln Leu Arg Ala Phe Tyr
 65                  70                  75                  80

Leu Gln Gln Leu Tyr Tyr Thr Leu Leu Glu Leu Glu Leu Pro Arg Leu
                 85                  90                  95

Leu Ala Pro Asp Leu Pro Ser Asn Gly Ser Ser Leu Lys Asp Leu Lys
            100                 105                 110

Trp Thr His Ser Asn Tyr Arg Ala Ser Lys Glu Ser Cys Ile Val Ile
        115                 120                 125
```

Phe Val Thr Thr Ser Pro Gly Arg Glu Trp Val Ile Cys Ala Pro Ala
130                 135                 140

Ala Phe Leu Gly Cys Gly Ser Leu Gln Ala Pro Ser Pro Glu Ser Glu
145                 150                 155                 160

Pro Ser Phe Pro Val Thr Arg Gly His His Gly Arg His Gly Asp Tyr
                165                 170                 175

His Arg Lys Leu Ile Gly Gln Thr Phe Glu Trp Val Val Arg Arg
            180                 185                 190

His Gly Gly Arg Ala Ile Gly Pro Arg Leu Ser Arg Val Thr Lys Ala
            195                 200                 205

Ala Gly Ala Arg Pro Pro Ala Gly Ala Gly Glu Gly Leu Arg Val Gly
210                 215                 220

Phe Asp Leu Ile Asn Ala Pro Ile Pro Pro Ala Lys Gly Val Ser Ala
225                 230                 235                 240

Arg Arg His Val Leu Ala Leu Glu Leu Pro Gln Leu Ser Lys
            245                 250

<210> SEQ ID NO 31
<211> LENGTH: 251
<212> TYPE: PRT
<213> ORGANISM: Mus musculus

<400> SEQUENCE: 31

Met Ala Trp Lys Gln Thr Pro Leu Leu Leu Val Tyr Met Val Thr
1               5                   10                  15

Thr Gly Ser Gly Arg Asp Arg Thr Asp Leu Leu Asn Val Cys Met Asp
            20                  25                  30

Ala Lys His His Lys Thr Lys Pro Gly Pro Glu Asp Lys Leu His Asp
        35                  40                  45

Gln Cys Ser Pro Trp Lys Lys Asn Ala Cys Cys Ser Val Asn Thr Ser
    50                  55                  60

Gln Glu Leu His Lys Ala Asp Ser Arg Leu Tyr Phe Asn Trp Asp His
65                  70                  75                  80

Cys Gly Lys Met Glu Pro Ala Cys Lys Ser His Phe Ile Gln Asp Ser
                85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
        115                 120                 125

Glu Asp Cys His Gln Trp Trp Glu Ala Cys Arg Thr Ser Phe Thr Cys
130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
                165                 170                 175

Pro Ala Ser Leu Cys Glu Gly Leu Trp Ser His Ser Tyr Lys Val Ser
            180                 185                 190

Asn Tyr Ser Arg Gly Ser Gly Arg Cys Ile Gln Met Trp Phe Asp Ser
        195                 200                 205

Thr Gln Gly Asn Pro Asn Glu Asp Val Val Lys Phe Tyr Ala Ser Phe
210                 215                 220

Met Thr Ser Gly Thr Val Pro His Ala Ala Val Leu Leu Val Pro Ser
225                 230                 235                 240

Leu Ala Pro Val Leu Ser Leu Trp Leu Pro Gly
            245                 250

<210> SEQ ID NO 32
<211> LENGTH: 255
<212> TYPE: PRT
<213> ORGANISM: Mus musculus

<400> SEQUENCE: 32

```
Met Ala His Leu Met Thr Val Gln Leu Leu Leu Val Met Trp Met
 1               5                  10                  15

Ala Glu Cys Ala Gln Ser Arg Ala Thr Arg Ala Arg Thr Glu Leu Leu
            20                  25                  30

Asn Val Cys Met Asp Ala Lys His His Lys Glu Lys Pro Gly Pro Glu
        35                  40                  45

Asp Asn Leu His Asp Gln Cys Ser Pro Trp Lys Thr Asn Ser Cys Cys
    50                  55                  60

Ser Thr Asn Thr Ser Gln Glu Ala His Lys Asp Ile Ser Tyr Leu Tyr
65                  70                  75                  80

Arg Phe Asn Trp Asn His Cys Gly Thr Met Thr Ser Glu Cys Lys Arg
                85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Gln Gln Trp Glu Asp Cys
    130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                245                 250                 255
```

<210> SEQ ID NO 33
<211> LENGTH: 243
<212> TYPE: PRT
<213> ORGANISM: Homo sapiens

<400> SEQUENCE: 33

```
Met Ala Trp Gln Met Met Gln Leu Leu Leu Leu Ala Leu Val Thr Ala
 1               5                  10                  15

Ala Gly Ser Ala Gln Pro Arg Ser Ala Arg Ala Arg Thr Asp Leu Leu
            20                  25                  30

Asn Val Cys Met Asn Ala Lys His His Lys Thr Gln Pro Ser Pro Glu
        35                  40                  45

Asp Glu Leu Tyr Gly Gln Cys Ser Pro Trp Lys Lys Asn Ala Cys Cys
    50                  55                  60

Thr Ala Ser Thr Ser Gln Glu Leu His Lys Asp Thr Ser Arg Leu Tyr
65                  70                  75                  80
```

```
Asn Phe Asn Trp Asp His Cys Gly Lys Met Glu Pro Thr Cys Lys Arg
                85                  90                  95
His Phe Ile Gln Asp Ser Cys Leu Tyr Glu Cys Ser Pro Asn Leu Gly
            100                 105                 110
Pro Trp Ile Arg Gln Val Asn Gln Ser Trp Arg Lys Glu Arg Ile Leu
        115                 120                 125
Asn Val Pro Leu Cys Lys Glu Asp Cys Glu Arg Trp Trp Glu Asp Cys
130                 135                 140
Arg Thr Ser Tyr Thr Cys Lys Ser Asn Trp His Lys Gly Trp Asn Trp
145                 150                 155                 160
Thr Ser Gly Ile Asn Glu Cys Pro Ala Gly Ala Leu Cys Ser Thr Phe
                165                 170                 175
Glu Ser Tyr Phe Pro Thr Pro Ala Ala Leu Cys Glu Gly Leu Trp Ser
            180                 185                 190
His Ser Phe Lys Val Ser Asn Tyr Ser Arg Gly Ser Gly Arg Cys Ile
        195                 200                 205
Gln Met Trp Phe Asp Ser Ala Gln Gly Asn Pro Asn Glu Glu Val Ala
210                 215                 220
Lys Phe Tyr Ala Ala Ala Met Asn Ala Gly Ala Pro Ser Arg Gly Ile
225                 230                 235                 240
Ile Asp Ser

<210> SEQ ID NO 34
<211> LENGTH: 255
<212> TYPE: PRT
<213> ORGANISM: Homo sapiens

<400> SEQUENCE: 34

Met Val Trp Lys Trp Met Pro Leu Leu Leu Leu Val Cys Val Ala
 1               5                  10                  15
Thr Met Cys Ser Ala Gln Asp Arg Thr Asp Leu Leu Asn Val Cys Met
                20                  25                  30
Asp Ala Lys His His Lys Thr Lys Pro Gly Pro Glu Asp Lys Leu His
            35                  40                  45
Asp Gln Cys Ser Pro Trp Lys Lys Asn Ala Cys Cys Thr Ala Ser Thr
        50                  55                  60
Ser Gln Glu Leu His Lys Asp Thr Ser Arg Leu Tyr Asn Phe Asn Trp
65                  70                  75                  80
Asp His Cys Gly Lys Met Glu Pro Ala Cys Lys Arg His Phe Ile Gln
                85                  90                  95
Asp Thr Cys Leu Tyr Glu Cys Ser Pro Asn Leu Gly Pro Trp Ile Gln
            100                 105                 110
Gln Val Asn Gln Thr Trp Arg Lys Glu Arg Phe Leu Asp Val Pro Leu
        115                 120                 125
Cys Lys Glu Asp Cys Gln Arg Trp Trp Glu Asp Cys His Thr Ser His
130                 135                 140
Thr Cys Lys Ser Asn Trp His Arg Gly Trp Asp Trp Thr Ser Gly Val
145                 150                 155                 160
Asn Lys Cys Pro Ala Gly Ala Leu Cys Arg Thr Phe Glu Ser Tyr Phe
                165                 170                 175
Pro Thr Pro Ala Ala Leu Cys Glu Gly Leu Trp Ser His Ser Tyr Lys
            180                 185                 190
Val Ser Asn Tyr Ser Arg Gly Ser Gly Arg Cys Ile Gln Met Trp Phe
        195                 200                 205
```

```
Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 35
<211> LENGTH: 255
<212> TYPE: PRT
<213> ORGANISM: RAT

<400> SEQUENCE: 35

Met Ala His Leu Met Ala Gly Gln Trp Leu Leu Leu Met Trp Met
  1               5                  10                  15

Ala Glu Cys Ala Gln Ser Arg Ala Thr Arg Ala Arg Thr Glu Leu Leu
                 20                  25                  30

Asn Val Cys Met Asp Ala Lys His His Lys Glu Lys Pro Gly Pro Glu
                35                  40                  45

Asp Lys Leu His Asp Gln Cys Ser Pro Trp Lys Thr Asn Ala Cys Cys
     50                  55                  60

Ser Thr Asn Thr Ser Gln Glu Asp Thr Lys Asp Ile Ser Tyr Leu Tyr
 65                  70                  75                  80

Arg Phe Asn Trp Asn His Cys Gly Thr Met Thr Pro Glu Cys Lys Arg
                 85                  90                  95

His Phe Ile Gln Asp Thr Cys Leu Tyr Glu Cys Ser Pro Asn Leu Gly
                100                 105                 110

Pro Trp Ile Gln Gln Val Asp Gln Ser Trp Arg Lys Glu Arg Ile Leu
                115                 120                 125

Asp Val Pro Leu Cys Lys Glu Asp Cys Val Leu Trp Trp Glu Asp Cys
    130                 135                 140

Lys Ser Ser Phe Thr Cys Lys Ser Asn Trp Leu Lys Gly Trp Asn Trp
145                 150                 155                 160

Thr Ser Gly His Asn Glu Cys Pro Val Gly Ala Ser Cys His Pro Phe
                165                 170                 175

Thr Phe Tyr Phe Pro Thr Pro Ala Val Leu Cys Glu Lys Ile Trp Ser
                180                 185                 190

His Ser Tyr Lys Leu Ser Asn Tyr Ser Arg Gly Ser Gly Arg Cys Ile
                195                 200                 205

Gln Met Trp Phe Asp Pro Ala Gln Gly Asn Pro Asn Glu Glu Val Ala
    210                 215                 220

Arg Phe Tyr Ala Glu Val Met Ser Gly Ala Gly Leu Arg Glu Ala Trp
225                 230                 235                 240

Leu Leu Val Cys Ser Leu Ser Leu Val Leu Phe Cys Val Val Ser
                245                 250                 255

<210> SEQ ID NO 36
<211> LENGTH: 46
<212> TYPE: PRT
<213> ORGANISM: chicken

<400> SEQUENCE: 36

Met Leu Arg Phe Ala Ile Thr Leu Phe Ala Val Ile Thr Ser Ser Thr
  1               5                  10                  15

Cys Gln Gln Tyr Gly Cys Leu Glu Gly Asp Thr His Lys Ala Asn Pro
                 20                  25                  30
```

Ser Pro Glu Pro Asn Met His Glu Cys Thr Leu Tyr Ser Glu
    35                  40                  45

<210> SEQ ID NO 37
<211> LENGTH: 238
<212> TYPE: PRT
<213> ORGANISM: chicken

<400> SEQUENCE: 37

Met Leu Arg Phe Ala Ile Thr Leu Phe Ala Val Ile Thr Ser Ser Thr
1               5                   10                  15

Cys Gln Gln Tyr Gly Cys Leu Glu Gly Asp Thr His Lys Ala Asn Pro
            20                  25                  30

Ser Pro Glu Pro Asn Met His Glu Cys Thr Leu Tyr Ser Glu Ser Ser
        35                  40                  45

Cys Cys Tyr Ala Asn Phe Thr Glu Gln Leu Ala His Ser Pro Ile Ile
    50                  55                  60

Lys Val Ser Asn Ser Tyr Trp Asn Arg Cys Gly Gln Leu Ser Lys Ser
65                  70                  75                  80

Cys Glu Asp Phe Thr Lys Lys Ile Glu Cys Phe Tyr Arg Cys Ser Pro
                85                  90                  95

His Ala Ala Arg Trp Ile Asp Pro Arg Tyr Thr Ala Ala Ile Gln Ser
            100                 105                 110

Val Pro Leu Cys Gln Ser Phe Cys Asp Asp Trp Tyr Glu Ala Cys Lys
        115                 120                 125

Asp Asp Ser Ile Cys Ala His Asn Trp Leu Thr Asp Trp Glu Arg Asp
130                 135                 140

Glu Ser Gly Glu Asn His Cys Lys Ser Lys Cys Val Pro Tyr Ser Glu
145                 150                 155                 160

Met Tyr Ala Asn Gly Thr Asp Met Cys Gln Ser Met Trp Gly Glu Ser
                165                 170                 175

Phe Lys Val Ser Glu Ser Ser Cys Leu Cys Leu Gln Met Asn Lys Lys
            180                 185                 190

Asp Met Val Ala Ile Lys His Leu Leu Ser Glu Ser Ser Glu Glu Ser
        195                 200                 205

Ser Ser Met Ser Ser Ser Glu Glu His Ala Cys Gln Lys Lys Leu Leu
    210                 215                 220

Lys Phe Glu Ala Leu Gln Gln Glu Glu Gly Glu Glu Arg Arg
225                 230                 235

<210> SEQ ID NO 38
<211> LENGTH: 251
<212> TYPE: PRT
<213> ORGANISM: Mus musculus

<400> SEQUENCE: 38

Met Ala Trp Lys Gln Thr Pro Leu Leu Leu Leu Val Tyr Met Val Thr
1               5                   10                  15

Thr Gly Ser Gly Arg Asp Arg Thr Asp Leu Leu Asn Val Cys Met Asp
            20                  25                  30

Ala Lys His His Lys Thr Lys Pro Gly Pro Glu Asp Lys Leu His Asp
        35                  40                  45

Gln Cys Ser Pro Trp Lys Lys Asn Ala Cys Cys Ser Val Asn Thr Ser
    50                  55                  60

Gln Glu Leu His Lys Ala Asp Ser Arg Leu Tyr Phe Asn Trp Asp His
65                  70                  75                  80

```
Cys Gly Lys Met Glu Pro Ala Cys Lys Ser His Phe Ile Gln Asp Ser
                85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
        115                 120                 125

Glu Asp Cys His Gln Trp Trp Glu Ala Cys Arg Thr Ser Phe Thr Cys
    130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
                165                 170                 175

Pro Ala Ser Leu Cys Glu Gly Leu Trp Ser His Ser Tyr Lys Val Ser
            180                 185                 190

Asn Tyr Ser Arg Gly Ser Gly Arg Cys Ile Gln Met Trp Phe Asp Ser
        195                 200                 205

Thr Gln Gly Asn Pro Asn Glu Asp Val Val Lys Phe Tyr Ala Ser Phe
    210                 215                 220

Met Thr Ser Gly Thr Val Pro His Ala Ala Val Leu Val Pro Ser
225                 230                 235                 240

Leu Ala Pro Val Leu Ser Leu Trp Leu Pro Gly
                245                 250

<210> SEQ ID NO 39
<211> LENGTH: 255
<212> TYPE: PRT
<213> ORGANISM: Mus musculus

<400> SEQUENCE: 39

Met Ala His Leu Met Thr Val Gln Leu Leu Leu Val Met Trp Met
  1               5                  10                  15

Ala Glu Cys Ala Gln Ser Arg Ala Thr Arg Ala Arg Thr Glu Leu Leu
            20                  25                  30

Asn Val Cys Met Asp Ala Lys His His Lys Glu Lys Pro Gly Pro Glu
        35                  40                  45

Asp Asn Leu His Asp Gln Cys Ser Pro Trp Lys Thr Asn Ser Cys Cys
    50                  55                  60

Ser Thr Asn Thr Ser Gln Glu Ala His Lys Asp Ile Ser Tyr Leu Tyr
65                  70                  75                  80

Arg Phe Asn Trp Asn His Cys Gly Thr Met Thr Ser Glu Cys Lys Arg
                85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Gln Gln Trp Trp Glu Asp Cys
    130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
```

```
                195                 200                 205
Gln Met Trp Phe Asp Pro Ala Gln Gly Asn Pro Asn Glu Val Ala
    210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                245                 250                 255

<210> SEQ ID NO 40
<211> LENGTH: 222
<212> TYPE: PRT
<213> ORGANISM: Cow
<220> FEATURE:
<221> NAME/KEY: MOD_RES
<222> LOCATION: (55)
<223> OTHER INFORMATION: Xaa = anything

<400> SEQUENCE: 40

Ala Gln Ala Pro Arg Thr Pro Arg Ala Arg Thr Asp Leu Leu Asn Val
1               5                   10                  15

Cys Met Asp Ala Lys His His Lys Ala Glu Pro Gly Pro Glu Asp Ser
            20                  25                  30

Leu His Glu Gln Cys Ser Pro Trp Arg Lys Asn Ala Cys Cys Ser Val
        35                  40                  45

Asn Thr Ser Ile Glu Ala Xaa Lys Asp Ile Ser Tyr Leu Tyr Arg Phe
    50                  55                  60

Asn Trp Asp His Cys Gly Lys Met Glu Pro Ala Cys Lys Arg His Phe
65                  70                  75                  80

Ile Gln Asp Thr Cys Leu Tyr Glu Cys Ser Pro Asn Leu Gly Pro Trp
                85                  90                  95

Ile Arg Glu Val Asn Gln Arg Trp Arg Lys Glu Arg Val Leu Gly Val
            100                 105                 110

Pro Leu Cys Lys Glu Asp Cys Gln Ser Trp Trp Glu Asp Cys Arg Thr
        115                 120                 125

Ser Tyr Thr Cys Lys Ser Asn Trp His Lys Gly Trp Asn Trp Thr Ser
    130                 135                 140

Gly Tyr Asn Gln Cys Pro Val Lys Ala Ala His Cys Arg Phe Asp Phe
145                 150                 155                 160

Tyr Phe Pro Thr Pro Ala Ala Leu Cys Asn Glu Ile Trp Ser His Ser
                165                 170                 175

Tyr Lys Val Ser Asn Tyr Ser Arg Gly Ser Gly Arg Cys Ile Gln Met
            180                 185                 190

Trp Phe Asp Pro Phe Gln Gly Asn Pro Asn Glu Glu Val Ala Arg Phe
        195                 200                 205

Tyr Ala Glu Asn Pro Thr Ser Gly Ser Thr Pro Gln Gly Ile
    210                 215                 220

<210> SEQ ID NO 41
<211> LENGTH: 261
<212> TYPE: PRT
<213> ORGANISM: Hamster sp.

<400> SEQUENCE: 41

Met Ala His Leu Met Thr Met Gln Leu Leu Leu Leu Ile Trp Val
1               5                   10                  15

Ser Glu Cys Ala Gln Ser Arg Ala Thr Arg Ala Arg Thr Glu Leu Leu
            20                  25                  30
```

```
Asn Val Cys Met Asp Ala Lys His His Lys Glu Lys Pro Gly Pro Glu
         35                  40                  45

Asp Asn Leu His Asn Gln Cys Ser Pro Trp Lys Lys Asn Ser Cys Cys
     50                  55                  60

Ser Thr Asn Thr Ser Gln Glu Ala His Glu Asp Ile Ser Tyr Leu Tyr
 65                  70                  75                  80

Arg Phe Asn Trp Asp His Cys Gly Lys Met Thr Leu Glu Cys Lys Arg
                 85                  90                  95

His Phe Ile Gln Asp Thr Cys Leu Tyr Glu Cys Ser Pro Asn Leu Gly
             100                 105                 110

Pro Trp Ile Gln Gln Val Asp Gln Ser Trp Arg Lys Glu Arg Ile Leu
         115                 120                 125

Asp Val Pro Leu Cys Lys Glu Asp Cys Gln Arg Trp Trp Glu Asp Cys
    130                 135                 140

Arg Thr Ser Phe Thr Cys Lys Ser Asn Trp His Lys Gly Trp Asn Trp
145                 150                 155                 160

Thr Ser Gly Tyr Asn Gln Cys Pro Val Gly Ala Ser Cys Arg His Phe
                165                 170                 175

Asp Phe Tyr Phe Pro Thr Pro Ala Ala Leu Cys Glu Glu Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Glu Ala Met Ser Gly Ala Gly Leu His Gly Ala Trp
225                 230                 235                 240

Pro Leu Met Cys Ser Leu Ser Leu Val Leu Leu Trp Val Phe Ser Arg
                245                 250                 255

Val Pro Leu Thr Phe
            260

<210> SEQ ID NO 42
<211> LENGTH: 249
<212> TYPE: PRT
<213> ORGANISM: Pig

<400> SEQUENCE: 42

Met Ala Leu Gly Arg Ala Arg Leu Leu Leu Leu Val Cys Val Ala
  1               5                  10                  15

Val Thr Trp Ala Ala Arg Pro Asp Leu Leu Asn Ile Cys Met Asp Ala
             20                  25                  30

Lys His His Lys Thr Lys Pro Gly Pro Glu Asp Gly Leu His Glu Gln
         35                  40                  45

Cys Ser Pro Trp Glu Met Asn Ala Cys Cys Ser Val Asn Thr Ser Gln
     50                  55                  60

Glu Ala His Asn Asp Ile Ser Tyr Leu Tyr Lys Phe Asn Trp Glu His
 65                  70                  75                  80

Cys Gly Lys Met Lys Pro Ala Cys Lys Arg His Phe Ile Gln Asp Thr
                 85                  90                  95

Cys Leu Tyr Glu Cys Ser Pro Asn Leu Gly Pro Trp Ile Gln Glu Val
             100                 105                 110

Asn Gln Lys Trp Arg Arg Glu Arg Ile Leu Asn Val Pro Leu Cys Lys
         115                 120                 125

Glu Asp Cys Gln Asn Trp Trp Glu Asp Cys Arg Thr Ser Tyr Thr Cys
    130                 135                 140
```

```
Lys Ser Asn Trp His Glu Gly Trp Asn Trp Ser Ser Gly Tyr Asn Arg
145                 150                 155                 160

Cys Pro Ala Asn Ala Ala Cys His Pro Phe Asp Phe Tyr Phe Pro Thr
            165                 170                 175

Pro Ala Ala Leu Cys Ser Gln Ile Trp Ser Asn Ser Tyr Lys Gln Ser
        180                 185                 190

Asn Tyr Ser Arg Gly Ser Gly Arg Cys Ile Gln Met Trp Phe Asp Pro
            195                 200                 205

Glu Gln Gly Asn Pro Asn Glu Val Val Ala Arg Tyr Tyr Ala Gln Ile
        210                 215                 220

Met Ser Gly Ala Gly Leu Ser Glu Ala Trp Pro Leu Gln Phe Gly Leu
225                 230                 235                 240

Ala Leu Thr Leu Leu Trp Leu Leu Ser
            245
```

<210> SEQ ID NO 43
<211> LENGTH: 252
<212> TYPE: PRT
<213> ORGANISM: Pig

<400> SEQUENCE: 43

```
Met Ala Trp Arg Leu Thr Leu Phe Val Leu Leu Gly Leu Val Ala Ala
1               5                   10                  15

Val Gly Gly Ala Arg Ala Lys Ser Asp Met Leu Asn Val Cys Met Asp
            20                  25                  30

Ala Lys His His Lys Pro Lys Pro Ser Pro Glu Asp Lys Leu His Asp
        35                  40                  45

Gln Cys Ser Pro Trp Arg Lys Asn Ser Cys Cys Ser Val Asn Thr Ser
    50                  55                  60

Leu Glu Ala His Lys Asp Ile Ser Tyr Leu Tyr Arg Phe Asn Trp Asp
65                  70                  75                  80

His Cys Gly Lys Met Glu Pro Ala Cys Lys Arg His Phe Ile Gln Asp
                85                  90                  95

Thr Cys Leu Tyr Glu Cys Ser Pro Asn Leu Gly Pro Trp Ile Gln Glu
            100                 105                 110

Val Asn Gln Lys Trp Arg Arg Glu Arg Ile Leu Asn Val Pro Leu Cys
        115                 120                 125

Lys Glu Asp Cys Gln Ile Trp Trp Glu Asp Cys Arg Thr Ser Tyr Thr
    130                 135                 140

Cys Lys Ser Asn Trp His Lys Gly Trp Asn Trp Thr Ser Gly Tyr Asn
145                 150                 155                 160

Gln Cys Pro Val Ser Ala Ala Cys His Arg Phe Asp Phe Tyr Phe Pro
                165                 170                 175

Thr Pro Ala Ala Leu Cys Asn Glu Ile Trp Ser His Ser Phe Glu Val
            180                 185                 190

Ser Ser Tyr Ser Arg Gly Ser Gly Arg Cys Ile Gln Met Trp Phe Asp
        195                 200                 205

Pro Ala Gln Gly Asn Pro Asn Glu Ala Val Ala Arg Tyr Tyr Ala Glu
    210                 215                 220

Asn Gly Asp Ala Gly Ala Val Ala Gln Gly Ile Gly Pro Leu Leu Thr
225                 230                 235                 240

Asn Leu Thr Glu Met Val Lys His Trp Val Thr Gly
                245                 250
```

-continued

```
<210> SEQ ID NO 44
<211> LENGTH: 42
<212> TYPE: PRT
<213> ORGANISM: Mus musculus

<400> SEQUENCE: 44

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
            20                  25                  30

Asn Val Cys Met Asp Ala Lys His His Lys
        35                  40

<210> SEQ ID NO 45
<211> LENGTH: 255
<212> TYPE: PRT
<213> ORGANISM: Mus musculus

<400> SEQUENCE: 45

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu Leu Leu
            20                  25                  30

Asn Val Cys Met Asp Ala Lys His His Lys Glu Lys Pro Gly Pro Glu
        35                  40                  45

Asp Asn Leu His Asp Gln Cys Ser Pro Trp Lys Thr Asn Ser Cys Cys
    50                  55                  60

Ser Thr Asn Thr Ser Gln Glu Ala His Lys Asp Ile Ser Tyr Leu Tyr
65                  70                  75                  80

Arg Phe Asn Trp Asn His Cys Gly Thr Met Thr Ser Glu Cys Lys Arg
                85                  90                  95

His Phe Ile Gln Asp Thr Cys Leu Tyr Glu Cys Ser Pro Asn Leu Gly
            100                 105                 110

Pro Trp Ile Gln Gln Val Asp Gln Ser Trp Arg Lys Glu Arg Ile Leu
        115                 120                 125

Asp Val Pro Leu Cys Lys Glu Asp Cys Gln Gln Trp Trp Glu Asp Cys
    130                 135                 140

Gln Ser Ser Phe Thr Cys Lys Ser Asn Trp His Lys Gly Trp Asn Trp
145                 150                 155                 160

Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
            180                 185                 190

His Ser Tyr Lys Leu Ser Asn Tyr Ser Arg Gly Ser Gly Arg Cys Ile
        195                 200                 205

Gln Met Trp Phe Asp Pro Ala Gln Gly Asn Pro Asn Glu Glu Val Ala
    210                 215                 220

Arg Phe Tyr Ala Glu Ala Met Ser Gly Ala Gly Phe His Gly Thr Trp
225                 230                 235                 240

Pro Leu Leu Cys Ser Leu Ser Leu Val Leu Leu Trp Val Ile Ser
                245                 250                 255

<210> SEQ ID NO 46
<211> LENGTH: 54
<212> TYPE: PRT
<213> ORGANISM: Homo sapiens

<400> SEQUENCE: 46
```

```
Met Ala Trp Gln Met Met Gln Leu Leu Leu Ala Leu Val Thr Ala
 1               5                  10                  15

Ala Gly Ser Ala Gln Pro Arg Ser Ala Arg Ala Arg Thr Asp Leu Leu
             20                  25                  30

Asn Val Cys Met Asn Ala Lys His His Lys Thr Gln Pro Ser Pro Glu
             35                  40                  45

Asp Glu Leu Tyr Gly Gln
         50

<210> SEQ ID NO 47
<211> LENGTH: 85
<212> TYPE: PRT
<213> ORGANISM: Homo sapiens

<400> SEQUENCE: 47

Thr Cys Leu Tyr Glu Cys Ser Pro Asn Leu Gly Pro Trp Ile Gln Gln
 1               5                  10                  15

Val Asp Gln Ser Trp Arg Lys Glu Arg Val Leu Asn Val Pro Leu Cys
             20                  25                  30

Lys Glu Asp Cys Glu Gln Trp Trp Glu Asp Cys Arg Thr Ser Tyr Thr
             35                  40                  45

Cys Lys Ser Asn Trp His Lys Gly Cys Asn Trp Thr Ser Gly Phe Asn
 50                  55                  60

Lys Cys Ala Val Gly Ala Ala Cys Gln Pro Phe His Phe Tyr Phe Pro
 65                  70                  75                  80

Thr Pro Ile Ala Arg
             85

<210> SEQ ID NO 48
<211> LENGTH: 245
<212> TYPE: PRT
<213> ORGANISM: Homo sapiens

<400> SEQUENCE: 48

Met Leu Pro Ala Ala Thr Glu Val Gln His Arg Leu Gln Gly Gln Lys
 1               5                  10                  15

Asp Met Val Trp Lys Trp Met Pro Leu Leu Leu Leu Val Cys Val
             20                  25                  30

Ala Thr Met Cys Ser Ala Gln Asp Arg Thr Asp Leu Leu Asn Val Cys
             35                  40                  45

Met Asp Ala Lys His His Lys Thr Lys Pro Gly Pro Glu Asp Lys Leu
 50                  55                  60

His Asp Gln Cys Ser Pro Trp Lys Lys Asn Ala Cys Cys Thr Ala Ser
 65                  70                  75                  80

Thr Ser Gln Glu Leu His Lys Asp Thr Ser Arg Leu Tyr Asn Phe Asn
             85                  90                  95

Trp Asp His Cys Gly Lys Met Glu Pro Ala Cys Ser Ala Thr Ser Ser
             100                 105                 110

Arg Thr Pro Val Ser Met Ser Ala His Gln Pro Gly Ala Leu Asp Pro
             115                 120                 125

Ala Gly Glu Ser Glu Leu Ala Ala Lys Asn Ala Ser Trp Met Cys Pro
             130                 135                 140

Tyr Ala Lys Ser Thr Val Ser Ala Gly Gly Arg Ile Val Thr Pro Pro
145                 150                 155                 160

Thr Arg Ala Arg Ala Thr Gly Thr Glu Asp Gly Thr Gly Pro Gln Glu
             165                 170                 175
```

```
Leu Thr Ser Ala Gln Leu Gly Leu Ser Ala Ala Pro Leu Ser Pro Thr
                180                 185                 190

Ser Pro Leu Gln Leu Pro Phe Val Lys Ala Ser Gly Val Thr His Thr
            195                 200                 205

Arg Ser Ala Thr Thr Ala Glu Gly Ala Ala Ala Ser Arg Cys Gly
        210                 215                 220

Leu Leu Gln Pro Arg Ala Thr Pro Thr Arg Lys Trp Arg Gly Ser Met
225                 230                 235                 240

Leu Gln Pro Cys Met
            245

<210> SEQ ID NO 49
<211> LENGTH: 253
<212> TYPE: PRT
<213> ORGANISM: Pig

<400> SEQUENCE: 49

Met Pro Trp Lys Leu Thr Ala Leu Leu Leu Phe Leu Ala Gly Val Val
  1               5                  10                  15

Ser Val Cys Arg Ala Arg Ala Arg Thr Asp Leu Leu Asn Val Cys Met
             20                  25                  30

Asp Ala Lys His His Lys Val Glu Pro Gly Pro Glu Asp Glu Leu His
         35                  40                  45

Asp Gln Cys Val Pro Trp Lys Lys Asn Ala Cys Cys Ser Ala Arg Val
     50                  55                  60

Ser His Glu Leu His Arg Asp Lys Ser Ser Leu Tyr Asn Phe Ser Trp
 65                  70                  75                  80

Glu His Cys Gly Arg Met Glu Pro Ala Cys Lys Arg His Phe Ile Gln
                 85                  90                  95

Asn Asn Cys Leu Tyr Glu Cys Ser Pro Asn Leu Gly Pro Trp Phe Gln
            100                 105                 110

Glu Val Asn Gln Lys Trp Arg Lys Glu Arg Phe Leu Asn Val Pro Leu
        115                 120                 125

Cys Lys Glu Asp Cys Leu Asp Trp Trp Glu Asp Cys Arg Thr Ser Tyr
130                 135                 140

Thr Cys Lys Ser Ser Trp His Lys Gly Trp Asn Trp Ser Ser Gly Ser
145                 150                 155                 160

Asn Gln Cys Pro Thr Gly Thr Thr Cys Asp Thr Phe Glu Ser Phe Phe
                165                 170                 175

Pro Thr Pro Ala Ala Leu Cys Glu Gly Ile Trp Asn His Asp Tyr Lys
            180                 185                 190

Phe Thr Asn Tyr Ser Arg Gly Ser Gly Arg Cys Ile Gln Met Trp Phe
        195                 200                 205

Asp Ala Ala Glu Gly Asn Pro Asn Glu Glu Val Ala Arg Phe Tyr Ala
    210                 215                 220

Leu Ala Leu Ser Ala Gly Thr Met Ser Leu Gly Thr Gly Pro Leu Leu
225                 230                 235                 240

Leu Ser Ala Ala Leu Met Leu Pro Leu Gly Leu Leu Asp
                245                 250

<210> SEQ ID NO 50
<211> LENGTH: 22
<212> TYPE: PRT
<213> ORGANISM: RAT

<400> SEQUENCE: 50
```

```
Gln Ala Thr Arg Ala Glu Thr Glu Asn Leu Asn Val Asp Met Asp Ala
  1               5                  10                  15

Lys His His Lys Glu Lys
             20
```

<210> SEQ ID NO 51
<211> LENGTH: 222
<212> TYPE: PRT
<213> ORGANISM: Cow
<220> FEATURE:
<221> NAME/KEY: MOD_RES
<222> LOCATION: (55)
<223> OTHER INFORMATION: Xaa = anything

<400> SEQUENCE: 51

```
Ala Gln Ala Pro Arg Thr Pro Arg Ala Arg Thr Asp Leu Leu Asn Val
  1               5                  10                  15

Cys Met Asp Ala Lys His His Lys Ala Glu Pro Gly Pro Glu Asp Ser
             20                  25                  30

Leu His Glu Gln Cys Ser Pro Trp Arg Lys Asn Ala Cys Cys Ser Val
             35                  40                  45

Asn Thr Ser Ile Glu Ala Xaa Lys Asp Ile Ser Tyr Leu Tyr Arg Phe
         50                  55                  60

Asn Trp Asp His Cys Gly Lys Met Glu Pro Ala Cys Lys Arg His Phe
 65                  70                  75                  80

Ile Gln Asp Thr Cys Leu Tyr Glu Cys Ser Pro Asn Leu Gly Pro Trp
                 85                  90                  95

Ile Arg Glu Val Asn Gln Arg Trp Arg Lys Glu Arg Val Leu Gly Val
            100                 105                 110

Pro Leu Cys Lys Glu Asp Cys Gln Ser Trp Trp Glu Asp Cys Arg Thr
            115                 120                 125

Ser Tyr Thr Cys Lys Ser Asn Trp His Lys Gly Trp Asn Trp Thr Ser
    130                 135                 140

Gly Tyr Asn Gln Cys Pro Val Lys Ala Ala His Cys Arg Phe Asp Phe
145                 150                 155                 160

Tyr Phe Pro Thr Pro Ala Ala Leu Cys Asn Glu Ile Trp Ser His Ser
                165                 170                 175

Tyr Lys Val Ser Asn Tyr Ser Arg Gly Ser Gly Arg Cys Ile Gln Met
            180                 185                 190

Trp Phe Asp Pro Phe Gln Gly Asn Pro Asn Glu Glu Val Ala Arg Phe
            195                 200                 205

Tyr Ala Glu Asn Pro Thr Ser Gly Ser Thr Pro Gln Gly Ile
    210                 215                 220
```

<210> SEQ ID NO 52
<211> LENGTH: 114
<212> TYPE: PRT
<213> ORGANISM: Homo Sapiens
<220> FEATURE:
<221> NAME/KEY: MOD_RES
<222> LOCATION: (12)..(92)
<223> OTHER INFORMATION: X = anything

<400> SEQUENCE: 52

```
Ile Ala Trp Ala Arg Thr Glu Leu Leu Asn Val Xaa Met Asn Ala Lys
  1               5                  10                  15

His His Lys Glu Lys Pro Gly Pro Glu Asp Lys Leu His Glu Gln Xaa
             20                  25                  30
```

```
Xaa Pro Trp Arg Lys Asn Ala Xaa Xaa Ser Thr Xaa Thr Xaa Gln Glu
        35                  40                  45

Ala Xaa Lys Asp Val Ser Tyr Leu Tyr Arg Phe Asn Ala Pro Ala Cys
     50                  55                  60

Lys Arg His Phe Ile Gln Asp Thr Cys Leu Tyr Glu Xaa Ser Pro Asn
 65                  70                  75                  80

Leu Gly Pro Xaa Ile Gln Gln Val Asp Gln Ser Xaa Arg Lys Glu Arg
             85                  90                  95

Val Leu Asn Val Trp Phe Asp Pro Ala Gln Gly Asn Pro Asn Glu Gln
            100                 105                 110

Val Ala

<210> SEQ ID NO 53
<211> LENGTH: 257
<212> TYPE: PRT
<213> ORGANISM: Homo Sapiens

<400> SEQUENCE: 53

Met Ala Gln Arg Met Thr Thr Gln Leu Leu Leu Leu Leu Val Trp Val
  1               5                  10                  15

Ala Val Val Gly Glu Ala Gln Thr Arg Ile Ala Trp Ala Arg Thr Glu
             20                  25                  30

Leu Leu Asn Val Cys Met Asn Ala Lys His His Lys Glu Lys Pro Gly
         35                  40                  45

Pro Glu Asp Lys Leu His Glu Gln Cys Arg Pro Trp Arg Lys Asn Ala
 50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
             85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
            165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
            195                 200                 205

Cys Ile Gln Met Trp Phe Asp Pro Ala Gln Gly Asn Pro Asn Glu Glu
210                 215                 220

Val Ala Arg Phe Tyr Ala Ala Met Ser Gly Ala Gly Pro Trp Ala
225                 230                 235                 240

Ala Trp Pro Phe Leu Leu Ser Leu Ala Leu Met Leu Leu Trp Leu Leu
            245                 250                 255

Ser

<210> SEQ ID NO 54
<211> LENGTH: 243
<212> TYPE: PRT
```

<213> ORGANISM: Homo Sapiens

<400> SEQUENCE: 54

Met Ala Trp Gln Met Met Gln Leu Leu Leu Ala Leu Val Thr Ala
1               5                   10                  15

Ala Gly Ser Ala Gln Pro Arg Ser Ala Arg Ala Arg Thr Asp Leu Leu
            20                  25                  30

Asn Val Cys Met Asn Ala Lys His His Lys Thr Gln Pro Ser Pro Glu
        35                  40                  45

Asp Glu Leu Tyr Gly Gln Cys Ser Pro Trp Lys Lys Asn Ala Cys Cys
    50                  55                  60

Thr Ala Ser Thr Ser Gln Glu Leu His Lys Asp Thr Ser Arg Leu Tyr
65                  70                  75                  80

Asn Phe Asn Trp Asp His Cys Gly Lys Met Glu Pro Thr Cys Lys Arg
                85                  90                  95

His Phe Ile Gln Asp Ser Cys Leu Tyr Glu Cys Ser Pro Asn Leu Gly
            100                 105                 110

Pro Trp Ile Arg Gln Val Asn Gln Ser Trp Arg Lys Glu Arg Ile Leu
        115                 120                 125

Asn Val Pro Leu Cys Lys Glu Asp Cys Glu Arg Trp Trp Glu Asp Cys
    130                 135                 140

Arg Thr Ser Tyr Thr Cys Lys Ser Asn Trp His Lys Gly Trp Asn Trp
145                 150                 155                 160

Thr Ser Gly Ile Asn Glu Cys Pro Ala Gly Ala Leu Cys Ser Thr Phe
                165                 170                 175

Glu Ser Tyr Phe Pro Thr Pro Ala Leu Cys Glu Gly Leu Trp Ser
            180                 185                 190

His Ser Phe Lys Val Ser Asn Tyr Ser Arg Gly Ser Gly Arg Cys Ile
        195                 200                 205

Gln Met Trp Phe Asp Ser Ala Gln Gly Asn Pro Asn Glu Glu Val Ala
    210                 215                 220

Lys Phe Tyr Ala Ala Ala Met Asn Ala Gly Ala Pro Ser Arg Gly Ile
225                 230                 235                 240

Ile Asp Ser

<210> SEQ ID NO 55
<211> LENGTH: 226
<212> TYPE: PRT
<213> ORGANISM: Homo Sapiens

<400> SEQUENCE: 55

Thr Arg Ile Ala Trp Ala Arg Thr Glu Leu Leu Asn Val Cys Met Asn
1               5                   10                  15

Ala Lys His His Lys Glu Lys Pro Gly Pro Glu Asp Lys Leu His Glu
            20                  25                  30

Gln Cys Arg Pro Trp Arg Lys Asn Ala Cys Cys Ser Thr Asn Thr Ser
        35                  40                  45

Gln Glu Ala His Lys Asp Val Ser Tyr Leu Tyr Arg Phe Asn Trp Asn
    50                  55                  60

His Cys Gly Glu Met Ala Pro Ala Cys Lys Arg His Phe Ile Gln Asp
65                  70                  75                  80

Thr Cys Leu Tyr Glu Cys Ser Pro Asn Leu Gly Pro Trp Ile Gln Gln
                85                  90                  95

Val Asp Gln Ser Trp Arg Lys Glu Arg Val Leu Asn Val Pro Leu Cys
            100                 105                 110

```
Lys Glu Asp Cys Glu Gln Trp Trp Glu Asp Cys Arg Thr Ser Tyr Thr
            115                 120                 125

Cys Lys Ser Asn Trp His Lys Gly Trp Asn Trp Thr Ser Gly Phe Asn
        130                 135                 140

Lys Cys Ala Val Gly Ala Ala Cys Gln Pro Phe His Phe Tyr Phe Pro
145                 150                 155                 160

Ser Pro Thr Val Leu Cys Asn Glu Ile Trp Thr His Ser Tyr Lys Val
                165                 170                 175

Ser Asn Tyr Ser Arg Gly Ser Gly Arg Cys Ile Gln Met Trp Phe Asp
            180                 185                 190

Pro Ala Gln Gly Asn Pro Asn Glu Val Ala Arg Phe Tyr Ala Ala
        195                 200                 205

Ala Met Ser Gly Ala Gly Pro Trp Ala Ala Trp Pro Phe Leu Leu Ser
210                 215                 220

Leu Ala
225

<210> SEQ ID NO 56
<211> LENGTH: 238
<212> TYPE: PRT
<213> ORGANISM: Chicken

<400> SEQUENCE: 56

Met Leu Arg Phe Ala Ile Thr Leu Phe Ala Val Ile Thr Ser Ser Thr
1               5                   10                  15

Cys Gln Gln Tyr Gly Cys Leu Glu Gly Asp Thr His Lys Ala Lys Pro
            20                  25                  30

Ser Pro Glu Pro Asn Met His Glu Cys Thr Leu Tyr Ser Glu Ser Ser
        35                  40                  45

Cys Cys Tyr Ala Asn Phe Thr Glu Gln Leu Ala His Ser Pro Ile Ile
    50                  55                  60

Lys Val Ser Asn Ser Tyr Trp Asn Arg Cys Gly Gln Leu Ser Lys Ser
65                  70                  75                  80

Cys Glu Asp Phe Thr Lys Lys Ile Glu Cys Phe Tyr Arg Cys Ser Pro
                85                  90                  95

His Ala Ala Arg Trp Ile Asp Pro Arg Tyr Thr Ala Ala Ile Gln Ser
            100                 105                 110

Val Pro Leu Cys Gln Ser Phe Cys Asp Asp Trp Tyr Glu Ala Cys Lys
        115                 120                 125

Asp Asp Ser Ile Cys Ala His Asn Trp Leu Thr Asp Trp Glu Arg Asp
130                 135                 140

Glu Ser Gly Glu Asn His Cys Lys Ser Lys Cys Val Pro Tyr Ser Glu
145                 150                 155                 160

Met Tyr Ala Asn Gly Thr Asp Met Cys Gln Ser Met Trp Gly Glu Ser
                165                 170                 175

Phe Lys Val Ser Glu Ser Cys Leu Cys Leu Gln Met Asn Lys Lys
            180                 185                 190

Asp Met Val Ala Ile Lys His Leu Leu Ser Glu Ser Ser Glu Glu Ser
        195                 200                 205

Ser Ser Met Ser Ser Glu Glu His Ala Cys Gln Lys Lys Leu Leu
    210                 215                 220

Lys Phe Glu Ala Leu Gln Gln Glu Glu Gly Glu Glu Arg Arg
225                 230                 235
```

```
<210> SEQ ID NO 57
<211> LENGTH: 251
<212> TYPE: PRT
<213> ORGANISM: Mus musculus

<400> SEQUENCE: 57
```

Met Ala Trp Lys Gln Thr Pro Leu Leu Leu Val Tyr Met Val Thr
1               5                   10                  15

Thr Gly Ser Gly Arg Asp Arg Thr Asp Leu Leu Asn Val Cys Met Asp
            20                  25                  30

Ala Lys His His Lys Thr Lys Pro Gly Pro Glu Asp Lys Leu His Asp
        35                  40                  45

Gln Cys Ser Pro Trp Lys Lys Asn Ala Cys Cys Ser Val Asn Thr Ser
    50                  55                  60

Gln Glu Leu His Lys Ala Asp Ser Arg Leu Tyr Phe Asn Trp Asp His
65                  70                  75                  80

Cys Gly Lys Met Glu Pro Ala Cys Lys Ser His Phe Ile Gln Asp Ser
                85                  90                  95

Cys Leu Tyr Glu Cys Ser Pro Asn Leu Gly Pro Trp Ile Gln Gln Val
            100                 105                 110

Asp Gln Ser Trp Arg Lys Glu Arg Phe Leu Asp Val Pro Leu Cys Lys
        115                 120                 125

Glu Asp Cys His Gln Trp Trp Glu Ala Cys Arg Thr Ser Phe Thr Cys
    130                 135                 140

Lys Arg Asp Trp His Lys Gly Trp Asp Trp Ser Ser Gly Ile Asn Lys
145                 150                 155                 160

Cys Pro Asn Thr Ala Pro Cys His Thr Phe Glu Tyr Tyr Phe Pro Thr
                165                 170                 175

Pro Ala Ser Leu Cys Glu Gly Leu Trp Ser His Ser Tyr Lys Val Ser
            180                 185                 190

Asn Tyr Ser Arg Gly Ser Gly Arg Cys Ile Gln Met Trp Phe Asp Ser
        195                 200                 205

Thr Gln Gly Asn Pro Asn Glu Asp Val Val Lys Phe Tyr Ala Ser Phe
    210                 215                 220

Met Thr Ser Gly Thr Val Pro His Ala Ala Val Leu Leu Val Pro Ser
225                 230                 235                 240

Leu Ala Pro Val Leu Ser Leu Trp Leu Pro Gly
                245                 250

```
<210> SEQ ID NO 58
<211> LENGTH: 30
<212> TYPE: PRT
<213> ORGANISM: Mus musculus

<400> SEQUENCE: 58
```

Met Ala His Leu Met Thr Val Gln Leu Leu Leu Val Met Trp Met
1               5                   10                  15

Ala Glu Cys Ala Gln Ser Arg Ala Thr Arg Ala Arg Thr Glu
            20                  25                  30

```
<210> SEQ ID NO 59
<211> LENGTH: 30
<212> TYPE: PRT
<213> ORGANISM: Mus musculus

<400> SEQUENCE: 59
```

Met Phe Gly Leu Lys Phe Phe Leu Val Leu Glu Ala Leu Leu Phe Leu
1               5                   10                  15

```
Phe Thr Cys Tyr Ile Val Leu Lys Ile Gly Leu Lys Ile Leu
                20                  25                  30

<210> SEQ ID NO 60
<211> LENGTH: 49
<212> TYPE: PRT
<213> ORGANISM: Mus musculus

<400> SEQUENCE: 60

Met Ala Trp Lys Gln Thr Pro Leu Leu Leu Val Tyr Met Val Thr
  1               5                  10                  15

Thr Gly Ser Gly Arg Asp Arg Thr Asp Leu Leu Asn Val Cys Met Asp
                20                  25                  30

Ala Lys His His Lys Thr Lys Pro Gly Pro Glu Asp Lys Leu His Asp
         35                  40                  45

Gln

<210> SEQ ID NO 61
<211> LENGTH: 54
<212> TYPE: PRT
<213> ORGANISM: Mus musculus

<400> SEQUENCE: 61

Met Ala His Leu Met Thr Val Gln Leu Leu Leu Val Met Trp Met
  1               5                  10                  15

Ala Glu Cys Ala Gln Ser Arg Ala Thr Arg Ala Arg Thr Glu Leu Leu
                20                  25                  30

Asn Val Cys Met Asp Ala Lys His His Lys Glu Lys Pro Gly Pro Glu
         35                  40                  45

Asp Asn Leu His Asp Gln
     50

<210> SEQ ID NO 62
<211> LENGTH: 255
<212> TYPE: PRT
<213> ORGANISM: Mus musculus

<400> SEQUENCE: 62

Met Ala His Leu Met Thr Val Gln Leu Leu Leu Val Met Trp Met
  1               5                  10                  15

Ala Glu Cys Ala Gln Ser Arg Ala Thr Arg Ala Arg Thr Glu Leu Leu
                20                  25                  30

Asn Val Cys Met Asp Ala Lys His His Lys Glu Lys Pro Gly Pro Glu
         35                  40                  45

Asp Asn Leu His Asp Gln Cys Ser Pro Trp Lys Thr Asn Ser Cys Cys
     50                  55                  60

Ser Thr Asn Thr Ser Gln Glu Ala His Lys Asp Ile Ser Tyr Leu Tyr
 65                  70                  75                  80

Arg Phe Asn Trp Asn His Cys Gly Thr Met Thr Ser Glu Cys Lys Arg
                85                  90                  95

His Phe Ile Gln Asp Thr Cys Leu Tyr Glu Cys Ser Pro Asn Leu Gly
             100                 105                 110

Pro Trp Ile Gln Gln Val Asp Gln Ser Trp Arg Lys Glu Arg Ile Leu
         115                 120                 125

Asp Val Pro Leu Cys Lys Glu Asp Cys Gln Gln Trp Trp Glu Asp Cys
     130                 135                 140

Gln Ser Ser Phe Thr Cys Lys Ser Asn Trp His Lys Gly Trp Asn Trp
```

```
                145                 150                 155                 160
Ser Ser Gly His Asn Glu Cys Pro Val Gly Ala Ser Cys His Pro Phe
                165                 170                 175

Thr Phe Tyr Phe Pro Thr Ser Ala Ala Leu Cys Glu Glu Ile Trp Ser
                180                 185                 190

His Ser Tyr Lys Leu Ser Asn Tyr Ser Arg Gly Ser Gly Arg Cys Ile
                195                 200                 205

Gln Met Trp Phe Asp Pro Ala Gln Gly Asn Pro Asn Glu Glu Val Ala
                210                 215                 220

Arg Phe Tyr Ala Glu Ala Met Ser Gly Ala Gly Leu His Gly Thr Trp
225                 230                 235                 240

Pro Leu Leu Cys Ser Leu Ser Leu Val Leu Leu Trp Val Ile Ser
                245                 250                 255

<210> SEQ ID NO 63
<211> LENGTH: 22
<212> TYPE: PRT
<213> ORGANISM: Homo Sapiens

<400> SEQUENCE: 63

Thr Arg Ile Ala Trp Ala Arg Thr Glu Leu Leu Asn Val Cys Met Asn
1               5                   10                  15

Ala Lys His His Lys Glu
            20

<210> SEQ ID NO 64
<211> LENGTH: 257
<212> TYPE: PRT
<213> ORGANISM: Homo Sapiens

<400> SEQUENCE: 64

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
                35                  40                  45

Pro Glu Asp Lys Leu His Glu Gln Cys Arg Pro Trp Arg Lys Asn Ala
            50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
                180                 185                 190

Trp Thr His Ser Tyr Lys Val Ser Asn Tyr Ser Arg Gly Ser Gly Arg
```

```
                195                 200                 205
Cys Ile Gln Met Trp Phe Asp Pro Ala Gln Gly Asn Pro Asn Glu Glu
    210                 215                 220
Val Ala Arg Phe Tyr Ala Ala Met Ser Gly Ala Gly Pro Trp Ala
225                 230                 235                 240
Ala Trp Pro Phe Leu Leu Ser Leu Ala Leu Met Leu Leu Trp Leu Leu
                245                 250                 255
Ser
```

<210> SEQ ID NO 65
<211> LENGTH: 257
<212> TYPE: PRT
<213> ORGANISM: Homo sapiens

<400> SEQUENCE: 65

```
Met Ala Gln Arg Met Thr Thr Gln Leu Leu Leu Leu Val Trp Val
1               5                   10                  15
Ala Val Val Gly Glu Ala Gln Thr Arg Ile Ala Trp Ala Arg Thr Glu
                20                  25                  30
Leu Leu Asn Val Cys Met Asn Ala Lys His His Lys Glu Lys Pro Gly
                35                  40                  45
Pro Glu Asp Lys Leu His Glu Gln Cys Arg Pro Trp Arg Lys Asn Ala
            50                  55                  60
Cys Cys Ser Thr Asn Thr Ser Gln Glu Ala His Lys Asp Val Ser Tyr
65                  70                  75                  80
Leu Tyr Arg Phe Asn Trp Asn His Cys Gly Glu Met Ala Pro Ala Cys
                85                  90                  95
Lys Arg His Phe Ile Gln Asp Thr Cys Leu Tyr Glu Cys Ser Pro Asn
                100                 105                 110
Leu Gly Pro Trp Ile Gln Gln Val Asp Gln Ser Trp Arg Lys Glu Arg
            115                 120                 125
Val Leu Asn Val Pro Leu Cys Lys Glu Asp Cys Glu Gln Trp Trp Glu
130                 135                 140
Asp Cys Arg Thr Ser Tyr Thr Cys Lys Ser Asn Trp His Lys Gly Trp
145                 150                 155                 160
Asn Trp Thr Ser Gly Phe Asn Lys Cys Ala Val Gly Ala Ala Cys Gln
                165                 170                 175
Pro Phe His Phe Tyr Phe Pro Thr Pro Thr Val Leu Cys Asn Glu Ile
                180                 185                 190
Trp Thr His Ser Tyr Lys Val Ser Asn Tyr Ser Arg Gly Ser Gly Arg
            195                 200                 205
Cys Ile Gln Met Trp Phe Asp Pro Ala Gln Gly Asn Pro Asn Glu Glu
    210                 215                 220
Val Ala Arg Phe Tyr Ala Ala Met Ser Gly Ala Gly Pro Trp Ala
225                 230                 235                 240
Ala Trp Pro Phe Leu Leu Ser Leu Ala Leu Met Leu Leu Trp Leu Leu
                245                 250                 255
Ser
```

<210> SEQ ID NO 66
<211> LENGTH: 255
<212> TYPE: PRT
<213> ORGANISM: Homo sapiens

<400> SEQUENCE: 66

Met Val Trp Lys Trp Met Pro Leu Leu Leu Leu Val Cys Val Ala
1               5                   10                  15

Thr Met Cys Ser Ala Gln Asp Arg Thr Asp Leu Leu Asn Val Cys Met
            20                  25                  30

Asp Ala Lys His His Lys Thr Lys Pro Gly Pro Glu Asp Lys Leu His
        35                  40                  45

Asp Gln Cys Ser Pro Trp Lys Lys Asn Ala Cys Cys Thr Ala Ser Thr
    50                  55                  60

Ser Gln Glu Leu His Lys Asp Thr Ser Arg Leu Tyr Asn Phe Asn Trp
65                  70                  75                  80

Asp His Cys Gly Lys Met Glu Pro Ala Cys Lys Arg His Phe Ile Gln
                85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255

<210> SEQ ID NO 67
<211> LENGTH: 243
<212> TYPE: PRT
<213> ORGANISM: Homo sapiens

<400> SEQUENCE: 67

Met Ala Trp Gln Met Met Gln Leu Leu Leu Leu Ala Leu Val Thr Ala
1               5                   10                  15

Ala Gly Ser Ala Gln Pro Arg Ser Ala Arg Ala Arg Thr Asp Leu Leu
            20                  25                  30

Asn Val Cys Met Asn Ala Lys His His Lys Thr Gln Pro Ser Pro Glu
        35                  40                  45

Asp Glu Leu Tyr Gly Gln Cys Ser Pro Trp Lys Lys Asn Ala Cys Cys
    50                  55                  60

Thr Ala Ser Thr Ser Gln Glu Leu His Lys Asp Thr Ser Arg Leu Tyr
65                  70                  75                  80

Asn Phe Asn Trp Asp His Cys Gly Lys Met Glu Pro Thr Cys Lys Arg
                85                  90                  95

His Phe Ile Gln Asp Ser Cys Leu Tyr Glu Cys Ser Pro Asn Leu Gly
            100                 105                 110

Pro Trp Ile Arg Gln Val Asn Gln Ser Trp Arg Lys Glu Arg Ile Leu
        115                 120                 125

```
Asn Val Pro Leu Cys Lys Glu Asp Cys Glu Arg Trp Trp Glu Asp Cys
    130                 135                 140
Arg Thr Ser Tyr Thr Cys Lys Ser Asn Trp His Lys Gly Trp Asn Trp
145                 150                 155                 160
Thr Ser Gly Ile Asn Glu Cys Pro Ala Gly Ala Leu Cys Ser Thr Phe
                165                 170                 175
Glu Ser Tyr Phe Pro Thr Pro Ala Ala Leu Cys Glu Gly Leu Trp Ser
            180                 185                 190
His Ser Phe Lys Val Ser Asn Tyr Ser Arg Gly Ser Gly Arg Cys Ile
        195                 200                 205
Gln Met Trp Phe Asp Ser Ala Gln Gly Asn Pro Asn Glu Glu Val Ala
    210                 215                 220
Lys Phe Tyr Ala Ala Ala Met Asn Ala Gly Ala Pro Ser Arg Gly Ile
225                 230                 235                 240
Ile Asp Ser

<210> SEQ ID NO 68
<211> LENGTH: 255
<212> TYPE: PRT
<213> ORGANISM: Homo sapiens

<400> SEQUENCE: 68

Met Val Trp Lys Trp Met Pro Leu Leu Leu Leu Val Cys Val Ala
  1               5                  10                  15
Thr Met Cys Ser Ala Gln Asp Arg Thr Asp Leu Leu Asn Val Cys Met
                20                  25                  30
Asp Ala Lys His His Lys Thr Lys Pro Gly Pro Glu Asp Lys Leu His
            35                  40                  45
Asp Gln Cys Ser Pro Trp Lys Lys Asn Ala Cys Cys Thr Ala Ser Thr
        50                  55                  60
Ser Gln Glu Leu His Lys Asp Thr Ser Arg Leu Tyr Asn Phe Asn Trp
65                  70                  75                  80
Asp His Cys Gly Lys Met Glu Pro Ala Cys Lys Arg His Phe Ile Gln
                85                  90                  95
Asp Thr Cys Leu Tyr Glu Cys Ser Pro Asn Leu Gly Pro Trp Ile Gln
            100                 105                 110
Gln Val Asn Gln Thr Trp Arg Lys Glu Arg Phe Leu Asp Val Pro Leu
        115                 120                 125
Cys Lys Glu Asp Cys Gln Arg Trp Trp Glu Asp Cys Leu Thr Ser His
    130                 135                 140
Thr Cys Lys Ser Asn Trp His Arg Gly Trp Asp Trp Thr Ser Gly Val
145                 150                 155                 160
Asn Lys Cys Pro Ala Gly Ala Leu Cys Arg Thr Phe Glu Ser Tyr Phe
                165                 170                 175
Pro Thr Pro Ala Ala Leu Cys Glu Gly Leu Trp Ser His Ser Tyr Lys
            180                 185                 190
Val Ser Asn Tyr Ser Arg Gly Ser Gly Arg Cys Ile Gln Met Trp Phe
        195                 200                 205
Asp Ser Ala Gln Gly Asn Pro Asn Glu Glu Val Ala Arg Phe Tyr Ala
    210                 215                 220
Ala Ala Met His Val Asn Ala Gly Glu Met Leu His Gly Thr Gly Gly
225                 230                 235                 240
Leu Leu Leu Arg Leu Ala Leu Met Leu Gln Leu Trp Leu Leu Gly
                245                 250                 255
```

<210> SEQ ID NO 69
<211> LENGTH: 478
<212> TYPE: DNA
<213> ORGANISM: Homo sapiens

<400> SEQUENCE: 69

```
tctcattggg tcccattggc ctgaccctaa agcctgggtt cttttccacc agacctaatc      60
tccatcgagc tggccttatc ctaagaacca cttggggtat ctataaaatc cagatgcccc     120
ctggtgatga gcaattctct agattttgat gaaagttgaa tgtgtggatg ctggaatgag     180
taaattaaca agtaaggaga tgaatgcaag caggaatgac taaatggaca gactcaggga     240
gccttgaaga gggtgggtc tggaagggaa ggaagagagg aaggagaata gctaagtagg      300
gagatttcac tcagtgctta ccagagcgcg ttgtctaccc tgtaccgaag acagaggctg     360
tggggacagc ctaggggcct ggatctattg cctacttaga gagaggccaa ctcagacaca     420
gccgtgtatg ctcccagcag caacggaggt tcaggcaaga tgcccgaaga gggaaggg      478
```

<210> SEQ ID NO 70
<211> LENGTH: 701
<212> TYPE: DNA
<213> ORGANISM: Salmon

<400> SEQUENCE: 70

```
gggggctggg acaggcggta gctcgcctcg cggcggaccg ccagctcgat cccgagatcc      60
aactacgagc tttttaactg cagcaacttt aagatacgct attggagctg aattaccgc      120
ggctgctggc accagacttg ccctccaatg gatcctcgtt aaaggattta agtgtactc      180
attccaatta cagggcctcg aaagagtcct gtattgttat ttttcgtcac tacctccccg     240
agtcgggagt gggtaatttg cgcgcctgct gccttccttg gatgtggtag ccgtttctca     300
ggctccctct ccggaatcga accctgattc cccgttaccc gtggtcacca tggtaggcac     360
agaaagtacc atcgaaagtt gatagggcag acattcgaat gagacgtcac cgccacaaag     420
ggcgcgcgat cggctcgagg ttatctagag tcaccaaagc ggccggggca accgagattg     480
gcccgcatgg gttttgggtc tgataaaatgc acgcatcccc ggaggtcagc gctcgtctgc     540
atgtattagc tctagaattg ccacagttat ccaagtaacg ttggagcgat caaaggaacc     600
ataactgatt taatgagcca ttcgcagttt cactgtaccg gccgtgtgta cttagacttg     660
catggcttaa tctttgagac aagcatatgc tactggcagg a                         701
```

<210> SEQ ID NO 71
<211> LENGTH: 356
<212> TYPE: DNA
<213> ORGANISM: Homo sapiens

<400> SEQUENCE: 71

```
gcggccgcct actactacta ctactgctcg aattcaagct tctaacgatg tacggggaca      60
tgccgacggg cgctgacccc cttcgcgggg gggatgcgtg catttatcag atcaaaacca     120
acccggtcag cccctctccg gccccggccg ggggcgggc gccggcggct ttggtgactc      180
tagataacct cgggccgatc gcacgccccc cgtgcggacg acgacccatt cgaacgtctg     240
ccctctccct taccaggacc acagctctgt ccttcggcc tctggtcctc tctggtcccc      300
tcctgggttt cttacgtagt tgatttttcc tctttagtct cccccgacct gcgccc         356
```

<210> SEQ ID NO 72

```
<211> LENGTH: 155
<212> TYPE: DNA
<213> ORGANISM: Frog

<400> SEQUENCE: 72 ttttttttttt tttcaaagta aacgcttcgg gccccggga cactcagtca agagcatcgg      60
ggaggcgccg agaggcaggg gctgggacag gcggtagctc gcctcgcggc ggaccgccag     120
ctcgatccca agatccaact acgagctttt taact                                155

<210> SEQ ID NO 73
<211> LENGTH: 944
<212> TYPE: DNA
<213> ORGANISM: Homo sapiens

<400> SEQUENCE: 73
tcaagattaa acgacaagga cagacatggc tcagcggatg acaacacagc tgctgctcct      60
tctagtgtgg gtggctgtag taggggaggc tcagacaagg attgcatggg ccaggactga     120
gcttctcaat gtctgcatga acgccaagca ccacaaggaa aagccaggcc ccgaggacaa     180
gttgcatgag cagtgtcgac cctggaggaa gaatgcctgc tgttctacca acaccagcca     240
ggaagcccat aaggatgttt cctacctata tagattcaac tggaaccact gtggagagat     300
ggcacctgcc tgcaaacggc atttcatcca ggacacctgc ctctacgagt gctccccaa      360 cttggggccc tggatccagc aggtggatca gagctggcgc aaagagcggg tactgaacgt     420
gcccctgtgc aaagaggact gtgagcaatg gtgggaagat tgtcgcacct cctacacctg     480
caagagcaac tggcacaagg gctggaactg gacttcaggg tttaacaagt gcgcagtggg     540
agctgcctgc aacctttcc atttctactt ccccacaccc actgttctgt gcaatgaaat      600
ctggactcac tcctacaagg tcagcaacta gccgaggg agtggccgct gcatccagat       660
gtggttcgac ccagcccagg caaccccaa tgaggaggtg gcgaggttct atgctgcagc      720
catgagtggg gctgggccct gggcagcctg gcctttcctg cttagcctgg ccctaatgct     780
gctgtggctg ctcagctgac ctccttttac cttctgatac ctggaaatcc ctgccctgtt     840
cagccccaca gctcccaact atttggttcc tgctccatgg tcgggcctct gacagccact     900
ttgaataaac cagacaccgc acatgtgtct tgagaattat ttgg                     944

<210> SEQ ID NO 74
<211> LENGTH: 7720
<212> TYPE: DNA
<213> ORGANISM: Homo sapiens

<400> SEQUENCE: 74
taagttgaca cttctcaggt tgtcacaaga ttcaggtatg gctcactgtt gcaggacata      60
agctgggatc tcctgggaat tggtctgctt gcaggcccta gagagccttc cttcttggtt     120
gattttcctc tagagatcca actgtcttct caggctcccc tgcctgcctc ctccttgggt     180 ccttcttgt ggcattgcca gattactggg cccccatttt ccctacactt actgccactc      240
atagtctgat ggttcccaca tctgcatcca acctggactc ttcccctgag cttcccctc      300 tacaaccacc ttccccggc caagggcaca caggcacctc gacaaaacag tgttctatgt     360
ttcttcctgc ccaaacctgc cctccctct ccttttccc atctgtggta ccaccatggg      420
ctcagagaat aaaaaaaatg aaggcttctg tcattgactg gggtggagat ggagggaaga     480
gttagcccag aatcacaggt gctgtagaaa ggatacctga gttgccggga gaggggtcc      540 atgagttggg gatggaagga gagcttggcc cttcaaacaa ttgaagatct gatcaaaaga     600
```

```
ttcagaacat ctgtgatttt gtggctggtg atgggtgaca cctggcctaa tggggttggg    660
ggagttggtg gctctacaat ttatggcctt gggagatcct tgctctctat agctgactgg    720
gaggttggaa gcctgggctc tagcccttgc cttgatcctc cggatctcat tttcctcatc    780
tgcctaacag gacagagggg ttggaaactg atgagattag ctcaaaggat cctggcagct    840
caggctgcaa gattttttc agacctcagt gtttgggaaa aaattgggta ggtggagctt    900
agggactggc cttaggcctg cactgttaat tcaccccctc ccactacccc atggaggcct    960
ggctggtgct cacatacaat aattaactgc tgagtggcct tcgcccaatc ccaggctcca   1020
ctcctgggct ccattcccac tccctgcctg tctcctaggc cactaaacca cagctgtccc   1080
ctggaataag gcaaggggga gtgtagagca gagcagaagc ctgagccaga cggagagcca   1140
cctcctctcc caggtatgtg acactcccca tcccccttca gaggccacac acccctatgc   1200
attcccacca tgtgttaagg attttctgaa ctggaagggc cctctgtttg cctgaaggcc   1260
agagaatctt gaagtggaga ctgaggccca gaccagagtg tggcctgctc aagattaaac   1320
gacaagttag tgttcatccc cctgaactag tacctgggct ctagcccttc agtccagagc   1380
tgagttctca gctcttctag tctggggccc caaggttggg tgtgggggtc atgattgttg   1440
gtggggaggg gtcacagctg gactaagacc tgaaggtgag actaggcagg tgggaaagga   1500
gcttgcagag tgatgctgct caaaaggaca ggaagagagc ctggcttcag aagcagccac   1560
agcaagagag actactgact gaacaggtgg gctccactgg gggctccgga aaggattttc   1620
tcagccccca tccccagcac tgtgtgttgg ccgcacccat gagagcctca gcactctgaa   1680
ggtgcagggg gcaaaggcca aaagagctct ggcctgaact tgggtggtcc ctactgtgtg   1740 acttgggca tggccctcat ctgtgctgaa atgattccac aaagattaaa ctggctatca   1800
tttgttgatt tccccttct tacatttaat ccttgcagga gaaagctaag cctcaagata   1860
gtttgcttct ctttccccca aggccaagga gaaggtggag tgagggctgg ggtcgggaca   1920
ggttgaacgg gaaccctgtg ctctaaacag ttagggtttg ttcccgcagg aactgaaccc   1980
aaaggatcac ctggtattcc ctgagagtac agatttctcc ggcgtggccc tcaaggttag   2040
tgagtgagca ggtccacagg ggcatgattg gatcctggaa tgaatgaatc aaccatgaga   2100
gagtgaatga acactggaat caatagagta gcagagtaat ggattgtgga gcaggaaaga   2160
gagctgctgg gtgggaattc aattccaggc ttatatgagc cctgctgtgc agtcggcctg   2220
gagacagccc agctcaggcc ctgcctagac ccctgtcaag gaggccctgt caagaggaga   2280 ggagggggcag cacggggggca aggcaagctt gtgagcggga aaggcatgtc cactttagcg   2340
actggtatgt ggaagatgag ttagaggaga cagatggaga gaagtcatag gaaataaatt   2400
ctgagcattt taggagggcc cagacacctg gtgtccagtg gagtgaagga aacagtcgcc   2460
tcccaaaatt cagtgtctga ggtcaaagga ttgaagttct gtgatgacca aggagaagcc   2520
agctctgtgg taggggcac aggagctccc caaggcccca gggctgtcca gctggctgtc   2580
ccctgccagc acccatgtcc tgtgacccca ccccaccaag atcccatggt tccgggaag   2640 ggcctactaa actagcttga gtgatgaggc tagaaagggg ctgggaccaa ggtttaaaaa   2700 gcaaacaaa ctaacaaaaa ccacactgca gcccccccaa ctaaaacatt tttataaact   2760
tttttttttt ttttgagatg gagtctcgct ctgtcaccca ggctagagtg caatggcaca   2820
atcttggctc actgtaacct ccacctcctg gattcaagtg attctcctgc ctcagcctcc   2880
cacgtagctg ggactacagg cacacgacac cgcacccagc tcattttgta tttttagtag   2940
```

```
agacagggtt tcactatgtt ggccaggctg gtctcaaact tctgacctca ggtgatccac    3000
ccacctcagc cttccaaagt gctgggatta caggcatgag ccaccgcgcc cagcccattt    3060
ttgtaaactt ttacaatgaa gtaatttggt gtcaaaatct gacctgaaaa ttaatgtgag    3120
tttatgtata gttttaattt atcccactag tgtaactgtt tcaccccaga atatacactt    3180
gattattggg tatatgaaaa aaatattttc tttgaatcac ctttgatgaa atcctaaaaa    3240
attttaaccc tgaaacattt gaataaggca ttgtggacct atggcaaact cctggctatt    3300
tctgcatttt gcccaaatcc atccttgaat tatatcacct gaacctcgtg accacctgga    3360
gaaggcaatg aggctcaagc cagggagggg tggtgtctaa tcctacccttt cattggatct    3420 gggaaaactg agggagatgg gggcagggct ctatctgccc caggcttccg tccaggcccc    3480
accctcctgg agccctgcac acaacttaag gccccacctc cgcattcctt ggtgccactg    3540
accacagctc tttcttcagg gacagacatg gctcagcgga tgacaacaca gctgctgctc    3600
cttctagtgt gggtggctgt agtagggggag gctcagacaa ggattgcatg ggccaggact    3660
gagcttctca atgtctgcat gaacgccaag caccacaagg aaaagccagg ccccgaggac    3720
aagttgcatg agcaggtggg ccaggggtg atctggggtg gtgagggact ggctcaggaa    3780
gaggaaacga ggacatggaa atgccaaacc ccattggcac tggtgaactg aagtggagga    3840
gcccttcagt ttgcattaat atgggtgact tatttcagag acactgtgcc aaatgtcggt    3900
acaatgccaa cagttcacct tcttggttgt tgagtttccg cattacagaa ataaggaagc    3960
aggcccaaag gagagcctgg gaaatgaagt tggagtgacc catcctgggg ttgcttgatt    4020
tagggattta gactgggaat gactcctcca aagatctgag ggaagaaact gcacactgtg    4080
catagtggcc tcttttctgc cagccctaaa cagctcaaga agggagagtc tctcacatta    4140
tgaggctgtg tgcaaagcat tctttttttt ttttcctgag acaaagtctc catatgttgc    4200
ccaggctggt ctcaaattcc tggactcaag tgatcctccc acctcagccc tcccaaagtg    4260
tgggattaca gaaatgagcc gtacgccctc ctgaagcatc ttggttcatg catctcgcaa    4320
aactttgggc tgtgtctctc gaccacattg gacctgaggt ctccctataa catttatttt    4380
gctaccaccc ctttaatatc ctgaacatga tgatataact aaagaaaaag cagaggaaaa    4440
gtaatttgta ggccaggtgt tacggctcac gcctgtaatc ccaacactgt gggatgtcga    4500
gatgggcaga tcacttgagc tcaggagttc gagaccagcc tgggcaagat ggcaaaaccc    4560
catctctact aaaaaataaa aaaattagt caggtgtggt ggcacatgcc tgcagtccca    4620
gctactcagg aggctgaggt gggcaggtca gttgagccca ggaggcagag attgtagatc    4680
gtgccactgc actccagcct gggcaacaga gtgagacctt gtcaaaagaa agaaagaacg    4740
aaaaaaagaa agaaaggaag gaaggaaggg gaggaaggaa agggagggag gaaagggagg    4800
gaggaaaggg agggaggcaa gggagagaaa cttgtaatac gcatttcttt ttttttttct    4860
tgagatagag ttttgctctt gttgcccagg gtggatggca gtggcacaat ctcagctcac    4920
tgcaacctcc acctcccagg ttcaagtgat tctcctgcct cagcctcctg agtaggcaca    4980
cgccaccaca cccagctaat ttttgtttg tttgtttgtt ttgtttgttg gtatttttag    5040
tagagatggg ggtttcacca tgttggccag gctggtctcg aactcctcac ctcataatcc    5100
gcccctcttg gcctcccaaa gtgctgagat tacaggtgtg agccactgcg cccggcctta    5160
agtgcacatt ttatttattt atttattttat ttatttattg agatggagtc ttgctctgtt    5220
gcccaggctg gagtgcagtg gcacaatctc agctcactgc aacctccacc tcccaggttc    5280
aagcaattct tctgccttgg cctccagagt agctgggact ataggcacct gccaccatgc    5340
```

```
ctagctaatt tttgtatttt tagtagaaat ggggttttgc catgttggcc aggctggtct    5400
ccattcttga ccttaagtga tctgtccacc tccacctccc aaagtgctgg gattacaggc    5460
actatgtgag ccactgtgcc ggcccacatt ttaatattta gcttgtcagc cttaagtaat    5520
gagattcagg aagcttgagg ataggcacac aggagcatag tttcaagttg tcctgaattt    5580
tgcagccatc acaagttagt ttttaaggaa aaagattagt tcctaagttg tttctcaata    5640
acttataata aataaacatc cacaattgat tggctataca ttgttttttt gtatcacaaa    5700
ttccacaaac agataatggg tgaggcagct agtcagggac aaaacacttc ccaagtagct    5760
gggattacag gtgtccgcca ccacacttgg ctagttttt gtttgtttat tttttgagat     5820
ggagtcttgc tctgtcgccc aggctggagt gcagtggcat gatctcggct cactgcaagc    5880
tccacctgcc gggttcacac cattctcctg cctcagcctc ccaagtagct gggactacag    5940
gtgccagcca ccacgcccgg ctaattttt gtattttag tagagacggg gtttcaccat      6000
gttggccagg atggtcttga tctcttagcc tcgtgatcca cccgcctcgg cctcccaaaa    6060
tgctgggatt acaggcgtga gccaccgcac ccggcctaat ttttatattt ttagtagaga    6120
cggggtttca ccatgttggc caggctggtc tcaaactctt gatctcaggt gatccacctg    6180
ccttggcctc ccaaagtgct gggattacac aagtaagcca ctgcacccag cctggggtta    6240
caatttaaat tgctttttta ccttcaaatc tttgacacct cagtgaggct taatctgacc    6300
gcactattac actacaagtc cccatccgtc tctgcttaat ttttgtccaa agcaaaaatc    6360
aggtgatgtg ttcattgttg taaccccagt ttctacaaaa gtacctgggt gagagtaagt    6420
aggatctcaa taaaggttga attaacaaat tttgtaatga ctgcaactcc agcaggagct    6480 ccctttttggg ctcccactgt ctctgacggc cctctcccct aaagaggtcc caatagcaag   6540
tattttcctg ggtgacttcc agtgggctgg ggaatcaagg actaagaggg gagacactgc    6600
atgtggaata ttctggctgt gctggctgtg ctggctgtgg actgagtcct ctgtcttccc    6660
ccatccagtg tcgaccctgg aggaagaatg cctgctgttc taccaacacc agccaggaag    6720
cccataagga tgtttcctac ctatatagat tcaactggaa ccactgtgga gagatggcac    6780
ctgcctgcaa acggcatttc atccaggaca cctgcctcta cgagtgctcc cccaacttgg    6840
ggccctggat ccagcaggta tgcatggctt cctgcaggta caagacctag cggagcagct    6900
gagctttcca ggcatctctg caggctgcaa ccccagctcc agttctattc ggggctgagt    6960
tgctgggatt cttgaacctg agcccttctt ttgtatcaaa atcacccagg tggatcagag    7020
ctggcgcaaa gagcgggtac tgaacgtgcc cctgtgcaaa gaggactgtg agcaatggtg    7080
ggaagattgt cgcacctcct acacctgcaa gagcaactgg cacaagggct ggaactggac    7140
ttcaggtgag gctggggtg gcaggaatg agggatttg gaagtggagg tgtgtgggtg       7200
tggaacaggt atgtgacaat ttggagttgt agggctggca gacctcaaga tagttccggg    7260
cccagtggct aaaggtcttc cctcctctct acagggttta acaagtgcgc agtgggagct    7320
gcctgccaac ctttccattt ctacttcccc acacccactg ttctgtgcaa tgaaatctgg    7380
actcactcct acaaggtcag caactacagc cgagggagtg gccgctgcat ccagatgtgg    7440
ttcgacccag cccaggcaa ccccaatgag gaggtggcga ggttctatgc tgcagccatg     7500
agtggggctg ggccctgggc agcctggcct ttcctgctta gcctggccct aatgctgctg    7560
tggctgctca gctgacctcc ttttaccttc tgatacctgg aaatccctgc cctgttcagc    7620
cccacagctc ccaactattt ggttcctgct ccatggtcgg gcctctgaca gccactttga    7680
```

```
ataaaccaga caccgcacat gtgtcttgag aattatttgg              7720
```

<210> SEQ ID NO 75
<211> LENGTH: 929
<212> TYPE: DNA
<213> ORGANISM: Homo sapiens

<400> SEQUENCE: 75

```
agggacagac atggctcagc ggatgacaac acagctgctg ctccttctag tgtgggtggc     60
tgtagtaggg gaggctcaga caaggattgc atgggccagg actgagcttc tcaatgtctg    120
catgaacgcc aagcaccaca aggaaaagcc aggccccgag acaagttgc atgagcagtg     180
tcgaccctgg aggaagaatg cctgctgttc taccaacacc agccaggaag cccataagga    240
tgtttcctac ctatatagat tcaactgaa ccactgtgga gagatggcac ctgcctgcaa     300
acggcatttc atccaggaca cctgcctcta cgagtgctcc cccaacttgg ggccctggat    360
ccagcaggtg gatcagagct ggcgcaaaga gcgggtactg aacgtgcccc tgtgcaaaga    420
ggactgtgag caatggtggg aagattgtcg caccctcctac acctgcaaga gcaactggca   480
caagggctgg aactggactt cagggtttaa caagtgcgca gtgggagctg cctgccaacc    540
tttccatttc tacttcccca cacccactgt tctgtgcaat gaaatctgga ctcactccta    600
caaggtcagc aactacagcc gagggagtgg ccgctgcatc cagatgtggt tcgacccagc    660
ccagggcaac cccaatgagg aggtggcgag gttctatgct gcagccatga gtggggctgg    720
gccctgggca gcctggcctt tcctgcttag cctggcccta atgctgctgt ggctgctcag    780
ctgacctcct tttaccttct gatacctgga aatccctgcc ctgttcagcc ccacagctcc    840
caactatttg gttcctgctc catggtcggg cctctgacag ccactttgaa taaaccagac    900
accgcacatg tgtcttgaga attatttgg                                      929
```

<210> SEQ ID NO 76
<211> LENGTH: 1331
<212> TYPE: DNA
<213> ORGANISM: Homo sapiens

<400> SEQUENCE: 76

```
ggaaaggatt ttctcagccc ccatccccag cactgtgtgt tggccgcacc catgagagcc     60
tcagcactct gaaggtgcag ggggcaaagg ccaaaagagc tctggcctga acttgggtgg    120
tccctactgt gtgacttggg gcatggccct catctgtgct gaaatgattc cacaaagatt    180
aaactggcta tcatttgttg atttccccct tcttacattt aatccttgca ggagaaagct    240
aagcctcaag atagtttgct tctctttccc ccaaggccaa ggagaaggtg gagtgagggc    300
tggggtcggg acaggttgaa cgggaaccct gtgctctaaa cagttagggt ttgttcccgc    360
aggaactgaa cccaaaggat cacctggtat tccctgagag tacagatttc tccggcgtgg    420
ccctcaaggg acagacatgg ctcagcggat gacaacacag ctgctgctcc ttctagtgtg    480
ggtggctgta gtagggagg ctcagacaag gattgcatgg gccaggactg agcttctcaa    540
tgtctgcatg aacgccaagc accacaagga aaagccaggc cccgaggaca agttgcatga    600
gcagtgtcga ccctggagga agaatgcctg ctgttctacc aacaccagcc aggaagccca    660
taaggatgtt tcctacctat atagattcaa ctggaaccac tgtggagaga tggcacctgc    720
ctgcaaacgg catttcatcc aggacacctg cctctacgag tgctccccca acttggggcc    780
ctggatccag caggtggatc agagctggcg caaagagcgg gtactgaacg tgcccctgtg    840
caaagaggac tgtgagcaat ggtgggaaga ttgtcgcacc tcctacacct gcaagagcaa    900
```

| | |
|---|---|
| ctggcacaag ggctggaact ggacttcagg gtttaacaag tgcgcagtgg gagctgcctg | 960 |
| ccaacctttc catttctact tccccacacc cactgttctg tgcaatgaaa tctggactca | 1020 |
| ctcctacaag gtcagcaact acagccgagg gagtggccgc tgcatccaga tgtggttcga | 1080 |
| cccagcccag ggcaaccccc atgaggaggt ggcgaggttc tatgctgcag ccatgagtgg | 1140 |
| ggctgggccc tgggcagcct ggcctttcct gcttagcctg ccctaatgc tgctgtggct | 1200 |
| gctcagctga cctccttta ccttctgata cctggaaatc cctgccctgt tcagccccac | 1260 |
| agctcccaac tatttggttc ctgctccatg gtcgggcctc tgacagccac tttgaataaa | 1320 |
| ccagacaccg c | 1331 |

<210> SEQ ID NO 77
<211> LENGTH: 939
<212> TYPE: DNA
<213> ORGANISM: Homo sapiens

<400> SEQUENCE: 77

| | |
|---|---|
| cattccttgg tgccactgac cacagctctt tcttcaggga cagacatggc tcagcggatg | 60 |
| acaacacagc tgctgctcct tctagtgtgg gtggctgtag taggggaggc tcagacaagg | 120 |
| attgcatggg ccaggactga gcttctcaat gtctgcatga acgccaagca ccacaaggaa | 180 |
| aagccaggcc ccgaggacaa gttgcatgag cagtgtcgac cctggaggaa gaatgcctgc | 240 |
| tgttctacca acaccagcca ggaagcccat aaggatgttt cctacctata tagattcaac | 300 |
| tggaaccact gtggagagat ggcacctgcc tgcaaacggc atttcatcca ggacacctgc | 360 |
| ctctacgagt gctcccccaa cttggggccc tggatccagc aggtggatca gagctggcgc | 420 |
| aaagagcggg tactgaacgt gcccctgtgc aaagaggact gtgagcaatg gtgggaagat | 480 |
| tgtcgcacct cctacacctg caagagcaac tggcacaagg gctggaactg gacttcaggg | 540 |
| tttaacaagt gcgcagtggg agctgcctgc aacctttcc atttctactt ccccacaccc | 600 |
| actgttctgt gcaatgaaat ctggactcac tcctacaagg tcagcaacta cagccgaggg | 660 |
| agtggccgct gcatccagat gtggttcgac ccagcccagg gcaacccca tgaggaggtg | 720 |
| gcgaggttct atgctgcagc catgagtggg gctgggccct gggcagcctg gccttcctg | 780 |
| cttagcctgg ccctaatgct gctgtggctg ctcagctgac ctcctttac cttctgatac | 840 |
| ctggaaatcc ctgccctgtt cagccccaca gctcccaact atttggttcc tgctccatgg | 900 |
| tcgggcctct gacagccact ttgaataaac cagacaccg | 939 |

<210> SEQ ID NO 78
<211> LENGTH: 1104
<212> TYPE: DNA
<213> ORGANISM: Homo sapiens

<400> SEQUENCE: 78

| | |
|---|---|
| tggaggcctg gctggtgctc acatacaata attaactgct gagtggcctt cgcccaatcc | 60 |
| caggctccac tcctgggctc cattcccact ccctgcctgt ctcctaggcc actaaaccac | 120 |
| agctgtcccc tggaataagg caagggggag tgtagagcag agcagaagcc tgagccagac | 180 |
| ggagagccac ctcctctccc aggacagac atggctcagc ggatgacaac acagctgctg | 240 |
| ctccttctag tgtgggtggc tgtagtaggg gaggctcaga caaggattgc atgggccagg | 300 |
| actgagcttc tcaatgtctg catgaacgcc aagcaccaca aggaaaagcc aggcccgag | 360 |
| gacaagttgc atgagcagtg tcgaccctgg aggaagaatg cctgctgttc taccaacacc | 420 |

| | |
|---|---|
| agccaggaag cccataagga tgtttcctac ctatatagat tcaactggaa ccactgtgga | 480 |
| gagatggcac ctgcctgcaa acggcatttc atccaggaca cctgcctcta cgagtgctcc | 540 |
| cccaacttgg ggccctggat ccagcaggtg gatcagagct ggcgcaaaga gcgggtactg | 600 |
| aacgtgcccc tgtgcaaaga ggactgtgag caatggtggg aagattgtcg cacctcctac | 660 |
| acctgcaaga gcaactggca aagggctgg aactggactt cagggtttaa caagtgcgca | 720 |
| gtgggagctg cctgccaacc tttccatttc tacttcccca cacccactgt tctgtgcaat | 780 |
| gaaatctgga ctcactccta caaggtcagc aactacagcc gagggagtgg ccgctgcatc | 840 |
| cagatgtggt tcgacccagc ccagggcaac cccaatgagg aggtggcgag gttctatgct | 900 |
| gcagccatga gtggggctgg gccctgggca gcctggcctt tcctgcttag cctggcccta | 960 |
| atgctgctgt ggctgctcag ctgacctcct tttaccttct gatacctgga aatccctgcc | 1020 |
| ctgttcagcc ccacagctcc caactatttg gttcctgctc catggtcggg cctctgacag | 1080 |
| ccactttgaa taaaccagac accg | 1104 |

<210> SEQ ID NO 79
<211> LENGTH: 1032
<212> TYPE: DNA
<213> ORGANISM: Homo sapiens

<400> SEQUENCE: 79

| | |
|---|---|
| ggcaagggg agtgtagagc agagcagaag cctgagccag acggagagcc acctcctctc | 60 |
| ccaggaactg aacccaaagg atcacctggt attccctgag agtacagatt tctccggcgt | 120 |
| ggccctcaag ggacagacat ggctcagcgg atgacaacac agctgctgct ccttctagtg | 180 |
| tgggtggctg tagtagggga ggctcagaca aggattgcat gggccaggac tgagcttctc | 240 |
| aatgtctgca tgaacgccaa gcaccacaag gaaaagccag gccccgagga caagttgcat | 300 |
| gagcagtgtc gaccctggag gaagaatgcc tgctgttcta ccaacaccag ccaggaagcc | 360 |
| cataaggatg tttcctacct atatagattc aactggaacc actgtggaga gatggcacct | 420 |
| gcctgcaaac ggcatttcat ccaggacacc tgcctctacg agtgctcccc caacttgggg | 480 |
| ccctggatcc agcaggtgga tcagagctgg cgcaaagagc gggtactgaa cgtgcccctg | 540 |
| tgcaaagagg actgtgagca atggtgggaa gattgtcgca cctcctacac ctgcaagagc | 600 |
| aactggcaca gggctggaa ctggacttca gggtttaaca agtgcgcagt gggagctgcc | 660 |
| tgccaacctt tccatttcta cttccccaca cccactgttc tgtgcaatga aatctggact | 720 |
| cactcctaca aggtcagcaa ctacagccga gggagtggcc gctgcatcca gatgtggttc | 780 |
| gacccagccc agggcaaccc caatgaggag gtggcgaggt tctatgctgc agccatgagt | 840 |
| ggggctgggc cctgggcagc ctggcctttc tgcttagcc tggccctaat gctgctgtgg | 900 |
| ctgctcagct gacctccttt taccttctga tacctggaaa tccctgccct gttcagcccc | 960 |
| acagctccca actatttggt tcctgctcca tggtcgggcc tctgacagcc actttgaata | 1020 |
| aaccagacac cg | 1032 |

<210> SEQ ID NO 80
<211> LENGTH: 765
<212> TYPE: DNA
<213> ORGANISM: Homo sapiens

<400> SEQUENCE: 80

| | |
|---|---|
| atggcctcag ttccgaaaac caacaaaata gaaccgcggt cctattccat tattcctagc | 60 |
| tgcagtatca ggcggctcgg gcctgctttg aacactccaa ttttttcaaag taaacgcaac | 120 |

```
gggcccgcg   gacactcagc   ttacagcatc   gaggggcgcc   agaggcaagg   ggcgggacgg         180
gcggtggtcc   ctcgcgcgga   ccgcccgccc   gctcccaaga   tccaactacg   agcttttac          240 ctgcagcaac   tttactatac   gctattggag   ctggaattac   cgcggctgct   ggcaccagac        300
ttgccctcca   atggctcctc   gttaaaggat   ttaaagtgga   ctcattccaa   ttacagggcc        360
tcgaaagagt   cctgtattgt   tattttcgtc   actacctccc   cgggtcggga   gtgggtaatt       420
tgcgcgcctg   ctgccttcct   tggatgtggt   agcctccagg   ctccctctcc   ggaatctgaa        480
ccctcattcc   ccgtcacccg   tggtcaccat   ggtcggcacg   gcgactacca   tcgaaagttg       540
atagggcaga   cgttcgaatg   ggtcgtcgtc   cgccgccacg   ggggcgtgc   gatcggcccg         600 aggttatcta   gagtcaccaa   agccgccggc   gcccgccccc   cggccggggc   cggagagggg       660
ctgagggttg   gttttgatct   gataaatgca   ccgatccccc   ccgcgaaggg   ggtcagcgcc       720
cgtcggcatg   tattagctct   agaattacca   cagttatcca   agtag                          765
```

<210> SEQ ID NO 81
<211> LENGTH: 1223
<212> TYPE: DNA
<213> ORGANISM: Mus musculus

<400> SEQUENCE: 81

```
gctttagagg   cagatcaggg   tgtagttttc   agctagcgcc   gtgccttccc   caccatgttc        60
cttgccatga   tgataatgta   ctagacctct   gaaactgtag   cttctttgtt   acagagtctc        120
cgtgaatctg   gaattcacca   attcggcgag   tctgaaagcc   tcagtgatct   ctcaggctcc        180
atctgtctcc   actccccagt   ggaaggcttg   cagctgtgtc   accgctccag   acttcacaca        240
ggtgctggaa   gactgaacta   agacagaaag   acatggcctg   gaaacagaca   ccactcttgc        300
ttttggtcta   catggtcaca   acaggcagtg   gccgggacag   aacagaccta   ctcaacgttt        360
gcatggatgc   caaacaccat   aagacaaagc   cgggccccga   ggacaagctg   catgaccagt       420
gtagtccatg   gaagaaaaat   gcctgttgct   cagtcaacac   cagccaggag   ctacacaagg       480
ctgactcccg   tctgtacttc   aactgggatc   actgtggcaa   gatggagcct   gcctgtaaga        540
gtcacttcat   ccaagactcc   tgcctgtatg   agtgctcccc   caaccttggg   ccttggatcc        600
agcaagtgga   ccagagttgg   cgtaaagagc   gtttcctgga   tgtgccctta   tgcaaagagg        660
actgtcacca   gtggtgggaa   gcctgtcgta   cctcctttac   ctgcaagaga   gactggcata        720
aaggctggga   ctggtcctca   ggcattaaca   agtgcccaaa   cacagcaccc   tgtcacacgt        780
ttgagtacta   cttcccgaca   ccagccagcc   tttgcgaggg   tctctggagt   cactcctaca        840
aggtcagcaa   ctacagcaga   gggagtggcc   gctgcatcca   gatgtggttt   gactcaaccc        900
agggcaatcc   caatgaggac   gtggtgaagt   tttatgcttc   ctttatgaca   tctgggactg        960
tgccccatgc   agcagtactt   cttgtgccca   gcctggcccc   agtgctgtca   ttatggctcc       1020
ctggctgaga   ggtcagtctt   cctctctaga   tttctcctct   atctacccct   ggtctggttc        1080
aactcttcaa   agaataagga   agtcttgagc   ctgcttccac   ccctctcctc   tgtcatccag       1140
ttcctgatcc   atgttggggg   ttggggttttc   tacaatcatt   ttcaataaat   ctatgacaca       1200
tctgggccta   atgaaaaaaa   aaa                                                      1223
```

<210> SEQ ID NO 82
<211> LENGTH: 979
<212> TYPE: DNA
<213> ORGANISM: Mus musculus

<400> SEQUENCE: 82

```
tggagctgag cacacacttg gaggttccac ttaccttagc tctgccttca gggtctgaca    60
tggctcacct gatgactgtg cagttgttgc tcctggtgat gtggatggcc gaatgtgctc   120
agtccagagc tactcgggcc aggactgaac ttctcaatgt ctgcatggat gccaagcacc   180
acaaagaaaa accgggccct gaggacaatt tacacgacca gtgcagcccc tggaagacga   240
attcctgctg ttccacgaac acaagccagg aagcacataa ggacatttcc tacctgtacc   300
ggttcaactg gaaccactgc ggaactatga catcggaatg caaacggcac tttatccaag   360
acacctgcct ctatgagtgt tccccgaact gggaccctg gatccagcag gtggaccaga    420
gctggcgcaa agagcggatc cttgatgttc ccctgtgcaa agaggactgt cagcagtggt   480
gggaggactg ccagagctct tttacctgca gagcaattg gcacaaggga tggaactggt    540
cctctgggca taacgagtgt cctgtgggag cctcctgcca tcccttcacc ttctacttcc   600
ccacatctgc tgctctgtgt gaggaaatct ggagtcactc ctacaagctc agcaactaca   660
gccgagggag cggccgctgc attcagatgt ggtttgaccc agcccaggc aaccccaacg    720
aggaagtggc gaggttctat gccgaggcca tgagtggagc tgggcttcat gggacctggc   780
cactcttgtg cagcctgtcc ttagtgctgc tctgggtgat cagctgagtt cctgttttac   840
cttcagttgt ctggagcgcc accctgcttg gctcagcctc ccagctccca gcctcctttg   900
tggtggggct ctgacagcct ctttaataaa ccagacattc acatgtgcc ttatgaatta    960
aaaaaaaaaa aaaaaaaa                                                 979
```

<210> SEQ ID NO 83
<211> LENGTH: 647
<212> TYPE: DNA
<213> ORGANISM: Solanum tuberosum

<400> SEQUENCE: 83

```
ctccgatccc gaaggccaac gtaataggac cgaaatccta taatgttatc ccatgctaat    60
gtatacagag cgtaggcttg ctttgagcac tctaatttct tcaaagtaac agcgccggag   120
gcacgacccg gccaattaag gccaggagcg catcgccgac agaagggacg agacgaccgg   180
tgcacaccta gggcggaccg gccggcccat cccaaagtcc aactacgagc ttttttaactg   240
caacaactta aatatacgct attggagctg gaattaccgc ggctgctggc accagacttg   300
ccctccaatg gatcctcgtt aagggattta gattgtactc attccaatta ccagactcat   360
agagcccggt attgttattt attgtcacta cctccccgtg tcaggattgg gtaatttgcg   420
cgcctgctgc cttccttgga tgtggtagcc gtttctcagg ctccctctcc ggaatcgaac   480
cctaattctc cgtcacccgt caccaccatg gtaggccact atcctaccat cgaaagttga   540
tagggcagaa atttgaatga tgcgtcgccg gcacgatggc cgtgcgatcc gtcgagttat   600
catgaatcat cgcagcaacg ggcagagccc gcgtcgacct tttatct                 647
```

<210> SEQ ID NO 84
<211> LENGTH: 280
<212> TYPE: DNA
<213> ORGANISM: Suaeda maritima supsb. salsa

<400> SEQUENCE: 84

```
cgacgcatca ttcaaatttc tgccctatca actttcgatg gtaggatagt ggcctaccat    60
ggtggtgacg ggtgacggag aattagggtt cgattccgga gagggagcct gagaaacggc   120
taccacatcc aaggaaggca gtaggcgcgc aaattaccca atcctgacac ggggaggtag   180
```

```
tgacaataaa taacaatacc gggctcttcg agtctggtaa ttggaatgag tacaatctaa    240
atcccttaac gaggatccat tggagggcaa gtctggtgcc                         280

<210> SEQ ID NO 85
<211> LENGTH: 300
<212> TYPE: DNA
<213> ORGANISM: Avicennia marina

<400> SEQUENCE: 85
gcacggccct cgtgccggcg acgcatcatt caaatttctg ccctatcaac tttcgatggt    60
aggatagtgg cctactatgg tggtgacggg tgacggagaa ttagggttcg attccggaga   120
gggagcctga gaaacggcta ccacatccaa ggaaggcagc aggcgcgcaa attacccaat   180
cctgatacgg ggaggtagtg acaataaata acaataccgg gctctcagag tctggtaatt   240
ggatgagtac aatctaatcc ttaacgagga tccattggag ggcaagtctg gtgcacgagc   300

<210> SEQ ID NO 86
<211> LENGTH: 453
<212> TYPE: DNA
<213> ORGANISM: Homo sapiens

<400> SEQUENCE: 86
gaagacacac gtttagtatt ttattatgaa tcattatttc aaagtcccat actgcatatt    60
catataaggc aacacggcac aatttcaggc ttcatcacaa aggatgaaaa agactgtttc   120
taactccctc ctaatttgca gacatgcttg aacacttaat ggaaggtgaa gtttattttg   180
tggcccctca gttctctttc aagtcctcta gtagaaagtc tccatggtgt gatcttctga   240
ctgggtagaa cccgcaattc tctgctgttt ttagtctttg ttccagatga ctaattacat   300
gacttggctg catttgtgag gggccgacac caacacaatt aaatcagtgc accattcagg   360
gccatagggt aggaggcacc agtggtcacc atggtaggca cggcgactac catcgaaagt   420
tgatagggca gacgttcgaa tgggtcgtcg ccg                                 453

<210> SEQ ID NO 87
<211> LENGTH: 70
<212> TYPE: DNA
<213> ORGANISM: RAT

<400> SEQUENCE: 87
gttgaagagt cacctggtgc ttcaacggga ctgatttcct gggcctggag ttggagatca    60
gaggtctgac                                                          70

<210> SEQ ID NO 88
<211> LENGTH: 381
<212> TYPE: DNA
<213> ORGANISM: RAT

<400> SEQUENCE: 88
cgctgatctg gaagcataaa caagaactga agctgaaggc tctaggggtt cccaacctgt    60
gatctccagc agacactcct ggtgtgtcac cggattcagg ctcctgggat aaagaaagca   120
aaggaagtct ggagtggaga cgaagaaacc ccaggcactc tgagagctgc tacctttttcc  180 atgtgtgctg ccagacactt ctcgtcaggg accaaatacc caagggagt ggagagaggc    240 ctgggctggg ccagcttcc tgggcttaa cctgtgctcc aagtaggtgg gtcacatttt     300
ccccagcggg agttgaagag tcacctggtg cttcaacggg actgatttcc tgggcctgga   360
```

```
gttggagatc agaggtctga c                                              381
```

<210> SEQ ID NO 89
<211> LENGTH: 916
<212> TYPE: DNA
<213> ORGANISM: RAT

<400> SEQUENCE: 89

```
ggggctggag ttggagatca gaggtctgac atggctcacc tgatggctgg gcagtggttg     60
ctcctgctga tgtggatggc cgaatgtgcc cagtccagag ctactcgggc caggaccgaa    120
cttctcaatg tctgcatgga tgccaagcac cacaaagaaa agccaggccc agaggacaag    180
ttacacgacc agtgcagccc ctggaagacg aatgcctgct gctccaccaa cacaagccag    240
gaagacacta aggacatttc ctacctgtac cgattcaact ggaatcactg tggaactatg    300
accccggagt gcaaacgtca cttttatcca gacacctgcc tctatgagtg ttccccgaac    360
ttgggaccct ggatccagca ggtggaccag agctggcgca agagcggat ccttgatgtt     420
cccctgtgca aagaagactg tgtgctgtgg tgggaggact gcaagagctc ttttacctgc    480
aagagcaact ggctcaaggg atggaactgg acctcgggc ataatgagtg ccctgtggga    540
gcctcctgcc atcccttcac tttctacttc cctacacctg ctgtgctgtg tgagaaaatc    600
tggagtcact cctacaagct cagcaactac agccgaggga gcggccgctg catccagatg    660
tggttcgacc cagcccaagg caaccccaac gaggaagtgg cgaggttcta tgccgaggtc    720
atgagtggag ctgggcttcg cgaggcctgg ctgctggtgt gcagcctgtc cttagtgctg    780
ttctgcgtcg tcagctgagt tcctgttact ccttgtctgg agctccaccc tgcccggctt    840
agcctcccag ctccagcctc ctttgtggtg gggctctgac agcctgttta gtaaaccaga    900
cattctaaaa aaaaaa                                                    916
```

<210> SEQ ID NO 90
<211> LENGTH: 478
<212> TYPE: DNA
<213> ORGANISM: Mus musculus
<400> SEQUENCE: 90

```
acccggtgag ctccctcccg gctccggccg ggggtcgggc gccggcggct ttggtgactc     60
tagataacct cgggccgatc gcacgccccc aggtcaagtt tgtttatgaa ggtatttgg    120
tattgttttc ctttgcttaa ttgcctcaca ttttgttctg aaaaacatgg gtccactgtt    180
aaaaccgaat gtatgtgtag ctttattctg tttcacaggc gcatgtgatt ggaaaactca    240
ttgtctcctc cagcctcagg agacttctaa aaagttttgc gtagctcaag ttgtgcatga    300
attaccgaat atattatttt tcagcttttc ttcatgaacg atatttgaca tgtgctttgg    360
taccccttctc tgaaagttga aaacctacct acttagtccc ttctgtgcct ttttttatttt   420
gccaaccatg ttttatggaa aagacattag caattacatt ttgcaaatgg aattatgt     478
```

<210> SEQ ID NO 91
<211> LENGTH: 821
<212> TYPE: DNA
<213> ORGANISM: Mastigamoeba balamuthi
<220> FEATURE:
<221> NAME/KEY: modified_base
<222> LOCATION: (560)
<223> OTHER INFORMATION: N = A, C, G, or T/U
<400> SEQUENCE: 91

```
ggcaccagag tagtcatatg cttgtgttaa agattaagcc atgcatgcct aagtacaaac     60
```

```
tattcttatg gtaaaactgc ggacggctcc atagatcagt aatagttcgt tcagtgattt     120
gaaaaagtac ttggataacc ctgttaattg tagagctaat acatgcaccg acggcctgat     180
cgggtgaccg agagggtcgc acttgtctta attcacagtg ccccggaact gaggctgttc     240
gacgtggtag gggaggacgc tgaatggggc tggtagaaac aactgggggt ataaaaccaa     300
ggaggaagca aaaaagccat aacccggcga tggccttggt ggaaacctct gggctcaagg     360
ttgttattat gttcattgtg gcctctcggg gttattttga atgtggtaat aaaccgaaag     420
caactctatc agtttggttt ggatgtccgt taatcctgcg tggccagcgg ctttggggac     480
tccagcggac agggcgaaac gaggcaattc aaagctgatc gctttctaac gagggcgaca     540
cactgttcga attcctgacn tatcaactcg atggtaggat agtggcctac catggttata     600
acgggtaacg gggaatcagg gctcgattcc ggagagggag cctgagaaac ggctaccact     660
tccaaggaag gcagcaggcg cgtaaattac tccctgccga cacggcgagg tagtgacgac     720
aaataccaag gaaaaccgcc tttggtggtt ttccattgga atgagcagaa ttcaaacccc     780
tctgcaagta acaattggag ggcaagtctg gtgccagcag c                        821
```

```
<210> SEQ ID NO 92
<211> LENGTH: 110
<212> TYPE: DNA
<213> ORGANISM: Mus musculus

<400> SEQUENCE: 92
tccctcgact gtagttgctg agcttgtagg agtgactcca gatttcctca cacagagcag      60
cagatgtggg gaagtagaag gtgaagggat ggcaggaggc tcccacagga                110

<210> SEQ ID NO 93
<211> LENGTH: 334
<212> TYPE: DNA
<213> ORGANISM: Frog

<400> SEQUENCE: 93
ctatcgatat ccgatggtac ttgttgtgcc taccatggtg accccagttc atagcgaatg      60
agggtgcgat ggcagagagg gaggatgtga tgcagctatc gcatgcggtg gatgctggag     120
gcgcgcatgt tgcaccctcc cgacggcgag aggtggtgac tacccatatc gtgcaggact     180 cttcgacgc gctgtagtct gaatgagtac actttaagtc cgtgagcgcg gatctatcgg     240
ttggcgagtt tagtgccagc agcgcgaggc tttacagcct caatgtcgtg tatgacagtt     300
gcgtgtcctt atggagcgtg agttggatca tggg                                 334

<210> SEQ ID NO 94
<211> LENGTH: 220
<212> TYPE: DNA
<213> ORGANISM: Homo sapiens
<220> FEATURE:
<221> NAME/KEY: modified_base
<222> LOCATION: (54) (77)
<223> OTHER INFORMATION: N = A, C, G, or T/U

<400> SEQUENCE: 94
gcggccgcct actactacta aattcgcggc cgcgtcgacc gacgacccat tcgntcgtct      60
gccctatcaa ctttcgntgg ttgtcgccgt gcctaccatg gtgaccacgg gtgacgggga     120
ttctgggttc gtttccggtg agggtgcctg tgggcggtt gcctcttctc tggttggctg     180
caggcgcgct ttttttcctcc tcccggcccg gggtggttgt                          220
```

<210> SEQ ID NO 95
<211> LENGTH: 630
<212> TYPE: DNA
<213> ORGANISM: Haemonchus contortus

<400> SEQUENCE: 95

```
ctggctgcag gaattcgcac gaggctatat gctcagttta aagattaagc catgcatgtc      60
gagttcatct ttgaagagaa actgcgaacg gctcattaga gcagatgtca tttattcgga     120
acgtcctttt ggataactgc ggtaattctg gagctaatac atgcaaataa accctgactt     180
ttgaaagggt gcaattatta gagcaaatca atcactttcg ggtgcagttt gctgactctg     240
aataacgcag catatcggcg gcttgttcgc cgatattccg aaaaagtgtc tgccctatca     300
acctgatggt agtctattag tctaccatgg ttattacggg taacgagaaa taagggttcg     360
actccggaga gggagcctta gaaacggcta ccacatccaa ggaaggcagc aggcgcgaaa     420
cttatccaat cttgaacaga tgagatagtg actaaaaata aaaagaccat tcctatggaa     480
cggtcatttc aatgagttga tcataaacct tttttcgagg atcaagtgga gggcaagtct     540
ggtgccagca gccgcggtaa ttccagctcc actagtgtaa atcgtcattg ctgcggttaa     600
aaagctcgta gttggatctg agttacatgc                                      630
```

<210> SEQ ID NO 96
<211> LENGTH: 340
<212> TYPE: DNA
<213> ORGANISM: Mus musculus

<400> SEQUENCE: 96

```
atcatccaga tttcgtttga tttcaccccg ggccttccgg aggaggacct cctgaaattt      60
tctccttcct atatgacatt agggactgtg ccccaagcag cagtactttt tgtccccagc     120
ctgccccccag tgccgtcatt atggctcccc gctgagaggt cagttttcct ctctagattt     180
ttcctctatt tacccttggt ctggttcaac ttttcaaaga ataaggaagt cttgacctg     240
cttccacccc tttcctctgt catccagttc ctgatccatg tgggggggttg gggtttctac     300
aatcattttc aataaattta tgacacatct gggcctaatg                           340
```

<210> SEQ ID NO 97
<211> LENGTH: 284
<212> TYPE: DNA
<213> ORGANISM: Mus musculus

<400> SEQUENCE: 97

```
aggacgtttg atgtcttatg cttcctttat gaaatccggg attgtgcccc atccagcagt      60
attcttgtgc ccagcctggc cccactgcag tcattatgcc tccctggctg agaggtcatt     120
cttcctcttt agatttctcc tcaatctacc cttgtctgg ttcaactctt caaagaataa     180
ggaagtcttg accctgcttc caccccttc ctctttcatc cagttcctga tccatgttgg     240
gggttggggt ttctacattc attttcaata aatctatgac acac                      284
```

<210> SEQ ID NO 98
<211> LENGTH: 263
<212> TYPE: DNA
<213> ORGANISM: Mus musculus

<400> SEQUENCE: 98

```
tccgggcctt tcccccaca caccaaaaac ttttctgcct actctggccc cagcgctttc       60
cttatgcctc cctggctgag aggtcatttt cttctataga tttctcctct atttaccctc    120
```

```
gctctggttc aactcttcaa agaataagga acttttgagc ctgcttccac ccttttcctc      180
tgtcatccag ttcctgatcc atgttggggg ttggggtttc tacaatcatt ttcaataaat      240
ctatgacaca tctgggccta atg                                              263
```

<210> SEQ ID NO 99
<211> LENGTH: 489
<212> TYPE: DNA
<213> ORGANISM: Homo sapiens

<400> SEQUENCE: 99

```
tttttgtgcg gtgtctggtt tattcaaagt ggctgtcaga ggcccgacca tggagcagga       60
accaaatagt tgggagctgt ggggctgaac agggcaggga tttccaggta tcagaaggta      120
aaaggaggtc agctgagcag ccacagcagc attagggcca ggctaagcag gaaaggccag      180
gctgcccagg gcccagcccc actcatggct gcagcataga acctcgccac ctcctcattg      240
gggttgccct gggctgggtc gaaccacatc tggatgcagc ggccactccc tcggctgtag      300
ttgctgacct tgtaggagtg agtccagatt tcattgcaca gaacagtggg tgtggggaag      360
tagaaatgga aaggttggca ggcagctccc actgcgcact tgttaaaccc tgaagtccag      420
tttcagccct tgtgccagtt gctcttgcag gtgtaggagg tgcgacaatc ttcccaccat      480
tgctcacag                                                              489
```

<210> SEQ ID NO 100
<211> LENGTH: 102
<212> TYPE: DNA
<213> ORGANISM: Mus musculus

<400> SEQUENCE: 100

```
ggatggaact ggtcctcggg gcataacgag tgtcctgtgg gagcctcctg ccatcccttc       60
accttctact tccccacatc tgctgctctg tgtgaggaaa tc                         102
```

<210> SEQ ID NO 101
<211> LENGTH: 583
<212> TYPE: DNA
<213> ORGANISM: Homo sapiens

<400> SEQUENCE: 101

```
tagtgtgggt ggctgtagta ggggaggctc agacaaggat tgcatgggcc aggactgagc       60
ttctcaatgt ctgcatgaac gccaagcacc acaaggaaaa gccaggcccc gaggacaagt      120
tgcttgtagc agtgtcgacc ctggaggaag aatgcctggt gttctaccaa caccagccag      180
gaagcccata aggatgtttc ctacctatat agattcaact ggaaccactg tggagagatg      240
gcacctgcct gcaaacggca tttcatccag gacacctgcc tctacgagtg ctcccccaac      300
ttggggccct ggatccagca ggtggatcag agctggcgca aagagcgggt actgaacgtg      360
cccctgtgca aagaggactg tgagcaatgg tgggaagatt gtcgcacctc ctacacctgc      420
aagagcaact ggcacaaggg ctggaactgg acttcagggt ttaacaagtg cgcagtggga      480
gctgcctgcc aaccttttcca tttctacttc cccacaccca ctgttctgtg caatgaaatc      540
tggactcact cctacaggtc agcaactaca gccgagggag tgg                        583
```

<210> SEQ ID NO 102
<211> LENGTH: 514
<212> TYPE: DNA
<213> ORGANISM: Homo sapiens
<220> FEATURE:

<221> NAME/KEY: modified_base
<222> LOCATION: (122)..(131)
<223> OTHER INFORMATION: N = A, C, G, or T/U

<400> SEQUENCE: 102

| | | |
|---|---|---|
| tgcggtgtct ggtttattca aagtggctgt cagaggcccg accatggagc aggaaccaaa | 60 |
| tagttgggag ctgtggggct gaacagggca ttttatttcc aggtatcata ttgtttgttg | 120 |
| tnggagctga ncagccacag cagcattagg gccaggctaa gcaggaaagg ccaggctgcc | 180 |
| cagggcccag ccccactcat ggctgcagca tagaacctcg ccacctcctc attggggttg | 240 |
| ccctgggctg ggtcgaacca catctggatg cagcggccac tccctcggct gtagttgctg | 300 |
| accttgtagg agtgagtcca gatttcattg cacagaacag tgggtgtggg gaagtagaaa | 360 |
| tggaaaggtt ggcaggcagc tcccactgcg cacttgttaa accctgaaga ccagttccag | 420 |
| cccttgtgcc agttgctctt ggaggtgtag gaggtgccac aatcttccca ccattgctca | 480 |
| cagtccttct tgcacagggg cacgttcaga accc | 514 |

<210> SEQ ID NO 103
<211> LENGTH: 321
<212> TYPE: DNA
<213> ORGANISM: Suaeda maritima supsb. salsa

<400> SEQUENCE: 103

| | | |
|---|---|---|
| cgacgcatca ttcaaatttc tgccctatca actttcgatg gtaggatagt ggcctaccat | 60 |
| ggtggtgacg ggtgacggag aattagggtt cgattccgga gagggagcct gagaaacggc | 120 |
| taccacatcc aaggaaggca gtaggcgcgc aaattaccca atcctgacac ggggaggtag | 180 |
| tgacaataaa taacaatacc gggctcttcg agtctggtaa ttggaatgag tacaatctaa | 240 |
| atcccttaac gaggatccat tggagggcaa gtctggtgcc agcagccgcg gtaattccag | 300 |
| ctccaatagc gtatatttaa g | 321 |

<210> SEQ ID NO 104
<211> LENGTH: 504
<212> TYPE: DNA
<213> ORGANISM: Haemonchus contortus

<400> SEQUENCE: 104

| | | |
|---|---|---|
| tatatgctca gtttaaagat taagccatgc atgtcgagtt catctttgaa gagaaactgc | 60 |
| gaacggctca ttagagcaga tgtcatttat tcggaacgtc cttttggata actgcggtca | 120 |
| ttctggagct aatacatgca aataaaccct gactttgaa agggtgcaat tattagagca | 180 |
| aatcaatcac tttcgggtgc agtttgctga ctctgaataa cgcagcatat cggcggcttg | 240 |
| ttcgccgata ttccgaaaaa gtgtctgccc tatcaacctg atggtagtct attagtctac | 300 |
| catggttatt acgggtaacg gagaataagg gttcgactcc ggagagggag ccttagaaac | 360 |
| ggctaccaca tccaaggaag gcagcaggcg cgaaacttat ccaatcttga acagatgaga | 420 |
| tagtgactaa aaataaaaag accattccta tggaacggtc atttcaatga gttgatcata | 480 |
| aaccttttt ccagttaatt ctac | 504 |

<210> SEQ ID NO 105
<211> LENGTH: 600
<212> TYPE: DNA
<213> ORGANISM: Meloidogyne incognita

<400> SEQUENCE: 105

| | | |
|---|---|---|
| tggccgggat tagaacaaaa ccacgcggct tcggctgctt cttgttgact cagaataact | 60 |

```
aagctgaccg catggccttg tgccggcggc gtgtctttca agcgtccact ttatcaactt    120
gacgggagca taatcgactc ccgtggtggt gacggataac ggaggatcag ggttcgactc    180
cggagaaggg gcctgagaaa tggccactac gtctaaggat ggcagcaggc gcgcaaatta    240
cccactctcg gctcgaggag gtagtgacga gaaataacga gatcgttctc tttgaggccg    300
gtcatcggaa tgagtacaat ttaaaccctt taacgagtat caagcagagg gcaagtctgg    360
tgccagcagc cgcggtaatt ccagctctgc taatacatag aattattgct gcggttaaaa    420
agctcgtagt tggattcgta tcggtaccct ggaaccctcc gggtgtttct gggtgttatc    480
gatttatcgt aatgttcggt tttgagtcct taacaggatt cttaacaggc attgcaagtt    540
tactttgaac aaatcagagt gcttcaaaca ggcgtttgcg ctgaatgatc gtgcatggat    600
```

<210> SEQ ID NO 106
<211> LENGTH: 634
<212> TYPE: DNA
<213> ORGANISM: Meloidogyne incognita

<400> SEQUENCE: 106

```
tgcctaatgt gccaccgctg agtgtgatga tattgacaat cggtagcatt atggccgggt     60
gtgtctattt caaagattaa gccatgcatg tataagttta aatcgttttg acgagaaacc    120
gcgaacggct cattacaatg gccatgattt acttgatctt gattatctaa atggattaac    180
tgtggaaaag ctagagctaa tacatgcacc aaaacttgtt cctctcggaa agcgcattt     240 attagaacaa aaccacgcgg cttcggctgc ttcttgtgac tcagaataac taagctgacc    300
gcatggcctt gtgccggcgg cgtgtctttc aagcgtccac tttatcaact tgacgggagc    360
ataatcgact cccgtggtgg tgacggataa cggaggatca gggttcgact ccggagaagg    420
ggcctgagaa atggccacta cgtctaagga tggcagcagg cgcgcaaatt acccactctc    480
ggctcgagga ggtagtgacg agaaataacg agatcgttct ctttgaggcc ggtcatcgga    540
atgggtacaa tttaaaccct taacgagta tcaagcagag ggcaagtctg gtgccagcag    600
ccgggtattc cagctctgct aatacataga atta                                634
```

<210> SEQ ID NO 107
<211> LENGTH: 222
<212> TYPE: DNA
<213> ORGANISM: Mus musculus
<220> FEATURE:
<221> NAME/KEY: modified_base
<222> LOCATION: (40)
<223> OTHER INFORMATION: N = A, C, G, or T/U

<400> SEQUENCE: 107

```
tccccaccct gccccagtg ctgtcattat ggatccctgn ctgagaggtc aatcttcctt     60
tctagatttt tcctctatct acccttggtc tggttcaaat tttcaaagaa taaggaagtc    120
ttgagcctgc ttccaccct ctcctctttc atccagttcc taatccatgt tgggggttgg    180
ggtttctaca atcatttca ataaatttat gacacatctg gg                       222
```

<210> SEQ ID NO 108
<211> LENGTH: 311
<212> TYPE: DNA
<213> ORGANISM: Mus musculus

<400> SEQUENCE: 108

```
gtagttgctg agcttgtagg agtgactcca gatttcctca cacagagcag cagatgtggg     60
```

```
gaagtagaag gtgaagggat ggcaggaggc tcccacagga cactcgttat gccccgagga    120
ccagttccat cccttgtgcc aattgctctt gcaggtaaaa gagctctggc agtcctccca    180
ccactgctga cagtcctctt tgcacagggg aacatcaagg atccgctctt tgcgccagct    240
ctggtccacc tgctggatcc agggtcccaa gttcggggaa cactcataga ggcaggtgtc    300
ttggataaag t                                                         311
```

<210> SEQ ID NO 109
<211> LENGTH: 272
<212> TYPE: DNA
<213> ORGANISM: Mus musculus

<400> SEQUENCE: 109

```
acacagagca gcagatgtgg ggaagtagaa ggtgaaggga tggcaggagg ctcccacagg     60
acactcgtta tgccccgagg accagttcca tcccttgtgc caattgctct tgcaggtaaa    120
agagctctgg cagtcctccc accactgctg acagtcctct ttgcacaggg gaacatcaag    180
gatccgctct ttgcgccagc tctggtccac ctgctggatc cagggtccca agttcgggga    240
acactcatag aggcaggtgt cttggataaa gt                                  272
```

<210> SEQ ID NO 110
<211> LENGTH: 315
<212> TYPE: DNA
<213> ORGANISM: Mus musculus
<220> FEATURE:
<221> NAME/KEY: modified_base
<222> LOCATION: (196)
<223> OTHER INFORMATION: N = A, C, G, or T/U

<400> SEQUENCE: 110

```
actgcggaac tatgacatcg gaatgcaaac ggcactttat ccaagacacc tgcctctatg     60
agtgttcccc gaacttggga ccctggatcc agcaggtgga ccagagctgg cgcaaagagc    120
ggatccttga tgttcccctg tgcaaagagg actgtcagca gtggtgggag gactgccaga    180 gctctttac ctgcangagc aattggcaca agggatggaa ctggtcctcg gggcataacg     240
agtgtcctgt gggagcctcc tgccatccct tcaccttcta cttccccaca tctgctgctc    300
tgtgtgagga aatct                                                     315
```

<210> SEQ ID NO 111
<211> LENGTH: 315
<212> TYPE: DNA
<213> ORGANISM: Mus musculus

<400> SEQUENCE: 111

```
actgcggaac tatgacatcg gaatgcaaac ggcactttat ccaagacacc tgcctctatg     60
agtgttcccc gaacttggga ccctggatcc agcaggtgga ccagagctgg cgcaaagagc    120
ggatccttga tgttcccctg tgcaaagagg actgtcagca gtggtgggag gactgccaga    180 gctctttac ctgcaagagc aattggcaca agggatggaa ctggtcctcg gggcataacg     240
agtgtcctgt gggagcctcc tgccatccct tcaccttcta cttccccaca tctgctgctc    300
tgtgtgagga aatct                                                     315
```

<210> SEQ ID NO 112
<211> LENGTH: 685
<212> TYPE: DNA
<213> ORGANISM: Cladosporium fulvum
<220> FEATURE:
<221> NAME/KEY: modified_base
<222> LOCATION: (197)..(683)
<223> OTHER INFORMATION: N = A, C, G, or T/U

<400> SEQUENCE: 112

| | | | | | |
|---|---|---|---|---|---|
| gaggccagta | gtcatatgct | tgtctcaaag | attaagccat | gcatgtctaa gtataagcaa | 60 |
| ctatacggtg | aaactgcgaa | tggctcatta | aatcagttat | cgtttatttg atagtaccat | 120 |
| actacatgga | taaccgtggt | aattctagag | ctaatacatg | ctaaaaaccc cgacttcgga | 180 |
| agggtgtat | ttattanata | aaaaccaac | gccctcggg | gctccttggt gaatcataat | 240 |
| aacttcacga | atcgcatggc | cttgcgccgg | cgatggttca | ttcaaatttc tgccctatca | 300 |
| actttcgatg | gtaggataga | ggcctaccat | ggtttcaacg | ggtaacgggg aattagggtt | 360 |
| cgactccgga | gagggagcct | gagaaacggc | taccacatcc | aaggaaggca gcaggcgcgc | 420 |
| aaattaccca | atcccgaccg | gggagggagn | gacaataaat | actgatncng gctnttgggg | 480 |
| gtcttgnaat | tggaatgagt | ncaattaaat | cccttaccag | gaacaattgg aggcaanttg | 540 |
| gngccccan | cncggnattc | cactccatag | cgttntaaag | tttgcaatta aaagttgaat | 600 |
| taacttggcc | tggtggcggc | ccctacgggt | ctggccggcg | gcnttntttg gggccgnncc | 660 |
| tttatgnggg | gggaacngct | ttntt | | | 685 |

<210> SEQ ID NO 113
<211> LENGTH: 440
<212> TYPE: DNA
<213> ORGANISM: Cladosporium fulvum
<220> FEATURE:
<221> NAME/KEY: modified_base
<222> LOCATION: (72)..(433)
<223> OTHER INFORMATION: N = A, C, G, or T/U

<400> SEQUENCE: 113

| | | | | | |
|---|---|---|---|---|---|
| tgacaattga | atacggatgc | ccccgactat | ccctattaat | cattacgggg gtcctagaaa | 60 |
| ccaacaaaat | anaaccacnc | gtcctattct | attattccat | gctaatgtat tcgagcaaag | 120 |
| gcctgctttg | aacactntaa | tttttcaaa | gnaaaagtcc | tggttcccg acncncccag | 180 |
| ngaagggcat | gcggctcccc | aaaaggaaag | gcccggccgg | accagtacac gcggngaggn | 240 |
| ggaccggcca | gccaggccca | aggttcaact | acgagctttt | taactgcaac aacttttaata | 300 |
| tacgctattg | gagctggaat | taccgnggnt | gctggcacca | aacttgccct ccaattgttc | 360 |
| ctcgttaagg | ggatttaaat | tgtactcatt | ccaattacaa | gacccaaaag agccctgtat | 420 |
| cagtatttat | tgncactact | | | | 440 |

<210> SEQ ID NO 114
<211> LENGTH: 246
<212> TYPE: DNA
<213> ORGANISM: Mus musculus

<400> SEQUENCE: 114

| | | | | | |
|---|---|---|---|---|---|
| tgtgcccat | gcaacagtaa | tttttgagcc | caccctggcc | ccagtgctgt cattatggct | 60 |
| ccctggctga | gaggtcagtt | ttcctatcta | gatttttcct | gtatctaccc ttggtctggt | 120 |
| tcaaattttc | aaagaataag | gaagtcttga | gcctgcttcc | acccctttcc tctgtcatcc | 180 |
| agttcctgat | ccatgttggg | ggttggggtt | tctacaatca | ttttcaataa atctatgaca | 240 |
| catctg | | | | | 246 |

<210> SEQ ID NO 115
<211> LENGTH: 694
<212> TYPE: DNA

```
<213> ORGANISM: Mesembryanthemum crystallinum
<220> FEATURE:
<221> NAME/KEY: modified_base
<222> LOCATION: (23) (609)
<223> OTHER INFORMATION: N = A, C, G, or T/U

<400> SEQUENCE: 115 cccctagat gctagtagca gtngncacga ggtcatatgc ttgtctcaaa gattaagcca      60
tgcatgtgta agtatgaact aattcagact gtgaaactgc gaatggctca ttaaatcagt   120
tatagtttgt ttgatggtac ctgctactcg gataaccgta gtaattctag agctaatacg   180
tgcaacaaac cccgacttct ggaagggatg catttattag ataaaaggtc gacgcgggct   240
ttgcccgttg ctctgatgat tcatgataac tcgacggatc gcacggnctt tgcgccggcg   300
acgcatcatt caaatttctg ccctatcaac tttcgatggt aggatagtgg cctaccatgg   360
tggtgacggg tgacggagaa ttagggttcg attccggaga gggagcctga gaaacggcta   420
ccacatccaa ggaaggcagc aggcgcgcaa attacccaat cctgcacggg gaggtaggga   480
caataaataa caataccggg ctcttcgagt ctggtaattg gaatgagtac aatctaaatc   540
ccttaacgag gatacattgg agggccaagt ctgttgccag cagccgcggt atattccagc   600
ttcaatagnc gtatatttaa agttgttggc agttaaaaag cttgtatttg gactctgggg   660
tgggcgaccc ggtcgtctag cggtgtgcac cggc                              694

<210> SEQ ID NO 116
<211> LENGTH: 1266
<212> TYPE: DNA
<213> ORGANISM: Mesembryanthemum crystallinum
<220> FEATURE:
<221> NAME/KEY: modified_base
<222> LOCATION: (16)..(1230)
<223> OTHER INFORMATION: N = A, C, G or T/U

<400> SEQUENCE: 116
gactactcat cagtgncagg ctagctgcac gaggtcatat gctcgtctca tagattaagc    60
catgcatgtg taagtatgaa ctaattcaga ctgtgaaact gcgaatggct cattaaatca   120
gttatagttt gtttgatggt acctgctact aggataaccg tagtaattct agagctaata   180
cgtgcaacaa accccgactt ctggaaggga tgcatttatt agataaaagg tcgacgcggg   240 cttttgcccgt tgctctgatg attcatgata actcgacgga tcgcacggcc tttgcgccgg   300
cgacgcatca ttcaaatttc tgccctatca actttcgatg gtaggatagt ggcctaccat   360
ggtggtgacg ggtgacggag aattagggtt cgattccgga gagggagcct gagaaacggc   420
taccacatcc aaggaaggca tcaggcgcgc atattaccca atcctgacac ggcgaggtag   480
tgacaataaa taacaatacc gggctcttcg agtctcggta atcggaatga gttcaatcta   540
tatcccttta cgaggatcca ttggagggca agtcctgctg ccagcagcct gctgtcckkk   600
cagctccaat agcgtatatt taagttgttg cagtttaaca agctcttatt cgaccttgtc   660
gtgcgaccgt tctcattacg ctatatgcct catcatatgt ccatatctat tctcgacttc   720
tcgctcccct cgtcttctct agtacttctg cctcttctat tatattcact atgatctatt   780
ctctacgcct cttcctctgc actcttatat tcatcgcact cttcactcta ctctctctta   840
tcgtctgcta gtctttcgct tcttcctctt tctactttct catgtctctc atcttatctt   900
accctctctc actctttctg ttcgtctcct tcactctgc gatttctcca ctgtatcacg   960
cttcgttctc tctactcttc tacttgttct ctctctatct cgtcctcatc tcctccgtct  1020
cgtctctatc gtcgtctacc gatactcttt ccttctctgt catcttcctc tctcttcctc  1080
```

```
tcttgcttac ttctcgtctc tcttcacgat tatcntctag cacgtcatct ctttactctc    1140
tctatcttca tgtctactca ctctctcctg tgcgtactac tcttggctat catcatctcc    1200
tagagtggct cgatgaggcg aatgtgcncn tctatctctc tacgttctct tactgatact    1260
tctttg                                                              1266
```

<210> SEQ ID NO 117
<211> LENGTH: 1162
<212> TYPE: DNA
<213> ORGANISM: Mesembryanthemum crystallinum
<220> FEATURE:
<221> NAME/KEY: modified_base
<222> LOCATION: (34)..(960)
<223> OTHER INFORMATION: N = A, C, G or T/U

<400> SEQUENCE: 117

```
gtcgacgcac tagtgctata gtagcgttca tgcnagcngc acgaggagag agagagagag     60
agagagagag agagagagag agagagagag agagagagag agagagagag agagagagag    120
agagagagag agagagcggc acgagcttgt ctcaaagatt aagccatgca tgtgtaagta    180
tgaactaatt cagactgtga aactgcgaat ggctcattaa atcagttata gtttgtttga    240
tggtacctgc tactaggata accgtagtaa ttctagagct aatacgtgca acaaaccccg    300
acttctggaa gggatgcatt tattagataa aaggtcgacg cgggctttgc ccgttgctct    360
gatgattcat gataactcga cggatcgcac ggcctttgcg ccggcgacgc atcattcaaa    420
tttctgccct atcaacttc gatggtagga tagtggccta ccatggtggt gacgggtgac    480
agagaattag ggttcgattc cggagaggga gcctgagaaa cggctaccac atccaaggaa    540
ggcagcatgc gcgcaaatta cccaatcctg acacggagag gtagtgacaa tatataacaa    600
taccgcgctc ttcgagtctg gtaattggaa tgagtacaat ctatatccct aacgaggat    660 ccattgtagg gcatgtctgg tgccagcagt cgcggtaatt tcagttccaa ttagcgatat    720
ttaattcgtt gcagtaaaaa gctcgtattt gaactttgcg tgggcccacc taccgtctag    780
cggtgtgcac tgtcttctct gctttttcg gcatagcctc tgccttaaag cttgtctcgc    840
actgctctta cttcgatatt tgatcttcat gcgctctctt ggatctcatc atggatacct    900
aatgatctgc ctttctttgc ttggattcgc atcatcattg tacctggtct ttcgttctan    960
ttagtatttc tcgattttat catcctgcta ccctactcga tttattttaa actatttgtc   1020
ttaacctatt tctttctctt cttacttcac tcttcctcgt aatctgtctt attatcactc   1080
ttcctcattt ctttattact gttcatttac ttatttactt tatttccttc tacatctttt   1140
ctctcatctt ctactcacgt cg                                           1162
```

<210> SEQ ID NO 118
<211> LENGTH: 537
<212> TYPE: DNA
<213> ORGANISM: Mesembryanthemum crystallinum
<220> FEATURE:
<221> NAME/KEY: modified_base
<222> LOCATION: (460)
<223> OTHER INFORMATION: N = A, C, G, or T/U

<400> SEQUENCE: 118

```
cccacactag ttctagagga ttcggcacga ggtctcaaag attaagccat gcatgtgtaa     60
gtatgaacta attcagactg tgaaactgcg aatggctcat taaatcagtt atagtttgtt    120
tgatggtacc tgctactagg ataaccgtag taattctaga gctaatacgt gcaacaaacc    180
```

```
ccgacttctg aagggatgc atttattaga taaaaggtcg acgcgggctt tgcccgttgc      240
tctgatgatt catgataact cgacggatcg cacggccttt cgccggcga cgcatcattc      300 aaatttctgc cctatcaact ttcgatggta ggatagtggc ctaccatggt ggtgacgggt     360
gacggagaat tagggttcga ttccggagag ggagcctgag aaacggctac cacatccaag     420
gaaggcagca ggcgcgcaaa ttacccaatc ctgacacggn gaggtagtga acaataataa     480
caataccggg ctcttcgagt ctggtaatgg gaatgagtac aatctaaatt ccttaac       537
```

<210> SEQ ID NO 119
<211> LENGTH: 968
<212> TYPE: DNA
<213> ORGANISM: Mesembryanthemum crystallinum
<220> FEATURE:
<221> NAME/KEY: modified_base
<222> LOCATION: (635) (658)
<223> OTHER INFORMATION: N = A, C, G, or T/U

<400> SEQUENCE: 119

```
gcacgagcga cgcgggcttt gcccgttgct ctgatgattc atgataactc gacggatcgc      60
acggcctttg cgccggcgac gcatcattca aatttctgcc ctatcaactt tcgatggtag     120
gatagtggcc taccatggtg gtgacgggtg acggagaatt agggttcgat tccggagagg     180
gagcctgaga acggctacc acatccaagg aaggcagcag gcgcgctaat tacccaatcc     240
tgacacgggg aggtagtgac aataaataac aataccgggc tcttcgagtc tggtaattgg     300
aatgagtaca atctaaatcc cttaacgagg atccattgga gggcaagtct ggtgccagca     360
gccgcggtaa ttccagctcc aatagcgtat atttaagttg ttgcagttaa aaagctcgta     420
gttggacctt ggggtgggcc gaccggtccg cctagcggtg tgcaccggtc gtcctgcctc     480
ttctgccggc gatgcgctcc tggccttaac tgggccggtc gtgccaccgg gcgctgtact     540
ttgaagaaat agagtgctca agcaggccta cgctctggat acattagcat gggataacat     600
cataggaatt ccgtcctatt ctgttgccct tcggnattcg agtaattgat aacaggnnac     660
agcgggggca ttcgtatttc atagtcagag gtgaaaatct tggattattg aagaccaaca     720
actgccaaag catttggcca ggatgttttc attattcaag accgaaagtt ggggcttcga     780
agaccaacag attcccgtct aatcttaaac cttaaacata tcccaccagg ggatcgggga     840
tgtaactttt aggaccccgc cggccccta tgagaaatta agttttggg gtcccggggg      900 gagtttggtg ccaaggcttt aacttaaggg aattgcgcgg aggggccccc cccgggaatg      960
ggccctgt                                                              968
```

<210> SEQ ID NO 120
<211> LENGTH: 893
<212> TYPE: DNA
<213> ORGANISM: Mesembryanthemum crystallinum
<220> FEATURE:
<221> NAME/KEY: modified_base
<222> LOCATION: (660)
<223> OTHER INFORMATION: N = A, C, G, or T/U

<400> SEQUENCE: 120

```
gcacgaggtc tcaaagatta agccatgcat gtgtaagtat gaactaattc agactgtgaa      60
actgcgaatg gctcattaaa tcagttatag tttgtttgat ggtacctgct actaggataa     120
ccgtagtaat tctagagcta atacgtgcaa caaaccccga cttctggaag ggatgcattt     180
attagataaa aggtcgacgc gggctttgcc cgttgctctg atgattcatg ataactcgac     240
ggatcgcacg gcctttgcgc cggcgacgca tcattcaaat ttctgcccta tcaactttcg     300
```

```
atggtaggat agtggcctac catggtggtg acgggtgacg gagaattagg gttcgattcc      360
ggagagggag cctgagaaac ggctaccaca tccaaggaag gcagcaggcg cgcaaattac      420
ccaatcctga cacggggagg tagtgacaat aaataacaat accgggctct tcgagtctgg      480
taattggaat gagtacaatc taaatccctt aacgaggatc cattggaggg caagtctggt      540
gccagcagcc gcggtaattc cagctccaat agcgtatatt taagttgttg cagttaaaaa      600
gctcgtagtt ggaccttggg gtgggccgac cggtccgcct agcggtgtgc accggtcggn      660
cttgcctctt ttgtcggcga tgcgctcctg gcctttaact ggccgggttg tgccaccggc      720
gctgttactt tgaagaaat aagagtgctc aaagcaagcc ctacgctctg gttacattag      780
catgggataa caatatagga tttccggtcc tattttgttg gcctttggga tcggagttat      840
gaataacagg gaccgtccgg gggcatttct tttttaatat tcaaaggtga aat             893
```

<210> SEQ ID NO 121
<211> LENGTH: 996
<212> TYPE: DNA
<213> ORGANISM: Mesembryanthemum crystallinum
<220> FEATURE:
<221> NAME/KEY: modified_base
<222> LOCATION: (676) (854)
<223> OTHER INFORMATION: N = A, C, G, or T/U

<400> SEQUENCE: 121

```
agctggtacg cctgcggtac cggtccggaa ttcccgggtc gacccacgcg tccgcggacg       60
cgtgggcgga cgcgtggggc taatacatgc aactcggtct ctaccggaaa tggtagggac      120
gcttttatta gaccaaaacc aatcgggcgt tctcgtccgt tttgccttgg tgactctgaa      180
taaattgtgt gcagatcgca cggtcctcgt accggcgacg catctttcaa atgtctgcct      240
tatcaacttt cgatggtagg tcctgcgcct accatggttg taacgggtaa cggggaatca      300
gggttcgatt ccggagaggg agcctgagaa acggctgcta catccaagga aggcagcagg      360
cgcgcaaatt acccactccc ggcacgggga ggtagtgacg acaaataacg atacgggact      420
catccgaggc cccgtaatcg gaatgaacac actttaaatc ctttaatgag tatccattgg      480
agggcaagtc tggtgccagc agccgcggta attccagctc caatagcgta tattaaagtt      540
gttgcggtta aaaagctcgt agtcggactt gtgtcacacg ctgccggttc accgcccgtc      600
ggtgctaact ggcatgcacg tgttgacgtc ctgctggtgg ccgtagccgg tccgggtgtt      660
ctgggatccc ttcggngttt cccggacccc ggtgcttggt gaaggcctac ttgacctacc      720
cgtcgcggtc ctcttaaccg agtgtctcga tgggccggca cttttacttt gaacaattag      780
agtgcttaaa gcaggcagta tcagccctga tactgagtgc atggaataat ggaataggaa      840
cctcggtcta tttntgtggt tttcggaatg ccctagatcg cgagcggccg ctctagaaga      900
tccaagctta cgtacgcctg cattgccaag tataagcttt tttatatggg gaaccctaaa      960
ttcaatcaac tggcgcgcgg tttaacacac gcggag                                996
```

<210> SEQ ID NO 122
<211> LENGTH: 607
<212> TYPE: DNA
<213> ORGANISM: Mus musculus
<220> FEATURE:
<221> NAME/KEY: modified_base
<222> LOCATION: (106)
<223> OTHER INFORMATION: N = A, C, G, or T/U

<400> SEQUENCE: 122

```
tgctgctcct tctagtgtgg gtggctgtag taggggaggc tcagacaagg attgcatggg      60
ccaggactga gcttctcaat gtctgcatga acgccaagca ccacanagga aaattctttc     120
cccgaggaca agttgcatgt tctgtggggg ccctggagga agaatgcctg ctgttctacc     180
aacaccagcc aggaagccca taaggatgtt tcctacctat atagattcaa ctggaaccac     240
tgtggagaga tggcacctgc ctgcaaacgg catttcatcc aggacacctg cctctacgag     300
tgctccccca acttggggcc ctggatccag caggtggatc agagctggcg caaagagcgg     360
gtactgaacg tgcccctgtg caaagaggac tgtgagcaat ggtgggaaga ttgtcgcacc     420
tcctacacct gcaagagcaa ctggcacaag ggcctggaac ctggacttca gggttttaac     480
aaggtgcgca ggtgggaggc tgccctgccc acctttttcca ttttctactt ctctcacacc     540
cactgttgct gttgcattgc aaatcttgtc ctcacttctt acaaggtaca gcaactacca     600
agaaaaa                                                              607

<210> SEQ ID NO 123
<211> LENGTH: 351
<212> TYPE: DNA
<213> ORGANISM: Mus musculus

<400> SEQUENCE: 123
aggacatttc ctacctgtac cggttcaact ggaaccactg cggaactatg acatcggaat      60
gcaaacggca ctttatccaa gacacctgcc tctatgagtg ttccccgaac ttgggaccct     120
ggatccagca ggtggaccag agctggcgca aagagcggat ccttgatgtt cccctgtgca     180
aagaggactc tcagcagtgg tgggaggact gccagagctc ttttacctgc aagagcaatt     240
ggcacaaggg atggaactgg tcctcggggc ataacgagtg tcctgtggga gcctcctgcc     300
atcccttcac cttctacttc cccacatctg ctgctctgtg tgaggaaatc t             351

<210> SEQ ID NO 124
<211> LENGTH: 365
<212> TYPE: DNA
<213> ORGANISM: Mus musculus

<400> SEQUENCE: 124
gcggccgctc cctcgactgt agttgctgag cttgtaggag tgactccaga tttcctcaca      60
cagagcagca gatgtgggga agtagaaggt gaagggatgg caggaggctc ccacaggaca     120
ctcgttatgc cccgaggacc agttccatcc cttgtgccaa ttgctcttgc aggtaaaaga     180
gctctggcag tcctcccacc actgctgaca gtcctctttg cacaggggaa catcaaggat     240
ccgctctttg cgccagctct ggtccacctg ctggatccag ggtcccaagt tcggggaaca     300
ctcatagagg caggtgtctt ggataaagtg ccgtttgcat tccgatgtca tagttccgca     360
gtggt                                                                365

<210> SEQ ID NO 125
<211> LENGTH: 653
<212> TYPE: DNA
<213> ORGANISM: Mus musculus
<220> FEATURE:
<221> NAME/KEY: modified_base
<222> LOCATION: (532)
<223> OTHER INFORMATION: N = A, C, G, or T/U

<400> SEQUENCE: 125
gggctgtgga cgaagactgt agagactacc cagagtctga cctagggaga ggccaactcg      60 gatacccta tgtgcgctcc cagaagctaa ggacattgag acagaaagac atggcctgga     120
```

```
aacagacacc actcttgctt ttggtctaca tggtcacaac aggcagtggc cgggacagaa    180
cagacctact caacgtttgc atggatgcca aacaccataa gacaaagccg ggccccgagg    240
acaagctgca tgaccagtgt agtccatgga agaaaaatgc ctgttgctca gtcaacacca    300
gccaggagct acacaaggct gactcccgtc tgtacttcaa ctgggatcac tgtggcaaga    360
tggagcctgc ctgtaagagt cacttcatcc aagactcctg cctgtatgag tgctccccca    420
accttgggcc ttggatccag caagtggacc agagttggcg taaagagcgt gtcctggatg    480
tgcccttatg caaagaggac tgtcaccagt ggtgggaagc ctgtcgtacc tnctttacct    540
gcaagagaga ctggcataaa ggctgggact ggtcctcagg catttacaag tgcccaaaca    600
cagcaccctg tcacacgttt gagtactact cccgacacc agccagccct tgc            653

<210> SEQ ID NO 126
<211> LENGTH: 649
<212> TYPE: DNA
<213> ORGANISM: Mus musculus

<400> SEQUENCE: 126
tttttttttt ttcccaaatg tgtcatagat ttattgaaaa tgattgtaga aaccccaacc     60
cccaacatgg atcaggaact ggatgacaga ggaaaggggt ggaagcaggc tcaagacttc    120
cttattcttt gaagagttga accaaaccaa gggtagatag aggagaaatc tagagaggaa    180
gactgacctc tcagccaggg agccataatg acagcactgg ggccaggctg gcacaaaaa     240 gtactgctgc atggggcaca gtcccagatg tcataaagga agcataaaac ttcaccacgt    300
cctcattcgg attgccctgg gttgagtcaa accacatttg gatgcagcgg ccactccctc    360
tgctgtagtt gctgaccttg taggagtgac tccagagacc ctcgcaaagg ctggctggtg    420
tcgggaagta gtactcaaac gtgtgacagg gtgctgtgtt tgggcacttg ttaatgcctg    480
aggaccagtc ccagccttta tgccagtctc tcttgcaggt aaaggaggta cgacaggctt    540
cccaccactg gtgacagtcc tttttgcata agggcaccat ccagaaaacg ctctttacgc    600
caactcttgt tccacttgct gatccaaagg ccaaagttgg gggagcact               649

<210> SEQ ID NO 127
<211> LENGTH: 668
<212> TYPE: DNA
<213> ORGANISM: chicken

<400> SEQUENCE: 127
cagcctcttg cacacagctt tactctgtca gccccagggt ggaaacaaag ggctggctgt     60
tcatcacact gcactttgtg taatcactcg ctctcacaac tggcaaatct cttttgccag    120
tggtgggact gaataacatt ttaaagggat gaagtacagc acagagctgt acaagatagt    180
ggatgactgc agactttttc ataattttgt accatttcta aaaagtgat gtttctcaaa     240 ttactacaag ttgattttaa ctccattctt tttaaaatgt gattgatgtg tgtttctcat    300
tttacacaca gatgtatgca aatgggaccg acatgtgcca gagtatgtgg ggggaatcct    360
ttaaggtgag cgaatcctcc tgcctctgct tgcaaatgaa caagaaggac atggtggcaa    420
tcaagcacct cctctccgaa agctcagagg aaagctccag tatgagcagc agtgaggagc    480
acgcctgcca aaagaaactc ctgaagtttg aggcactgca gcaagaggaa ggggaagaga    540
gaagatgaat tttggtggat gaatatcagg aggagaggaa tcattgtgga ggttgtgctc    600
ggggcatcac agcagcctgt cttatccctc acttctgaga acacaataaa tcaatggttg    660
```

```
gctatatt                                                              668

<210> SEQ ID NO 128
<211> LENGTH: 3632
<212> TYPE: DNA
<213> ORGANISM: chicken

<400> SEQUENCE: 128
acaagcagat taatttcatt agcacgcatc accatatata ataaagctgt aataggccaa     60
atgctccaat ttacacttgt gaaactccgt ctcactccag ccacactgtt gttacacttt    120
catgatgcca aggagggaaa cagatctggc agctgtcaca agttggaagt acaacaatt     180
tttcccttca ccactacagc tttgcagagt taacaaaaat ataaaaccag aaaagcttac    240
ttcagtcatt agagagatct gcctcactaa aaagggatca ctgtgttgag ttaggagatg    300
tcagtttgac atagatacta actcaatggc cagaagctgt gaagttagca actagctgga    360
gttcttgtat ctcttttgca ttttttccc tcattaccca atggtagctc ttgcagaagg     420
aattcatgca ggcaggtagc ggctcctgag agctcaaata gctgcgtctg tgatttcgga    480
ataaatacat ccttctgcta acatcgctgg ccattatcag atagtcagat gataatgtaa    540
taataataat gtacccgtgc cagaattact gtctgtggca atatctgtaa catcatgcat    600
gctttaacgc tgtataaaaa ctttgagaag atgaatataa gttcatagg caatgatatt     660
aatgttaaaa ataaatgata acaggagttt tatcagtaca aaaatatgag cgagtacttg    720
caaataaatt cagcattaac aaatgaggtt aacaacccat tcaagtattg aaagcaataa    780
gaaacattct ttaataaatt tctcaatata agacttacgg tcttatactg agacttttct    840
tactcagaat aagaaaaaga agactcaaga tgatgaagat gtgtggctga atctctaga    900
agctcctgtg cttgagcctg cctacatcta ttgttaacca aagccaagtc tgagaaatca    960
caaacatatg acaattttcc ttcctgctgt tagaaattct gcctaatctc ccagcaagtg   1020
gtcccatttg gctcatattc aaagcttgaa aaagatccca gtctcctata gcttaatata   1080
atttgtatgt caattccata acaaaggca ttacatgaaa cctcctggct cctaacacct    1140
ttacaagagt gaatacattt catacaaacc aagcagtaag gaacagaaca cgtgctttt    1200
caccaggctg gctagcacag ccactcatcc tcagattgaa agggatgtt tatgtggcac     1260
agtggtcttt actttgtatg aatacactga tcttagtacc aagcaatatg cacaagtcct   1320
ttacactaca aatcagcaag aagctccatt aatttcagcc agcacaaaat caagccacat   1380
gaagtgaagg cacaggcaat aaggtcttac atttacttca gtttctccta tacttatatt   1440
atgtctcttt gtatttgttt taattaaatt cactctggaa agcagaaaac actagggttt   1500
caaatgatct gaaaatggtc ttgtaaaggc agcagcactt ttgcctcaag gaaggcttca   1560
gccagagcag gaattggtgc ttacagctca gcagagatca ttatcatact gtgagtttgc   1620
tcagtgagat tcattccaca cttccactgt gccagtgttt gttttattca agcaaaaaag   1680
ttttgtaaat actgacccac agttactatt tgacaaacca ctgttgtgtt ttaaaataga   1740
aacaagagat gctattttcc atttgcatct gaataattgc aaagtagtca gtggcgtgtt   1800
gctagttagg gagctcactg ggatttgacc tatggaagta agtgcaccta tttgtaatga   1860
ccacgtctgc tttctgtgat ggtccatgtt cagatgtgga atccctctg cagaaagcac    1920
acctggtaag gaaatccagt cagcaactgc tgtcagtggt actcgcaaca gtttctccta   1980
gtgtttgtga caccccttgga aagcacaaac atggcaggta gagaaagaag acaaacatc    2040
agcaggttaa aaaaagaatc ttctgggcaa agagcaaagg cctgagaatc aggagaccaa   2100
```

```
ttctccttca ggggctgcag taaaattact gagtaaccca aagcaaactg atatgtttac    2160
ggtcaaaatt aagccagaca ggttgaaata tgaagagttg tttgaaatgt ctataattca    2220
gtgaagttgg tgataagaac ccaattaagc tgttgtagaa atgaatctaa taattataac    2280
aaaaggaatc attgcaaaat caggcagggg gtgggaggta gttgtattgg gtacactgga    2340
gagctgttgt ttttctaatt ctagtctatg tttgtacttt cctgtttatt atgtccacat    2400
ttgcaagcaa taaagggca ttatgtgctg gtcattccat ctgcttttga gataaatcta    2460
tgttagcatt tcaaagggtc aaggaactct ccagggcaaa caaattctgg agcgctgctg    2520
ccagatggcg cgtatataaa gtggaaagcg agaaaagcaa tttgctgtgt ttctgttcca    2580
gggagaagtc tcacccagaa ggacagcaaa agaggtgaga aactaccgag aaattgtaca    2640
ggcggttttc ttctgtaaca tgttgctttc tttgcatctg aaaagtttag gtacggagag    2700
aagctcagtt cttgttcagg caaagctctt ccaaaaaggt atcaggaata tttaaccaaa    2760
gaattgaagg ttaagttaat aacacctata aagaattatg cacttcttta tgtgggaggt    2820
tctagattta tctgtataac tcactaatat gtagtctgta cttacagaaa ctctatgctc    2880
gcagaccaaa tggtggttat cttgcatatt tgactgaact ctacaaaagc agacacaaaa    2940
ccattgatca gattattagg ttcaaataag cgtgacctca acaaaggcaa gttatctgca    3000
taatttatcc agctcaattg ccaccttatg ctctgctatt agcttgtcaa ttctgtaaac    3060
agaagcactg caattaaatg ggtaatttcc cagcacacaa aagaactctg taagtttcgg    3120
agctgatcaa tcttgccttc aaatctagtg tagcagtggg atgggaaatc catatctgca    3180
tgagaaattt aaaaaccttt tgttaaatac tgaaaaccat aacatatagc cttcattctt    3240
catatagcct gtattcttca taggtcacca gaaactgaaa atatgtagca gaagcattaa    3300
gtgtttggac atgagcaaag gaaagggaga atgagtgacc caatatttat atgcgtacct    3360
ctcttgagca tatttaattg tatatatatg tagctttttt acagcagccc ttcttttttac    3420 tatcaggact tttcctacaa ataaaggata tcagtaaaga cttctctccg cacaggaaaa    3480
gaagggaaca acaatgctga ggtttgccat caccctcttt gctgtcatca catcatctac    3540
ctgccagcag tatggatgtc tggaagggga cacccacaaa gcgaatccaa gtcctgagcc    3600
aaacatgcat gaatgcactc tgtattctga at                                 3632
```

<210> SEQ ID NO 129
<211> LENGTH: 713
<212> TYPE: DNA
<213> ORGANISM: Mus musculus

<400> SEQUENCE: 129

```
tttccccagt cagctggctg atctggaagt ataaacaaga aaggaggctg acggctctag      60
aagtccccaa cctgttgtga tcttcagtag acaaacactc tggtgtgtc acaggattca     120 ggccactaaa cctcggccgg ctgtctcctg gaatgaagaa agcaaaggaa gcctagagtg     180
gagacaaaga aacccgaggc actctgagag ctgccatctt atccttgttt gccgcctgac     240
acttctcagc aggatccaca taccctaagg agtggaagac tccttggcgc ttggtgcttc     300
aaccggactg acttcctggg cctggagttg gcgattagag gtctgacatg gctcacctga     360
tgactgtgca gttgttgctc ctggtgatgt ggatggccga atgtgctcag tccagagcta     420
ctcgggccag gactgaactt ctcaatgtct gcatggatgc catacaccac agagaaaaac     480
cgggccctga tgacaattta cacgaccagt gcagcctctg gaaacgaatt cctgctgttc     540
```

```
cacgaacact agccatgaag cacataagga catgtcctac ctgttccaga tcaactggaa    600
ccactgcggg actatgacat cggaatgcag actgcactgt atgcaagaca cctgcctcta    660
tgagtgtaca cagaacttgg gacgctggat tcatctagtg aaccaaagct ggc           713

<210> SEQ ID NO 130
<211> LENGTH: 444
<212> TYPE: DNA
<213> ORGANISM: Mus musculus

<400> SEQUENCE: 130
cacctgatga ctgtgcagtt gttgctcctg gtgatgtgga tggccgaatg tgctcagtcc     60
agagctactc gggccaggac tgaacttctc aatgtctgca tggatgccaa acaccacaaa    120
gaaaaaccgg gccctgagga caatttacac gaccagtgca gccctggaa gacgaattcc     180 tgctgttcca cgaacacaag ccaggaagca cataaggaca tttcctacct gtaccggttc    240
aactggaacc actgcggaac tatgacatcg gaatgcaaac ggcactttat ccaagacacc    300
tgcctctatg agtgttcccc gaacttggga ccctggatcc agcaggtgga ccagagctgg    360
cgcaaagagc ggatccttga tgttcccctg tgcaagagg actgtcagca gtggtgggag    420
gactgccaga gctcttttac ctgc                                           444

<210> SEQ ID NO 131
<211> LENGTH: 286
<212> TYPE: DNA
<213> ORGANISM: Mus musculus
<220> FEATURE:
<221> NAME/KEY: modified_base
<222> LOCATION: (263)
<223> OTHER INFORMATION: N = A, C, G, or T/U

<400> SEQUENCE: 131
caacaaccca ttcaaacatc taccctatca actttcaata atagtcacca tacctaccat     60
aataaccacg aataacaaaa aatcataatt caattccaaa taagaatcct aagaaactac    120
taccacatcc aaataataca gcatacactc aaattaccca ctcccgaccc aagaaaattt    180
aacgaaaaat aacaatacaa tactctttcg aagccctata attaaaataa atccacttta    240
aatcctttaa cgaagatcca ttngagaaca attctgctga tatcac                   286

<210> SEQ ID NO 132
<211> LENGTH: 590
<212> TYPE: DNA
<213> ORGANISM: Homo sapiens
<220> FEATURE:
<221> NAME/KEY: modified_base
<222> LOCATION: (18)..(577)
<223> OTHER INFORMATION: N = A, C, G, or T/U

<400> SEQUENCE: 132
aagattatgc ctcccccnaa ttcggcacga ngcggggagc gagcggnccc cctccctgtc     60
cgtctcctgg tcggggtcct tttttaataa cgcgtaaacc tatccaangg tacacaacga    120
agaagcttgg acaaaaggcg gaaaagcgtc ttgccaaaag ggggactgga ngtnaactgg    180
aaaaaaacta attttccaag agaagaactt ggnagaangg ggaattgngt ttcngggtg     240 nccttctcgn tctccggggn cgnanttctg natncgcaac aagcaaggac caatccaatc    300
ccgggnacgc gggcggnccc anccgcgaag nttttcannc ccganaatcc aaacaatcct    360
ggccnaagaa atatgccctt gngtaacaaa ccntcccaat ttttttaata tatcccaaan    420
tnttattatt aaaacaaatg ctnaaanccc tccactcccn nanggttaaa naaatggggt    480
```

```
ccnnttggca ccaactttaa tgggangttt gggnttanaa anaaacaccc cttccntttt    540
cccggggngc gttatttggg gnngcacccc ccccgcnctt taattttgtt              590
```

<210> SEQ ID NO 133
<211> LENGTH: 247
<212> TYPE: DNA
<213> ORGANISM: Mus musculus

<400> SEQUENCE: 133

```
atgggaatat cccccataca atagtacttc ttgtgcccaa tctggcccca gtgccgtcat    60
tatgggtccc tgcgtgagag gtcatttttct tctttagatt tttcctctat ttacccttgg   120
tctggttcaa ttcttcaaag aataaggaag ttttgagcct gcttccaccc ctttcttctt   180
tcatccagtt cctgatccat gttgggggtt ggggtttcta caatcatttt caataaatct   240
atgacac                                                             247
```

<210> SEQ ID NO 134
<211> LENGTH: 665
<212> TYPE: DNA
<213> ORGANISM: Pseudopleuronectes americanus
<220> FEATURE:
<221> NAME/KEY: modified_base
<222> LOCATION: (40)   (596)
<223> OTHER INFORMATION: N = A, C, G, or T/U

<400> SEQUENCE: 134

```
gaattcggca cgagccagta gcatatgctt gtctcaaagn ttaagccatg caagtctaag    60
tacacacggc cggtacagtg aaactgcgaa tggctcatta aatcagttat ggttcctttg   120
atcgctctca cgttacttgg ataactgtgg caattccaga gctaatacat gccaacgggc   180
gctgacctcc ggggacgcgt gcatttatca gacccaaaac ccatgcgggg tgctcctcac   240
ggggtgcccc ggccgctttg gtgactctag ataacctcga gctgatcgct ggccctcgtg   300
gcggcgacgt ctcattcgaa tgtctgccct atcaactttc gatggtactt tttgtgccta   360
ccatggtgac cacgggtaac ggggaatcag ggttcgattc cggagaggga gcctgagaaa   420
cggctaccac atccaaggaa ggcagcaggc gcgcaaatta cccactcccg actcggggag   480
gtagtgacga aaaataacaa tacaggactc tttcgaggcc ctgtaattgg aatgagtaca   540
cttttaaatc tttaacgaag atccattgga gggcaagtct ggtgccagca gccgcnggta   600
attcagctcc aatagcgtat cttaaagttg ctgcaattaa aaagctccgt attggacctc   660
ggatc                                                               665
```

<210> SEQ ID NO 135
<211> LENGTH: 666
<212> TYPE: DNA
<213> ORGANISM: Pseudopleuronectes americanus

<400> SEQUENCE: 135

```
gaattcggca cgagcagtag catatgcttg tctcaaagat taagccatgc aagtctaagt    60
acacacggcc ggtacagtga aactgcgaat ggctcattaa atcagttatg gttcctttga   120
tcgctctcac gttacttgga taactgtggc aattccagac taatacatgc caacgggcg    180 ctgacctccg gggacgcgtg catttatcag acccaaaacc catgcggggt gctcctcacg   240
gggtgccccg gccgctttgg tgactctaga taacctcgag ctgatcgctg gccctcgtgg   300
cggcgacgtc tcattcgaat gtctgcccta tcaactttcg atggtactt tttgtgcctac    360
```

```
catggtgacc acgggtaacg gggaatcagg gttcgattcc ggagagggag cctgagaaac    420
ggctaccaca tccaaggaag gcagcaggcg cgcaaattac ccactcccga ctcggggagg    480
tagtgacgaa aaataacaat acaggactct ttcgaggccc tgtaattgga atgagtacac    540
tttaaatcct ttaacgagga tccattggaa ggcaagtctg gtgccagcag ccgcggtaat    600
tccagctcca atagcgtatc ttaaagttgc tgcagttcaa caagcctcgt attggacctc    660
ggattc                                                              666
```

<210> SEQ ID NO 136
<211> LENGTH: 645
<212> TYPE: DNA
<213> ORGANISM: Pseudopleuronectes americanus
<220> FEATURE:
<221> NAME/KEY: modified_base
<222> LOCATION: (508)..(569)
<223> OTHER INFORMATION: N = A, C, G or T/U

<400> SEQUENCE: 136

```
gaattcggca cgaggcggta ttcaggcgac cgggcctgct ttgaacactc taattttttc     60
aaagtaaacg cttcggaccc cgcgggacac tcagctaaga gcatcgaggg ggcgccgaga    120
ggcaggggct gggacagacg gtagctcgcc tcgcggcgga ccgtcagctc gatcccgagg    180
tccaactacg agcttttaa  ctgcagcaac tttaagatac gctattggag ctggaattac    240
cgcggctgct ggcaccagac ttgccctcca atggatcctc gttaaaggat ttaaagtgta    300
ctcattccaa ttacagggcc tcgaaagagt cctgtattgt tattttcgt cactacctcc     360 ccgagtcggg agtgggtaat ttgcgcgcct gctgccttcc ttggatgtgg tagccgtttc    420
tcaggctccc tctccggaat cgaaccctga ttccccgtta cccgtggtca ccatggtagg    480
cacaaaaagt accatcgaaa gttgatangg cagacattcg aatgacgt  cccgccacga    540 aggccagcga tcagctcgag gttatctana gtcaccacag cggccggggc cacccgttga    600
ggaaccaccg ccgcattggg ggttttgggt ctgaataaat tgcac                   645
```

<210> SEQ ID NO 137
<211> LENGTH: 542
<212> TYPE: DNA
<213> ORGANISM: Pseudopleuronectes americanus
<220> FEATURE:
<221> NAME/KEY: modified_base
<222> LOCATION: (18)..(504)
<223> OTHER INFORMATION: N = A, C, G, or T/U

<400> SEQUENCE: 137

```
gaattcggca cgaggctnga cctccgggga cgcgtgcatt tatcagaccc aaaacccatg     60
cggggtgctc ctcacggggt gccccggccg ctttggtgac tctagataac ctcgagctga    120
tcgctggccc tcgtggcggc gacgtctcat tcgaatgtct gccctatcaa ctttcgatgg    180 tacttttgt  gcctaccatg gtgaccacgg gtaacgggga atcagggttc gattccggag    240
agggagcctg agaacggct accacatcca aggaaggcag caggcgcgca aattacccac    300
tcccgactcg gggaggtagt gacgaaaaat aacaatacag gactctttcg aggccctgta    360
attggaatga gtacacttta aatcctttaa cnaggatcca ttggagggca agtctggtgc    420
catcagccgc ggtaattcca gctccaatan cgtatcttaa agttgctgc  acttaaaaag    480 ctcntanttg gacctcggga tccnagctga cggtccgccg ctaagcgaac ttaccgtctg    540
tc                                                                  542
```

-continued

```
<210> SEQ ID NO 138
<211> LENGTH: 650
<212> TYPE: DNA
<213> ORGANISM: Pseudopleuronectes americanus
<220> FEATURE:
<221> NAME/KEY: modified_base
<222> LOCATION: (626)
<223> OTHER INFORMATION: N = A, C, G or T/U

<400> SEQUENCE: 138
gaattcggca cgagcagtag catatgcttg tctcaaagat taagccatgc aagtctaagt      60
acacacggcc ggtacagtga aactgcgaat ggctcattaa atcagttatg gttcctttga     120
tcgctctcac gttacttgga taactgtggc aattccagag ctaatacatg ccaacgggcg     180
ctgacctccg gggacgcgtg catttatcag acccaaaacc catgcggggt gctcctcacg     240
gggtgccccg gccgctttgg tgactctaga taacctcgag ctgatcgctg ccctcgtgg     300 cggcgacgtc tcattcgaat gtctgcccta tcaactttcg atggtacttt tgtgcctac     360 catggtgacc acgggtaacg gggaatcagg gttcgattcc ggagagggag cctgagaaac     420
ggctaccaca tccaaggaag gcagcaggcg cgcaaattac ccactcccga ctcggggagg     480
tagtgacgaa aaataacaat acaggactct ttcgaggccc tgtaattgga atgagtacac     540
tttaaatcct ttaacgagga tccattggag ggcaagtctg gtgccagcag ccgccggtaa     600
ttccagctcc atagcgtatc ttaaanttgc ctgccagtta ataagcctc                 650

<210> SEQ ID NO 139
<211> LENGTH: 709
<212> TYPE: DNA
<213> ORGANISM: Pseudopleuronectes americanus

<400> SEQUENCE: 139
gaattcggca cgagtggccg tccctcttaa tcatggcccc agttcagaga agaaaaccca      60
caaaatagaa ccggagtcct attccattat tcctagctgc ggtattcagg cgaccgggcc     120
tgctttgaac actctaattt tttcaaagta aacgcttcgg accccgcggg acactcagct     180
aagagcatcg agggggcgcc gagaggcagg ggctgggaca gacggtagct cgcctcgcgg     240
cggaccgtca gctcgatccc gaggtccaac tacgagcttt ttaactgcag caactttaag     300
atacgctatt ggagctggaa ttaccgcggc tgctggcacc agacttgccc tccaatggat     360
cctcgttaaa ggatttaaag tgtactcatt ccaattacag ggcctcgaaa gagtcctgta     420
ttgttatttt tcgtcactac ctccccgagt cgggagtggg taatttgcgc gcctgctgcc     480
ttccttggat gtggtagccg tttctcaggc tccctctccg gaatcgaacc ctgattcccc     540
gttacccgtg gtcaccatgg taggcacaaa aagtaccatc gaaagttgat agggcagaca     600
ttccgaatga gacgtcgccg ccaccgaggg ccagcggatc tagctcgagg ttatctagag     660
tcaccaaaag ccggccgggg caccccgtga ggaacacccc gccattggg                  709

<210> SEQ ID NO 140
<211> LENGTH: 679
<212> TYPE: DNA
<213> ORGANISM: Pseudopleuronectes americanus

<400> SEQUENCE: 140
gaattcggca cgaggtcagc tcgatcccga ggtccaacta cgagcttttt aactgcagca      60
actttaagat acgctattgg agctggaatt accgcggctg ctggcaccag acttgccctc     120
caatggatcc tcgttaaagg atttaaagtg tactcattcc aattacaggg cctcgaaaga     180
```

```
gtcctgtatt gttattttc gtcactacct ccccgagtcg ggagtgggta atttgcgcgc    240
ctgctgcctt ccttggatgt ggtagccgtt tctcaggctc cctctccgga atcgaaccct    300
gattccccgt tacccgtggt caccatggta ggcacaaaaa gtaccatcga aagttgatag    360
ggcagacatt cgaatgagac gtcgccgcca cgagggccag cgatcagctc gaggttatct    420
agagtcacca aagcggccgg ggcaccccgt gaggagcacc ccgcatgggt tttgggtctg    480
ataaatgcac gcgtcccgg  aggtcagcgc ccgttggcat gtattagctc tggaattgcc    540
acagttatcc aagtaacgtg agagcgatca aaggaaccat aactgattta atgagccatt    600
cgcagtttca ctgtaccggc cgtgtgtatt agacttgcat ggcttaatct ttgagacaag    660
catatctcgt gccgaattc                                                 679
```

```
<210> SEQ ID NO 141
<211> LENGTH: 611
<212> TYPE: DNA
<213> ORGANISM: Pseudopleuronectes americanus

<400> SEQUENCE: 141
gaattcggca cgaggcccta tcaactttcg atggtacttt ttgtgcctac catggtgacc     60
acgggtaacg gggaatcagg gttcgattcc ggagagggag cctgagaaac ggctaccaca    120
tccaaggaag gcagcaggcg cgcaaattac ccactcccga ctcggggagg tagtgacgaa    180
aaataacaat acaggactct ttcgaggccc tgtaattgga atgagtacac tttaaatcct    240
ttaacgagga tccattggag ggcaagtctg gtgccagcag ccgcggtaat tccagctcca    300
atagcgtatc ttaaagttgc tgcagttaaa aagctcgtag ttggacctcg ggatcgagct    360
gacggtccgc cgcgaggcga gctaccgtct gtcccagccc ctgcctctcg gcgccccctc    420
gatgctctta gctgagtgtc ccgcggggtc cgaaacgttt actttgaaaa aattagagtg    480
ttcaaagcag gcccggtcgc ctgaataccg catctaggaa taatggaata ggactccggt    540
tctattttgt gggttttctt ctctgaactg gggccatgat taagaaggac ggccgggctc    600
gtgccgaatt c                                                         611
```

```
<210> SEQ ID NO 142
<211> LENGTH: 476
<212> TYPE: DNA
<213> ORGANISM: Pseudopleuronectes americanus
<220> FEATURE:
<221> NAME/KEY: modified_base
<222> LOCATION: (335)
<223> OTHER INFORMATION: N = A, C, G, or T/U

<400> SEQUENCE: 142
gaattcggca cgaggtgccc ttccgtcaat tcctttaagt ttcagctttg caaccatact     60 cccccccggaa cccaaagact ttggtttccc ggacgctgcc cggcgggtca tgggaataac    120
gccgccggat cgctagttgg catcgtttac ggtcggaact acgacggtat ctgatcgtct    180
tcgaacctcc gactttcgtt cttgattaat gaaaacattc ttggcaaatg ctttcgcttt    240
cgtccgtctt gcgccggtcc aagaatttca cctctagcgg cacaatacga atgcccccgg    300
ccgtccctct taatcatggc cccagttcag agaanaaaac ccacaaaata gaaccggagt    360
cctattccat tattcctagc tgcggtattc aggcgaccgg gcctgctttg aacactctaa    420
ttttttcaaa gtaaacgctt cggaccccgc gggacactca gcctcgtgcc gaattc         476
```

```
<210> SEQ ID NO 143
<211> LENGTH: 740
```

<212> TYPE: DNA
<213> ORGANISM: Pseudopleuronectes americanus
<220> FEATURE:
<221> NAME/KEY: modified_base
<222> LOCATION: (526)
<223> OTHER INFORMATION: N = A, C, G or T/U

<400> SEQUENCE: 143

```
gaattcggca cgaggctgcg gtattcaggc gaccgggcct gctttgaaca ctctaatttt      60
ttcaaagtaa acgcttcgga ccccgcggga cactcagcta agagcatcga ggggggcggaa    120
ttcggcacga gctgggacag acggtagctc gcctcgcggc ggaccgtcag ctcgatcccg    180
aggtccaact acgagctttt taactgcagc aactttaaga tacgctattg gagctggaat    240
taccgcggct gctggcacca gacttgccct ccaatggatc ctcgttaaag gatttaaagt    300
gtactcattc caattacagg gcctcgaaag agtcctgtat tgttattttt cgtcactacc    360
tccccgagtc gggagtgggt aatttgcgcg cctgctgcct tccttggatg tggtagccgt    420
ttctcaggct ccctctccgg aatcgaaccc tgattcccg ttacccgtgg tcaccatggt      480
aggcacaaaa agtaccatcg aaagttgata gggcagacat tcgaangaga cgtcgccgcc    540
acgagggcca gcgatcagct cgaggttatc tagagtcacc aaagcggccg ggcaccccg    600
tgaggagcac cccgcatggg ttttgggtct gataaatgca cgcgctctct ctctctctct    660
ctctctctct ctctctctct ctctctctct ctctctctct ctctctctct ctctctctct    720
ctctccctcg tgccgaattc                                                 740
```

<210> SEQ ID NO 144
<211> LENGTH: 334
<212> TYPE: DNA
<213> ORGANISM: Pseudopleuronectes americanus

<400> SEQUENCE: 144

```
gaattcggca cgaggctgcg gtattcaggc gaccgggcct gctttgaaca ctctaatttt      60
ttcaaagtaa acgcttcgga ccccgcggga cactcagcta agagcatcga ggggggcgccg   120
agaggcaggg gctgggacag acggtagctc gcctcgcggc ggaccgtcag ctcgatcccg    180
aggtccaact acgagctttt taactgcagc aactttaaga tacgctattg gagctggaat    240
taccgcggct gctggcacca gacttgccct ccaatggatc ctcgttaaag gatttaaagt    300
gtactcattc caattacagg gcctcgaaag agtc                                 334
```

<210> SEQ ID NO 145
<211> LENGTH: 542
<212> TYPE: DNA
<213> ORGANISM: Pseudopleuronectes americanus
<220> FEATURE:
<221> NAME/KEY: modified_base
<222> LOCATION: (516)..(521)
<223> OTHER INFORMATION: N = A, C, G, or T/U

<400> SEQUENCE: 145

```
gaattcggca cgagtacttg gataactgtg gcaattccag agctaataca tgccaacggg      60
cgctgacctc cggggacgcg tgcatttatc agacccaaaa cccatgcggg gtgctcctca    120
cggggtgccc cggccgcttt ggtgactcta gataacctcg agctgatcgc tggccctcgt    180
ggcggcgacg tctcattcga atgtctgccc tatcaacttt cgatggtact ttttgtgcct    240
accatggtga ccacgggtaa cggggaatca gggttcgatt ccggagaggg agcctgagaa    300
acggctacca catccaagga aggcagcagg cgcgcaaatt acccactccc gactcgggga    360
```

```
ggtagtgacg aaaaataaca atacaggact ctttcgaggc cctgtaattg gaatgagtac    420
actttaaatc ctttaacgag gatccattgg agggcaagtc tggtgccagc agccgcggta    480
attccagctc caatagcgta tcttaaagtt gcctcntgcc naatcctgca gccggggat    540 cc                                                                    542

<210> SEQ ID NO 146
<211> LENGTH: 532
<212> TYPE: DNA
<213> ORGANISM: Pseudopleuronectes americanus

<400> SEQUENCE: 146
cgtccgtctt gggccggtcc aagaatttca cctctagcgg cacaatacga atgccccgg     60 ccgtccctct taatcatggc cccagttcag agaagaaaac ccacaaaata gaaccggagt    120
cctattccat tattcctagc tgcggtattc aggcgaccgg gcctgctttg aacactctaa    180 tttttttcaaa gtaaacgctt cggaccccgc gggacactca gctaagagca tcgaggggggc   240 gccgagaggc aggggctggg acagacgtta gctcgcctcg cggcggaccg tcagctcgat   300
cccgaggtcc aactacgagc tttttaactg cagcaactt aagatacgct attggagctg    360
gaattaccgc ggctgctggc accagacttg ccctccaatg gatcctcgtt aaaggattta    420
aagtgtactc attccaatta cagggcctcg aaagagtcct gtattgttat ttttcgtcac    480
tacctccccg agtcgggagt gggtaatttg cgcgcctgct gccttccttg ga           532

<210> SEQ ID NO 147
<211> LENGTH: 1135
<212> TYPE: DNA
<213> ORGANISM: Cricetulus griseus

<400> SEQUENCE: 147
gggcggcgac ggtttcctgg tggccgcgcg ctgctctgtg agcggcgggt ggcagacgga     60
cctgggccct cacccccagac gcaccgcgga tctggcatgg ctcacctgat gacaatgcag   120
ttgctgctcc tgctgatatg ggtatctgag tgtgcccaat caagagctac tcgggccaga    180
actgaactgc tcaatgtttg catggatgca aagcaccaca agaaaaagcc aggccctgag    240
gacaatttac acaaccagtg cagtccctgg aagaagaatt cctgctgttc caccaacaca    300
agccaggaag cccacgagga catttcctac ctgtaccgat caactgggaa ccactgtgga    360
aagatgacat tgaatgcaa gcgacacttt atccaggata cctgtctcta tgagtgttct     420
cctaacttgg gaccctggat tcagcaggtg gaccagagct ggcgaaaaga gcgaatcctt    480
gatgttcctc tgtgcaaaga ggactgtcag cgatggtggg aggactgccg cacctctttc    540
acctgcaaga gcaactggca aaggggtgg aactggacct cggggtataa ccagtgccct    600
gtgggagcct cctgtcgcca cttcgacttc tatttcccta cacctgctgc tctgtgtgag    660
gaaatctgga gtcactccta caaactcagt aactacagcc gagggagtgg ccgctgtatc    720
cagatgtggt tcgacccagc ccaaggcaac cccaacgagg aagtggcaag gttctatgct    780
gaggccatga gtggagctgg gcttcacggg gcctggccac taatgtgcag cctgtctta    840 gtgctgctct gggtgttcag ccgagttcct ttaaccttct gatccccagg aactccctgc    900
cgggcttaga ctcccagctc ccaacctcct ttgtggtggg gcctctgaca ggcattcaat    960
atctctctta tgaattattt gggtgtgaat gggaatataa ttattttgca tcctacttac   1020
cactgattga agttgtttaa acttggttag ttccctgctc taacacttac tgtgggcaag   1080
ttaaataaac ttaattttcc tgtgctgttc cacaaaaaaa aaaaaaaaaa aaaaa        1135
```

<210> SEQ ID NO 148
<211> LENGTH: 70
<212> TYPE: DNA
<213> ORGANISM: Mus musculus

<400> SEQUENCE: 148

```
atcggacgcc ccccgtgtcg gtgacgaccc attcgaacgt ctgccctatc aactttcgat      60
ggtagtcgct                                                              70
```

<210> SEQ ID NO 149
<211> LENGTH: 470
<212> TYPE: DNA
<213> ORGANISM: Mus musculus

<400> SEQUENCE: 149

```
gtggacgaag actgtagaga ctacccagag tctgacctag ggagaggcca actcggatac      60
ccctatgtgc gctcccagaa gctaaggaca ttgagacaga aagacatggc ctggaaacag     120
acaccactct tgcttttggt ctacatggtc acaacaggca gtggcgggac agaacagacc     180
tactcaacgt ttgcatggat gccaaacacc ataagacaaa gccggcccc gaggacaagc     240 tgcatgacca gtgtagtcca tggaagaaaa atgcctgttg ctcagtcaac accagccagg     300
agctacacaa ggctgactcc cgtctgtact tcaactggga tcactgtggc aagatggagc     360
ctgcctgtaa gagtcacttc atccaagact cctgcctgta tgagtgctcc ccaaccttgg     420
ccttggatca gcaagtggac agagttggcg taagagcgtt ctggatgtgc                 470
```

<210> SEQ ID NO 150
<211> LENGTH: 387
<212> TYPE: DNA
<213> ORGANISM: Mus musculus

<400> SEQUENCE: 150

```
gagaattagg gttcgattcc ggagagggag cctgagaaac ggctaccaca tccaaggaag      60
gcagcaggcg cgcaaattac ccaatcctga cacggggagg tagtgacaat aaataacaat     120
accgggctct tcgagtctgg taattggaat gagtacaatc taaatccctt aacgaggatc     180
cattggaggg caagtctggt gccagcagcc gcggtaattc cagctccaat agcgtatatt     240
taagttgttg cagttaaaaa gctcgtagtt gctgtcttta ggggactctc actctcctgc     300
ttgtcgttgt gttcttaagg tcttgtcttt attgccggtt gatgtactgc tagtcgtaat     360
tgctctcatt tgccctgtcg tttccgt                                         387
```

<210> SEQ ID NO 151
<211> LENGTH: 22
<212> TYPE: DNA
<213> ORGANISM: Mus musculus

<400> SEQUENCE: 151

```
cgccgtgcct accatggtga cc                                               22
```

<210> SEQ ID NO 152
<211> LENGTH: 46
<212> TYPE: DNA
<213> ORGANISM: Homo sapiens

<400> SEQUENCE: 152

```
gggccccgcg ggacactcag ctaaaagcat cgaggggggcg ccgaga                    46
```

<210> SEQ ID NO 153
<211> LENGTH: 635
<212> TYPE: DNA
<213> ORGANISM: Gossypium hirsutum
<220> FEATURE:
<221> NAME/KEY: modified_base
<222> LOCATION: (565)
<223> OTHER INFORMATION: N = A, C, G, or T/U

<400> SEQUENCE: 153

```
ctaaatccct taacgaggat ccattggagg gcaagtctgg tgccagcagc cgcggtaatt      60
ccagctccaa tagcgtatat ttaagttgtt gcagttaaaa agctcgtagt tggacttagg     120
ggtgggtcgg ccggtccgcc tcacggtgag caccggtctg ctcgtcccta ctgccggcga     180
tgcgctcctg gccttaattg gccgggtcgt tcctccggcg ctgttacttt gaagaaatta     240
gagtgctcaa agcaggccta cgcttgtata cattagcatg gataacatc ataggatttc      300
gatcctattg tgttggcctt cgggatcgga gtaatgatta acaggacag tcgggggcat      360
tcgtatttca tagtcagagg tgaaattctt ggatttatga aagacgaaca actgcgatag     420
catttgccaa ggatgttttc attaatcaag aacgaaagtt gggggctcga aaacgatcag     480
ataccgtcct agtctcaacc ataaatctcc tccagttccg gaaccacatc ctccgccagt     540
tccagtctat aagaaaacac atccnactcc agttccagta tacaagatac catgtcctcc     600
ccagttccag tctataaatc tcctccggtt ccatt                                635
```

<210> SEQ ID NO 154
<211> LENGTH: 584
<212> TYPE: DNA
<213> ORGANISM: Gossypium hirsutum
<220> FEATURE:
<221> NAME/KEY: modified_base
<222> LOCATION: (389) (513)
<223> OTHER INFORMATION: N = A, C, G, or T/U

<400> SEQUENCE: 154

```
ggataaccgt agtaattcta gagctaatac gtgcaacaaa ccccgacttc tggaagggat      60
gcatttatta aataaaaggt cgacgcgggc tttgcccgtt gctctgatga ttcatgataa     120
ctcgacggat cgcacggcct ttgtgccggc gacgcatcat tcaaatttct gccctatcaa     180
ctttcgatgg taggatagtg gcctactatg gtggtgacgg gtgacggaga attagggttc     240
gattccggag agggagcctg agaaacggct accacatcca aggaaggcag caggcgcgca     300
aattacccaa tcctgacacg gggaggtatt gacaataaat aacaataccg ggctctatga     360
gtctggtaat tggaatgagt acaatctana tcccttaacg aagatccatt ggagggcaat     420
tctggtgcca ncanccgcgg taattccact cccatancgt atatttaagt gtttgcagtc     480
aaaaagctcg taattggact taggggtggg tcngccggtc cccctcacgg tgagcacggg     540
tctgctcttc cctactgcgg gcgatgccct cctggcctta attg                      584
```

<210> SEQ ID NO 155
<211> LENGTH: 65
<212> TYPE: DNA
<213> ORGANISM: Pig

<400> SEQUENCE: 155

```
ggattcctgc tgcttttgac cacagttctt tctgcaggac aagcatggcc cttgggagag      60
cacgg                                                                  65
```

```
<210> SEQ ID NO 156
<211> LENGTH: 959
<212> TYPE: DNA
<213> ORGANISM: Pig

<400> SEQUENCE: 156
gatgagggag tccaggagtt ccagcaagct cgacctgctt aacactccca gacggtcaca      60
ggattcagga caagcatggc ccttgggaga gcacggctgc tgctgctctt ggtgtgtgtg     120
gctgtcacat gggcggcccg gcctgatctc ctcaacatct gcatggacgc caagcaccac     180
aagaccaagc ccggcccgga agatggcctg catgagcagt gcagcccctg ggagatgaac     240
gcctgctgct ccgtcaacac cagccaagaa gcccataacg acatctccta cctgtacaaa     300
ttcaactggg agcactgcgg caagatgaag ccggcctgca agcgccactt cattcaagac     360
acctgtctct atgagtgctc gcccaacctg gggcctggga tccaggaggt gaaccagaag     420
tggcgcagag agcggatcct gaacgtgccc ctctgcaaag aggactgtca gaactggtgg     480
gaagactgcc gcacctccta cacctgcaag agcaactggc acgagggctg aactggagc      540 tcagggtata accggtgccc cgcgaacgcc gcctgccacc ccttcgactt ctacttcccc     600
acgcctgctg ccctgtgcag ccagatctgg agcaactcct acaaacaaag caactacagc     660
cggggcagcg gccgctgcat ccagatgtgg ttcgacccgg aacagggcaa ccccaacgag     720
gtggtggcga gatactacgc ccagatcatg agtggcgctg ggctctccga ggcctggcct     780
ctccagttcg gcctggccct gacgctgctc tggctgctga gctgagcttc tgtcttcgga     840
gagctggaca gccctcccct gttcggcccc acagcaccca gctcgtcagt gcctcagtgg     900
tggtggtagt ggtggtggtg gtggcggcgg ggggactctg aataaaccag tcaccccac     959

<210> SEQ ID NO 157
<211> LENGTH: 1218
<212> TYPE: DNA
<213> ORGANISM: Pig

<400> SEQUENCE: 157
gacactgctt ccgggtgggc ctccaggagg gccgaggcag aggagcctct gcctgtgggt      60
gaagcactgg ctggcgaact ccggaagggg aggtccggag aggtggtgcc tcccccgca     120 gcaaagctca gactgcactg tcctcaggtg gcagtggtgt cctaccactt ggcacagacc     180
tccacgggcc cttcatcgct tggctccact gtgctgtggg gtaagcggcg cggggaggga     240
cgacgatctg ggcttggaag ggaaacagga atctggcca agaagcttac ggcagctttc      300
tggcagaagt ggatcaacat ggcctggcgg ctgacgctct tcgtgctcct gggtttggtg     360
gctgctgtgg ggggcgcccg gccaagtcg acatgctca atgtctgcat ggatgccaag     420
caccacaagc caaagccaag cccggaggac aagctgcacg accagtgcag ccctggagg     480 aagaactcct gctgctcagt caacaccagc ctagaagccc ataaagacat ctcctacctg     540
tacagattca actgggacca ctgcggcaag atggagccgg cctgcaagcg ccacttcatt     600
caagacacct gtctctatga gtgctcgccc aacctggggc cctggatcca ggaggtgaac     660
cagaagtggc gcagagagcg gatcctgaac gtgcccctct gcaaagagga ctgtcagatc     720
tggtgggaag actgccgtac ctcctacacc tgcaagagca ctggcacaa gggctggaac     780 tggacctcag gtataaccag tgcccagtg agcgccgcct gccaccgctt cgacttctac     840
ttccccacgc ccgctgccct gtgcaacgag atctggagcc actcctttga agtcagcagc     900
tacagccggg gcagcggccg ctgcatccag atgtggttcg acccggccca gggcaacccc     960
```

| aacgaggcgg tggcgagata ctatgcagag aatggggatg ctggggccgt ggcccagggg | 1020 |
| atcgggcctc tcctgaccaa cttgacggag atggtgaaac actgggtcac cggctaagct | 1080 |
| gttccccgc cgacccctgc tttccgccca caccccctgg gttactctcc gggtggcctc | 1140 |
| agcaccccgg tcattggctc ctgatctaag atccgatggg gagcctctga tggcctcttc | 1200 |
| caatacaata tccacgtg | 1218 |

<210> SEQ ID NO 158
<211> LENGTH: 406
<212> TYPE: DNA
<213> ORGANISM: Mus musculus

<400> SEQUENCE: 158

| ctcagtcgca catagataaa attggccttt atttggagac gggtttgttc ttctatgttt | 60 |
| aatcctcggg tgaaatgacc tgaagatatt tgtgtctgtt ttccgcatgg tcaagcaggg | 120 |
| agtggagaga ggcctgggct gggccaggtt ttctgggctt tttcctgtgc tccgagtagg | 180 |
| tgggttgtat tttacccagt aggagtggaa gactccttgg cgcttggtgc ttcaaccgga | 240 |
| ctgacttcct gggcctggag ttggcgatta gaggtctgac atggctcacc tgatgactgt | 300 |
| gcagttgttg ctcctggtga tgtggatggc cgaatgtgct cagtccagag ctactcgggc | 360 |
| caggactgaa cttctcaatg tctgcatgga tgccaaacac cacaaa | 406 |

<210> SEQ ID NO 159
<211> LENGTH: 1303
<212> TYPE: DNA
<213> ORGANISM: Mus musculus

<400> SEQUENCE: 159

| gctgacggct ctagaagtcc ccaacctgtt gtgatcttca gtagacaaac actcctggtg | 60 |
| tgtcacagga ttcaggccac taaacctcgg ccggctgtct cctggaatga agaaagcaaa | 120 |
| ggaagcctag agtggagaca aagaagcccg aggcactctg agagctgcca tcttttcctt | 180 |
| gtttgccgcc tgacacttct cagcaggatc cacatacct aagggagtgg agagaggcct | 240 |
| gggctgggcc aggttttctg ggcttttcc tgtgctccga gtaggtgggt tgtatttac | 300 |
| ccagtaggag tggaagactc cttggcgctt ggtgcttcaa ccggactgac ttcctgggcc | 360 |
| tggagttggc gattagaggt ctgacatggc tcacctgatg actgtgcagt tgttgctcct | 420 |
| ggtgatgtgg atggccgaat gtgctcagtc cagagctact cgggccagga ctgaacttct | 480 |
| caatgtctgc atggatgcca aacaccacaa agaaaaccg ggccctgagg acaatttaca | 540 |
| cgaccagtgc agcccctgga agacgaattc ctgctgttcc acgaacacaa gccaggaagc | 600 |
| acataaggac atttcctacc tgtaccggtt caactggaac cactgcggaa ctatgacatc | 660 |
| ggaatgcaaa cggcactttta tccaagacac ctgcctctat gagtgttccc cgaacttggg | 720 |
| accctggatc cagcaggtgg accagagctg gcgcaaagag cggatccttg atgttcccct | 780 |
| gtgcaaagag gactgtcagc agtggtggga ggactgccag agctctttta cctgcaagag | 840 |
| caattggcac aagggatgga actggtcctc ggggcataac gagtgtcctg tgggagcctc | 900 |
| ctgccatccc ttcaccttct acttcccac atctgctgct ctgtgtgagg aaatctggag | 960 |
| tcactcctac aagctcagca actacagtcg agggagcggc cgctgcattc agatgtggtt | 1020 |
| cgacccagcc cagggcaacc ccaacgagga agtggcgagg ttctatgccg aggccatgag | 1080 |
| tggagctggg tttcatggga cctggccact cttgtgcagc ctgtccttag tgctgctctg | 1140 |
| ggtgatcagc tgagctcctg ttttaccttc agttgtctgg agcgccaccc tgcttggctc | 1200 |

```
agcctcccag ctcccagcct cctttgtggt ggggctctga cagcctcttt aataaaccag    1260
acattccaca tgtgccttat gaattaaaaa aaaaaaaaaa aaa                      1303

<210> SEQ ID NO 160
<211> LENGTH: 70
<212> TYPE: DNA
<213> ORGANISM: Mus musculus

<400> SEQUENCE: 160
cccgttaaag gatttaaagt ggacctcatc caattacagg gccttgaaag aatcctgtat     60
tgttatattt                                                           70

<210> SEQ ID NO 161
<211> LENGTH: 822
<212> TYPE: DNA
<213> ORGANISM: Mus musculus
<220> FEATURE:
<221> NAME/KEY: modified_base
<222> LOCATION: (719)   (781)
<223> OTHER INFORMATION: N = A, C, G, or T/U

<400> SEQUENCE: 161
ataaggcaca tgtggaatgt ctggttgatt aaagaggctg tcagagcccc accacaaagg     60
aggctgggag ctgggaggct gagccaagca gggtggcgct ccagacaact gaaggtaaaa    120
caggagctca gctgatcacc cagagcagca ctaaggacag gctgcacaag agtggccagg    180
tcccatgaaa cccagctcca ctcatggcct cggcatagaa cctcgccact tcctcgttgg    240
ggttgccctg ggctgggtcg aaccacatct gaatgcagcg gccgctccct cgactgtagt    300
tgctgagctt gtaggagtga ctccagattt cctcacacag agcagcagat gtggggaagt    360
agaaggtgaa gggatggcag gaggctccca caggacactc gttatgcccc gaggaccagt    420
tccatccctt gtgccaattg ctcttgcagg taaaagagct ctggcagtcc tcccaccact    480
gctgacagtc ctctttgcac aggggaacat caaggatccg ctctttgcgc cagctctggt    540
ccacctgctg gatccagggt cccaagttcg gggaacactc atagaggcag gtgtcttgga    600
taaagtgccg tttgcattcc gatgtcatag tttcgcaggg ttccagttga accgtacag    660 gtaggaaatg tccctatgtg cttcctggct ttgtgtcgtg aacagcagga atcgtcttnc    720
aggggctgcc actgtcgtgt aaattgcctc angggcccgt ttttttcttg tgtggtgcat    780
ncatgcagac aatttgaaat cagtcctggc cgagtagctc tg                      822

<210> SEQ ID NO 162
<211> LENGTH: 185
<212> TYPE: DNA
<213> ORGANISM: Mus musculus

<400> SEQUENCE: 162
aaggcctggt aattaaaaag gctgcaaagc cccacccaaa ggaggttggg agctgggagg     60
ttgacccaac cagggtggcc ctccaaacaa ctgaaggtaa aacaggagct cagttgatca    120
cccaaagcag cattaaggac aggcttgcca aaagtggcca ggtcccatga aacccagttc    180
cattc                                                              185

<210> SEQ ID NO 163
<211> LENGTH: 347
<212> TYPE: DNA
<213> ORGANISM: Mus musculus
```

<400> SEQUENCE: 163

```
gtagttgctg agcttgtagg agtgactcca gatttcctca cacagagcag cagatgtggg      60
gaagtagaag gtgaagggat ggcaggaggc tcccacagga cactcgttat gccccgagga     120
ccagttccat cccttgtgcc aattgctctt gcaggtaaaa gagctctggc agtcctccca    180
ccactgctga cagtcctctt tgcacagggg aacatcaagg atccgctctt tgcgccagct    240
ctggtccacc tgctggatcc agggtcccaa gttcggggaa cactcataga ggcaggtgtc    300
ttggataaag tgccgtttgc attccgatgt catagttccg cagtggt                  347
```

<210> SEQ ID NO 164
<211> LENGTH: 43
<212> TYPE: DNA
<213> ORGANISM: Mus musculus

<400> SEQUENCE: 164

```
taccacaacc aaagaaagca ttacacgcgc atattaccca ctg                       43
```

<210> SEQ ID NO 165
<211> LENGTH: 556
<212> TYPE: DNA
<213> ORGANISM: Mus musculus
<220> FEATURE:
<221> NAME/KEY: modified_base
<222> LOCATION: (501)
<223> OTHER INFORMATION: N = A, C, G or T/U

<400> SEQUENCE: 165

```
gagagttgaa cttgccaccc acttcaggga tctctggtac cacaaggtct tgtttctctc      60
tctctcttgg aggcaggcta ctcaggtcta gctactggcg gctctccaca cctgtagctc    120
atagaagctg aaggctgata aagggcagt gggtggagcg ccctcagccc gctcacctct     180
ttggcatcag gaggagcaac aggagggccc tgccttgaag gtcatggcac agtggtggca    240
gatcctcttg gggttgtggg cagtcctacc caccttggca ggggacaaac tgctcagcgt    300
ctgcatgaat tccaagcgcc acaagcaaga acctggccca gaagacgaac tctaccagga    360
gtgcaggcct tgggaggaca atgcctgctg cacacgttcc acaagttggg aagcccacct    420
tgaggagccc ttgctctttta acttcagcat gatgcactgt ggactgctga ccccggcctg    480
tcgcaaagca ctcattccag nccatttgtt tccatgatgt tcccccaacc tggggccctg    540
gatcccaccc gtgtcc                                                     556
```

<210> SEQ ID NO 166
<211> LENGTH: 353
<212> TYPE: DNA
<213> ORGANISM: Mus musculus

<400> SEQUENCE: 166

```
acacagagca gcagatgtgg ggaagtagaa ggtgaaggga tggcaggagg ctcccacagg      60
acactcgtta tgccccgagg accagttcca tcccttgtgc caattgctct tgcaggtaaa    120
agagctctgg cagtcctccc accactgctg acagtcctct ttgcacaggg gaacatcaag    180
gatccgctct ttgcgccagc tctggtccac ctgctggatc cagggtccca agttcgggga    240
acactcatag aggcaggtgt cttggataag tgccgttgca ttccgatgtc atagttccgc    300
agtggttcag ttgacccgta cggtaggaat gtcctatgtg cttctggctg tgt           353
```

<210> SEQ ID NO 167
<211> LENGTH: 58

```
<212> TYPE: DNA
<213> ORGANISM: Mus musculus

<400> SEQUENCE: 167
cccccggggc cggaagggggg aaatttgccc cccggcgccc ttcctgggag ggggaacc        58

<210> SEQ ID NO 168
<211> LENGTH: 49
<212> TYPE: DNA
<213> ORGANISM: Homo sapiens

<400> SEQUENCE: 168
cggcgaacac catcgaaagt taatagggca gacgttcaaa taggtcgtc                  49

<210> SEQ ID NO 169
<211> LENGTH: 448
<212> TYPE: DNA
<213> ORGANISM: RAT
<220> FEATURE:
<221> NAME/KEY: modified_base
<222> LOCATION: (387)
<223> OTHER INFORMATION: N = A, C, G or T/U

<400> SEQUENCE: 169
cggccgctcc ctcggctgta gttgctgagc ttgtaggaat gactccagat tttctcacac      60
agaacagcag gtgtagggaa gtagaaagtg aagggatggc aggaggctcc cacagggcac     120
tcattatgcc ccgaggtcca gttccatccc ttgtgccagt tgctcttgca ggtaaaagag     180
ctcttgcagt cctcccacca cagcacacag tcttctttgc acaggggaac atcaaggatc     240
cgctctttgc gccagctctg gtccacctgc tggatccagg gtcccaagtt cggggaacac     300
tcatagaggc aagtgtcttg gataaagtga cgtttgcact ccggggtcat agttccacag     360
tgattccagt tgaatcggta caggtangaa atgtccttat gtgcttggca tccatgcaga     420
cattgagaag ttcgcctcgt gccgaatt                                        448

<210> SEQ ID NO 170
<211> LENGTH: 435
<212> TYPE: DNA
<213> ORGANISM: RAT
<220> FEATURE:
<221> NAME/KEY: modified_base
<222> LOCATION: (378)
<223> OTHER INFORMATION: N = A, C, G, or T/U

<400> SEQUENCE: 170 ttttttttttt tttttttaga tgtgtcatag atttattgaa aatgattgtt gtagaaaccc    60
caagccccaa catggatcag gaactggatg gcagaggaga ggggtggaag caggctcaag    120
acttccttat tctttgaaga gttgaaccaa ccgagaccaa gggtagctag aggagaagac    180
tggcctcagt cagggagcca taatgacagc actgggggcca ggctgggcac aagaagtatt    240
gctgcatggt acacagtccc agatgtcata aggaagcat agaacttcac cacttcctca     300
ttgggattgc cctgggttga gtcaaaccac atctggatgc actggccact ccctctgcta    360
tagttgctga ccttgtanga gtgactccag agaccctcac aaaggctggc tggtgtcggg    420
aaatagtact gaaat                                                     435

<210> SEQ ID NO 171
<211> LENGTH: 429
<212> TYPE: DNA
<213> ORGANISM: RAT
<220> FEATURE:
```

<221> NAME/KEY: modified_base
<222> LOCATION: (387)
<223> OTHER INFORMATION: N = A, C, G or T/U

<400> SEQUENCE: 171

```
cggccgctcc ctcggctgta gttgctgagc ttgtaggagt gactccagat tttctcacac    60
agaacagcag gtgtagggaa gtagaaagtg aagggatggc aggaggctcc cacagggcac   120
tcattatgcc ccgaggtcca gttccatccc ttgtgccagt tgctcttgca ggtaaaagag   180
ctcttgcagt cctcccacca cagcacacag tcttctttgc acaggggaac atcaaggatc   240
cgctctttgc gccagctctg gtccacctgc tggatccagg gtcccaagtt cggggaacac   300
tcatagaggc aggtgtcttg gataaagtga cgtttgcact ccggggtcat agttccacag   360
tgattccagt tgaatcggta caggtangaa atgtccttat gtgcttcctg gcttgtgttg   420
gtggagcag                                                          429
```

<210> SEQ ID NO 172
<211> LENGTH: 427
<212> TYPE: DNA
<213> ORGANISM: RAT

<400> SEQUENCE: 172

```
cggccactcc ctcggctgta gttgctgagc ttgtaggagt gactccagat tttctcacac    60
agaacagcag gtgtagggaa gtagaaagtg aagggatggc aggaggctcc cacagggcac   120
tcattatgcc ccgaggtcca gttccatccc ttgtgccagt tgctcttgca ggtaaaagag   180
ctcttgcagt cctcccacca cagcacacag tcttctttgc acaggggaac atcaaggatc   240
cgctctttgc gccagctctg gtccacctgc tggatccagg gtcccaagtt cggggaacac   300
tcatagaggc aggtgtcttg gataaagtga cgtttgcact ccggggtcat agttccacag   360
tgattccagt tgaatcggta caggtaggaa atgtccttat gtgcttcctg gcttgtgttg   420
gtggagc                                                            427
```

<210> SEQ ID NO 173
<211> LENGTH: 382
<212> TYPE: DNA
<213> ORGANISM: RAT

<400> SEQUENCE: 173

```
cggccgctcc ctcggctgta gttgctgagc ttgtaggagt gactccagat tttctcacac    60
agaacagcag gtgtagggaa gtagaaagtg aagggatggc aggaggctcc cacagggcac   120
tcattatgcc ccgaggtcca gttccatccc ttgtgccagt tgctcttgca ggtaaaagag   180
ctcttgcagt cctcccacca cagcacacag tcttctttgc acaggggaac atcaaggatc   240
cgctctttgc gccagctctg gtccacctgc tggatccagg gtcccaagtt cggggaacac   300
tcatagaggc aggtgtcttg gataaagtga cgtttgcact ccggggtcat agttccacag   360
tgattccagt tgaatcggta ca                                           382
```

<210> SEQ ID NO 174
<211> LENGTH: 52
<212> TYPE: DNA
<213> ORGANISM: Homo sapiens

<400> SEQUENCE: 174

```
aaggcccggg aactcccatc aaaagttgtt agggcaaact ttcaaatggg tc            52
```

```
<210> SEQ ID NO 175
<211> LENGTH: 847
<212> TYPE: DNA
<213> ORGANISM: Mus musculus
<220> FEATURE:
<221> NAME/KEY: modified_base
<222> LOCATION: (520)..(717)
<223> OTHER INFORMATION: N = A, C, G or T/U

<400> SEQUENCE: 175
aattcggatc catgggctga tctggaagta taaacaagaa aggaggctga cggctctaga      60
agtccccaac ctgttgtgat cttcagtata caaacactcc tggtgtgtca caggattcag     120
ctctgtttcc taggccacta aacctcggcc ggctgtctcc tggaatgaag aaagcaaagg     180
aagcctatag tggagacaaa gaagcccgag gcactctgag agctgccatc tttccttgt      240 ttgccgcctg acacttctca gcaggatcca catccctaa ggagtggaag actccttggc      300
gcttggtgct tcaaccggac tgacttcctg tgcctggagt tggcgattag actctgcctt     360
cagggtctga catggctcac ctgatgactg tgcagttgtt gctcctggtg atgtggatgg     420
ccgaatgtgc tcagtccata gctactcggg ccaggactga acttctcaat gtctgcatgg     480
atgcctaaca ccacaaagat aaaccgtccc tgaggacatn tacacgacca gtgcagcccc     540
tgcaagacaa ttactgctgt tccactaaca caagccagga agcacataat gacatttcct     600
acctgtaccg tttcactgga accactgctg aactatgaca tcggaatgca tacggcacta     660
tatccaagac acttgctcta tgagtgttcc cccgacttgt gaccctgtat tcagcangtg     720
gaacatgact tgcgcatata cggatccttg atgttcccct gtgcaaagag gactgtcagc     780
attgatgtga tgactgccat agctctttac ctgtcagaac atttgtccat ggtatgtaac     840
tgttcct                                                               847

<210> SEQ ID NO 176
<211> LENGTH: 326
<212> TYPE: DNA
<213> ORGANISM: Homo sapiens

<400> SEQUENCE: 176
gggtcatttc cacatgcttt attccagcaa tcaaataat taaaaacatc tcaaattatt       60
atacacatac aaaataggta cagagtcttt tgcttcctcc caccccctagg gggaaaaact    120 gctttgtgct ttgggaagtt gtctctgaaa cccggggaca gaggacgcag acagactag      180 gagggagccg ggaggatggg ctgcagctgt ggaggagggt ttcagaggag agaggtcgga    240
gagcagaggc ctgagaagcc tgattccccg tcacccgtgg tcaccatggt aggcacggca    300
actaccatcg aaagttgatg ggcaga                                          326

<210> SEQ ID NO 177
<211> LENGTH: 4409
<212> TYPE: DNA
<213> ORGANISM: Homo sapiens

<400> SEQUENCE: 177
actagttgtc tgttgctgca taacaaatca ttccataatt ttgtggtgta ttgctgcaga      60
caatgttaaa ctaagtggat gaaaaggata ttcacatagt ctcagagtgt ctccctacaa     120
ggtaggatta ctaacaaagg gaaactaata attatatagt aaggaaatct ccttaaccca     180
ataatcacca gcaataagat gcagcaaccc tcatcatgta cctcttgata tgatgcactg     240
acaaaagcac ctctcttctc taattttctt gccaaaatcg ataagctcaa gctaattaca     300
```

```
ggaaaatata gacaaaccca aattgaggga cattctgcaa ataactgaa cagtaattct      360 ccaaaagtgt caaggtcata aaagacaaag acattgagga ctgtcacaga ttggagggag    420
actaagggga catgacaact acatgcaacc tggaatcatg gactgaatcc tgggccagag    480
aaggacattg gggggggaact ggtgtaaagg gcataaagct tgtagattag ttaacagtat   540
tgcctcaata ttaatttcct gattttttta agaactgggc tttggttaca taagatgcca   600
atatttgggg aagttgcata aaaacatacg ggaaatcttt tgacgatgtt ttgcagtttt   660
tctgcaaatc taaaattatt tcaaaacaaa aagtttaaaa atcaaataca catagttgct   720
tgaaatagta actattttat tatattccaa gatgttgtga gtcaggaatt tggccaaaac   780
tcaggtgggc gattcttctg caaagacccc cacaacacat tcaaagtcac aggcagaggt   840
tgttggggga gggcattgaa aagaagagaa gagtcatagg tgggtgcaat ggagggaggg   900
cagagggctg ctgactatgt gcaggactca tccataatgg agccctgggg aggcaagggc   960
ttcataacta gacactggtc ttgtcacctc agactcacct gtagcaggac cagatactga   1020
ggtcagactg aaaacacagg ctctgcctca ggagaggctc tctactagct gagtaaatga   1080
tgacagtatt ggaaatgttc ccaacatcat aatgggaaaa catcacttca cactacataa   1140
gcaatacaca gggcagtgc cggtcgtctt cccaggttag tagcagttct actgcctcca    1200
agagtgttgg agaaatacaa accaagcatt aggcactttt aacttgaaaa catgaagttc   1260
tctttcctaa ctttctttgt ttccttattt cttcttcttc ttcttcttct tcttcttctt   1320
cttcttcttc ttcttcttct tcttcttctt cttcttcttc ttcctcttct tcttcttctt   1380
cttctttctt cttcttctcc ttctccttttt ccttcttctt tttttgctga cagggtct    1440 cactctgaca gtacagtggt gccatcacag ctcactgcag cctcgacctc cagggctcaa   1500
gcaatcctcc cagctcaccc tcccaaatgg ctgaaactac aagctcgcac caccatacgt   1560
ggctaatttt tctattttg tgtgcagatg aagttttcct atgttgccca agtggtctca    1620
aactcctggg atcaagtgat ccatccacct caacctccca aaacgctggg attacaggtg   1680
taagccacca cacccagccc actaactttt ttatatcggc taatgaaata gttttaagtt   1740
tagaccctac gaggcataaa gaaataattt tagttatgtt atcagatgta cagtaatact   1800
caagtgtgca actgtggata acttgagttc atgaggtttt tgttttttg tcaaaagaat    1860 aaatttatag tgaaactacc caaaaaagca aagtacagaa cagtatgcta ccatttgtgc   1920
acagaaatgg gatatatatg gtgtaactgc atcgaattta ctggatgtat gtccagggac   1980
cagaactctt ggtggcttca tgttcatact tttgcaagca catgtgtagt atccttaact   2040
taaaggtact gttgtataca ttctagtgtt atcaaaattt acatacatat tatcaagtca   2100
gagaggtcat tctgtgtctt agtattttca cttcatattt ggtatattta tgtatgtata   2160
cacacatacc tatatgtatt taaataagat ttatagtcac atggtccaaa aatcaaaaca   2220
atgtggaaag gtttacagag aaaagtctca agcctaatcc tgttctctac tgccaggtga   2280
ccatgttatt aatttctttt cataccttgc cacagaattt tcacctgcaa acacagatat   2340
tcttttcttt tttaatgaca gagtcacgtt ctgttatcca ggctggagtg cagtggcgtg   2400
atcttggctc actgcaaact cctcccgggt tcaagtgatt ctcctgtctc agcctcctga   2460
gtagctggga ttacaggcat gtgccaccac acccagctaa ttttttgtatt tttagtacag   2520 atggggtttt atcatattga ccaggctgat gtcgaactcc tgacctcaag tgatccgcct   2580
gcctcggcct cccacagtgc tgggattaca ggcgtgagcc accacgccca gtcaacacag   2640
acattcttac tcctttttta cagagaattt attattatta tttttacat agcatttttc    2700
```

```
tgcacctttc ttttttccact taacaatgca cttgaagatt tttccatatt tgtacatcag    2760
gagctttctc tttctttgtt accacattaa attccactgg gtagatgtac cataatttaa    2820
ctgggtcctt attgaaagac aattgagctg tctcctagac aaagccttgt gcaccttccc    2880
gaacagaggg tctaaccaag caggcaggat gggttataa agtaggtggg gaggtgggag      2940
agactccacc ttcccaggtg ggctgagaat ggaggtaagg ccctgcaaca ggacagaggg    3000
aaaagtgggg atgagaggtg ggaggcgaga tagcgcccac tgttctcgct cagccccctc    3060
ctccgtttgc cgctgacctg ttggcctccc ccaacctctg agcctgcctc tgcctaggta    3120
atttcccaag acccagaagg ggtgaagggt gaggtgtgat tgcccccacc tccttgcctc    3180
ccgcagcatc tgctccggga ccatgaacaa tagctgacag ctccatggcc cttgctgtcc    3240
ccatctcagc ttccctgggc atctaaacct cagctgccat ggggtaggag acaggctga    3300 ggaagcagaa gcctgaggct gtctagagtc tcactcctgc atcagcaggc caccacctgt    3360
ggttcctcct tgtgcaaatt tgaaaagaat tgcataaaac actggagaaa tccaagaggg    3420
gaagtccaca agggcggtgg ctccctacaa ggtcacagag caagctggtg tcagagcctg    3480
gacctacagc gctgttggtg gaggtcctgc ctccaggtag gggaagggct ccctctcacc    3540
tctacacgca gcgcatttct tggctcagct gccctgtagg ggatgcaggg tggggacagc    3600
agagatctgg gcctgggagg gagagagtac acaatcacat ggctgttgcc cctgtctcag    3660
gccttgtcta cctctgactg tggctctctg gcaggaatag atggacatgg cctggcagat    3720
gatgcagctg ctgcttctgg ctttggtgac tgctgcgggg agtgcccagc ccaggagtgc    3780
gcgggccagg acggacctgc tcaatgtctg catgaacgcc aagcaccaca agacacagcc    3840
cagccccgag gacgagctgt atggccaggt gagggcagcc tggtgtagga cagcatgcac    3900
acaggtcaga gggtgatggc acgagcaatg gcaggtccag tgtggtcaga accaagggtg    3960
ccgctgctga caaggaaggg gaggggcggc caggccacc atgccacagg taaggccact     4020
gaggcagctt ggggaatatg agctccaatt tgaactccag gctcaggagt gtgcttgtat    4080
ttcattcctc tggtctcctg gcctgctccc tacaaggttt cacattccca gagggctggg    4140
gatgtgccta gggagagact gtggcgtgga cacaatctgt gggttaaagc gaagacagga    4200
cagcctggaa gccccatgac atctgagtca ctcccaacat tccatttgct tatttttaaa    4260
tcggggttaa aaaaaaaaaa caaatacata acatacattt tccactttgg ccattttaaa    4320
ctgtacggtt cagtggcatt aggtatgctc atgtggttgt gcaaccatca ccaccatcca    4380
tctcctgacc tctgtgattc tccaaaact                                       4409
```

<210> SEQ ID NO 178
<211> LENGTH: 847
<212> TYPE: DNA
<213> ORGANISM: Mus musculus
<220> FEATURE:
<221> NAME/KEY: modified_base
<222> LOCATION: (645)..(712)
<223> OTHER INFORMATION: N = A, C, G, or T/U

<400> SEQUENCE: 178

```
aattcggatc catgggctga tctggaagta taaacaagaa aggaggctga cggctctaga      60
agtccccaac ctgttgtgat cttcagtaga caaacactcc tggtgtgtca caggattcag    120
ctctgtttcc taggccacta aacctcggcc ggctgtctcc tggaatgaag aaagcaaagg    180
aagcctagag tggagacaaa gaagcccgag gcactctgag agctgccatc ttttccttgt    240
```

```
ttgccgcctg acacttctca gcaggatcca catacccctaa ggagtggaag actccttggc    300
gcttggtgct tcaaccggac tgacttcctg ggcctggagt tggcgattag actctgcctt    360
cagggtctga catggctcac ctgatgactg tgcagttgtt gctcctggtg atgtggatgg    420
ccgaatgtgc tcagtccaga gctactcggg cccagactga acctctcatg tctgatggat    480
gccaaacacc acatagaata accgggccct gaggacaatt tacacgacca gtgcagcccc    540
tggaagacga aatcctgctg ttccacgaac acaagccagg aagcacataa ggacatttcc    600
tacctgtacc ggttcaactg gaaccactgc ggaactatga catcngcaat gcanacggca    660
ctttatccaa gacacctgcc tctatgagtg ttccccgaac ttgggacact gnatccagca    720
ggtgggacca agcttgcgc caaagagcgg atcccttgat gtttcccctg gcaaagagg     780 actgtccagc agttgtgggg aggactgcca gaagctcttt tacctgccag agcaatttgc    840
accaggg                                                             847
```

<210> SEQ ID NO 179
<211> LENGTH: 541
<212> TYPE: DNA
<213> ORGANISM: Mus musculus

<400> SEQUENCE: 179

```
gtagttgctg agcttgtagg agtgactcca gatttcctca cacatagcag cagatgtggg    60
gaagtagaag gtgaagggat ggcaggaggc tcccacagga cactcgttat gccccgagga   120
ccagttccat cccttgtgcc aattgctctt gcaggtaaaa gagctctggc agtcctccca   180
ccactgctga cagtcctctt tgcacagggg aacatcaagg atccgctctt tgcgccagct   240
ctggtccacc tgctggatcc agggtcccaa gttcgggaa cactcataga ggcaggtgtc    300
ttggataaag tgccgtttgc attccgatgt catagttccg cagtggttcc agttgaaccg   360
gtacaggtag gaaatgtcct tatgtgcttc ctggcttgtg ttcgtggaac agcaggaatt   420
cgtcttccag gggctgcact ggtcgtgtaa attgtcctca gggcccggtt tttctttgtg    480
gtgtttggca tccatgcaga cattgagaag ttcagtcctg cccgagtag ctctggactg    540 a                                                                    541
```

<210> SEQ ID NO 180
<211> LENGTH: 525
<212> TYPE: DNA
<213> ORGANISM: Mus musculus

<400> SEQUENCE: 180

```
acacagtagt tttcagatgt ggggaagtag aaggtgaagg gagggcagga tgctcccaca    60
ggacactcgt tatgccccga ggaccagttc catcccttgt gccaattgct cttgcaggta   120
aaagagctct ggcagtcctc ccaccactgc tgacagtcct ctttgcacag gggaacatca   180
aggatccgct ctttgcgcca gctctggtcc acctgctgga tccagggtcc caagttcggg   240
gaacactcat agaggcaggt gtcttggata agtgccgtt tgcattccga tgtcatagtt    300
ccgcagtggt tccagttgaa ccggtacagg taggaaatgt ccttatgtgc ttcctggctt   360
gtgttcgtgg aacagcagga attcgtcttc caggggctgc actggtcgtg taaattgtcc   420
tcagggcccg gttttctttt gtggtgtttg gcatccatgc agacattgag aagttcagtc   480
ctggcccgag tagctctgga ctgagcacat tcggccatcc acatc                    525
```

<210> SEQ ID NO 181
<211> LENGTH: 805

```
<212> TYPE: DNA
<213> ORGANISM: Mus musculus
<220> FEATURE:
<221> NAME/KEY: modified_base
<222> LOCATION: (535)..(740)
<223> OTHER INFORMATION: N = A, C, G or T/U

<400> SEQUENCE: 181
gtggacgaag actgtagaga ctacccagag tctgacctag ggagaggcca actcggatac    60
ccctatgtgc gctcccagaa gctaaggaca ttgagacaga aagacatggc ctggaaacag   120
acaccactct tgcttttggt ctacatggtc acaacaggca gtggccggga cagaacagac   180
ctactcaacg tttgcatgga tgccaaacac cataagacaa agcccgggcc cgaggacaag   240
ctgcatgacc agtgtagtcc atggaagaaa aatgcctgtt gctcagtcaa caccagccag   300
gagctacaca aggctgactc ccgtctgtac ttcaactggg atcactgtgg caagatggag   360
cctgcctgta agagtcactt catccaagac tcctgcctgt atgagtgctc ccccaacctt   420
gggccttgga tccagcaagt ggaccagagt tggcgtaaag agcgttttct ggatgtgccc   480
ctatgcaaag aggactgtca ccagtggtgg gaagcctgtc gtacctcctt taccntgcag   540
agagactggc atanaggctg ggactggtcc tcaggcatta acaagtgccc anacacagca   600
ccctgtcaca cgtntgagta ctacttcccg acaccagcca gcctttgcga gggtctctgg   660
agtcactcct acaaggtcag caaactacag cagaggagtg gccgctgcat ccagatgtgg   720
ttgactcacc ccanngcann tcgaaatgag acgtggtgaa gtttatgctt ctttatacat   780
ctgggatgtg cccatgcaca gtact                                         805

<210> SEQ ID NO 182
<211> LENGTH: 585
<212> TYPE: DNA
<213> ORGANISM: Mus musculus
<220> FEATURE:
<221> NAME/KEY: modified_base
<222> LOCATION: (511)..(513)
<223> OTHER INFORMATION: N = A, C, G or T/U

<400> SEQUENCE: 182
acacagagca gcagatgtgg ggaagtagaa ggtgaaggga tggcaggagg ctcccacagg    60
acactcgtta tgccccgagg accagttcca tcccttgtgc caattgctct tgcaggtaaa   120
agagctctgg cagtcctccc accactgctg acagtcctct ttgcacaggg gaacatcaag   180
gatccgctct ttgcgccagc tctggtccac ctgctggatc cagggtccca agttcgggga   240 acactccatag aggcaggtgt cttggataaa gtgccgtttg cattccgatg tcatagttcc   300
gcagtggttc cagttgaacc ggtacaggta ggaaatgtcc ttatgtgctt cctggcttgt   360
gttcgtggaa cagcaagaat tcgtcttcca ggggctgcac tggtcgtgta aattgtgctc   420
atggccctgg tcttctttag tgtgtttagc atccatgcag acatcgagaa gatcagtcct   480
ggtccgagta gctctggact gagcacagtc ngncattcac atcatccaga gcaacaactg   540
cacagtcatc aggtgagcca tgtcagaccc tgatgcagag tctaa                   585

<210> SEQ ID NO 183
<211> LENGTH: 584
<212> TYPE: DNA
<213> ORGANISM: Mus musculus
<220> FEATURE:
<221> NAME/KEY: modified_base
<222> LOCATION: (557)
<223> OTHER INFORMATION: N = A, C, G or T/U
```

```
<400> SEQUENCE: 183
tgggtcataa attgattgaa aatgattgta gaaaccccaa cccccaacat ggatcaggaa      60
ctggatgaca gaggagaggg gtggaagcag gctcaaaact tccttattct ttgaagagtt     120
gaaccagacc aagggtagat agaggagaaa tctaaagagg aagactgacc tctcagccag     180
ggagccataa tgacagcact ggggccaggc tgggcacaag aagtactgct gcatggggca     240
cagtcccaga tgtcataaag gaagcataaa acttccaccac gtcctcattc ggattgccct    300
gggttgagtc aaaccacatc tggatgcagc ggccactccc tctgctgtag ttgctgacct     360
tgtaggagtg actccagaga ccctcgcaaa ggctggcttg tgtcgggaag tagtactcaa     420
acgtgtgaca gggtgctgtt gttgggcacc ttgttaatgc ctgaggacca gtcccagcct    480
tattgcaatc tttcttgcag gtaaaggagg acgacaggct tccaccactg gtgcagtcct    540
ctttgataag ggacatncag aaacgctctt acgccactct ggtc                    584

<210> SEQ ID NO 184
<211> LENGTH: 85
<212> TYPE: DNA
<213> ORGANISM: Mus musculus

<400> SEQUENCE: 184
ctatccattc gaacgtgtgc catatcatct tctgatgtac caacccgtgc ctaccatgtg      60
gaccacgggt gactggcaat ccaga                                          85

<210> SEQ ID NO 185
<211> LENGTH: 70
<212> TYPE: DNA
<213> ORGANISM: Mus musculus
<220> FEATURE:
<221> NAME/KEY: modified_base
<222> LOCATION: (9)
<223> OTHER INFORMATION: N = A, C, G or T/U

<400> SEQUENCE: 185
attccccgnc ccccggggtc accaggggag gcgcggggac taccattaaa agttgatagg      60
gcaaactttt                                                           70

<210> SEQ ID NO 186
<211> LENGTH: 576
<212> TYPE: DNA
<213> ORGANISM: Manduca sexta
<220> FEATURE:
<221> NAME/KEY: modified_base
<222> LOCATION: (187)..(530)
<223> OTHER INFORMATION: N = A, C, G or T/U

<400> SEQUENCE: 186
gaactagggc ggtatctaat cgccttcgaa cctctaactt tcgttcttga ttgatgaaaa      60
cacctttggc aaatgctttc gctgatgttc gtcttgcgac gatccaagaa tttcacctct     120
aacgtcgcaa tacgaatgcc cccagttatc cctattaatc attacctcgg agttctgaaa     180
accaacnaaa tagaaccgag atcatattct attattccat gcacgaaata ttcaagcagc     240
attttgagcc cgctttgagc actctaattt gttcaaagna aaattgtcgg cccatctcga     300
cactcaccga agagcaccgc gataggattt tgatattgaa ccgacgtttg ttacaacgcc     360
ggctcaccga cnatatgctc cgcagacgtg tcagtatcac cgcggatgcg gtgcaccgac     420
agcncggcgc acaaatgcan ctacnagctt tttaaccgca acaattttag tatacgctat     480
tggagctggg aattaccgcg gctgctggca ccagacttgc cctcaattgn cctcgttaaa     540
```

```
atatttaaag tgtctcattc cgattacgaa gcctcg                              576

<210> SEQ ID NO 187
<211> LENGTH: 295
<212> TYPE: DNA
<213> ORGANISM: Mus musculus
<220> FEATURE:
<221> NAME/KEY: modified_base
<222> LOCATION: (154)..(195)
<223> OTHER INFORMATION: N = A, C, G or T/U

<400> SEQUENCE: 187
cagcgagcct tgcgggggt gtctggagtg actcctacga ggtgagcgac tacagcagag     60
ggagtggccg ctgcgtccag atgtggtttg agtcagccca gggcgatccc aatgaggacg   120
tggtggagtt ttatgcttcc tttatgacat ctgngactgt gccccatgca gcagtagttc   180
ttgtgcccag cctnngccca gtgctgtcat tatagctccc tggctgagag gtcagtgttc   240
ctctctagat ttcgtcctct atctacccct tggtgctggtt cagctcttca gagaa       295

<210> SEQ ID NO 188
<211> LENGTH: 85
<212> TYPE: DNA
<213> ORGANISM: Mus musculus

<400> SEQUENCE: 188
cagctcacct cctgttttac cttcacttct ctccacgccc caccctcgct tcgcgctcac     60
gcctcccagc tcccacgcct cctttt                                         85

<210> SEQ ID NO 189
<211> LENGTH: 88
<212> TYPE: DNA
<213> ORGANISM: Mus musculus

<400> SEQUENCE: 189
cctcccggct cctgcccgag ggtcgggcgc ctgcggcttt ggtgacttta gattacctcg     60
ggccgatcgc acgccccccg tggcggcg                                       88

<210> SEQ ID NO 190
<211> LENGTH: 369
<212> TYPE: DNA
<213> ORGANISM: Mus musculus
<220> FEATURE:
<221> NAME/KEY: modified_base
<222> LOCATION: (93)..(353)
<223> OTHER INFORMATION: N = A, C, G or T/U

<400> SEQUENCE: 190
gtctctctct ctcttctctt gcttcgctct cttgcttttc tctctctctt gcttttttcgc    60 tctcttgctt ctcgctctct cttgcttctt gcnctctttt cctgaagatg taagaataaa   120
gctttgccgc agaagattct ggtctgtggt gttcttcctg gccggtcgtg anaacgcgtc   180
taataacaat tggtgccgaa ttccgggang anaaaatccg ggacgagaaa aaaactccgg   240
antggcgcag gagggatact tcattccagg aancagaact gcgaatcaag gttanaangg   300
atcncgtnac acagattgat tgagaagnnn tccnactggc cgaattcnag aanctcatcg   360
cttggggaa                                                           369

<210> SEQ ID NO 191
<211> LENGTH: 332
<212> TYPE: DNA
```

<213> ORGANISM: Mus musculus
<220> FEATURE:
<221> NAME/KEY: modified_base
<222> LOCATION: (309)
<223> OTHER INFORMATION: N = A, C, G, or T/U

<400> SEQUENCE: 191

```
ggtttttcga dacagggttt ctctgtgtag ccctggctgt ccttgaactc actttgtaga      60
ccaggctggc ctcgaactca gaaatccgcc tgcctctgcc tcccaagtgc tgggattaaa     120
ggcattcgcc accaccaacc ggcgataaac aaattttata cgaaagaaaa gaagcaagta     180
agattatgag aaacataagc tattttaaga gagtttagag aagatccttc aaatatttta     240
aaagagatct gaataaatca gaaagcatta ttcctggata aataatgggg agagaaataa     300
tagattaana tacaacctat caaaatttaa tc                                   332
```

<210> SEQ ID NO 192
<211> LENGTH: 331
<212> TYPE: DNA
<213> ORGANISM: Mus musculus
<220> FEATURE:
<221> NAME/KEY: modified_base
<222> LOCATION: (295)..(308)
<223> OTHER INFORMATION: N = A, C, G or T/U

<400> SEQUENCE: 192

```
cgagacaggg tttctctgtg cagtcctgga actcactctg tagaccaggc tggccttgaa      60
ctcagaaatc cacctgcctc tgcctcccaa gtgctgggat tgcaggcatg cgccaccact     120
gcctggctgc ctggtttttt aattactggc tttagcctaa atggcaaatt ctataactag     180
gttataagaa tagttttaaa agaaagagcc tcaggagagt gggaacagga acatggagaa     240
gtaagaggac acctgggctt tagtcaagat cctgtctaaa acaaaacaga ggggncggna     300
gagctngngc aatggctcag ttggttagag c                                    331
```

<210> SEQ ID NO 193
<211> LENGTH: 67
<212> TYPE: DNA
<213> ORGANISM: Homo sapiens

<400> SEQUENCE: 193

```
ccgccacggg ggggtcgcga tcggtccgag gttatctaga gtcaccaaag ccgccggcgt      60
cgtcccc                                                                67
```

<210> SEQ ID NO 194
<211> LENGTH: 593
<212> TYPE: DNA
<213> ORGANISM: Mus musculus
<220> FEATURE:
<221> NAME/KEY: modified_base
<222> LOCATION: (489)..(578)
<223> OTHER INFORMATION: N = A, C, G or T/U

<400> SEQUENCE: 194

```
ctctctccag gtattcctac ctaaccttaa cttttcctcg ggttcaagac ccttggaaag      60
gcctgtatac ttattttgtg aaccatattt tctctttgtt cctactcttt cttcccgctt     120
tacttctgat agcttgtcct gaatttcctc tagaattttc agcccatctc taaccactat     180
ataacatgtg aaaaggaaca aaagggcttc taacactaga aaaaattcaa ggccaaacat     240
aacttgtaaa gccattttcc actttacttc tgatagactg tcttgaattt ccttagaaag     300
ttcaagatca gacttaccte gttccccage tgaaaagttc tgaattcata cagttgaatc     360
```

```
ctcttaacag tctggcttta cgggaacctt atcaccgtcg ttccccagct ggatgagttc      420
tgaatcggca gttgaatcct tctcaacagt ctgtgttacg ggaaccttat aacctggatt      480
cgcagttcng ggttctggga aggaaagtaa tccnctcctg gcggccagtn ccgggagntt      540
ttttcctcgg tcccgggatt tttcctcggt ccccgggnaa ttcgggcacc caa             593
```

```
<210> SEQ ID NO 195
<211> LENGTH: 58
<212> TYPE: DNA
<213> ORGANISM: Homo sapiens

<400> SEQUENCE: 195
tgggtccgtt cctaaaacaa aaaaaaaaa acagcggtcc tattccaata ttcctagc         58
```

```
<210> SEQ ID NO 196
<211> LENGTH: 22
<212> TYPE: DNA
<213> ORGANISM: Homo sapiens

<400> SEQUENCE: 196
tgggcagacg ttcgaatggg tc                                               22
```

```
<210> SEQ ID NO 197
<211> LENGTH: 324
<212> TYPE: DNA
<213> ORGANISM: Mus musculus

<400> SEQUENCE: 197
gacatcgagc tcactcagtc tccagcttct ttggctgtgt ctctagggca gagggccatc      60
atctcctgca aggccagcca agtgtcagt tttgctggta ctagtttaat gcactggtac      120
caccagaaac caggacagca acccaaactc ctcatctatc gtgcatccaa cctagaagct      180
ggggttccta ccaggtttag tggcagtggg tctaagacag acttcaccct caatatccat      240
cctgtggagg aggaggatgc tgcaacctat tactgtcagc aaagtaggga atatccgtac      300
acgttcggag gggggacaaa gttg                                             324
```

```
<210> SEQ ID NO 198
<211> LENGTH: 351
<212> TYPE: DNA
<213> ORGANISM: Mus musculus

<400> SEQUENCE: 198
caggtgcagc tgcagcagtc tggagctgag ctggtgaagc ctggggcttc agtgaagata      60
tcctgcaagg cttctggtta ctcatttact ggctacttta tgaactgggt gaagcagagc      120
catgaaaaga gccttgagtg gattggacgt attcatcctt acgatggtga tactttctac      180
aaccagaact tcaaggacaa ggccacattg actgtagaca atcctctaa cacagcccac       240 atggagctcc tgagcctgac atctgaggac tttgcagtct attattgtac aagatacgac      300
ggtagtcggg ctatggacta ctggggccaa gggaccacgg tcaccgtctc c               351
```

```
<210> SEQ ID NO 199
<211> LENGTH: 360
<212> TYPE: DNA
<213> ORGANISM: Homo sapiens

<400> SEQUENCE: 199
caggtgcagc tggtggagtc tgggggaggc ttggtacagc cagggcggtc cctgagactc      60
```

```
tcctgcacaa cttctggatt cacttttggt gattatgcta tgatctgggc ccgccaggct    120
ccagggaagg ggctggagtg ggtctcatcc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gagagaacga    300
tacgattttt ggagtggaat ggacgtctgg ggcaaaggga ccacggtcac cgtgtcgagt    360

<210> SEQ ID NO 200
<211> LENGTH: 333
<212> TYPE: DNA
<213> ORGANISM: Homo sapiens

<400> SEQUENCE: 200
cagtctgccc tgactcagcc tgcctcagtg tccgggtctc ctggacagtc cgtctccatc     60
tcctgcactg gaaccatcaa tgatgttggt ggatataggt ttgtctcctg gtaccaacga    120
cgccccggca aagcccccaa actcatcatt tctgatgtca ttaggcggcc atcagggguc    180
cctgatcgct tctctagttc caagtctgac aacacggcct acctgaccat ctctgggctc    240
caggctgagg acgaggctga ttattactgc agctcatata caagcagcag cactctctat    300
gtcttcggaa ctgggaccaa ggtcaccgtc cta                                  333

<210> SEQ ID NO 201
<211> LENGTH: 330
<212> TYPE: DNA
<213> ORGANISM: Homo sapiens

<400> SEQUENCE: 201
cagtctgccc tgactcagcc tgcctccgtg tctgggtctc ctggacagtc gatcaccatc     60
tcctgcactg gaaccagcag tgatgttggg agttataacc ttgtctcctg gtaccaacag    120
cacccaggca aagcccccaa actcatgatt tatgagggca gtaagcggcc ctcaggggtt    180
tctaatcgct tctctggctc caagtctggc aacgcggcct ccctgacaat ctctgggctc    240
caggctgagg acgaggctga ttattactgc cagtcctatg acagcagcct gagtgtggta    300
ttcggcggag ggaccaagct gaccgtccta                                      330

<210> SEQ ID NO 202
<211> LENGTH: 349
<212> TYPE: DNA
<213> ORGANISM: Mus musculus

<400> SEQUENCE: 202
acacagagca gcagatgtgg ggaagtagaa ggtgaaggga tggcaggagg ctcccacagg     60
acactcgtta tgccccgagg accagttcca tcccttgtgc caattgctct tgcaggtaaa    120
agagctctgg cagtcctccc accactgctg acagtcctct ttgcacaggg gaacatcaag    180
gatccgctct ttgcgccagc tctggtccac ctgctggatc cagggtccca agttcgggga    240
acactcatag aggcaggtgt cttggataaa gtgccgtttg cattccgatg tcatagttcc    300
gcagtggttc cagttgaacc ggtacaggta ggaaatgtcc tcctcgtgc                 349

<210> SEQ ID NO 203
<211> LENGTH: 276
<212> TYPE: DNA
<213> ORGANISM: Homo sapiens

<400> SEQUENCE: 203 tttttttta aattcatgtt tttaattggc ttaatacaaa ggtcccccag gaggccctgg      60
```

| gaggaggggg acagcctggg agaggcagag attcatggcc agcagcccac ccccacctgc | 120 |
| cacccactcc ccaacaaggg tcccagactc tttcaataat cctaaaaaaa ccgacgagag | 180 |
| cgcaggcaga tgaagagccc cttcatcctc aaacggcgac taccatcgaa agttgatagg | 240 |
| gcagacgttc gaatgggtcg tcgccgccac gggggg | 276 |

<210> SEQ ID NO 204
<211> LENGTH: 668
<212> TYPE: DNA
<213> ORGANISM: Mus musculus

<400> SEQUENCE: 204

| gatccttcga ctccttggcg cttggtgctt caaccggact gacttcctgg gcctggagtt | 60 |
| ggcgattaga ggtctgacat ggctcacctg atgactgtgc agttgttgct cctggtgatg | 120 |
| tggatggccg aatgtgctca gtccagagct actcgggcca ggactgaact tctcaatgtc | 180 |
| tgcatggatg ccaaacacca caagaaaaa ccgggccctg aggacaattt acacgaccag | 240 |
| tgcagcccct ggaagacgaa ttcctgctgt tccacgaaca caagccagga agcacataag | 300 |
| gacatttcct acctgtaccg gttcaactgg aaccactgcg gaactatgac atcggaatgc | 360 |
| aaacggcact ttatccaaga cacctgcctc tatgagtgtt ccccgaactt gggaccttgg | 420 |
| atccagcagg tggaccagag ctggcgcaaa gagcggatcc ttgattgttc ccctgtgcaa | 480 |
| agaggactgt catcagtggt gggaggactt gcagagctct tttccctgca agagcaattt | 540 |
| ggacaaggga tggaacttgg tctcggggca taacagtgt cctgtggggc ctccttgcaa | 600 |
| tccttcacgt tttatttccc agattggttg gtcttgttgt gaggaatctg gggttcactc | 660 |
| ttacagct | 668 |

<210> SEQ ID NO 205
<211> LENGTH: 73
<212> TYPE: DNA
<213> ORGANISM: Mus musculus

<400> SEQUENCE: 205

| ccagctccaa taacgtatat gagagttgca gcagataagg ggcaagtagt agagtatgga | 60 |
| gagagggaga gcg | 73 |

<210> SEQ ID NO 206
<211> LENGTH: 542
<212> TYPE: DNA
<213> ORGANISM: Mus musculus

<400> SEQUENCE: 206

| ctgtcaccag tggtgggaag cctgtcgtac ctcctttacc tgcaagagag actggcataa | 60 |
| aggctgggac tggtcctcag gcattaacaa gtgcccaaac acagcaccct gtcacacgtt | 120 |
| tgagtactac ttcccgacac cagccagcct ttgcgagggt ctctggagtc actcctacaa | 180 |
| ggtcagcaac tacagcagag ggagtggccg ctgcatccag atgtggtttg actcaaccca | 240 |
| gggcaatccc aatgaggacg tggtgaagtt ttatgcttcc tttatgacat ctgggactgt | 300 |
| gccccatgca gcagtacttc ttgtgcccag cctggcccca gtgctgtcat tatggctccc | 360 |
| tggctgagag gtcagtcttc ctctctagat ttctcctcta tctacccttg gtctggttca | 420 |
| actcttcaaa gaataaggaa gtcttgagcc tggttccacc cctctcctct gtcatccagt | 480 |
| tcctgatcca tgttggggga tggggtttct acatcatttc aataaactat gaacatctgg | 540 |

| gc | 542 |

<210> SEQ ID NO 207
<211> LENGTH: 269
<212> TYPE: DNA
<213> ORGANISM: Mus musculus

<400> SEQUENCE: 207

| gacatttcct aactgtaacg ggtcaactgg aagcactgcg gaaatatgac atcggaatgc | 60 |
| aaacgggact tttttcaaga cacctgcctc tatgagtgtt ccccgaattt ggaccttgat | 120 |
| tcagcaggtg gagcaaaact tgcgcaagaa ggggttcctg aagttcccct gtgcaaaaag | 180 |
| gactttcaca attggttgga ggatttccaa agctctttta cccgcaagag gaatttgcac | 240 |
| aagggtttga acatgtcctc ggggaataa | 269 |

<210> SEQ ID NO 208
<211> LENGTH: 785
<212> TYPE: DNA
<213> ORGANISM: Mus musculus

<400> SEQUENCE: 208

| attcggatcc ttcaaacctc ggccggctgt ctcctggaat gaagaaagca aaggaagcct | 60 |
| agagtggaga caaagaagcc cgaggactct gagagctgcc atcttttcct tgtttgccgc | 120 |
| ctgacacttc tcagcaggat ccacataccc taaggagtgg aagactcctt ggcgcttggt | 180 |
| gcttcaaccg gactgacttc ctgggcctgg agttggcgat tagaggtctg acatggctca | 240 |
| cctgatgact gtgcagttgt tgctcctggt gatgtggatg gccgaatgtg ctcagtccag | 300 |
| agctactcgg gccaggactg aacttctcaa tgtctgcatg gatgccaaac accacaaaga | 360 |
| aaaaccgggc cctgaggaca atttacacga ccagtcagc ccctggaaga cgaattcctg | 420 |
| ctgttccacg aacacaagcc aggaagcaca taaggacatt tcctacctgt accggttcaa | 480 |
| ctggaaccac tgcggaacta tgacatcgga atgcaaacgg cactttatcc aagacacctg | 540 |
| cctctatgag tgttccccga acttgggacc ctggatccag caggtggacc agagctggcg | 600 |
| caaagagcgg atccttgatg ttcccctgtg caagaggact gtcagcagtg gtgggaggac | 660 |
| tgccagagct ctttacccct gcagagcaat tggcacaagg gtggaatggt ccccgggca | 720 |
| taacgatttc ccgtggaggc ttctggaatc ccttaacctc taattcccaa tctgcggcct | 780 |
| gtgtg | 785 |

<210> SEQ ID NO 209
<211> LENGTH: 718
<212> TYPE: DNA
<213> ORGANISM: Mus musculus

<400> SEQUENCE: 209

| attcggatcc ttcctggaag tataaacaag aaaggaggct gacggctcta gaagtcccaa | 60 |
| cctgttgtga tcttcagtag acaaacactc ctggtgtgtc acaggattca ggccactaaa | 120 |
| cctcggccgg ctgtctcctg gaatgaagaa agcaaaggaa gcctagagtg gagacaaaga | 180 |
| agcccgaggc actctgagag ctgccatctt tccttgtttt gccgcctgac acttctcagc | 240 |
| aggatccaca taccctaagg agtggaagac tccttggcgc ttggtgcttc aaccggactg | 300 |
| acttcctggg cctggagttg gcgattagag gtctgacatg gctcacctga tgactgtgca | 360 |
| gttgttgctc ctgctgatgt ggatggccga atgtgctcag tccagagcta ctcgggccag | 420 |
| gactgaactt ctcaatgtct gcatggatgc caaacaccac aaagaaaaac cgggccctga | 480 |

```
ggacaattta cacgaccagt gcagccctg gaagacgaat tcctgctgtt tcacgaacac      540
aagccaggaa gcacataagg acagttccta cctgtaccgg ttcaactggg accactgcgg      600
aactatgaca tcggaatgca aacggcactt tatccagaaa cctgcctcta ttagtgttcc      660
cccacattgg gaccctggat tcaccagtgg gacaaagatg gcgcgaaaaa acgggtcc       718
```

<210> SEQ ID NO 210
<211> LENGTH: 323
<212> TYPE: DNA
<213> ORGANISM: Mus musculus

<400> SEQUENCE: 210

```
attcggatcc ttcggaacta tgacatcgga atgcaaacgg cactttatcc aagacacctg       60
cctctatgag tgttccccga acttgggacc ctggatccag caggtggacc agagctggcg      120
caaagagcgg atccttgatg ttcccctgtg caaagaggac tgtcagcagt ggtgggagga      180
ctgccagagc tcttttacct gcaagagcaa ttggcacaag gatgaaact ggtcctcggg      240 gcataacgag tgtcctgtgg gagcctcctg ccatccttc accttctact tccccacatc      300
tgctgctctg tgtgaggaaa tct                                             323
```

<210> SEQ ID NO 211
<211> LENGTH: 450
<212> TYPE: DNA
<213> ORGANISM: Mus musculus

<400> SEQUENCE: 211

```
attcggatcc ttcctggaag tataaaccag aaaggaggct gacggctcta gaagtcccca       60
acctgttgtg atcttcagta gacaaacact cctggtgtgt cacaggattc aggccactaa      120
acctcggccg gctgtctcct ggaatgaaga agcaaaggga agcctagagt ggagacaaag      180
aagcccgagg cactctgaga gctggcatct tttccttgtt tgccgcctga caattctcag      240
cagggtccac atatcctaag taagagtggg agactccttt gcgcttggtg cttcaaccgg      300
actgaattcc tgggcctgga attggcgatt agaggtccga catggctcaa ctgatgacct      360
tgcaattgtt ggccccggtg atgtggatgg gcgaaagtgc ttcagttcaa gaagctactt      420
cgggccaagg actgaaactt tctcaaatgt                                      450
```

<210> SEQ ID NO 212
<211> LENGTH: 682
<212> TYPE: DNA
<213> ORGANISM: Mus musculus

<400> SEQUENCE: 212

```
gaagactcct tggcgcttgg tgcttcaacc ggactgactt cctgggcctg gagttggcga       60
ttagaggtct gacatggctc acctgatgac tgtgcagttg ttgctcctgg tgatgtggat      120
ggccgaatgt gctcagtcca gagctactcg ggccaggact gaacttctca atgtctgcat      180
ggatgccaaa caccacaaag aaaaaccggg ccctgaggac aatttacacg accagtgcag      240
cccctggaag acgaattcct gctgttccac gaacacaagc caggaagcac ataaggacat      300
ttcctacctg taccggttca actggaacca ctgcggaact atgacatcgg aatgcaaacg      360
gcactttatc aagacacct gcctctatga gtgttccccg aacttgggac cctggatcca      420
gcaggtggac cagagctggc gcaaagagcg gatccttgat gttcccctgt gcaaagagga      480
ctgtcagcag tggtgggagg actgccagag ctcttttacc tgcaagagca attggcacaa      540
```

```
gggatggaac tggtcctcgg ggcataacga gtgtcctgtg ggagcctcct gccatccctt      600
caccttccta cttcccaaca tctgctgctc tgtgtgagga aatctggagt cactcctcaa      660
gctcagcaac tacagttcga gg                                              682
```

```
<210> SEQ ID NO 213
<211> LENGTH: 411
<212> TYPE: DNA
<213> ORGANISM: Mus musculus

<400> SEQUENCE: 213
cgggccctga ggacaattta cacgaccagt gcagccctg gaagacgaat tcctgctgtt       60
ccacgaacac aagccaggaa gcacataagg acatttccta cctgtaccgg ttcaactgga     120
accactgcgg aactatgaca tcggaatgca acggcactt tatccaagac acctgcctct     180
atgagtgttc cccgaacttg ggaccctgga tccagcaggt ggaccagagc tggcgcaaag     240
agcggatcct tgatgttccc ctgtgcaaag aggactgtca gcagtggacg gaggactgcc     300
agagctcttt tacctgcaag agcaattggc acaagggatg gaactggtcc tctgggcata     360
acgagtgtcc tgtgggagcc tcctgccatc ccttcacctt ctacttcccc a              411
```

```
<210> SEQ ID NO 214
<211> LENGTH: 653
<212> TYPE: DNA
<213> ORGANISM: Mus musculus

<400> SEQUENCE: 214
ctggagctga gcacacactt ggaggttcca cttaccttag ctctgccttc agggtctgac      60
atggctcacc tgatgactgt gcagttgtgg ctgctggtga tgtggatggc cgaatgtgct     120
cagtccagag ctactcgggc caggactgaa cttctcaatg tctgcatgga tgccaaacac     180
cacaaagaaa aaccgggccc tgaggacaat ttacacgacc agtgcagccc ctggaagacg     240
aattcctgct gttccacgaa cacaagccag gaagcacata aggacatttc ctacctgtac     300
cggttcaact ggaaccactg cggaactatg acatcggaat gcaaacggca ctttatccaa     360
gacacctggc tctatgagtg ttccccgaac ttgggaccct ggattcagca ggtgaccaa      420 agctggcgca agagagggat cctttatgtt cccctggtgc aaagaggact tgtcagcagt     480
tggtgggagg actgccagaa ctcgtgtacc tgccaggagc aattggcaca agggatggaa     540
ttggttcttc gggcataac gaagtgctct gtgtggagcc tcctgcagtc ctgtaacgtc      600
taattcccac atttggcggt ctgtgtaatg aatctcgggc actccacagg ctc            653
```

```
<210> SEQ ID NO 215
<211> LENGTH: 256
<212> TYPE: DNA
<213> ORGANISM: Homo sapiens

<400> SEQUENCE: 215
acacctgcct ctacgagtgc tcccccaact tggggccctg gatccagcag gtggatcaga      60
gctggcgcaa agagcgggta ctgaacgtgc ccctgtgcaa agaggactgt gagcaatggt     120
gggaagattg tcgcacctcc tacacctgca gagcaactg gcacaagggc tgcaactgga     180
cttcagggtt taacaagtgc gcagtgggag ctgcctgcca acctttccat ttctacttcc     240
ccacacccat tgcccg                                                     256
```

```
<210> SEQ ID NO 216
<211> LENGTH: 1282
```

```
<212> TYPE: DNA
<213> ORGANISM: Homo sapiens

<400> SEQUENCE: 216
gtgtccccag aagtggcctt gaaccgaata tctccaatgg acagggctgg ggagcccaca      60
gggctggtgc ggcgggagtc agtggaggcg aagatgcaga gtgccagctg gaaggtcaga     120
atacgctcca ccaccatggc ctggccctgc gttgtgttgt tggtagagcg cgttgtctac     180
cctgtaccga agacagaggc tgtggggaca gcctaggggc cctggatcta ttgcctactt     240
agagagaggc caactcagac acagccgtgt atgctcccag cagcaacgga ggttcagcac     300
cgcctgcagg gacagaaaga catggtctgg aaatggatgc cacttctgct gcttctggtc     360
tgtgtagcca ccatgtgcag tgcccaggac aggactgatc tcctcaatgt ctgtatggat     420
gccaagcacc acaagacaaa gccaggtcct gaggacaagc tgcatgacca atgcagtccc     480
tggaagaaga atgcctgctg cacagccagc accagccagg agctgcacaa ggacacctcc     540
cgcctgtaca actttaactg ggaccactgc ggcaagatgg agcccgcctg cagcgccact     600
tcatccagga cacctgtctc tatgagtgct caccaacctg gggccctgga tccagcaggt     660
gaatcagagc tggcggcaaa gaacgcttcc tggatgtgcc cttatgcaaa gagcactgtc     720
agcgctggtg ggaggattgt cacacctccc acacgtgcaa gagcaactgg cacagaggat     780
gggactggac ctcaggagtt aacaagtgcc agctggggc tctctgccgc acctttgagt      840
cctacttccc cactccagct gcccttgtc aaggcctctg gagtcactca tacaaggtca      900
gcaactacag ccgagggagc ggccgctgca tccagatgtg gtttacttca gcccagggca     960
accccaacga ggaagtggcg aggttctatg ctgcagccat gcatgtgaat gctggtgaga    1020
tgcttcatgg gactggggt ctcctgctca gtctggccct gatgctgacc ctctggctcc     1080
tcggctgcgt tcagtcctcc cagactacct gccctcagct tggataacca ggctgggctc    1140
agctcagctc ccacaaatga cagcccctta agcatgcttc tattagtcac ctaaccctct    1200
gtcacccagt ctgttgctgc tccatggtgg ggccaagagt cacttctaat aaacagactg    1260
ttttctaata aaaaaaaaaa aa                                             1282

<210> SEQ ID NO 217
<211> LENGTH: 211
<212> TYPE: DNA
<213> ORGANISM: Mus musculus

<400> SEQUENCE: 217
aggattctat gccgaggcca tgagtggagc tgggcttcat gggacctggc cactcttgtg      60
cagcctgtcc ttagtgctgc tctgggtgat cagctgagtt cctgttttac cttcagttgt     120
ctggagcgcc accctgcttg gctcagcctc ccagctccca gcctcctttg tggtggggct     180
ctgacagcct ctttaataaa ccagacattc c                                    211

<210> SEQ ID NO 218
<211> LENGTH: 559
<212> TYPE: DNA
<213> ORGANISM: Mus musculus

<400> SEQUENCE: 218
attaggatcc ttccttctca gcaggatcca catacccaa ggagtggaag actccttggc       60
gcttggtgct tcaaccggac tgacttcctg ggcctggagt tggcgattag aggtctgaca     120
tggctcaact gatgactgtg cagttgttgc tcctggtgat gtggatggcc gaatgtgctc     180
```

```
agtccagagc tactcgggcc aggactgaac ttctcaatgt ctgcatggat gccaaacacc    240
acaaagaaaa accgggccct gaggacaatt tacacgacca gtgcagcccc tggaagacga    300
attcctgctg ttccacgaac acaagccagg aagcacataa ggacatttcc tacctgtacc    360
ggttcaactg gaaccactgc ggaaatatga atcggaatg caaacggcac tttatccaag     420
aaaccttgac tcaatgagtg ttacacgaaa cttgggacac tggataagca agtggaacag    480
agatgggcga aaagagcgga tacattgatg taaccctgtg acaagaggac tgttcagcag    540
tggtgggagg actgccaga                                                559
```

<210> SEQ ID NO 219
<211> LENGTH: 661
<212> TYPE: DNA
<213> ORGANISM: Mus musculus

<400> SEQUENCE: 219

```
aattcggatc catgatctgg aagtataaac aagaaaggag gctgacggct ctagaagtcc    60
ccaacctgtt gtgatcttca gtagacaaac actcctggtg tgtcacagga ttcaggccac   120
taaacctcgg ccggctgtct cctggaatga agaaagcaaa ggaagcctag agtggagaca   180
aagaagcccg aggcactctg agagctgcca tcttttcctt gtttgccgcc tgacacttct   240
cagcaggatc cacataccct aagcaggag tggagagagg cctgggctgg gccaggtttt    300
ctgggctttt cctgtgctc cgagtaggtg ggttgtattt tacccagtag gagtggaaga    360
ctccttggcg cttggtgctt caaccggact gacttcctgg gcctggagtt ggcgattaga    420
ggtctgacat ggctcacctg atgactgtgc agttgttgct cctggtgatg tggatggccg    480
aatgtgctca gtccagagct actcgggcca ggactgaact tctcaatgtc tgcatggatg    540
ccaaacacca caaagaaaaa ccgggccctg aggacaattt acacgaccag tgcagccct    600 ggaagacgaa ttcctgctgt tcaacgacac aagcaggaag cactaaggac ttttctactg    660
t                                                                   661
```

<210> SEQ ID NO 220
<211> LENGTH: 695
<212> TYPE: DNA
<213> ORGANISM: Mus musculus

<400> SEQUENCE: 220

```
ttcggatcct tctctggaag tataaacaag aaaggaggct gacggctcta gaagtcccca    60
acctgttgtg atcttcagta gacaaacact cctggtgtgt cacaggattc aggccactaa   120
acctcggccg gctgtctcct ggaatgaaga agcaaagga agcctagagt ggagacaaag    180
aagcccgagg cactctgaga gctgccatct ttttccttgtt tgccgcctga cacttctcag   240
caggatccac ataccctaag gagtggaaga ctccttggcg cttggtgctt caaccggact    300
gacttcctgg gcctggagtt ggcgattaga ggtctgacat ggctcacctg atgactgtgc    360
agttgttgct cctggtgatg tggatggccg aatgtgctca gtccagagct actcggggcc    420
aggactgaac ttctcaatgt ctgcatggat gccaaacacc acaaagaaaa accgggccct    480
gaggacaatt tacacgacca gtgcagcccc tggaagacga attcctgctg ttccacgaac    540
acaagccagg aagcacataa ggacatttcc tacctgtacc ggttcaactg gaaccactgc    600
ggaactatga catcggaatg caaacggcac tttatccaag acacctgcct ctatgagtgt    660
tccccgaact tgggactgga ttcagcaggt ggacc                               695
```

<210> SEQ ID NO 221
<211> LENGTH: 567
<212> TYPE: DNA
<213> ORGANISM: Mus musculus

<400> SEQUENCE: 221

```
tggaagactc cttggcgctt ggtgcttcaa ccggactgac ttcctgggcc tggagttggc      60
atttagaggt ctgacatggc tcacctgatg actgtgcagt tgttgctcct ggtgatgtgg     120
atggccgaat gtgctcagtc cagagctact cgggccagga ctgaacttct caatgtctgc    180
atggatgcca agcaccacaa agaaaaaccg ggccctgagg acaatttaca cgaccagtgc    240
agccctggaa gacgaattc ctgctgttcc acgaacacaa gccaggaagc acataaggac     300
atttcctacc tgtaccggtt caactggaac cactgcggaa ctatgacatc ggaatggcaa    360
cggcactttt atcaaagaca cctgcctcta tgagtgttcc ccgaactttg gaacctgga    420
ttccagaagt tggacagagc ctgcgcaaaa gagcggattc ttgatggttc cctgtgcaaa    480
gaggactgtc agcagtggtg ggagactgcc aagctcttta cctgcaagag cattggcaca   540
aggatggaat ggtcctctgg caaacga                                        567
```

<210> SEQ ID NO 222
<211> LENGTH: 600
<212> TYPE: DNA
<213> ORGANISM: Mus musculus

<400> SEQUENCE: 222

```
atggctccct gatgactgtg cagttgttgc tcctgctgat gtggatggcc gaatgtgctc      60
agtccagagc tactcgggcc aggactgaac ttctcagtgt ctgcatggat gccagacacc    120
acaaagagaa accgggccct gaggacaatt tacacgacca gtgcagcccc tggaagacga    180
attcctgctg ttccacgaac acaagccagt aagcacataa ggacatttcc tacctgtacc    240
ggttcaactg gaaccactgc ggaactatga catcggaatg caaacggcac tttatccaag    300
acagctgcct ctatgagtgt tccccgaact tgggagcctg tatgcagcag gtggacgaga    360
gctgtcgcaa agagcggatc cttgatgtgc ccctgtgcaa agaggactgt cagcagtggt    420
gcgagtgctg cggagctctt gtacctgcag agaggaattt gcacagggga tggaactggt    480
tccctggggc ataacaagtg tcctgtggta gcctgccggc aggccgttag cgttgtagtt    540
tcgcggatcg gctggtcggg tgaagaagtt gtggggcatg ccacatgtca gtagtttgtt    600
```

<210> SEQ ID NO 223
<211> LENGTH: 582
<212> TYPE: DNA
<213> ORGANISM: Mus musculus

<400> SEQUENCE: 223

```
aattcgcatc cttcataaac aagacaggag gctgacggct ctagaagtcc ccaacctgtt      60
gtgatcttca gtagacaaac actcctggtg tgtcacagga ttcaggccac taaacctcgg    120
ccggctgtct cctggaatga agaaagcaaa ggaagcctag agtggagaca agaagcccg     180
aggcactctg agagctgcca tcttttcctt gtttgccgcc tgacttct cagcaggatc      240
cacatacct aaggagtgga agactccttg gcgcttggtg cttcaaccgg actgacttcc     300
tgggcctgga gttggcgatt agaggtctga catggctcac ctgatgactg tgcagttgtt    360
gctcctggtg atgttgatgg ccgaatgtgc tcagtccaga gctactcggg ccaggactga    420
acttctcaat gtctgcatgg atgccaaaca ccacaaagaa aaaccgggcc ctgaggacaa    480
```
tttacacgac cagtgcagcc cctggaagac gaatttctgc tgttccacga acacaagcca     540
ggaagcacat aaggacattt cctaactgta acggttcaat gg                         582

<210> SEQ ID NO 224
<211> LENGTH: 372
<212> TYPE: DNA
<213> ORGANISM: Mus musculus

<400> SEQUENCE: 224
tcccatttcc tacctgtacc ggttcaactg gaaccactgc ggaactatga catcggaatg      60
caaacggcac tttatccaag acacctgcct ctatgagtgt tccccgaact tgggaccctg     120
gatccagcag gtggaccaga gctggcgcaa agagcggatc cttgatgttc ccctgtgcaa     180
agaggactgt cagcagtggt gggaggactg ccagagctct tttacctgca agagcaattg     240
gcacaaggga tggaactggt cctcggggca taacgagtgt cctgtgggag cctcctgcca     300
tcccttcacc ttctacttcc ccacatctgc tgctctgtgt gaggaaatct ggagtcactc     360
ctacgagctc ag                                                         372

<210> SEQ ID NO 225
<211> LENGTH: 375
<212> TYPE: DNA
<213> ORGANISM: Mus musculus

<400> SEQUENCE: 225
ctatcccatt tcctacctgt accggttcaa ctggaaccac tgcggaacta tgacatcgga      60
atgcaaacgg cactttatcc aagacacctg cctctatgag tgttccccga acttgggacc     120
ctggatccag caggtggacc agagctggcg caaagagcgg atccttgatg ttcccctgtg     180
caaagaggac tgtcagcagt ggtgggagga ctgccagagc tctttttacct gcaagagcaa    240 ttggcacaag ggatggaact ggtcctcggg gcataacgag tgtcctgtgg gagcctcctg     300
ccatcccttc accttctact tccccacatc tgctgctctg tgtgaggaaa tctggagtca     360
ctcctacaag ctcag                                                      375

<210> SEQ ID NO 226
<211> LENGTH: 440
<212> TYPE: DNA
<213> ORGANISM: Mus musculus

<400> SEQUENCE: 226
tatccctgag agctgccatc ttttccttgt ttgccgcctg acacttctca gcaggatcca      60
cataccctaa gggagtggag agaggcctgg gctgggccag gttttctggg cttttttcctg    120 tgctccgagt cagtgggttg tattttaccc agtaggagtg gaagactcct ggcgcttgg      180 tgcttcaacc ggaactgact tcctgggcct ggagttggcg attagaggtc ctacatggct     240
cacctgatga ctgtgcaagt tgtgcccccg gtgatgttga atggcggatg tgctcagtcc     300
agaagtaatt tgggccaaga ctggacttct ccatggctgc attgatggca aacaccccaa     360
aggaaaacgg ggccttgggg caattatcac ggccctgtaa cccttggaaa ccaattcccg     420
ggttccgaaa cacagccgga                                                 440

<210> SEQ ID NO 227
<211> LENGTH: 544
<212> TYPE: DNA
<213> ORGANISM: Mus musculus

<400> SEQUENCE: 227

```
aattcggatc catgggctga tctggaagta taaacaagaa aggaggctga cggctctaga      60
agtccccaac ctgttgtgat cttcagtaga caaaacactcc tggtgtgtca caggattcag    120
gccactaaac ctcggccggc tgtctcctgg aatgaagaaa gcaaaggaag cctagagtgg    180
agacaaagaa gcccgaggac tctgagagct gccatctttt ccttgtttgc cgcctgacac    240
ttctcagcag gatccacata ccctaaggga gtggagagag gcctgggctg gcaggtttt    300 ctgggctttt tcctgtgctc cgagtaggtg ggttgtattt tacccagtag gagtggaaga    360
ctccttggcg cttggtgctt caaccggact gacttcctgg gcctggagtt ggcgattaga    420
ggtctgacat ggctcacctg atgactgtgc agttgttgct cctggtgatg tggatggccg    480
aatgtgctca gtccagagct actcgggcca ggactgaact tctcaatgtc tgcatggatg    540
ccaa                                                                 544
```

<210> SEQ ID NO 228
<211> LENGTH: 350
<212> TYPE: DNA
<213> ORGANISM: Mus musculus
<400> SEQUENCE: 228

```
ttggcatcca tgcagacatt gagaagttca gtcctggccc gagtagctct ggactgagca     60
cattcggcca tccacatcac caggagcaac aactgcacag tcatcaggtg agccatgtca    120
gacctctaat cgccaactcc aggcccagga agtcagtccg gttgaagcac caagcgccaa    180
ggagtcttcc actcctactg ggtaaaatac aacccaccta ctcggagcac aggaaaaagc    240
ccagaaaacc tggcccagcc caggcctctc tccactccct tagggtatgt ggatcctgct    300
gagaagtgtc aggcggcaaa caaggaaaag atggcagctc tcagagtgcc                350
```

<210> SEQ ID NO 229
<211> LENGTH: 563
<212> TYPE: DNA
<213> ORGANISM: Mus musculus
<400> SEQUENCE: 229

```
ttcggatcca tggtgctccg agtaggtggg ttgtatttta cccagtagga gtggaagact     60
ccttggcgct tggtgcttca accggactga cttcctgggc ctggagttgg cgattagagg    120
tctgacatgg ctcacctgat gactgtgcag ttgttgctcc tggtgatgtg gatggccgaa    180
tgtgctcagt ccagagctac tcgggccagg actgaacttc tcaatgtctg catggatgcc    240
aaacaccaca agaaaaaacc gggccctgag gacaatttac acgaccagtg cagcccctgg    300
aagacgaatt cctgctgttc cacgaacaca agccaggaag cacataagga catttcctac    360
ctgtaccggt tcaactggaa ccactgcgga actatgacat cggaatgcaa acggcacttt    420
atccaagaca cctgcctcta tgagtgttcc ccgaacttgg accctggat ccagcaagtg    480 gaccagagct ggcgcaagag cggatccttg aatgtccctg tgcaagagga ctgtcagcag    540
tggtgggaga ctgcagagct ctt                                            563
```

<210> SEQ ID NO 230
<211> LENGTH: 587
<212> TYPE: DNA
<213> ORGANISM: Mus musculus
<400> SEQUENCE: 230

```
aattcgggat ccatgggctg atctggaagt ataaacaaga aaggaggctg acggctctag     60
```

| | |
|---|---|
| aagtccccaa cctgttgtga tcttcagtag acaaacactc ctggtgtgtc acaggattca | 120 |
| gctctgtttc ctaggccact aaacctcggc cggctgtctc ctggaatgaa gaaagcaaag | 180 |
| gaagcctaga gtggagacaa agaagcccga ggcactctga gctgccat cttttccttg | 240 |
| tttgccgcct gacacttctc agcaggatcc acatacccta aggagtggaa gactccttgg | 300 |
| cgcttggtgc ttcaaccgga ctgacttcct gggcctggag ttggcgatta gaggtctgac | 360 |
| atggctcacc tgatgactgt gcagttgttg ctcctggtga tgtggatggc cgaatgtgct | 420 |
| cagtccagag ctactcgggc caggactgaa cttctcaatg tctgcatgga tgccaaacac | 480 |
| cacaaagaaa aaccgggccc tgaggacaat ttacacgacc agtgcagccc tggaagacg | 540 |
| aattcctgct gttccacgaa cacaagccag gaagcacata aggacat | 587 |

<210> SEQ ID NO 231
<211> LENGTH: 557
<212> TYPE: DNA
<213> ORGANISM: Mus musculus

<400> SEQUENCE: 231

| | |
|---|---|
| attcggatcc acgtataaac aagaaaggag gctgacggct ctagaagtcc ccaacctgtt | 60 |
| gtgatcttca gtagacaaac actcctggtg tgtcacagga ttcagctctg tttcctaggc | 120 |
| cactaaacct cggccggctg tctcctggaa tgaagaaagc aaaggaagcc tagagtggag | 180 |
| acaagaagc ccgaggcact ctgagagctg ccatctttc cttgtttgcc gcctgacact | 240 |
| tctcagcagg atccacatac cctaagggag tggagagagg cctgggctgg caggttttc | 300 |
| tgggcttttt cctgtgctcc gagtaggtgg gttgtatttt acccagtagg agtggaagac | 360 |
| tccttggcgc ttggtgcttc aaccggactg acttcctggg cctggagttg gcgattagag | 420 |
| gtctgacatg gctcacctga tgactgtgca gttgttgctc ctggtgatgt ggatggccga | 480 |
| attggctcat tccaaagcta ctcgggccgg aactgaactc ctcaaggtct gcatggatgc | 540 |
| aaacgccaca aagaaaa | 557 |

<210> SEQ ID NO 232
<211> LENGTH: 613
<212> TYPE: DNA
<213> ORGANISM: Mus musculus

<400> SEQUENCE: 232

| | |
|---|---|
| gttcggatcc atgggctgat ctggaagtat aaacaagaaa ggaggctgac ggctctagaa | 60 |
| gtccccaacc tgttgtgatc ttcagtagac aaacactcct ggtgtgtcac aggattcagc | 120 |
| tctgtttcct aggccactaa acctcggccg gctgtctcct ggaatgaaga agcaaagga | 180 |
| agcctagagt ggagacaaag aagcccgagg cactctgaga gctgccatct tttccttgtt | 240 |
| tgccgcctga cacttctcag caggatccac atacccaag ggagtggaga ggcctgggg | 300 |
| ctgggccagg ttttctgggc ttttcctgtg ctccgagtag gtgggttgta ttacccag | 360 |
| taggagtgga agactccttg gcgcttggtg cttcaaccgg actgacttcc tgggcctgga | 420 |
| gttggcgatt agaggtctga catggctcac ctgatgactg tgcagttgtt gctcctggtg | 480 |
| atgtggatgg cgaatgtgct cagtccagag ctactcgggc caagactgaa cttctcaatg | 540 |
| tctgcatgga tgccaacacc acaagaaaaa cggggcttga acaatttca cgacagtgca | 600 |
| gccctggaaa aga | 613 |

<210> SEQ ID NO 233
<211> LENGTH: 1230

<212> TYPE: DNA
<213> ORGANISM: Pig

<400> SEQUENCE: 233

```
gaattcgcgg ccgctccggg aagggggaa gggcacaact ccctcgggaa gctcgccgct      60
gcctcctgga gcagaaggca gacaaagcca tgccctggaa gctgacagcc cttctgctct     120
ttctggccgg ggtggtctcc gtgtgccgcg cccgggccag gacggacctg ctcaacgtct     180
gcatggatgc caagcaccac aaggtagagc caggccctga ggacgagctg cacgaccagt     240
gcgtccctg gaagaagaac gcctgctgct ccgccagagt cagccacgag ctgcaccggg      300
acaagtcctc cctgtataac ttttcctggg agcactgcgg caggatggag ccggcctgca     360
agcgccactt cattcagaac aactgtctgt acgagtgctc gcccaacctg ggccctggt      420
tccaggaggt gaaccagaag tggcgcaaag agcggttcct gaacgtgccc ctctgcaaag     480
aggactgtct ggactggtgg gaagactgcc gcacctccta cacctgcaag agcagctggc     540
acaagggctg gaactggagc tcaggatcta accagtgtcc cacggggacc acctgcgaca     600
catttgagtc cttcttcccc acacccgcag cgctgtgtga gggcatctgg aatcacgatt     660
ataagttcac caactacagc cggggcagcg gccgctgcat ccagatgtgg tttgacgcgg     720
ccgagggcaa ccccaacgag gaggtagcga ggttctacgc cttggccttg agtgcgggga     780
ccatgtccct gggaccgggg cctcctcctgc tcagcgcagc cctgatgctg ccacttgggc    840
tccttgactg agtccggcgt ctccagacgg tccttctgcc tgtccccagc tttgatgacc     900
aggctggtct caactcagct cccaccaatg agggagccct aagcccgcct catctgttac     960
ccatccctct gtcatcaagt tcctgccgta gggtgggcct tggggtctct ctgacagcca    1020
gttctaacag gcagattaac agcactgtgt ctgatgggct gttttggttg tgagctggtg    1080
tgtggcagag gacagagccc atagcttttg gattccttca gcttagagaa atgagacctg    1140
ggtttgaatt ccagctctgc cactcactat gtcaagtgaa gcagttgcgc gacggctcta    1200
aaccataggc tcctcctcaa taaaatgaag                                     1230
```

<210> SEQ ID NO 234
<211> LENGTH: 317
<212> TYPE: DNA
<213> ORGANISM: Mus musculus

<400> SEQUENCE: 234

```
aatctggagt cactcctaca agctcagcaa ctacagtcga gggagcggcc gctgcattca      60
gatgtggttc gacccagccc agggcaaccc caacgaggaa gtggcgaggt tctatgccga     120
ggccatgagt ggagctgggt ttcatgggac ctggccactc ttgtgcagcc tgtccttagt     180
gctgctctgg gtgatcagct gagctcctgt tttaccttca gttgtctgga gcgccaccct    240
gcttggctca gcctcccagc tcccagcctc ctttgtggtg gggctctgac agcctcttta    300
ataaaccaga cattcca                                                    317
```

<210> SEQ ID NO 235
<211> LENGTH: 529
<212> TYPE: DNA
<213> ORGANISM: Mus musculus

<400> SEQUENCE: 235

```
cacgaacaca agccaggaag cacataagga catttcctac ctgtaccggt tcaactggaa      60
ccactgcgga actatgacat cggaatgcaa acggcacttt atccaagaca catgcctcta    120
```

```
tgagtattcc ccgaacttgg gaccctggat ccagcaggtg gaccagagct ggcgcaaaga    180
gcggatcctt gatgttcccc tgtgcaaaga ggactgtcag cagtggtggg aggactgcca    240
gagctctttt acctgcaaga gcaattggca caagggatgg aactggtcct cggggcataa    300
cgagtgtcct gtgtgagcct cctgccatcg cttcaccttc tacttcccca catctgctgc    360
tctgtgtgaa gaaatctgga gtcactccta caagcttaac aactacagtc gagggaagcg    420
gccgctgcag tcagatgtgg ttcgacccag ccatggcaaa cccagcgagg aagttgcgag    480
gtctatgccg aggcaatagt gagctggtgt ctgggactgg gcactttgt                529
```

<210> SEQ ID NO 236
<211> LENGTH: 557
<212> TYPE: DNA
<213> ORGANISM: Mus musculus

<400> SEQUENCE: 236

```
aagactgtag agactaccca gagtctgacc tagggacagg ccaactcgga tacccctatg     60
tgcgctccca gaagctaagg acattgagac agaaagacat ggcctggaaa cagacaccac    120
tcttgctttt ggtctacatg gtcacaacag gcagtggcgg gacagaacag acctactcaa    180
cgtttgcatg gatgccaaac accataagac aaagccgggc cccgaggaca agctgcatga    240
ccagtgtagt ccatggaaga aaaatgcctg ttgctcagtc aacaccagcc aggagctaca    300
caaggctgac tcccgtctgt acttcaactg ggatcactgt ggcaagatgg agcctgcctg    360
taagagtcac ttcatccaag actcctgcct gtatgattgt ttcccaaacc ttggcccttg    420
attcagtcaa gtggatcaag attgggctta aaaaggtttt cctgatgtgc ccctaatgca    480
agaagacctg tcaccagtgt tggaaagctt gtggtacctc ctttactggc agaagagact    540
ggcataaagc tcggact                                                   557
```

<210> SEQ ID NO 237
<211> LENGTH: 616
<212> TYPE: DNA
<213> ORGANISM: Mus musculus

<400> SEQUENCE: 237

```
attcggatcc atgggctgat ctggaagtat aaacaagaaa ggaggctgac ggctctagaa     60
gtcccaacct gttgtgatct tcagtagaca aacactcctg gtgtgtcaca ggattcagct    120
ctgtttccta ggccactaaa cctcggccgg ctgtctcctg gaatgaagaa agcaaaggaa    180
gcctagagtg gagacaaaga agcccgaggc actctgagag ctgccatctt tccttgttt    240 gccgcctgac acttctcagc aggatccaca taccctaagg agtggaagac tccttggcgc    300
ttggtgcttc aaccggactg acttcctggg cctggagttg gcgattagac tctgccttca    360
gggtctgaca tggctcacct gatgactgtg cagttgttgc tcctggtgat gtggatggcc    420
gaatgtgctc agtccagagc tactcgggcc aggactgaac ttctcaatgt ctgcatggat    480
gccaaacacc acagagaaag accgggccct gaggacaatt ttacacgaca gtgcagcccc    540
tggaagacga attcctgttg ttcacgaaca caagcaggat gacataggac atttctactg    600
taccgttcac tggaac                                                    616
```

<210> SEQ ID NO 238
<211> LENGTH: 648
<212> TYPE: DNA
<213> ORGANISM: Mus musculus
<220> FEATURE:
<221> NAME/KEY: modified_base
<222> LOCATION: (605)
<223> OTHER INFORMATION: N = A, C, G, or T/U

<400> SEQUENCE: 238

```
aattcggatc catgggctga tctggaagta taaacaagaa aggaggctga cggctctaga      60
agtccccaac ctgttgtgat cttcagtaga caaaacactcc tggtgtgtca caggattcag    120
ctctgtttcc taggccacta aacctcggcc ggctgtctcc tggaatgaag aaagcaaagg    180
aagcctagag tggagacaaa gaagcccgag gcactctgag agctgccatc ttttccttgt    240
ttgccgcctg acacttctca gcaggatcca catacccctaa ggagtggaag actccttggc    300
gcttggtgct tcaaccggac tgacttcctg ggcctggagt tggcgattag actctgcctt    360
cagggtctga catggctcac ctgatgactg tgcagttgtt gctcctggtg atgtggatgg    420
ccgaatgtgc tcagtccaga gctactcggg ccaggactga acttctcaat gtctgcatgg    480
atgccaaaca ccacaaagaa aaaccgggcg ctgaggacaa tttacacgac cagtgcagca    540
cctggaagac gaattcctgg ctgttcacga gcacaagcta ggaagcacat aaggacattt    600
tctanctgta ccggttcaac tggacccact gcggactatg acatcgga                 648
```

<210> SEQ ID NO 239
<211> LENGTH: 636
<212> TYPE: DNA
<213> ORGANISM: Mus musculus

<400> SEQUENCE: 239

```
attcggatcc atgcagctta gaagggcctc cagctttagg ctttatagat acctggccca      60
cccttcccca gtcagcaggc tgatctggaa gtataaacaa gaaaggaggc tgacggctct    120
agaagtcccc aacctgttgt gatcttcagt agacaaacac tcctggtgtg tcacaggatt    180
caggccacta aacctcggcc ggctgtctcc tggaatgaag aaagcaaagg aagcctagag    240
tggagacaaa gaagcccgag gcactctgag agctgccatc ttttccttgt ttgccgcctg    300
acacttctca gcaggatcca catacccctaa gtaggagtgg aagactcctt ggcgcttggt    360
gcttcaaccg gactgacttc ctgggcctgg agttggcgat tagaggtctg acatggctca    420
cctgatgact gtgcagttgt tgctcctggt gatgtggatg ggcgaatgtg ctcagtccag    480
agctactcgg gccaggactg aacttctcaa tgtctgcatg gatgtcaaac accacaaaga    540
aacaccgggc ctgaggacaa tttacacgac cagtgcagcc cctggaagac gaattcctgct    600
gttccagaaa caagcaggag cataggcc attcct                                 636
```

<210> SEQ ID NO 240
<211> LENGTH: 660
<212> TYPE: DNA
<213> ORGANISM: Mus musculus

<400> SEQUENCE: 240

```
attcggatcc atgggctgat ctggaagtat aaacaagaaa ggaggctgac ggctctagaa      60
gtccccaacc tgttgtgatc ttcagtagac aaacactcct ggtgtgtcac aggattcagg    120
ccactaaacc tcggccggct gtctcctgga atgaagaaag caaggaagc ctagagtgga    180
gacaaagaag cccgaggcac tctgagagct gccatctttt ccttgtttgc cgcctgacac    240
ttctcagcag gatccacata cccctaaggag tggaagactc cttggcgctt ggtgcttcaa    300
ccggactgac ttcctgggcc tggagttggc gattagaggt ctgacatggc tcacctgatg    360
actgtgcagt tgttgctcct ggtgatgtgg atggccgaat gtgctcagtc cagagctact    420
```

| | |
|---|---|
| cgggccagga ctgaacttct caatgtctgc atggatgcca acaccacaa agaaaaaccg | 480 |
| ggccctgagg acaatttaca cgaccagtgc atgccctgga agacgaattc ctgctgttcc | 540 |
| acgaacacaa gccaggaagc acatagagac atttcctgct gtaccggttc aactggacca | 600 |
| ctgcggaact atgacatcga atgcagacgc actttgccag acactggct ctatgagtgt | 660 |

<210> SEQ ID NO 241
<211> LENGTH: 578
<212> TYPE: DNA
<213> ORGANISM: Mus musculus

<400> SEQUENCE: 241

| | |
|---|---|
| aattcggatc catgggctct agaagtcccc aacctgttgt gatcttcagt agacaaacac | 60 |
| tccgtggtgt gtcacaggat tcaggccact aaacctcggc cggctgtctc ctggaatgaa | 120 |
| gaaagcaaag gaagcctaga gtggagacaa agaagcccga ggcactctga gagctgccat | 180 |
| cttttccttg tttgccgcct gacacttctc agcaggatcc acatacccta aggagtggaa | 240 |
| gactccttgg cgcttggtgc ttcaaccgga ctgacttcct gggcctggag ttggcgatta | 300 |
| gaggtctgac atggctcacc tgatgactgt gcagttgttg ctcctggtga tgtggatggc | 360 |
| cgaatgtgct aagtccagag ctactcgggc caggactgaa ctcctaaatg tctgcatgga | 420 |
| tgccaaacac cacaaggaaa aacgggcccc tgaggacaat tacacgacca gtgcaagccc | 480 |
| tggaagacga aattctgctg ttcaagacca caagccagta gcatagggg acattccaac | 540 |
| ctgtaccgtt caacttgaac actgcggaat atgactcg | 578 |

<210> SEQ ID NO 242
<211> LENGTH: 403
<212> TYPE: DNA
<213> ORGANISM: Mus musculus

<400> SEQUENCE: 242

| | |
|---|---|
| ccactaacca cataaggaca tttcctacct gtaccggttg acctgcaacg actgccgaac | 60 |
| tatgacatcg caatgcacac gccactttat cgaccacacc tgcctctatg agtgttaccc | 120 |
| gaacttcgca ccctccatcc accaggtgca cgacagctgg cccacagagc gcatccttca | 180 |
| tgttccctg tccacagacg actgtcagca gtcgtcccag cactcccaca gctctcttac | 240 |
| ctgcaacacc aattcccaca acggatgaa ctcgtcctcg cggcatcacg agtgtcctgt | 300 |
| agcaccctcc tgccatccct tcaccttcta cttccgcaca tctcgtgctc tgtgtgatga | 360 |
| actctggagt cactcctaga cactcagcaa ctacagtcga cgg | 403 |

<210> SEQ ID NO 243
<211> LENGTH: 477
<212> TYPE: DNA
<213> ORGANISM: Mus musculus

<400> SEQUENCE: 243

| | |
|---|---|
| aattcggatc catgcatgga tccgatcca tggccctgg aagacgaatt cctgctgttc | 60 |
| cacgaacaca agccaggaag cacataagga catttcctac ctgtaccggt tcaactggaa | 120 |
| ccactgcgga actatgacat cggaatgcaa acggcacttt atccaagaca cctgcctcta | 180 |
| tgagtgttcc ccgaacttgg gaccctggat ccagcaggtg gaccagagct ggcgcaaaga | 240 |
| gcggatcctt gatgttcccc tgtgcaaaga ggactgtcag cagtggtggg aggactgcca | 300 |
| gagctctttt acctgcaaga gcaattgcca caagggatgg aactggtcct cggggcataa | 360 |
| cgagtgtcct gtgggagcct cctgccatcc cttcaccttc tacttcccac atctgctgct | 420 |

```
ctgtgtgagg aatctggagt cactctacaa gctcagcact acagtcgagg agccgcc      477
```

<210> SEQ ID NO 244
<211> LENGTH: 643
<212> TYPE: DNA
<213> ORGANISM: Mus musculus

<400> SEQUENCE: 244

```
ctgagtctga ggccagctgg tcgacaaggg tctgacatgg ctcacctgat gactgtgcag      60
ttgttgctcc tggtgatgtg gatggccgaa tgtgctcagt ccagagctac tcgggccagg     120
actgaacttc tcaatgtctg catggatgcc aaacaccaca agaaaaaacc gggccctgag     180
gacaatttac acgaccagtg cagccccctgg aagacgaatt cctgctgttc cacgaacaca    240
agccaggaag cacataagga catttcctac ctgtaccggt tcaactggaa ccactgcgga     300
actatgacat cggaatgcaa acggcacttt atccaagaca cctgcctcta tgagtgttcc     360
ccgaacttgg gaccctggat ccagcaggtg accagagct ggcgcaaaga gcggatcctt      420
gatgttcccc tgtgcaaaga ggactgtcag cagtggtggg aggactgcca gagctctttt     480
acctgcaaga gcaattggca caagggatgg aactggtcct cggggcataa cgagtgtcct     540
gtgggagcct cctgccatcc gttcacttct acttcgcaca tctgctgtct gtgtgaggaa     600
tctggagtca ctctacaagt ctagaataca gtcgaggacc ggc                      643
```

<210> SEQ ID NO 245
<211> LENGTH: 351
<212> TYPE: DNA
<213> ORGANISM: Mus musculus

<400> SEQUENCE: 245

```
aaccactgcg gaactatgac atcggaatgc aaacggcact ttatccaaga cacctgcctc      60
tatgagtgtt ccccgaactt gggaccctgg atccagcagg tggaccagag ctggcgcaaa     120
gagcggatcc ttgatgttcc cctgtgcaaa gaggactgtc agcagtggtg ggaggactgc     180
cagagctctt ttacctgcaa gagcaattgg cacaagggat ggaactggtc ctcgggggca     240
taacgagtgt cctgtgggag cctcctggca tcccttcagc ttctacttcc ccacatctgg     300
ctgctcctgt gttaggaaaa tcttggattc actcctacca agcttcagca a              351
```

<210> SEQ ID NO 246
<211> LENGTH: 423
<212> TYPE: DNA
<213> ORGANISM: Mus musculus

<400> SEQUENCE: 246

```
aattcggcac taggggaggc tgacggctct agaagtcccc aacctgttgt gatcttcagt      60
agacaaacac tcctggtgtg tcacaggatt cagctctgtt tcctaggcca ctaaacctcg     120
gccggctgtc tcctggaatg aagaaagcaa aggaagccta gagtggagac aaagaagccc     180
gaggcactct gagagctgcc atcttttcct tgtttgccgc ctgacacttc tcagcaggat     240
ccacataccc taaggagtgg aagactcctt ggcgcttagt gctgctctgg gtgatcagct     300
gagctcctgt tttaccttca gttgtctgga gcgccaccct gcttggctca gcctcccagc     360
tcccagcctc ctttgtggtg gggctctgac agcctcttta ataaaccaga cattccaaaa     420
aag                                                                  423
```

<210> SEQ ID NO 247

```
<211> LENGTH: 638
<212> TYPE: DNA
<213> ORGANISM: Mus musculus

<400> SEQUENCE: 247
gtggacgaag actgtagaga ctacccagag tctgacctag ggagaggcca actcggatac      60
ccctatgtgc gctcccagaa gctaaggaca ttgagacaga aagacatggc ctggaaacag     120
acaccactct tgcttttggt ctacatggtc acaacaggca gtggccggga cagaacagac     180
ctactcaacg tttgcatgga tgccaaacac cataagacaa agccgggccc cgaggacaag     240
ctgcatgacc agtgtagtcc atggaagaaa aatgcctgtt gctcagtcaa caccagccag     300
gagctacaca aggctgactc ccgtctgtac ttcaactggg atcactgtgg caagatggag     360
cctgcctgta agagtcactt catccaagac tcctgcctgt atgagtgctc ccccaacctt     420
gggccttgga tccagcaagt ggaccagagt tggcgtaaag agcgtttcct ggatgtgccc     480
ttatgcagag aggactgtca ccagtggtgg aagcctgtc gtacctcctt tacctgcaag     540
agagactggc ataaaggctg ggaatggtcg tcaggcatgt acaagtgcgc aacacagcac     600
ctgtacacgt gtgagtactc ttccgaacca gcagcttt                             638

<210> SEQ ID NO 248
<211> LENGTH: 638
<212> TYPE: DNA
<213> ORGANISM: Mus musculus

<400> SEQUENCE: 248
gggctgtgga cgaagactgt agagactacc cagagtctga cctagggaga ggccaactcg      60
gataccccta tgtgcgctcc cagaagctaa ggacattgag acagaaagac atggcctgga     120
aacagacacc actcttgctt ttggtctaca tggtcacaac aggcagtggc cgggacagaa     180
cagacctact caacgtttgc atggatgcca acaccataa gacaaagccg gccccgagg      240
acaagctgca tgaccagtgt agtccatgga agaaaaatgc tgttgctca gtcaacacca      300
gccaggagct acacaaggct gactcccgtc tgtacttcaa ctgggatcac tgtggcaaga     360
tggagcctgc ctgtaagagt cacttcatcc aagactcctg cctgtatgag tgctccccca     420
accttgggcc ttggatccag caagtggacc agagttggcg taaagagcgt tcctggatg      480
tgccttatgc aaagaggact gtcaccagtg gtgggaagcc tgtcgtacgt cctttacctg     540
caagagagac tggcataaag gctgggactg gtctcaggca ttaccagtgc aaacacagg     600
accctgtaaa cgttgagtac tattccgaaa cagcagcc                             638

<210> SEQ ID NO 249
<211> LENGTH: 502
<212> TYPE: DNA
<213> ORGANISM: Mus musculus

<400> SEQUENCE: 249
ttcggcacag ggggctgtgg acgaagactg tagagactac ccagagtctg acctagggag      60
aggccaactc ggataccccct atgtgcgctc ccagaagcta aggacattga acagaaaga     120
catggcctgg aaacagacac cactcttgct tttggtctac atggtcacaa caggcagtgg     180
ccgggacaga acagacctac tcaacgtttg catggatgcc aaacaccata gacaaagcc      240
gggccccgag acaagctgc atgaccagtg tagtccatgg aagaaaaatg cctgttgctc     300
agtcaacacc agccaggagc tacacaaggc tgactcccgt ctgtacttca actgggatca     360
ctgtggcaag atggagcctg cctgtaagag tcacttcatc caagactcct gcctgtatga     420
```

| | |
|---|---|
| gtgctccccc aaccttgggc cttggatcca gcaagtggac cagagttggc gtaaagagcg | 480 |
| tttcctggat gtgcccttat gc | 502 |

<210> SEQ ID NO 250
<211> LENGTH: 1325
<212> TYPE: DNA
<213> ORGANISM: Homo sapiens

<400> SEQUENCE: 250

| | |
|---|---|
| ggaaaggatt ttctcagccc ccatctccag cactgtgtgt tggccgcacc catgagagcc | 60 |
| tcagcactct gaaggtgcag ggggcaaagg ccaaaagagc tctggcctga acttgggtgg | 120 |
| tccctactgt gtgacttggg gcatggcctc atctgtgctg aaatgattcc acaaagatta | 180 |
| aactggctat catttgttga tttccccctt cttacattta atccttgcag agaaagcta | 240 |
| agcctcaaga tagtttgctt ctctttcccc caaggccaag gagaaggtgg agtgagggct | 300 |
| ggggtcggga caggttgaac gggaaccctg tgctctaaca gttagggccc gccgaggaac | 360 |
| tgaacccaaa ggatcacctg gtattccctg agagtacaga tttctccggc gtggccctca | 420 |
| agggacagac atggctcagc ggatgacaac acagctgctg ctccttctag tgtgggtggc | 480 |
| tgtagtaggg gaggctcaga caaggattgc atgggccagg actgagcttc tcaatgtctg | 540 |
| catgaacgcc aagcaccaca aggaaaagcc aggccccgag acaagttgc atgagcagtg | 600 |
| tcgaccctgg aggaagaatg cctgctgttc taccaacacc agccaggaag cccataagga | 660 |
| tgtttcctac ctatatagat tcaactgaa ccactgtgga gagatggcac ctgcctgcaa | 720 |
| acggcatttc atccaggaca cctgcctcta cgagtgctcc cccaacttgg ggccctggat | 780 |
| ccagcaggtg gatcagagct ggcgcaaaga gcgggtactg aacgtgcccc tgtgcaaaga | 840 |
| ggactgtgag caatggtggg aagattgtcg cacctcctac acctgcaaga gcaactggca | 900 |
| caagggctgg aactggactt cagggtttaa caagtgcgca gtgggagctg cctgccaacc | 960 |
| tttccatttc tacttcccca cacccactgt tctgtgcaat gaaatctgga ctcactccta | 1020 |
| caaggtcagc aactacagcc gagggagtgg ccgctgcatc cagatgtggt tcgacccagc | 1080 |
| ccagggcaac cccaatgagg aggtggcgag gttctatgct gcagccatga gtggggctgg | 1140 |
| gccctgggca gcctggcctt tcctgcttag cctggcccta atgctgctgt ggctgctcag | 1200 |
| ctgacctcct tttaccttct gatacctgaa aatccctgcc ctgttcagcc ccacagctcc | 1260 |
| caactatttg gttcctgctc catggtcggg cctctgacag ccactttgaa taaaccagac | 1320 |
| accgc | 1325 |

<210> SEQ ID NO 251
<211> LENGTH: 819
<212> TYPE: DNA
<213> ORGANISM: Homo sapiens

<400> SEQUENCE: 251

| | |
|---|---|
| cgcaggaata gatggacatg gcctggcaga tgatgcagct gctgcttctg gctttggtga | 60 |
| ctgctgcggg gagtgcccag cccaggagtg cgcgggccag gacggacctg ctcaatgtct | 120 |
| gcatgaacgc caagcaccac aagacacagc ccagccccga ggacgagctg tatgccagt | 180 |
| gcagtccctg gaagaagaat gcctgctgca cggccagcac cagccaggag ctgcacaagg | 240 |
| acacctcccg cctgtacaac tttaactggg atcactgtgg taagatggaa cccacctgca | 300 |
| agcgccactt tatccaggac agctgtctct atgagtgctc acccaacctg ggccctgga | 360 |

| | |
|---|---:|
| tccggcaggt caaccagagc tggcgcaaag agcgcattct gaacgtgccc ctgtgcaaag | 420 |
| aggactgtga cgctggtgg gaggactgtc gcacctccta cacctgcaaa agcaactggc | 480 |
| acaaaggctg gaattggacc tcagggatta atgagtgtcc ggccggggcc ctctgcagca | 540 |
| cctttgagtc ctacttcccc actccagccg cctttgtga aggcctctgg agccactcct | 600 |
| tcaaggtcag caactatagt cgagggagcg gccgctgcat ccagatgtgg tttgactcag | 660 |
| cccagggcaa ccccaatgag gaggtggcca agttctatgc tgcggccatg aatgctgggg | 720 |
| ccccgtctcg tgggattatt gattcctgat ccaagaaggg tcctctgggg ttcttccaac | 780 |
| aacctattct aatagacaaa tccacatgaa aaaaaaaa | 819 |

```
<210> SEQ ID NO 252
<211> LENGTH: 283
<212> TYPE: DNA
<213> ORGANISM: Homo sapiens
<220> FEATURE:
<221> NAME/KEY: modified_base
<222> LOCATION: (259)
<223> OTHER INFORMATION: N = A, C, G, or T/U

<400> SEQUENCE: 252
```

| | |
|---|---:|
| catgagcagt gtcgaccctg gaggaagaat gcctgctgtt ctaccaacac cagccaggaa | 60 |
| gcccataagg atgttttccta cctatataga ttcaactgga accactgtgg agagatggca | 120 |
| cctgcctgca acggcatttt catccaggac acctgcctct acgagtgctc ccccaacttg | 180 |
| gggccctgga tccagcaggt ggatcagagc tggcgcaaag agcgggtact gaacgtgccc | 240 |
| ctgtgcaaag aggactgtna gcaaatggtg gggaagattg tcg | 283 |

```
<210> SEQ ID NO 253
<211> LENGTH: 834
<212> TYPE: DNA
<213> ORGANISM: Homo sapiens

<400> SEQUENCE: 253
```

| | |
|---|---:|
| gaattccgga caaggattgc atgggccagg actgagcttc tcaatgtctg catgaacgcc | 60 |
| aagcaccaca aggaaaagcc aggccccgag gacaagttgc atgagcagtg tcgaccctgg | 120 |
| aggaagaatg cctgctgttc taccaacacc agccaggaag cccataagga tgtttcttac | 180 |
| ctatatagat tcaactggaa ccactgtgga gagatggcac ctgcctgcaa acggcatttc | 240 |
| atccaggaca cctgcctcta cgagtgctcc cccaacttgg ggccctggat ccagcaggtg | 300 |
| gatcagagct ggcgcaaaga gcgggtactg aacgtgcccc tgtgcaaaga ggactgtgag | 360 |
| caatggtggg aagattgtcg cacctcctac acctgcaaga gcaactggca caagggctgg | 420 |
| aactggactt cagggtttaa caagtgcgca gtgggagctg cctgccaacc tttccatttc | 480 |
| tacttcccct ctcccactgt tctgtgcaat gaaatctgga ctcactccta caaggtcagc | 540 |
| aactacagcc gagggagtgg ccgctgcatc cagatgtggt tcgacccagc ccagggcaac | 600 |
| cccaatgagg aggtggcgag gttctatgct gcagccatga gtgggctggg cctgggca | 660 |
| gcctggcctt tcctgcttag cctggcctaa tgctgctgtg gctgctcagc tgacctcctt | 720 |
| ttaccttctg atacctggaa atccctgccc tgttcagccc cacagctccc aactatttgg | 780 |
| ttcctgctcc atggtcgggc ctctgacagc cattttgaat aaaccagaca ccgc | 834 |

```
<210> SEQ ID NO 254
<211> LENGTH: 1067
<212> TYPE: DNA
<213> ORGANISM: Homo sapiens
```

<400> SEQUENCE: 254

```
cctgtgtctt cccgcatcca gtgtagtctc tggagaaaga atgcctgagc tttaccagca    60
ccacccagga agcccataag aatattccca tctatatgga ttcaactgga accactgtgg   120
agagatggta cctgcctgca aacggcactt tatccaggac acctgccttt acgagtgacc   180
ccccaacttg gggccctgga tccagcaggt atgcatggct tcctggcatc aagagctag    240
cagaggagct gaattttcca ggcgtctctg caggcagcaa ccccagctcc acttctattc   300
agggctgggt tcctgggatt cttgagcctg agcccttctt ttctaccaaa atctcccagg   360
tggatcagag ctggtgcaaa gagtgggtgc tgaatgtgcc cctgtgcaaa gaggactgtg   420
agcaatggtg ggaagattgt cgcacctcct acacctgcaa gagcaatggg cacaagggct   480
ggaactggac ctcaggtgag ggctggggtg gcaggaaag  gagggatttg gaagtgaagg    540
tgtgttgggt gtggaacagg tgtgtgacat tttggggttg tagggctggc agaatcagag   600
acctttgggg cccagtggct aaaggtcttc cctcttccta cagggtctaa caagtgccag   660
gtggcagctg cctgactacc tttccatctc tactttctca cacccactgc tctgtgcagt   720
gaaatctgga ctcactccta cagggtcagc aactacaacc gagggagcag ccgctgcatc   780
cagatgtggt tcgacctggc ccagggcaac cccaatgagg aggtggcaag gttctatgct   840
gcagctctga gtggggctgg gccctgggca gcctggcctc tcctgctcaa cctgccccta   900
atgctgctgt ggctgctcag ctgacctcct tttaccttct gatacttgga catccctgcc   960
ctgtttagcc ccacagctcc caactatttg gttcctcttc tatggtcttg tctctgacag  1020
ccactttgaa taaaccacac accacacatg tatcttgaga attattt                1067
```

<210> SEQ ID NO 255
<211> LENGTH: 900
<212> TYPE: DNA
<213> ORGANISM: chicken

<400> SEQUENCE: 255

```
gaattcctct agggagaagt ctcacccaga aggacagcaa agaggaaaaa gaagggaaca    60
acaatgctga ggtttgccat caccctcttt gctgtcatca catcatctac ctgccagcag   120
tatggatgtc tggaagggga cacccacaaa gcgaagccaa gtcctgagcc aaacatgcat   180
gaatgcactc tgtattctga atcttcctgt tgctatgcaa acttcacaga gcaattggct   240
cattccccaa taattaaagt aagcaacagc tactggaaca gatgtgggca gctcagtaaa   300
tcctgtgaag atttcacaaa gaaaatcgag tgcttttacc ggtgttctcc gcacgctgct   360
cgctggatcg atcccagata tactgctgct attcagtctg ttccactgtg tcagagcttc   420
tgtgatgact ggtatgaagc ctgcaaagat gattccattt gtgctcataa ctggctgacg   480
gactgggaac gggatgaaag tggagaaaac cactgtaaga gtaaatgcgt accatacagt   540
gagatgtatg caaatgggac cgacatgtgc cagagtatgt gggggaatc ctttaaggtg    600
agcgaatcct cctgcctctg cttgcaaatg aacaagaagg acatggtggc aatcaagcac   660
ctcctctccg aaagctcaga ggaaagctcc agtatgagca gcagtgagga gcacgcctgc   720
caaaagaaac tcctgaagtt tgaggcactg cagcaagagg aaggggaaga gagaagatga   780
attttggtgg atgaatatca ggaggagagg aatcattgtg gaggttgtgc tcggggcatc   840
acagcagcct gtcttatccc tcacttctga gaacacaata aatcaatggt tggctatatt   900
```

<210> SEQ ID NO 256

```
<211> LENGTH: 1223
<212> TYPE: DNA
<213> ORGANISM: Mus musculus

<400> SEQUENCE: 256
gctttagagg cagatcaggg tgtagttttc agctagcgcc gtgccttccc caccatgttc    60
cttgccatga tgataatgta ctagacctct gaaactgtag cttctttgtt acagagtctc   120
cgtgaatctg gaattcacca attcggcgag tctgaaagcc tcagtgatct ctcaggctcc   180
atctgtctcc actccccagt ggaaggcttg cagctgtgtc accgctccag acttcacaca   240
ggtgctggaa gactgaacta agacagaaag acatggcctg gaaacagaca ccactcttgc   300
ttttggtcta catggtcaca acaggcagtg gccgggacag aacagaccta ctcaacgttt   360
gcatggatgc caaacaccat aagacaaagc cgggccccga ggacaagctg catgaccagt   420
gtagtccatg gaagaaaaat gcctgttgct cagtcaacac cagccaggag ctacacaagg   480
ctgactcccg tctgtacttc aactgggatc actgtggcaa gatggagcct gcctgtaaga   540
gtcacttcat ccaagactcc tgcctgtatg agtgctcccc caaccttggg ccttggatcc   600
agcaagtgga ccagagttgg cgtaaagagc gtttcctgga tgtgccctta tgcaaagagg   660
actgtcacca gtggtgggaa gcctgtcgta cctcctttac ctgcaagaga gactggcata   720
aaggctggga ctggtcctca ggcattaaca agtgcccaaa cacagcaccc tgtcacacgt   780
ttgagtacta cttcccgaca ccagccagcc tttgcgaggg tctctggagt cactcctaca   840
aggtcagcaa ctacagcaga gggagtggcc gctgcatcca gatgtggttt gactcaaccc   900
agggcaatcc caatgaggac gtggtgaagt tttatgcttc ctttatgaca tctgggactg   960
tgccccatgc agcagtactt cttgtgccca gcctggcccc agtgctgtca ttatggctcc  1020
ctggctgaga ggtcagtctt cctctctaga tttctcctct atctaccctt ggtctggttc  1080
aactcttcaa agaataagga agtcttgagc ctgcttccac ccctctcctc tgtcatccag  1140
ttcctgatcc atgttggggg ttggggtttc tacaatcatt tcaataaat  ctatgacaca  1200 tctgggccta atgaaaaaaa aaa                                           1223

<210> SEQ ID NO 257
<211> LENGTH: 1565
<212> TYPE: DNA
<213> ORGANISM: Mus musculus

<400> SEQUENCE: 257
ggatccaaga gattttatac tgtccttcag cactgtcctt cagttctttt tgttttttg    60 ttttttgttt tgttttgttt ttggttttc gagacagggt ttctctgtgt agccctggct   120
gtcctggaac tcactctgta gaccaggctg gcctcgaact cagaaatcca cctgcctctg   180
cctcccaagt gctgggttta aaggcatacg ccaccacagc ccggctcttc ggttctttag   240
gtcattattt ttggggtag ggggacaaac aaattctcac tatgtatcac agattggcct   300
agaccccaca agccttcccc cttcccgtcc tccatgtcct gggggttgcag gcgtgtctca   360 ccaattgcag ctgggcttgt tttgtgtgtt tccttttgag aggtttcggt cgggtcgggt   420
gcttttgctg cagatgccgc tgtcaggatg gctgtcagg gcagaatggc ttttggagaa   480
caggaaagga aaatactgag gaagcaaaac tttacaaagc agcactcttt cttgtgtacc   540
ctctaaccac accatcctgt gggctgtcac ttggtcctcc tgccaatctg gagaacttgg   600
cagggctggg tcaccacctc cctcaggct aacaggactt ctaggctgac atgatgaccc   660
agctgataca gagtggaatg ccgagaacct cctgtgacag gatgaaggat ctgtgtgtcc   720
```

```
ctggcccttg tcaaggtagc aagcagcagg aacctgaact atttaactat gtgtcataaa        780
gtctggaaat aagatgaaag catggggcat cccatcttct ctaggttgga aagctttgct        840
tcttttataa ccccctccc caatgccatg gggccatggg ataaaagagt ctccttgctg         900
acctctattc cagcttcagg gagcctgagg acatgaatgc tgaaggagaa gggactgatc        960
taatctttca ctatagggac agagagtctg agtcagggaa taaatgaagt ccctccccccc      1020 tctggtctag gtctccctaa ctttagctcc ctctgcacag acagaaagac atggcctgga      1080
aacagacacc actcttgctt ttggtctaca tggtcacaac aggcagtggc cgggacagaa      1140
cagacctact caacgtttgc atggatgcca aacaccataa cacaaagccg ggccccgagg      1200
acaagctgca tgaccaggtt ctgtgccagt gtggtcctga tgggagggtg atagagggca      1260
gggtggggtt agtgagcagc cagacacacc cacaccctga gctcttgttg gcagagatgg      1320
cttggtggaa agtagtgagg tgattttctg agggctgtcc ccagaagagg acacagtagt      1380
ggcaatgaag cagttgatca ttagaagcct ctaattagag gccacgtgag gtcatgtgat      1440
gataatctct atatctctca aataagggcc cgtggaagca cagggactca ctctcacagg      1500
ttagacacac ctgattttttt ttttttgag agcattggtg ttttgcctac atatgtgttg      1560
gatcc                                                                  1565

<210> SEQ ID NO 258
<211> LENGTH: 1000
<212> TYPE: DNA
<213> ORGANISM: Mus musculus

<400> SEQUENCE: 258
tctagaattt tcagccctat cttaagcact atataacatg tgaaaaggaa caaagggct         60 tctaacacta gaaaaattt aaggccaaac ataacttgta aagccatttt ccactttact        120
tctgatagac tgtcttgaat ttccttagaa agttcaagat cagacttacc tcgttcccca       180
gctgaaaagt tctgaattca tacagttgaa tccttcttaa cagtctgctt tacgggaacc       240
tttatcaccg tcgttcccca gctgatgagt tctgaattcg gcagttgaat ccttctcaac       300
agtctgtgtt acgggaacct tataaccttg attcgcagtt ctggtctgg aatgagggat        360 cttccttgcg ccagtcccga gttttttctc gtcccggatt ttctcgtccc ggaattcggc       420
accaattgtt attcgacgcg ttctcacgac cggccaggaa gaacaccaca gaccagaatc       480
ttctgcgaca aagctttatt cttacatctt caggaaaaga gagcaagaag caagagagag       540
caagaagcaa gagagggaag caagagagag caagaagcaa gagagggaag caagagagag       600
caaagcaaga gagagagaaa aacgaaaccc cttctatttt aaagagaaca accattgcct       660
agggcgcatc actccctgat tggctgcagc ccatggccga gctgacgttc acgggaaaaa       720
cagagtacaa gtagtcgtaa ataccccttgg ctcatgcgca gattatttgt ttaccaactt      780
agaacacagg atgtcagcgc catcttgtga cggcgaatgt gggggcggct tcccacaagg       840
ctccacccac tggagctgag cacacacttg gaggttccac ttaccttagc tctgccttca       900
gggtctgaca tggctcacct gatgactgtg cagttgttgc tcctggtgat gtggatggcc       960
gaatgtgctc agtccagagc tactcgggcc aggactgaac                            1000

<210> SEQ ID NO 259
<211> LENGTH: 1391
<212> TYPE: DNA
<213> ORGANISM: Mus musculus
```

<400> SEQUENCE: 259

```
actagttgtg tctagatcct attgcactga tggtcatgaa gttgaaacat gggggaaaat      60
gaactttata cccttcttca tgacttctgt ccttttgcct gcctcctttc tcatctccta     120
atattacagt cttggtttcc tctctaaatt tttagacttt taacccacac ctaaacctgt     180
atcagctttt ataaaaatct tttcaaaact tcacactgaa gcatctgcct ccaaaggttt     240
tgaatgtgaa cgtgggtaaa ctctgttttt gcaaatggcc catctcttat tttttaattg     300
ccctgtgtga gtctcaggac cactaagtct aacaggctgt gaccagtgat tgtctctagg     360
gcatctgagc ctcacagagt ctgggaagac tgacaggagg aggtgaccca aggtctgtga     420
gtgcaggctc cacccactgg agctgagcac acacttggag gttccactta ccttagctct     480
gccttcaggg tctgacatgg ctcacctgat gactgtgcag ttgttgctcc tggtgatgtg     540
gatggccgaa tgtgctcagt ccagagctac tcgggccagg actgaacttc tcaatgtctg     600
catggatgcc aagcaccaca agaaaaaacc gggccctgag gacaatttac acgaccaggt     660
aggacgaagg gtgatgtgtg gctgactaag ggctcgtggg tcaggagaaa gaagtatcta     720
gtcccagttt atggtggagg tggtcagacc tacctgagga gaccttcggt tctctctagt     780
gtgggtgact ttgacagtac atattggctg ccaactgcca gtgtgatatt atcagctcat     840
cttcctggta gctgaatttt gacgttgcat aagtaaggaa gtagattcaa ggaggaactt     900
gggaatggaa caggcaaacc attgtgatgg ttttagattt aaactgattg gggaggacgc     960
ctctgggagt ctcaggggag ggactgtatg ctgcccagtc acttttctgc cagccttga     1020
agacttgaga aggagactct catatctgag aagcctttgg aggcaggcat ctagcgaaca    1080
cttggactgt ggtcctcagc ttgagggctg gagggcttga gggctctgtg ttataacagt    1140
tgtttgccat agtgcttttca gtatcccaaa gctcactaaa catttaataa aatcagtgtg    1200
atgcaacaac tatgaagtca accagcagca ggtctgctat ggggaggta caatcagtgc     1260
agacaacaaa gtggggagggg ggtctcaaaa aagccaagat gagggctgga gagttggctc    1320
agtggttaaa agcacttgtt gagcttgcag aataccaagg tctgatccac aacatccaag    1380
gtggtggatc c                                                          1391
```

<210> SEQ ID NO 260
<211> LENGTH: 979
<212> TYPE: DNA
<213> ORGANISM: Mus musculus

<400> SEQUENCE: 260

```
tggagctgag cacacacttg gaggttccac ttaccttagc tctgccttca gggtctgaca      60
tggctcacct gatgactgtg cagttgttgc tcctggtgat gtggatggcc gaatgtgctc     120
agtccagagc tactcgggcc aggactgaac ttctcaatgt ctgcatggat gccaagcacc     180
acaaagaaaa accgggccct gaggacaatt tacacgacca gtgcagcccc tggaagacga     240
attcctgctg ttccacgaac acaagccagg aagcacataa ggacatttcc tacctgtacc     300
ggttcaactg gaaccactgc ggaactatga catcggaatg caaacggcac tttatccaag     360
acacctgcct ctatgagtgt tccccgaact tgggaccctg gatccagcag gtggaccaga     420
gctggcgcaa agagcggatc cttgatgttc ccctgtgcaa agaggactgt cagcagtggt     480
gggaggactg ccagagctct tttacctgca gagcaattg gcacaaggga tggaactggt     540
cctctgggca taacgagtgt cctgtgggag cctcctgcca tcccttcacc ttctacttcc     600
ccacatctgc tgctctgtgt gaggaaatct ggagtcactc ctacaagctc agcaactaca     660
```

```
gccgagggag cggccgctgc attcagatgt ggtttgaccc agcccagggc aaccccaacg    720
aggaagtggc gaggttctat gccgaggcca tgagtggagc tgggcttcat gggacctggc    780
cactcttgtg cagcctgtcc ttagtgctgc tctgggtgat cagctgagtt cctgttttac    840
cttcagttgt ctggagcgcc accctgcttg gctcagcctc ccagctccca gcctcctttg    900
tggtggggct ctgacagcct ctttaataaa ccagacattc cacatgtgcc ttatgaatta    960
aaaaaaaaaa aaaaaaaa                                                  979

<210> SEQ ID NO 261
<211> LENGTH: 66
<212> TYPE: DNA
<213> ORGANISM: Homo sapiens

<400> SEQUENCE: 261
acaaggattg catgggccag gactgagctt ctcaatgtct gcatgaacgc caagcaccac     60
aaggaa                                                                66

<210> SEQ ID NO 262
<211> LENGTH: 1108
<212> TYPE: DNA
<213> ORGANISM: Homo sapiens

<400> SEQUENCE: 262
ctggaggcct ggctggtgct cacatacaat aattaactgc tgagtggcct tcgcccaatc     60
ccaggctcca ctcctgggct ccattccac tccctgcctg tctcctaggc cactaaacca    120
cagctgtccc ctggaataag gcaaggggga gtgtagagca gagcagaagc ctgagccaga    180
cggagagcca cctcctctcc cagggacaga catggctcag cggatgacaa cacagctgct    240
gctccttcta gtgtgggtgg ctgtagtagg ggaggctcag acaaggattg catgggccag    300
gactgagctt ctcaatgtct gcatgaacgc caagcaccac aaggaaaagc caggccccga    360
ggacaagttg catgagcagt gtcgaccctg gaggaagaat gcctgctgtt ctaccaacac    420
cagccaggaa gcccataagg atgtttccta cctatataga ttcaactgga accactgtgg    480
agagatggca cctgcctgca aacggcattt catccaggac acctgcctct acgagtgctc    540
ccccaacttg gggccctgga tccagcaggt ggatcagagc tggcgcaaag agcgggtact    600
gaacgtgccc ctgtgcaaag aggactgtga gcaatggtgg gaagattgtc gcacctccta    660
cacctgcaag agcaactggc acaagggctg gaactggact tcagggttta acaagtgcgc    720
agtgggagct gcctgccaac cttttccatt ctacttcccc acacccactg ttctgtgcaa    780
tgaaatctgg actcactcct acaaggtcag caactacagc cgagggagtg gccgctgcat    840
ccagatgtgg ttcgacccag cccagggcaa ccccaatgag gaggtggcga ggttctatgc    900
tgcagccatg agtggggctg ggccctgggc agcctggcct ttcctgctta gcctggccct    960
aatgctgctg tggctgctca gctgacctcc ttttaccttc tgatacctgg aaatccctgc   1020
cctgttcagc cccacagctc ccaactattt ggttcctgct ccatggtcgg gcctctgaca   1080
gccactttga ataaaccaga caccgcac                                      1108

<210> SEQ ID NO 263
<211> LENGTH: 991
<212> TYPE: DNA
<213> ORGANISM: Homo sapiens

<400> SEQUENCE: 263
```

```
ggagagccac ctcctctccc aggaactgaa cccaaaggat cacctggtat tccctgagag      60
tacagatttc tccggcgtgg ccctcaaggg acagacatgg ctcagcggat gacaacacag     120
ctgctgctcc ttctagtgtg ggtggctgta gtagggggagg ctcagacaag gattgcatgg    180
gccaggactg agcttctcaa tgtctgcatg aacgccaagc accacaagga aaagccaggc    240
cccgaggaca agttgcatga gcagtgtcga ccctggagga agaatgcctg ctgttctacc    300
aacaccagcc aggaagccca taaggatgtt tcctacctat atagattcaa ctggaaccac    360
tgtggagaga tggcacctgc ctgcaaacgg catttcatcc aggacacctg cctctacgag    420
tgctccccca acttgggggcc ctggatccag caggtggatc agagctggcg caaagagcgg    480
gtactgaacg tgcccctgtg caaagaggac tgtgagcaat ggtgggaaga ttgtcgcacc    540
tcctcaccct gcaagagcaa ctggcacaag ggctggaact ggacttcagg gtttaacaag    600
tgcgcagtgg gagctgcctg ccaacctttc catttctact tccccacacc cactgttctg    660
tgcaatgaaa tctggactca ctcctacaag gtcagcaact acagccgagg gagtggccgc    720
tgcatccaga tgtggttcga cccagcccag ggcaaccccca atgaggaggt ggcgaggttc    780
tatgctgcag ccatgagtgg ggctgggccc tgggcagcct ggcctttcct gcttagcctg    840
gccctaatgc tgctgtggct gctcagctga cctccttttta ccttctgata cctggaaatc    900
cctgccctgt tcagccccac agctcccaac tatttggttc ctgctccatg gtcgggcctc    960
tgacagccac tttgaataaa ccagacaccg c                                    991

<210> SEQ ID NO 264
<211> LENGTH: 1230
<212> TYPE: DNA
<213> ORGANISM: Homo sapiens

<400> SEQUENCE: 264
gaatcaattc ctccaaaccg caagaacagt aacatttatt attcaaaaaa acaaaaacca      60
gattatagga tatgacattt ggtataacaa taatgttatt gaaaaatgga aaatgatcc     120 attaatggct tgggctaaaa attcgggggga cagcctaggg gcctggatct attgcctact    180
tagagagagg ccaactcaga cacagccgtg tatgctccca gcagcaacgg aggttcacgt    240
ccgcctgcag ggacagaaag acatggtctg gaaatggatg ccacttctgc tgcttctggt    300
ctgtgtagcc accatgtgca gtgcccagga caggactgat ctcctcaatg tctgtatgga    360
tgccaagcac cacaagacaa agccaggtcc tgaggacaag ctgcatgacc aatgcagtcc    420
ctggaagaag aatgcctgct gcacagccag caccagccag gagctgcaca aggacacctc    480
ccgcctgtac aactttaact gggaccactg cggcaagatg gagcccgcct gcaagcgcca    540
cttcatccag acacctgtc tctatgagtg ctcacccaac ctggggccct ggatccagca    600
ggtgaatcag acgtggcgaa agaacgcttt cctggatgtg cccttatgca agaggactg     660 tcagcgctgg tgggaggatt gtcacacctc ccacacgtgc aagagcaact ggcacagagg    720
atgggactgg acctcaggag ttaacaagtg cccagctggg gctctctgcc gcacctttga    780
gtcctacttc cccactccag ctgcccttttg tgaaggcctc tggagtcact catacaaggt    840
cagcaactac agccgaggga gcggccgctg catccagatg tggtttgatt cagcccaggg    900
caaccccaac gaggaagtgg cgaggttcta tgctgcagcc atgcatgtga atgctggtga    960
gatgcttcat gggactgggg gtctcctgct cagtctggcc ctgatgctgc aactctggct   1020
ccttggctga gttcagtcct cccagactac ctgccctcag cttggataac caggctgggc   1080
tcagctcagc tcccacaaat gacagcccct taagcatgct tctattagtc acctaaccct   1140
```

```
ctgtcaccca gtctgttgct gctccatggt ggggccaaga gtcacttcta ataaacagac    1200
tgttttctaa taaaaaaaaa aaaaaaaaaa                                    1230

<210> SEQ ID NO 265
<211> LENGTH: 819
<212> TYPE: DNA
<213> ORGANISM: Homo sapiens

<400> SEQUENCE: 265
cgcaggaata gatggacatg gcctggcaga tgatgcagct gctgcttctg gctttggtga     60
ctgctgcggg gagtgcccag cccaggagtg cgcgggccag gacggacctg ctcaatgtct    120
gcatgaacgc caagcaccac aagacacagc ccagccccga ggacgagctg tatggccagt    180
gcagtccctg gaagaagaat gcctgctgca cggccagcac cagccaggag ctgcacaagg    240
acacctcccg cctgtacaac tttaactggg atcactgtgg taagatggaa cccacctgca    300
agcgccactt tatccaggac agctgtctct atgagtgctc acccaacctg ggccctgga    360 tccggcaggt caaccagagc tggcgcaaag agcgcattct gaacgtgccc ctgtgcaaag    420
aggactgtga cgctggtgg gaggactgtc gcacctccta cacctgcaaa agcaactggc    480
acaaaggctg gaattggacc tcagggatta atgagtgtcc ggccggggcc ctctgcagca    540
cctttgagtc ctacttcccc actccagccg ccctttgtga aggcctctgg agccactcct    600
tcaaggtcag caactatagt cgagggagcg gccgctgcat ccagatgtgg tttgactcag    660
cccagggcaa ccccaatgag gaggtggcca agttctatgc tgcggccatg aatgctgggg    720
ccccgtctcg tgggattatt gattcctgat ccaagaaggg tcctctgggg ttcttccaac    780
aacctattct aatagacaaa tccacatgaa aaaaaaaa                            819

<210> SEQ ID NO 266
<211> LENGTH: 1123
<212> TYPE: DNA
<213> ORGANISM: Homo sapiens

<400> SEQUENCE: 266
gaggagggta tggggaggca cttagttcct gtgtcttccc cacccagtgc agtccctgga     60
agaagaatgc ctgctgcaca gccagcacca gccaggagct gcacaaggac acctcccgcc    120
tgtacaactt taactgggac cactgcgca agatggagcc cgcctgcaag cgccacttca    180
tccaggacac ctgtctctat gagtgctcac ccaacctggg ccctggatc agcaggtag      240 ggtgtctccc ccccacccac cccagcagac tgccatcccc ctcagtcact tcaaggcgat    300
ggctgccagc atccctggct gagaggagcc ctgcctcccc acctccacc caggtgaatc     360 agacgtggcg caaagaacgc ttcctggatg tgcccttatg caagaggac tgtcagcgct    420 ggtgggagga ttgtctcacc tcccacacgt gcaagagcaa ctggcacaga ggatgggact    480
ggacctcagg tgagggtgat tgagttgggg ttaggaaaaa ggagattgag gtagggtttg    540
gaaaatcctc aaggatttgg ggtggggtga agatttctgg gggtggccag aaatgagctt    600
tgggcccagg ggctgaaagt ctgtgtccac catgcctctc cctgcaggag ttaacaagtg    660
cccagctggg gctctctgcc gcacctttga gtcctacttc cccactccag ctgccctttg    720
tgaaggcctc tggagtcact catacaaggt cagcaactac agccgaggga gcggccgctg    780
catccagatg tggtttgatt cagcccaggg caaccccaac gaggaagtgg cgaggttcta    840
tgctgcagcc atgcatgtga atgctggtga gatgcttcat gggactgggg gtctcctgct    900
```

```
caggctggcc ctgatgctgc aactctggct ccttggctga gttcagtcct cccagactac    960
ctgccctcag cttggataac caggctgggc tcagctcagc tcccacaaat gccagcccct   1020
taagcatgct tctattagtc acctaaccct ctgtcaccca gtctgttgct gctccatggt   1080
ggggccaaga gtcacttcta ataaacagac tgttttctaa taa                     1123

<210> SEQ ID NO 267
<211> LENGTH: 374
<212> TYPE: DNA
<213> ORGANISM: Homo sapiens

<400> SEQUENCE: 267
agcttcaggg ccccagcatc gaaggaacag gtctgacct catttgccac cgtagggatg      60
gggagactga ggcaggaggt gaatggctcc cagcttggag ccctttcccc tcaggacttg    120
gtttccctac cctacgtccg cctgcaggga cagaaagaca tggtctggaa atggatgcca    180
cttctgctgc ttctggtctg tgtagccacc atgtgcagtg cccaggacag gactgatctc    240
ctcaatgtct gtatggatgc caagcaccac aagacaaagc caggtcctga ggacaagctg    300
catgaccaag tacggctgga gtgtgcctct gctaaggagg ggcttgttct aacagggagg    360
agaaagtcag gatg                                                      374

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 268

Glu Ile Trp Thr His Ser Tyr Lys Val
  1               5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 269

Leu Leu Ser Leu Ala Leu Met Leu Leu
  1               5

<210> SEQ ID NO 270
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 270

Ser Tyr Lys Val
  1

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence:  Synthetic
```

```
    Peptide

<400> SEQUENCE: 271

Phe Ile Trp Thr Phe Ser Thr Lys Val
 1               5
```